US012807674B2

(12) United States Patent
Wang et al.

(10) Patent No.: US 12,807,674 B2
(45) Date of Patent: Nov. 24, 2026

(54) BINDING PROTEINS RECOGNIZING MAGEA1 PEPTIDE-MHC COMPLEX

(71) Applicants: TScan Therapeutics, Inc., Waltham, MA (US); Dana-Farber Cancer Institute, Inc., Boston, MA (US)

(72) Inventors: Yifan Wang, Arlington, MA (US); Jenny Tadros, Brighton, MA (US); Nancy Nabilsi, Lynnfield, MA (US); Gavin MacBeath, Wakefield, MA (US); Jonathan Schoenfeld, Brookline, MA (US); Kai Wucherpfennig, Brookline, MA (US)

(73) Assignees: TScan Therapeutics, Inc., Waltham, MA (US); Dana-Farber Cancer Institute, Inc., Boston, MA (US)

( * ) Notice: Subject to any disclaimer, the term of this patent is extended or adjusted under 35 U.S.C. 154(b) by 1050 days.

(21) Appl. No.: 17/984,647

(22) Filed: Nov. 10, 2022

(65) Prior Publication Data

US 2023/0270832 A1 Aug. 31, 2023

Related U.S. Application Data

(60) Provisional application No. 63/342,415, filed on May 16, 2022, provisional application No. 63/317,337, filed on Mar. 7, 2022, provisional application No. 63/277,924, filed on Nov. 10, 2021.

(51) Int. Cl.

*C07K 16/30* (2006.01)
*C07K 14/705* (2006.01)
*A61K 39/00* (2006.01)
*C07K 14/47* (2006.01)

(52) U.S. Cl.

CPC .......... *C07K 14/7051* (2013.01); *C07K 16/30* (2013.01); *A61K 39/001186* (2018.08); *A61K 39/00119* (2018.08); *A61K 2039/876* (2018.08); *C07K 14/4748* (2013.01); *C07K 14/70539* (2013.01)

(58) Field of Classification Search

CPC .......................... C07K 14/7051; C07K 16/30; C07K 14/4748; C07K 14/70539; A61K 39/001186

See application file for complete search history.

(56) References Cited

U.S. PATENT DOCUMENTS

| | | | |
|---|---|---|---|
| 2006/0073159 A1 | 4/2006 | Vonderheide et al. |
| 2008/0260762 A1 | 10/2008 | Grey et al. |
| 2011/0318380 A1 | 12/2011 | Brix et al. |
| 2019/0106477 A1 | 4/2019 | Vander Elst |
| 2020/0254106 A1 | 8/2020 | Alten et al. |
| 2021/0198341 A1 | 7/2021 | Zhou et al. |
| 2022/0370584 A1 | 11/2022 | Gifford et al. |

FOREIGN PATENT DOCUMENTS

| | | |
|---|---|---|
| WO | WO-1995/004542 A1 | 2/1995 |
| WO | WO-2010/037395 A2 | 4/2010 |
| WO | WO-2020/194195 A1 | 10/2020 |
| WO | WO-2020/201318 A1 | 10/2020 |
| WO | WO-2021/119545 A1 | 6/2021 |
| WO | WO-2022/232148 A2 | 11/2022 |
| WO | WO-2023/086480 A2 | 5/2023 |
| WO | WO-2023/215183 A1 | 11/2023 |

OTHER PUBLICATIONS

Luoma et al, 2022. Cell. 185(16): 2918-2935; published on-line Jul. 7, 2022 (Year: 2022).*

Ferretti et al., "Unbiased Screens Show CD8+ T Cells of COVID-19 Patients Recognize Shared Epitopes in SARS-CoV-2 that Largely Reside outside the Spike Protein" Immunity 53, 1095-1107 (2020).

International Search Report and Written Opinion for Application No. PCT/US2022/049556 dated Apr. 27, 2023.

Invitation to Pay Additional Fee's for application No. PCT/US2022/049556 dated Jan. 30, 2023.

Database Geneseq [Online], Jan. 4, 2024 (Jan. 4, 2024), "Magea TCR 32-41 MGTM optimized DNA encoded protein, Seq ID 12.", retrieved from EBI accession No. GSP:BNY88192 and submitted herewith as WO2023215183A1 [TScan Therapeutics, Inc.; published Nov. 9, 2023], see Seq ID No. 12 (SVFSS).

Database Geneseq [Online], Jan. 4, 2024 (Jan. 4, 2024), "Magea TCR 32-41 MGTM optimized DNA encoded protein, Seq ID 14.", retrieved from EBI accession No. GSP:BNY88194 BNY88192 and submitted herewith as WO2023215183A1 [TScan Therapeutics, Inc.; published Nov. 9, 2023], see Seq ID No. 14 (SGHDY).

Richman et al., "Structural features of T cell receptor variable regions that enhance domain stability and enable expression as single-chain VaVβ fragments." Molecular Immunology 46(5) (2009): 902-916.

Supplementary Partial European Search Report for EP Application No. 22893612.6 dated Jan. 21, 2026.

* cited by examiner

*Primary Examiner* — Zachary C Howard

(74) *Attorney, Agent, or Firm* — Foley Hoag LLP; Philip S. Choi; Mi Cai

(57) ABSTRACT

Provided herein are MAGEA1 immunogenic peptides, binding proteins recognizing MAGEA1 immunogenic peptides, and uses thereof.

35 Claims, 20 Drawing Sheets

Specification includes a Sequence Listing.

*Denotes broad lung cancer expression.
Source: American Cancer Society

| TCR | Target | HLA |
|---|---|---|
| HN-P32-39 | MAGEA1 | C*07:02 |
| HN-P32-41 | | |

GREHSAYGEPRKLLTQDLVQEKYLEYRQVPDSDPARYEFLWGPRALAETSYVKVLEYVIKVSARVRFFFPSLREAALREEEEGV*SELSP
YLEYRQVPDSDPARYEFLWGPRALAETSYVKVLEYVIKVSARVRFFFPSLREAALREEEEGV*SELSPRADPCV*VDYSISRDGETHYRT
Figure 2C
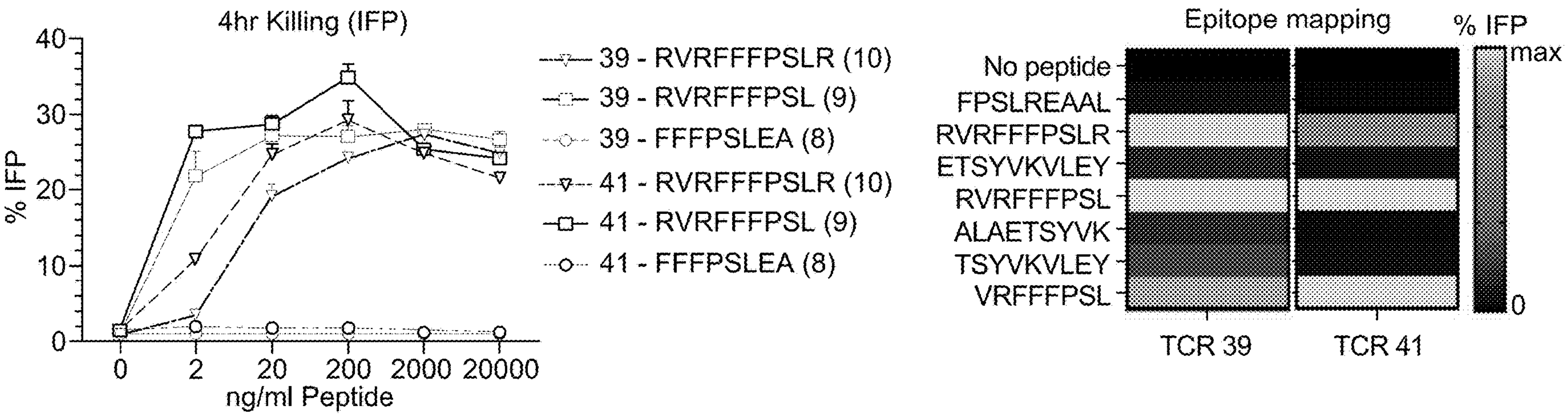
Figure 2D
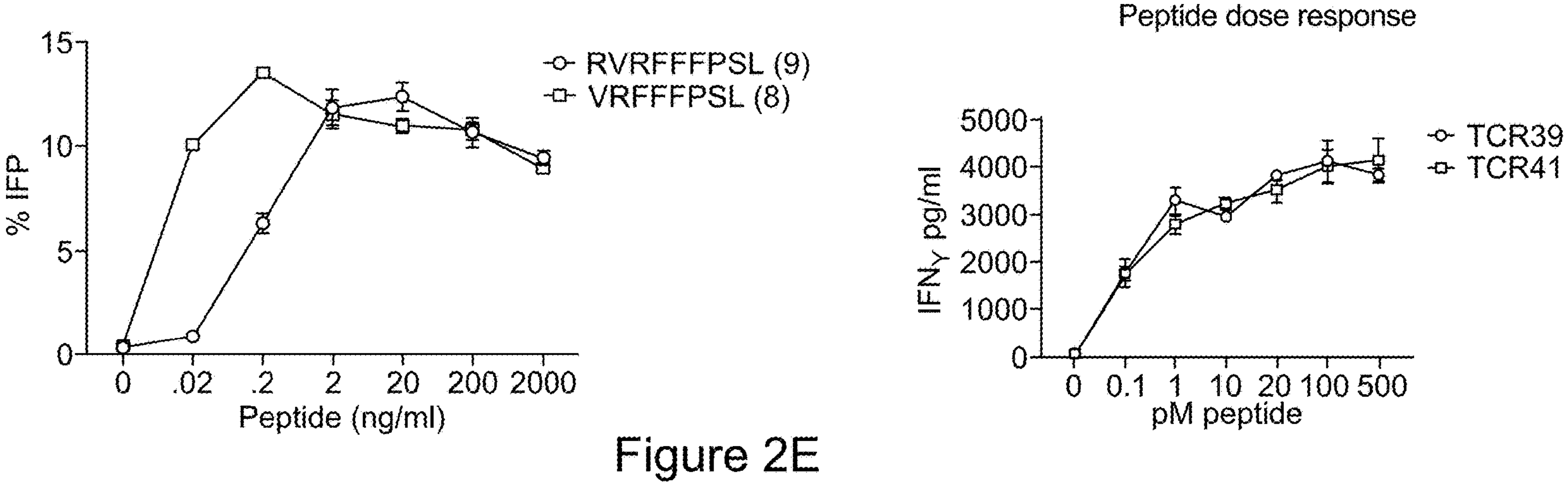
Figure 2E

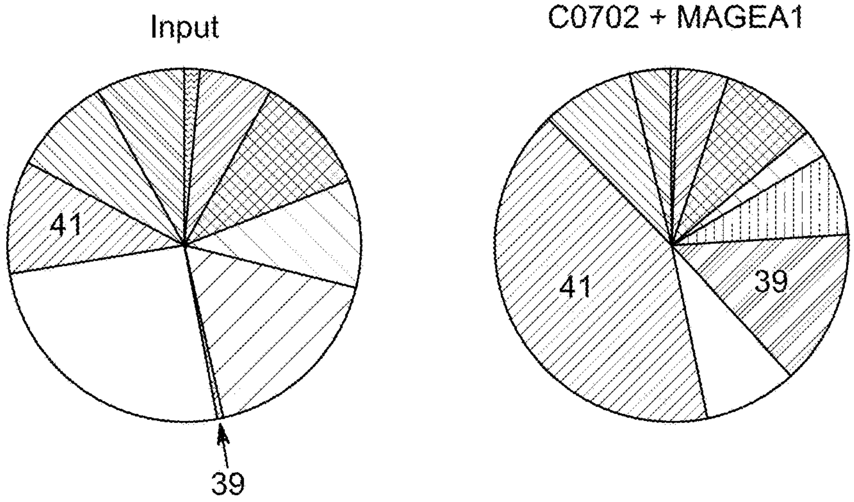
Figure 3A
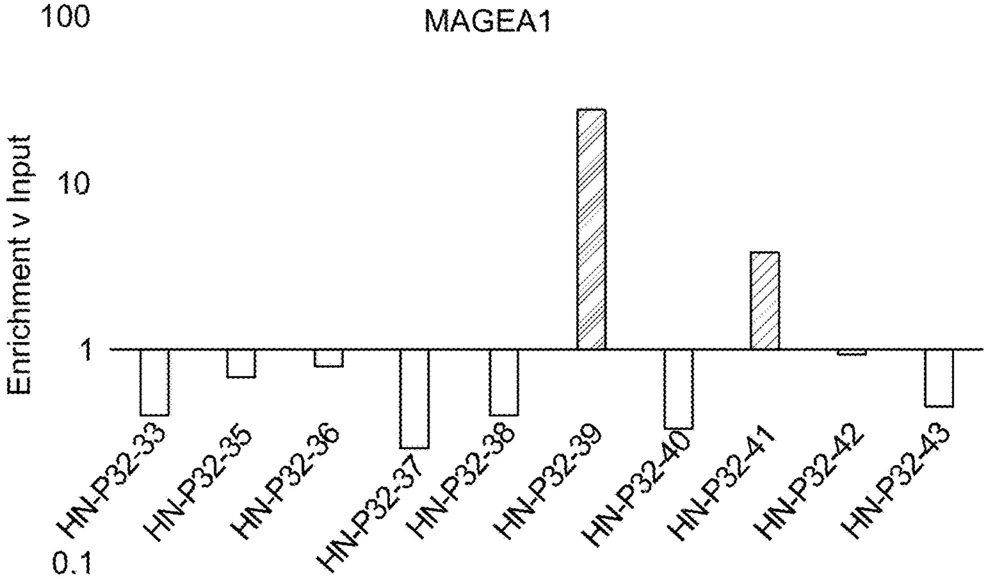
Figure 3B
| Cell line | | MAGEA1 TPM |
|---|---|---|
| U266B1 | Plasma cell myeloma | 657 |
| A101D | Melanoma | 359 |
| SKMEL5 | Melanoma | 8 |
| 786-O | Renal cell carcinoma | 0.4 |
Figure 4A

| Cell line | Disease | MAGEA1 TPM |
|---|---|---|
| U266B1 | Plasma cell myeloma | 657 |
| A101D | Melanoma | 359 |
| HS294T | Melanoma | 267 |
| A2058 | Melanoma | 128 |
| NCIH1437 | Lung adenocarcinoma | 25 |
| HEK-C0702 | Embryonic kidney | 0 |

• TCR 41 T cells co-cultured with HEK cells expressing different MHC Class I alleles

| Hit | Validated 90mers | Validated ORF | Peptide EC50 |
|---|---|---|---|
| MAGEA1 | Yes | Yes | ~250 pM |
| LAMB4 IR | Yes | Yes | > µM range |
| PIGO | Yes | No | |
| SLC6A13 | Yes | No | |
| TLE3 | Yes | No | |
| BTBD2 | No | | |
| SLC16A2 | No | | |
| RXFP1 | No | | |

BINDING PROTEINS RECOGNIZING MAGEA1 PEPTIDE-MHC COMPLEX

CROSS-REFERENCE TO RELATED APPLICATIONS

This application claims the benefit of U.S. Provisional Application No. 63/342,415, filed on 16 May 2022; U.S. Provisional Application No. 63/317,337, filed on 7 Mar. 2022; and U.S. Provisional Application No. 63/277,924, filed on 10 Nov. 2021; the entire contents of each of said applications are incorporated herein in their entirety by this reference.

SEQUENCE LISTING

The instant application contains a Sequence Listing which has been submitted electronically in XML format and is hereby incorporated by reference in its entirety. Said XML copy, created on Jan. 5, 2023, is named TTC-01025_SL.xml and is 125,706 bytes in size.

BACKGROUND OF THE INVENTION

Adoptive cell transfer (ACT) using engineered T cells has demonstrated great efficacy in treating certain types of liquid tumor and holds promise for treating solid tumor. T cell receptor-engineered T cells (TCR-T) are T cells expressing an exogenous TCR that recognizes an antigen that exist in cancer cells. The TCR-antigen interaction is the core component of the targeting mechanism that allows the TCR-T cells to kill cancer cells. One of the challenges for the broad testing and adoption of TCR-T therapy is the lack of TCR-antigen pairs that are applicable to a wide range of patients and indications. Although several TCR and antigens have been explored in clinical trials, most pursued antigens are restricted to one HLA allele, namely HLA-A*02:01, which limits the number of patients who are eligible for the therapy and also allowing cancer cells to develop potential resistance by mutating the HLA-A*02:01 allele.

In addition, the number of pursued antigens is limited due to the difficulty of discovering novel TCR-antigen pairs which commonly require prediction of the MHC presented epitope. However, such epitopes may not be immunogenic, thereby making it difficult to identify a reactive TCR, or the epitope may not be processed and presented physiologically by the cancer cells. Accordingly, there is a great need in the art to identify TCR-antigen pairs in the context of a variety of widely applicable HLA alleles in order to develop useful reagents to diagnose, prognose, treat, and screen agents relevant for disorders characterized by the expression of the antigens.

SUMMARY OF THE INVENTION

The present invention is based, at least in part, on the discovery of MAGEA1 immunogenic peptides and binding proteins recognizing such MAGEA1 immunogenic peptides based on unbiased functional screens used to discover the antigen of TCR clonotypes identified from subjects having disorders associated with MAGEA1 expression (e.g., subjects afflicted with a melanoma, head & neck cancer, lung cancer, cervical cancer, hepatocellular carcinoma, colorectal cancer, gastrointestinal cancer, breast invasive carcinoma, or bladder urothelial carcinoma). The identified TCRs recognized MAGEA1 immunogenic peptides, such as those listed in Table 1, in the context of a variety of HLA alleles (e.g., HLA-C*07:02). MAGEA1 is demonstrated herein to be selectively expressed in cancer and testis tissue, but not in normal somatic tissues, thereby making it an ideal target for ACT. The ability of MAGEA1 binding proteins (e.g., TCRs described herein) to bind MAGEA1 immunogenic peptides and to elicit immune responses that kill cells expressing MAGEA1 (e.g., cancer cells) demonstrates the utility of such binding proteins in a diversity of uses, including methods of diagnosis, prognosis, treatment, and screening of agents relevant for disorders characterized by MAGEA1 expression.

In one aspect, an immunogenic peptide comprising a peptide epitope selected from peptide sequences listed in Table 1, is provided.

In another aspect, an immunogenic peptide consisting of a peptide epitope selected from peptide sequences listed in Table 1, is provided.

Numerous embodiments are further provided that may be applied to any aspect encompassed by the present invention and/or combined with any other embodiment described herein. For example, in one embodiment, the immunogenic peptide is derived from a MAGEA1 protein, optionally wherein the immunogenic peptide is 8, 9, 10, 11, 12, 13, 14, 15, 16, 17, 18, 19, 20, 21, 22, 23, 24, or 25 amino acids in length. In another embodiment, the immunogenic peptide is capable of eliciting an immune response against MAGEA1 and/or MAGEA1-expressing cells in a subject, optionally wherein the immune response is i) a T cell response and/or a CD8+ T cell response and/or ii) selected from the group consisting of T cell expansion (e.g., proliferation), cytokine release, and/or cytotoxic killing.

In still another aspect, an immunogenic composition comprising at least one immunogenic peptide described herein, is provided.

Numerous embodiments are further provided that may be applied to any aspect encompassed by the present invention and/or combined with any other embodiment described herein. For example, in one embodiment, the immunogenic composition further comprises an adjuvant. In another embodiment, the immunogenic composition is capable of eliciting an immune response against MAGEA1 and/or MAGEA1-expressing cells in a subject, optionally wherein the immune response is i) a T cell response and/or a CD8+ T cell response and/or ii) selected from the group consisting of T cell expansion (e.g., proliferation), cytokine release, and/or cytotoxic killing.

In yet another aspect, a composition comprising a peptide epitope selected from peptide sequences listed in Table 1, and an MHC molecule, is provided.

Numerous embodiments are further provided that may be applied to any aspect encompassed by the present invention and/or combined with any other embodiment described herein. For example, in one embodiment, the MHC molecule is an MHC multimer, optionally wherein the MHC multimer is a tetramer. In another embodiment, the MHC molecule is an MHC class I molecule. In still another embodiment, the MHC molecule comprises an MHC alpha chain that is an HLA serotype selected from the group consisting of HLA-A*02, HLA-A*03, HLA-A*01, HLA-A*11, HLA-A*24, HLA-B*07, HLA-C*07, HLA-C*01, HLA-C*02, HLA-C*03, HLA-C*04, HLA-C*05, HLA-C*06, HLA-C*08, HLA-C*12, HLA-C*14, HLA-C*15, HLA-C*16, HLA-C*17, and HLA-C*18, optionally wherein the HLA allele is selected from the group consisting of HLA-A*0201, HLA-A*0202, HLA-A*0203, HLA-A*0204, HLA-A*0205, HLA-A*0206, HLA-A*0207, HLA-A*0210, HLA-A*0211, HLA-A*0212, HLA-A*0213, HLA-A*0214, HLA-A*0216, HLA-A*0217, HLA-A*0219, HLA-A*0220, HLA-A*0222, HLA-A*0224, HLA-A*0230, HLA-A*0242, HLA-A*0253, HLA-A*0260, HLA-A*0274 allele, HLA-A*0301, HLA-A*0302, HLA-A*0305, HLA-A*0307, HLA-A*0101, HLA-A*0102, HLA-A*0103, HLA-A*0116 allele, HLA-A*1101, HLA-A*1102, HLA-A*1103, HLA-A*1104, HLA-A*1105, HLA-A*1119 allele, HLA-A*2402, HLA-A*2403, HLA-A*2405, HLA-A*2407, HLA-A*2408, HLA-A*2410, HLA-A*2414, HLA-A*2417, HLA-A*2420, HLA-A*2422, HLA-A*2425, HLA-A*2426, HLA-A*2458 allele, HLA-B*0702, HLA-B*0704, HLA-B*0705, HLA-B*0709, HLA-B*0710, HLA-B*0715, HLA-B*0721, HLA-C*0702, HLA-C*0701, HLA-C*0401, HLA-C*0602, HLA-C*0304, HLA-C*0501, HLA-C*1601, HLA-C*0202, HLA-C*0303, HLA-C*1203, HLA-C*0802, HLA-C*0102, HLA-C*1701, HLA-C*1502, HLA-C*1402, HLA-C*1202, HLA-C*0704, HLA-C*0801, HLA-C*0302, HLA-C*1801, HLA-C*1505, HLA-C*1602, HLA-C*0804, HLA-C*0305, and HLA-C*1403 allele.

In another aspect, a stable MHC-peptide complex, comprising an immunogenic peptide described herein in the context of an MHC molecule, is provided.

Numerous embodiments are further provided that may be applied to any aspect encompassed by the present invention and/or combined with any other embodiment described herein. For example, in one embodiment, the MHC molecule is an MHC multimer, optionally wherein the MHC multimer is a tetramer. In another embodiment, the MHC molecule is an MHC class I molecule. In still another embodiment, the MHC molecule comprises an MHC alpha chain that is an HLA serotype selected from the group consisting of HLA-A*02, HLA-A*03, HLA-A*01, HLA-A*11, HLA-A*24, HLA-B*07, HLA-C*07, HLA-C*01, HLA-C*02, HLA-C*03, HLA-C*04, HLA-C*05, HLA-C*06, HLA-C*08, HLA-C*12, HLA-C*14, HLA-C*15, HLA-C*16, HLA-C*17, and HLA-C*18, optionally wherein the HLA allele is selected from the group consisting of HLA-A*0201, HLA-A*0202, HLA-A*0203, HLA-A*0204, HLA-A*0205, HLA-A*0206, HLA-A*0207, HLA-A*0210, HLA-A*0211, HLA-A*0212, HLA-A*0213, HLA-A*0214, HLA-A*0216, HLA-A*0217, HLA-A*0219, HLA-A*0220, HLA-A*0222, HLA-A*0224, HLA-A*0230, HLA-A*0242, HLA-A*0253, HLA-A*0260, HLA-A*0274 allele, HLA-A*0301, HLA-A*0302, HLA-A*0305, HLA-A*0307, HLA-A*0101, HLA-A*0102, HLA-A*0103, HLA-A*0116 allele, HLA-A*1101, HLA-A*1102, HLA-A*1103, HLA-A*1104, HLA-A*1105, HLA-A*1119 allele, HLA-A*2402, HLA-A*2403, HLA-A*2405, HLA-A*2407, HLA-A*2408, HLA-A*2410, HLA-A*2414, HLA-A*2417, HLA-A*2420, HLA-A*2422, HLA-A*2425, HLA-A*2426, HLA-A*2458 allele, HLA-B*0702, HLA-B*0704, HLA-B*0705, HLA-B*0709, HLA-B*0710, HLA-B*0715, HLA-B*0721, HLA-C*0702, HLA-C*0701, HLA-C*0401, HLA-C*0602, HLA-C*0304, HLA-C*0501, HLA-C*1601, HLA-C*0202, HLA-C*0303, HLA-C*1203, HLA-C*0802, HLA-C*0102, HLA-C*1701, HLA-C*1502, HLA-C*1402, HLA-C*1202, HLA-C*0704, HLA-C*0801, HLA-C*0302, HLA-C*1801, HLA-C*1505, HLA-C*1602, HLA-C*0804, HLA-C*0305, and HLA-C*1403 allele. In yet another embodiment, the peptide epitope and the MHC molecule are covalently linked and/or wherein the alpha and beta chains of the MHC molecule are covalently linked. In another embodiment, the stable MHC-peptide complex comprises a detectable label, optionally wherein the detectable label is a fluorophore.

In still another aspect, an immunogenic composition comprising a stable MHC-peptide complex described herein, and an adjuvant, is provided.

In yet another aspect, an isolated nucleic acid that encodes an immunogenic peptide described herein, or a complement thereof, is provided.

In another aspect, a vector comprising an isolated nucleic acid described herein, is provided.

In still another aspect, a cell that a) comprises an isolated nucleic acid described herein, b) comprises a vector described herein, and/or c) produces one or more immunogenic peptides described herein and/or presents at the cell surface one or more stable MHC-peptide complexes described herein, optionally wherein the cell is genetically engineered, is provided.

In yet another aspect, a device or kit comprising a) one or more immunogenic peptides described herein and/or b) one or more stable MHC-peptide complexes described herein, said device or kit optionally comprising a reagent to detect binding of a) and/or b) to a binding protein, optionally wherein the binding protein is an antibody, an antigen-binding fragment of an antibody, a TCR, an antigen-binding fragment of a TCR, a single chain TCR (scTCR), a chimeric antigen receptor (CAR), or a fusion protein comprising a TCR and an effector domain, is provided.

In another aspect, a method of detecting T cells that bind a stable MHC-peptide complex comprising: a) contacting a sample comprising T cells with a stable MHC-peptide complex described herein; and b) detecting binding of T cells to the stable MHC-peptide complex, optionally further determining the percentage of stable MHC-peptide-specific T cells that bind to the stable MHC-peptide complex, optionally wherein the sample comprises peripheral blood mononuclear cells (PBMCs), is provided.

Numerous embodiments are further provided that may be applied to any aspect encompassed by the present invention and/or combined with any other embodiment described herein. For example, in one embodiment, T cells are CD8+ T cells. In another embodiment, detecting and/or determining is performed using fluorescence activated cell sorting (FACS), enzyme linked immunosorbent assay (ELISA), radioimmune assay (RIA), immunochemically, Western blot, or intracellular flow assay. In still another embodiment, a sample comprises T cells contacted with, or suspected of having been contacted with, one or more MAGEA1 proteins or fragments thereof.

In still another aspect, a method of determining whether a T cell has had exposure to MAGEA1 comprising: a) incubating a cell population comprising T cells with an immunogenic peptide described herein or a stable MHC-peptide complex described herein; and b) detecting the presence or level of reactivity, wherein the presence of or a higher level of reactivity compared to a control level indicates that the T cell has had exposure to MAGEA1, optionally wherein the cell population comprising T cells is obtained from a subject, is provided.

In yet another aspect, a method for predicting the clinical outcome of a subject afflicted with a disorder characterized by MAGEA1 expression comprising: a) determining the presence or level of reactivity between T cells obtained from the subject and one more immunogenic peptides described herein or one or more stable MHC-peptide complexes described herein; and b) comparing the presence or level of reactivity to that from a control, wherein the control is obtained from a subject having a good clinical outcome, wherein the presence or a higher level of reactivity in the subject sample as compared to the control indicates that the subject has a good clinical outcome, is provided.

In another aspect, a method of assessing the efficacy of a therapy for a disorder characterized by MAGEA1 expression comprising: a) determining the presence or level of reactivity between T cells obtained from the subject and one more immunogenic peptides described herein or one or more stable MHC-peptide complexes described herein, in a first sample obtained from the subject prior to providing at least a portion of the therapy to the subject, and b) determining the presence or level of reactivity between the one more immunogenic peptides described herein, or the one or more stable MHC-peptide complexes described herein, and T cells obtained from the subject present in a second sample obtained from the subject following provision of the therapy to the subject, wherein the presence or a higher level of reactivity in the second sample, relative to the first sample, is an indication that the therapy is efficacious for treating the disorder characterized by MAGEA1 expression in the subject, is provided.

Numerous embodiments are further provided that may be applied to any aspect encompassed by the present invention and/or combined with any other embodiment described herein. For example, in one embodiment, the level of reactivity is indicated by a) the presence of binding and/or b) T cell activation and/or effector function, optionally wherein the T cell activation or effector function is T cell proliferation, killing, or cytokine release. In another embodiment, a method further comprises repeating steps a) and b) at a subsequent point in time, optionally wherein the subject has undergone treatment to ameliorate the disorder characterized by MAGEA1 expression between the first point in time and the subsequent point in time. In still another embodiment, T cell binding, activation, and/or effector function is detected using fluorescence activated cell sorting (FACS), enzyme linked immunosorbent assay (ELISA), radioimmune assay (RIA), immunochemically, Western blot, or intracellular flow assay. In yet another embodiment, a control level is a reference number. In another embodiment, a control level is a level of a subject without the disorder characterized by MAGEA1 expression.

In still another aspect, a method of preventing and/or treating a disorder characterized by MAGEA1 expression in a subject comprising administering to the subject a therapeutically effective amount of a composition described herein.

In yet another aspect, a method of identifying a peptide-binding molecule, or antigen-binding fragment thereof, that binds to a peptide epitope selected from the peptide sequences listed in Table 1 comprising: a) providing a cell presenting a peptide epitope selected from the peptide sequences listed in Table 1 in the context of an MHC molecule on the surface of the cell; b) determining binding of a plurality of candidate peptide-binding molecules or antigen-binding fragments thereof to the peptide epitope in the context of the MHC molecule on the cell; and c) identifying one or more peptide-binding molecules or antigen-binding fragments thereof that bind to the peptide epitope in the context of the MHC molecule, is provided.

Numerous embodiments are further provided that may be applied to any aspect encompassed by the present invention and/or combined with any other embodiment described herein. For example, in one embodiment, a step a) comprises contacting the MHC molecule on the surface of the cell with a peptide epitope selected from the peptide sequences listed in Table 1. In another embodiment, a step a) comprises expressing the peptide epitope selected from the peptide sequences listed in Table 1 in the cell using a vector comprising a heterologous sequence encoding the peptide epitope.

In another aspect, a method of identifying a peptide-binding molecule or antigen-binding fragment thereof that binds to a peptide epitope selected from the peptide sequences listed in Table 1 comprising: a) providing a peptide epitope either alone or in a stable MHC-peptide complex, comprising a peptide epitope selected from the peptide sequences listed in Table 1, either alone or in the context of an MHC molecule; b) determining binding of a plurality of candidate peptide-binding molecules or antigen-binding fragments thereof to the peptide or stable MHC-peptide complex; and c) identifying one or more peptide-binding molecules or antigen-binding fragments thereof that bind to the peptide epitope or the stable MHC-peptide complex, optionally wherein the MHC or MHC-peptide complex is as described herein, is provided.

Numerous embodiments are further provided that may be applied to any aspect encompassed by the present invention and/or combined with any other embodiment described herein. For example, in one embodiment, a plurality of candidate peptide binding molecules comprises an antibody, an antigen-binding fragment of an antibody, a TCR, an antigen-binding fragment of a TCR, a single chain TCR (scTCR), a chimeric antigen receptor (CAR), or a fusion protein comprising a TCR and an effector domain. In another embodiment, a plurality of candidate peptide binding molecules comprises at least 2, 5, 10, 100, $10^3$, $10^4$, $10^5$, $10^6$, $10^7$, $10^8$, $10^9$, or more, different candidate peptide binding molecules. In still another embodiment, a plurality of candidate peptide binding molecules comprises one or more candidate peptide binding molecules that are obtained from a sample from a subject or a population of subjects; or the plurality of candidate peptide binding molecules comprises one or more candidate peptide binding molecules that comprise mutations in a parent scaffold peptide binding molecule obtained from a sample from a subject. In yet another embodiment, a subject or population of subjects are a) not afflicted with a disorder characterized by MAGEA1 expression and/or have recovered from a disorder characterized by MAGEA1 expression, or b) are afflicted with a disorder characterized by MAGEA1 expression. In another embodiment, a subject or population of subjects has been administered a composition described herein. In still another embodiment, a subject is an animal model of a disorder characterized by MAGEA1 expression and/or a mammal, optionally wherein the mammal is a human, a primate, or a rodent. In yet another embodiment, a subject is an animal model of a disorder characterized by MAGEA1 expression, an HLA-transgenic mouse, and/or a human TCR transgenic mouse. In another embodiment, a sample comprises peripheral blood mononuclear cells (PBMCs), T cells, and/or CD8+ memory T cells.

In still another aspect, a peptide-binding molecule or antigen-binding fragment thereof identified according to a method described herein, optionally wherein the peptide-binding molecule or antigen-binding fragment thereof is an antibody, an antigen-binding fragment of an antibody, a TCR, an antigen-binding fragment of a TCR, a single chain TCR (scTCR), a chimeric antigen receptor (CAR), or a fusion protein comprising a TCR and an effector domain, is provided.

In yet another aspect, a method of treating a disorder characterized by MAGEA1 expression in a subject comprising administering to the subject a therapeutically effective amount of genetically engineered T cells that express a peptide-binding molecule or antigen-binding fragment thereof that i) binds to a peptide epitope selected from the sequences listed in Table 1, ii) is identified according to a method described herein, and/or iii) binds to a stable MHC-peptide complex comprising a peptide epitopes selected from the sequences listed in Table 1 in the context of an MHC molecule, optionally wherein the peptide-binding molecule or antigen-binding fragment thereof is an antibody, an antigen-binding fragment of an antibody, a TCR, an antigen-binding fragment of a TCR, a single chain TCR (scTCR), a chimeric antigen receptor (CAR), or a fusion protein comprising a TCR and an effector domain, optionally wherein the MHC or MHC-peptide complex is as described herein, is provided.

Numerous embodiments are further provided that may be applied to any aspect encompassed by the present invention and/or combined with any other embodiment described herein. For example, in one embodiment, T cells are isolated from a) the subject, b) a donor not afflicted with the disorder characterized by MAGEA1 expression, or c) a donor recovered from a disorder characterized by MAGEA1 expression.

In another aspect, a method of treating a disorder characterized by MAGEA1 expression in a subject comprising transfusing antigen-specific T cells to the subject, wherein the antigen-specific T cells are generated by: a) stimulating immune cells from a subject with a composition described herein; and b) expanding antigen-specific T cells in vitro or ex vivo, optionally i) isolating immune cells from the subject before stimulating the immune cells and/or ii) wherein the immune cells comprise PBMCs, T cells, CD8+ T cells, naive T cells, central memory T cells, and/or effector memory T cells, is provided.

Numerous embodiments are further provided that may be applied to any aspect encompassed by the present invention and/or combined with any other embodiment described herein. For example, in one embodiment, agents are placed in contact under conditions and for a time suitable for the formation of at least one immune complex between the peptide epitope, immunogenic peptide, stable MHC-peptide complex, T cell receptor, and/or immune cells. In another embodiment, a peptide epitope, immunogenic peptide, stable MHC-peptide complex, and/or T cell receptor is expressed by cells and the cells are expanded and/or isolated during one or more steps. In still another embodiment, a disorder characterized by MAGEA1 expression is a cancer or relapse thereof, optionally wherein the cancer is selected from the group consisting of melanoma, head & neck cancer, lung cancer, cervical cancer, hepatocellular carcinoma, colorectal cancer, gastrointestinal cancer, breast invasive carcinoma, and bladder urothelial carcinoma. In yet another embodiment, a subject is an animal model of a disorder characterized by MAGEA1 expression and/or a mammal, optionally wherein the mammal is a human, a primate, or a rodent.

In still another aspect, a binding protein that binds a polypeptide comprising an immunogenic peptide sequence described herein, an immunogenic peptide described herein, and/or the stable MHC-peptide complex described herein, optionally wherein the binding protein is an antibody, an antigen-binding fragment of an antibody, a TCR, an antigen-binding fragment of a TCR, a single chain TCR (scTCR), a chimeric antigen receptor (CAR), or a fusion protein comprising a TCR and an effector domain, is provided.

Numerous embodiments are further provided that may be applied to any aspect encompassed by the present invention and/or combined with any other embodiment described herein. For example, in one embodiment, a binding protein comprises: a) a T cell receptor (TCR) alpha chain CDR sequence with at least about 80% identity to a TCR alpha chain CDR sequence selected from the group consisting of TCR alpha chain CDR sequences listed in Table 2; and/or b) a TCR beta chain CDR sequence with at least about 80% identity to a TCR beta chain CDR sequence selected from the group consisting of TCR beta chain CDR sequences listed in Table 2, wherein the binding protein is capable of binding to a MAGEA1 immunogenic peptide-MHC (pMHC) complex, optionally wherein the binding affinity has a $K_d$ less than or equal to about $5\times10^{-4}$ M. In another embodiment, a binding protein comprises: a) a TCR alpha chain variable ($V_\alpha$) domain sequence with at least about 80% identity to a TCR $V_\alpha$ domain sequence selected from the group consisting of TCR $V_\alpha$ domain sequences listed in Table 2; and/or b) a TCR beta chain variable ($V_\beta$) domain sequence with at least about 80% identity to a TCR $V_\beta$ domain sequence selected from the group consisting of TCR $V_\beta$ domain sequences listed in Table 2, wherein the binding protein is capable of binding to a MAGEA1 immunogenic peptide-MHC (pMHC) complex, optionally wherein the binding affinity has a $K_d$ less than or equal to about $5\times10^{-4}$ M. In still another embodiment, a binding protein comprises: a) a TCR alpha chain sequence with at least about 80% identity to a TCR alpha chain sequence selected from the group consisting of TCR alpha chain sequences listed in Table 2; and/or b) a TCR beta chain sequence with at least about 80% identity to a TCR beta chain sequence selected from the group consisting of TCR beta chain sequences listed in Table 2, wherein the binding protein is capable of binding to a MAGEA1 immunogenic peptide-MHC (pMHC) complex, optionally wherein the binding affinity has a $K_d$ less than or equal to about $5\times10^{-4}$ M. In yet another embodiment, a binding protein comprises: a) a TCR alpha chain CDR sequence selected from the group consisting of TCR alpha chain CDR sequences listed in Table 2; and/or b) a TCR beta chain CDR sequence selected from the group consisting of TCR beta chain CDR sequences listed in Table 2, wherein the binding protein is capable of binding to a MAGEA1 immunogenic peptide-MHC (pMHC) complex, optionally wherein the binding affinity has a $K_d$ less than or equal to about $5\times10^{-4}$ M. In yet another embodiment, a binding protein comprises: a) a TCR alpha chain variable ($V_\alpha$) domain sequence selected from the group consisting of TCR $V_\alpha$ domain sequences listed in Table 2; and/or b) a TCR beta chain variable ($V_\beta$) domain sequence selected from the group consisting of TCR $V_\beta$ domain sequences listed in Table 2, wherein the binding protein is capable of binding to a MAGEA1 immunogenic peptide-MHC (pMHC) complex, optionally wherein the binding affinity has a $K_d$ less than or equal to about $5\times10^{-4}$ M, is provided. In another embodiment, a binding protein comprises: a) a TCR alpha chain sequence selected from the group consisting of TCR alpha chain sequences listed in Table 2; and/or b) a TCR beta chain sequence selected from the group consisting of TCR beta chain sequences listed in Table 2, wherein the binding protein is capable of binding to a MAGEA1 immunogenic peptide-MHC (pMHC) complex, optionally wherein the binding affinity has a $K_d$ less than or equal to about $5\times10^{-4}$ M, is provided. In another embodiment, 1) a TCR alpha chain CDR, TCR $V_\alpha$ domain, and/or TCR alpha chain is encoded by a TRAY, TRAJ, and/or TRAC gene or fragment thereof selected from the group of TRAY, TRAJ, and TRAC genes listed in Table 2, and/or 2) a TCR beta chain CDR, TCR VB domain, and/or TCR beta chain is encoded by a TRBV, TRBJ, and/or TRBC gene or fragment thereof selected from the group of TRBV, TRBJ, and TRBC genes listed in Table 2, and/or 3) each CDR of the binding protein has up to five amino acid substitutions, insertions, deletions, or a combination thereof as compared to the cognate reference CDR sequence listed in Table 2. In still another embodiment, a binding protein is chimeric, humanized, or human. In yet another embodiment, a binding protein comprises a binding domain having a transmembrane domain, and an effector domain that is intracellular. In another embodiment, a TCR alpha chain and a TCR beta chain are covalently linked, optionally wherein the TCR alpha chain and the TCR beta chain are covalently linked through a linker peptide. In still another embodiment, a TCR alpha chain and/or a TCR beta chain are covalently linked to a moiety, optionally wherein the covalently linked moiety comprises an affinity tag or a label. In yet another embodiment, an affinity tag is selected from the group consisting of aCD34 enrichment tag, glutathione-S-transferase (GST), calmodulin binding protein (CBP), protein C tag, Myc tag, HaloTag, HA tag, Flag tag, His tag, biotin tag, and V5 tag, and/or wherein the label is a fluorescent protein. In another embodiment, a covalently linked moiety is selected from the group consisting of an inflammatory agent, cytokine, toxin, cytotoxic molecule, radioactive isotope, or antibody or antigen-binding fragment thereof. In still another embodiment, a binding protein binds to the pMHC complex on a cell surface. In yet another embodiment, an MHC or MHC-peptide complex is as described herein. In another embodiment, binding of a binding protein to the MAGEA1 peptide-MHC (pMHC) complex elicits an immune response, optionally wherein the immune response is i) a T cell response and/or a CD8+ T cell response and/or ii) selected from the group consisting of T cell expansion, cytokine release, and/or cytotoxic killing. In still another embodiment, a binding protein is capable of specifically and/or selectively binding to a MAGEA1 immunogenic peptide-MHC (pMHC) complex with a $K_d$ less than or equal to about $1\times10^{-4}$ M, less than or equal to about $5\times10^{-5}$ M, less than or equal to about $1\times10^{-5}$ M, less than or equal to about $5\times10^{-6}$ M, less than or equal to about $1\times10^{-6}$ M, less than or equal to about $5\times10^{-7}$ M, less than or equal to about $1\times10^{-7}$ M, less than or equal to about $5\times10^{-8}$ M, less than or equal to about $1\times10^{-8}$ M, less than or equal to about $5\times10^{-9}$ M, less than or equal to about $1\times10^{-9}$ M, less than or equal to about $5\times10^{-10}$ M, less than or equal to about $1\times10^{-10}$ M, less than or equal to about $5\times10^{-11}$ M, less than or equal to about $1\times10^{-11}$ M, less than or equal to about $5\times10^{-12}$ M, or less than or equal to about $1\times10^{-12}$ M. In yet another embodiment, a binding protein has a higher binding affinity to the peptide-MHC (pMHC) than does a known T-cell receptor, optionally wherein the higher binding affinity is at least 1.05-fold higher. In another embodiment, a binding protein induces higher T cell expansion, cytokine release, and/or cytotoxic killing than does a known T-cell receptor when contacted with target cells with a heterozygous expression of MAGEA1, optionally wherein the induction is at least 1.05-fold higher. As used herein, references to fold changes, in some embodiments, may be in comparison to any reference modality of interest, such as comparison to a different binding protein; comparison to the same binding protein under different context like expression of the same binding protein in a different immune cell, at a different level, in combination with other agents described herein; and the like. In still another embodiment, cytotoxic killing is of a target cancer cell. In yet another embodiment, cancer is selected from the group consisting of melanoma, head & neck cancer, lung cancer, cervical cancer, hepatocellular carcinoma, colorectal cancer, gastrointestinal cancer, breast invasive carcinoma, and bladder urothelial carcinoma. In another embodiment, a binding protein does not bind to a peptide-MHC (pMHC) complex comprising a LAMB4-IR, TLE3, SLC16A2, SLC6A13, BTBD2, RXFP1, and/or PIGO peptide epitope. These genes are well-known and are art-recognized to be annotated according to the following NCBI Gene ID numbers, each of which is available on the World Wide Web at ncbi.nlm.nih.gov/gene: TLE3: Gene ID 7090 and NM_005078.4 NP_005069.2 as representative clones; SLC16A2: Gene ID 6567 and NM_006517.5 and NP_006508.2 as representative clones; SLC6A13: Gene ID 6540 and NM_016615.5 and NP_057699.2 as representative clones; BTBD2: Gene ID 55643 and NM_017797.4 and NP_060267.2 as representative clones; RXFP1: Gene ID 59350 and NM_021634.4 and NP_067647.2 as representative clones; and PIGO: Gene ID 84720 and NM_032634.4 and NP_116023.2 as representative clones. LAMB4-IR is a bioinformatically predicted transcript that has yet to be identified in cells and which coding (CDS) and protein sequences are provided in Table 3 below. LAMB4-IR has a chromosomal location of chr7: 108043489-108123164 as referenced according to the Genome Reference Consortium Human GRCh38.p13 (GCA_000001405.28) (UCSC HG38) assembly (accession available on the World Wide Web at ncbi.nlm.nih.gov/assembly/GCA_000001405.28/).

In yet another aspect, a TCR alpha chain and/or beta chain selected from the group consisting of TCR alpha chain and beta chain sequences listed in Table 2, is provided.

In another aspect, an isolated nucleic acid molecule i) that hybridizes, under stringent conditions, with the complement of a nucleic acid encoding a polypeptide selected from the group consisting of polypeptide sequences listed in Table 2, ii) a sequence with at least about 80% homology to a nucleic acid encoding a polypeptide selected from the group consisting of the polypeptide sequences listed in Table 2, and/or iii) ii) a sequence with at least about 80% homology to a nucleic acid encoding listed in Table 2, optionally wherein the isolated nucleic acid molecule comprises 1) a TRAY, TRAJ, and/or TRAC gene or fragment thereof selected from the group of TRAY, TRAJ, and TRAC genes listed in Table 2 and/or 2) a TRBV, TRBJ, and/or TRBC gene or fragment thereof selected from the group of TRBV, TRBJ, and TRBC genes listed in Table 2, is provided.

Numerous embodiments are further provided that may be applied to any aspect encompassed by the present invention and/or combined with any other embodiment described herein. For example, in one embodiment, a nucleic acid is codon optimized for expression in a host cell.

In still another aspect, a vector comprising an isolated nucleic acid described herein, optionally wherein i) the vector is a cloning vector, expression vector, or viral vector and/or ii) the vector comprises a vector sequence listed in Table 3, is provided.

Numerous embodiments are further provided that may be applied to any aspect encompassed by the present invention and/or combined with any other embodiment described herein. For example, in one embodiment, a vector further comprises a nucleic acid sequence encoding CD8α CD8β, a dominant negative TGFβ receptor II (DN-TGFβRII), selectable protein marker, optionally wherein the selectable protein marker is dihydrofolate reductase (DHFR). In another embodiment, a nucleic acid sequence encoding CD8α, CD8β, the DN-TGFβRII, and/or the selectable protein marker is operably linked to a nucleic acid encoding a tag. In still another embodiment, a nucleic acid encoding a tag is at the 5' upstream of the nucleic acid sequence encoding CD8α, CD8β, the DN-TGFβRII, and/or the selectable protein such that the tag is fused to the N-terminus of CD8α, CD8β, the DN-TGFβRII, and/or the selectable protein marker. In yet another embodiment, a tag is a CD34 enrichment tag. In another embodiment, an isolated nucleic acid described herein, either alone or in combination with a nucleic acid sequence encoding CD8α, CD8β, the DN-TGFβRII, and/or the selectable protein marker are interconnected with an internal ribosome entry site or a nucleic acid sequence encoding a self-cleaving peptide. In still another embodiment, a self-cleaving peptide is P2A, E2A, F2A or T2A.

In yet another aspect, a host cell which comprises an isolated nucleic acid described herein, comprises a vector described herein, and/or expresses a binding protein described herein, optionally wherein the cell is genetically engineered, is provided.

Numerous embodiments are further provided that may be applied to any aspect encompassed by the present invention and/or combined with any other embodiment described herein. For example, in one embodiment, a host cell comprises a chromosomal gene knockout of a TCR gene, an HLA gene, or both. In another embodiment, a host cell comprises a knockout of an HLA gene selected from anal macroglobulin gene, α2 macroglobulin gene, α3 macroglobulin gene, (31 microglobulin gene, (32 microglobulin gene, and combinations thereof. In still another embodiment, a host cell comprises a knockout of a TCR gene selected from a TCR α variable region gene, TCR β variable region gene, TCR constant region gene, and combinations thereof. In yet another embodiment, a host cell expresses CD8α, CD8β, a DN-TGFβRII, and/or a selectable protein marker, optionally wherein the selectable protein marker is DHFR, and further optionally wherein the CD8α, CD8β, the DN-TGFβRII, and/or the selectable protein marker is fused to a CD34 enrichment tag. In another embodiment, host cells are enriched using the CD34 enrichment tag. In still another embodiment, a host cell is a hematopoietic progenitor cell, peripheral blood mononuclear cell (PBMC), cord blood cell, or immune cell. In yet another embodiment, an immune cell is a T cell, cytotoxic lymphocyte, cytotoxic lymphocyte precursor cell, cytotoxic lymphocyte progenitor cell, cytotoxic lymphocyte stem cell, $CD4^+$ T cell, $CD8^+$ T cell, CD4/CD8 double negative T cell, gamma delta (γδ) T cell, natural killer (NK) cell, NK-T cell, dendritic cell, or a combination thereof. In yet another embodiment a T cell is a naive T cell, central memory T cell, effector memory T cell, or a combination thereof. In another embodiment, a T cell is a primary T cell or a cell of a T cell line. In still another embodiment, a T cell does not express or has a lower surface expression of an endogenous TCR. In yet another embodiment, a host cell is capable of producing a cytokine or a cytotoxic molecule when contacted with a target cell that comprises a peptide-MHC (pMHC) complex comprising a MAGEA1 peptide epitope in the context of an MHC molecule. In another embodiment, a host cell is contacted with the target cell in vitro, ex vivo, or in vivo. In still another embodiment, a cytokine is TNF-α, IL-2, and/or IFN-γ. In yet another embodiment, a cytotoxic molecule is perforins and/or granzymes, optionally wherein the cytotoxic molecule is granzyme B. In another embodiment, a host cell is capable of producing a higher level of cytokine or a cytotoxic molecule when contacted with a target cell with a heterozygous expression of MAGEA1. In still another embodiment, a host cell is capable of producing an at least 1.05-fold higher level of cytokine or a cytotoxic molecule. In yet another embodiment, a host cell is capable of killing a target cell that comprises a peptide-MHC (pMHC) complex comprising the MAGEA1 peptide epitope in the context of an MHC molecule. In another embodiment, killing is determined by a killing assay. In still another embodiment, a ratio of the host cell and the target cell in the killing assay is from 20:1 to 1:4. In yet another embodiment, a target cell is a target cell pulsed with 1 μg/mL to 50 pg/mL of MAGEA1 peptide, optionally wherein the target cell is a cell monoallelic for an MHC matched to the MAGEA1 peptide. In another embodiment, a host cell is capable of killing a higher number of target cells when contacted with target cells with a heterozygous expression of MAGEA1, optionally wherein the cell killing is at least 1.05-fold higher. In still another embodiment, a target cell is cell line or a primary cell, optionally wherein the target cell is selected from the group consisting of a HEK293 derived cell line, a cancer cell line, a primary cancer cell, a transformed cell line, and an immortalized cell line. In yet another embodiment, a MAGEA1 immunogenic peptide is as described herein and/or wherein an MHC or MHC-peptide complex is as described herein. In another embodiment, a host cell does not induce T cell expansion, cytokine release, or cytotoxic killing when contact with a target cell that comprises a peptide-MHC (pMHC) complex comprising a LAMB4-IR, TLE3, SLC16A2, SLC6A13, BTBD2, RXFP1, and/or PIGO peptide epitope. In still another embodiment, a host cell does not express MAGEA1 antigen, is not recognized by a binding protein described herein, is not of serotype HLA-C*07, and/or does not express an HLA-C*07 allele.

In another aspect, a population of host cells described herein, is provided.

In still another aspect, a composition comprising a) a binding protein described herein, b) an isolated nucleic acid described herein, c) a vector described herein, d) a host cell described herein, and/or e) a population of host cells described herein, and a carrier, is provided.

In yet another aspect, a device or kit comprising a) a binding protein described herein, b) an isolated nucleic acid described herein, c) a vector described herein, d) a host cell described herein, and/or e) a population of host cells described herein, said device or kit optionally comprising a reagent to detect binding of a), d) and/or e) to a pMHC complex, is provided.

In another aspect, a method of producing a binding protein described herein, wherein the method comprises the steps of: (i) culturing a transformed host cell which has been transformed by a nucleic acid comprising a sequence encoding a binding protein described herein under conditions suitable to allow expression of said binding protein; and (ii) recovering the expressed binding protein, is provided.

In still another aspect, a method of producing a host cell expressing a binding protein described herein, wherein the method comprises the steps of: (i) introducing a nucleic acid comprising a sequence encoding a binding protein described herein into the host cell; and (ii) culturing the transformed host cell under conditions suitable to allow expression of said binding protein, is provided.

In yet another aspect, a method of detecting the presence or absence of a MAGEA1 antigen and/or a cell expressing MAGEA1, optionally wherein the cell is a hyperproliferative cell, comprising detecting the presence or absence of said MAGEA1 antigen in a sample by use of at least one binding protein described herein, at least one host cell described herein, or a population of host cells described herein, wherein detection of the MAGEA1 antigen is indicative of the presence of a MAGEA1 antigen and/or cell expressing MAGEA1, is provided.

Numerous embodiments are further provided that may be applied to any aspect encompassed by the present invention and/or combined with any other embodiment described herein. For example, in one embodiment, at least one binding protein, or at least one host cell, forms a complex with the MAGEA1 peptide in the context of an MHC molecule, and the complex is detected in the form of fluorescence activated cell sorting (FACS), enzyme linked immunosorbent assay (ELISA), radioimmune assay (RIA), immunochemically, Western blot, or intracellular flow assay. In another embodiment, a method further comprises obtaining a sample from a subject.

In another aspect, a method of detecting the level of a disorder characterized by MAGEA1 expression in a subject, comprising: a) contacting a sample obtained from the subject with at least one binding protein described herein, at least one host cell described herein, or a population of host cells described herein; and b) detecting the level of reactivity, wherein the presence or a higher level of reactivity compared to a control level indicates the level of the disorder characterized by MAGEA1 expression in the subject, is provided.

Numerous embodiments are further provided that may be applied to any aspect encompassed by the present invention and/or combined with any other embodiment described herein. For example, in one embodiment, a control level is a reference number. In another embodiment, a control level is a level from a subject without the disorder characterized by MAGEA1 expression.

In still another aspect, a method for monitoring the progression of a disorder characterized by MAGEA1 expression in a subject, the method comprising: a) detecting in a subject sample the presence or level of reactivity between a sample obtained from the subject and at least one binding protein described herein, at least one host cell described herein, or a population of host cells described herein; b) repeating step a) at a subsequent point in time; and c) comparing the level of MAGEA1 or the cell of interest expressing MAGEA1 detected in steps a) and b) to monitor the progression of the disorder characterized by MAGEA1 expression in the subject, wherein an absent or reduced MAGEA1 level or the cell of interest expressing MAGEA1 detected in step b) compared to step a) indicates an inhibited progression of the disorder characterized by MAGEA1 expression in the subject and a presence or increased MAGEA1 level or the cell of interest expressing MAGEA1 detected in step b) compared to step a) indicates a progression of the disorder characterized by MAGEA1 expression in the subject, is provided.

Numerous embodiments are further provided that may be applied to any aspect encompassed by the present invention and/or combined with any other embodiment described herein. For example, in one embodiment, a subject has undergone treatment to treat a disorder characterized by MAGEA1 expression between the first point in time and the subsequent point in time.

In yet another aspect, a method for predicting the clinical outcome of a subject afflicted with a disorder characterized by MAGEA1 expression comprising: a) determining the presence or level of reactivity between a sample obtained from the subject and at least one binding protein described herein, at least one host cell described herein, or a population of host cells described herein; and b) comparing the presence or level of reactivity to that from a control, wherein the control is obtained from a subject having a good clinical outcome; wherein the absence or a reduced level of reactivity in the subject sample as compared to the control indicates that the subject has a good clinical outcome, is provided.

In another aspect, a method of assessing the efficacy of a therapy for a disorder characterized by MAGEA1 expression comprising: a) determining the presence or level of reactivity between a sample obtained from the subject and at least one binding protein described herein, at least one host cell described herein, or a population of host cells described herein, in a first sample obtained from the subject prior to providing at least a portion of the therapy for the disorder characterized by MAGEA1 expression to the subject, and b) determining the presence or level of reactivity between a sample obtained from the subject and at least one binding protein described herein, at least one host cell described herein, or a population of host cells described herein, in a second sample obtained from the subject following provision of the therapy for the disorder characterized by MAGEA1 expression, wherein the absence or a reduced level of reactivity in the second sample, relative to the first sample, is an indication that the therapy is efficacious for treating the disorder characterized by MAGEA1 expression in the subject, and wherein the presence or an increased level of reactivity in the second sample, relative to the first sample, is an indication that the therapy is not efficacious for treating the disorder characterized by MAGEA1 expression in the subject, is provided.

Numerous embodiments are further provided that may be applied to any aspect encompassed by the present invention and/or combined with any other embodiment described herein. For example, in one embodiment, a level of reactivity is indicated by a) the presence of binding and/or b) T cell activation and/or effector function, optionally wherein the T cell activation or effector function is T cell proliferation, killing, or cytokine release. In another embodiment, a T cell binding, activation, and/or effector function is detected using fluorescence activated cell sorting (FACS), enzyme linked immunosorbent assay (ELISA), radioimmune assay (RIA), immunochemically, Western blot, or intracellular flow assay.

In still another aspect, a method of preventing and/or treating a disorder characterized by MAGEA1 expression comprising contacting target cells expressing MAGEA1 with a therapeutically effective amount of a composition comprising cells expressing at least one binding protein described herein, optionally wherein the composition is administered to a subject, is provided.

Numerous embodiments are further provided that may be applied to any aspect encompassed by the present invention and/or combined with any other embodiment described herein. For example, in one embodiment, a cell is an allogeneic cell, syngeneic cell, or autologous cell. In another embodiment, a cell is host cell described herein or a population of host cells described herein. In still another embodiment, a target cell is a cancer cell expressing MAGEA1. In yet another embodiment, a cell composition further comprises a pharmaceutically acceptable carrier. In another embodiment, a cell composition induces an immune response against the target cell expressing MAGEA1 in the subject. In still another embodiment, a cell composition induces an antigen-specific T cell immune response against the target cell expressing MAGEA1 in the subject. In yet another embodiment, an antigen-specific T cell immune response comprises at least one of a $CD4^+$ helper T lymphocyte (Th) response and a CD8+ cytotoxic T lymphocyte (CTL) response. In another embodiment, a method further comprises administering at least one additional treatment for the disorder characterized by MAGEA1 expression, optionally wherein the at least one additional treatment for the disorder characterized by MAGEA1 expression is administered concurrently or sequentially with the composition. In still another embodiment, a disorder characterized by MAGEA1 expression is a cancer or relapse thereof, optionally wherein the cancer is selected from the group consisting of melanoma, head & neck cancer, lung cancer, cervical cancer, hepatocellular carcinoma, colorectal cancer, gastrointestinal cancer, breast invasive carcinoma, and bladder urothelial carcinoma. In yet another embodiment, a subject is an animal model of a disorder characterized by MAGEA1 expression and/or a mammal, optionally wherein the mammal is a human, a primate, or a rodent.

BRIEF DESCRIPTION OF THE DRAWINGS

FIG. 2A-FIG. 2E demonstrate the identification of a MAGEA1 antigenic peptide and HLA restriction. Overlapping peptide sequences from MAGEA1 were evaluated for predicted binding to HLA-C*07:02. The top predicted MHC binding peptides were synthesized and used to pulse HLA-C*07:02-expressing HEK293T cells. Reactivity of TCR-transduced T cells was measured using granzyme-IFP reporter. FIG. 2A shows results of and frequencies for a pool of TCR-transduced T cells co-cultured with HEK293T cells expressing a granzyme-activated fluorescent reporter, six HLA alleles: A*01:01, A*03:01, B*07:02, B*08:01, C*07:01 and C*07:02, and an overlapping library of ~600,000 90-mer peptides spanning the human proteome. Tiles with a fold enrichment >2.5 with identical overlapping peptide sequences area highlighted with dots corresponding to the underlying shared gene. FIG. 2B shows HLA deconvolution of MAGEA1 to C*07:02. HEK293T cells expressing the granzyme-activated fluorescent reporter and individual HLA alleles as indicated, or all six HLA alleles (Pt.32 6Mer) as used in FIG. 2A were transduced ± the MAGEA1 90-mer, and co-cultured with a pool of TCR-transduced T-cells. Heatmaps representing % IFP+ cells for each coculture condition are shown in triplicate. Each row represents a reporter cell line expressing the indicated HLA. The key to the right indicates the range of IFP signal. FIG. 2C shows representative sequences of MAGEA1 peptides identified in screening data. Overlapping sequences (solid box) were analyzed for HLA-C*07:02-predicted binding to identify a top predicted binder having a sequence VBFFFPSL (SEQ ID NO: 1). FIGS. 2D and 2E (left panel) show reactivity of the TCR-transduced T cells co-cultured with HLA-C*07:02 monoallelic HEK293T cells expressing a granzyme-activated fluorescent reporter pulsed with the indicated peptides measured, which confirmed VBFFFPSL (SEQ ID NO: 1) as a minimal MAGEA1 epitope. FIG. 2E (right panel) shows that both TCR39 and TCR41 show similar affinity for peptide VBFFFPSL (SEQ ID NO: 1) pulsed into suspension HEK293 cells. Each point shows the average of 2-3 technical replicates measuring IFNg levels with standard deviations indicated. Figure discloses SEQ ID NOS 66-70, 6, 5, 71, 6, 5, 71, 72, 6, 73, 5, 74-75, 1, 5, and 1, respectively, in order of appearance.

FIG. 3A and FIG. 3B show identification of MAGEA1-reactive TCRs from pools of TCR-transduced t cells. Target cells were transduced with a 90-mer from MAGEA1 and co-cultured with a pool of TCR-transduced T cells. Reactive TCRs were identified by sequencing the exogenous TCR from sorted CD137/CD69 double-positive cells. FIG. 3A shows proportion of cells expressing the indicated TCRs in the input (left) and sorted cells (right) (TCR 32-39 and TCR 32-41 labeled as "39" and "41", respectively).

FIG. 3B shows the fold enrichment of sorted TCRs reacting to MAGEA1-transduced cells over the input library.

FIG. 4A-FIG. 4C show that TCR 32-39 (also known as TCR 39) and TCR 32-41 (also known as TCR 41) recognize cancer cells that express MAGEA1. FIG. 4A reports mRNA expression data from publicly available datasets (CCLE Cancer cell line encyclopedia) in transcripts per million (TPM). FIG. 4B demonstrates reactivity of the TCRs to cancer cell lines as measured by IFNγ release. FIG. 4C demonstrates reactivity of the TCRs to cancer cell lines as measured by CD137/CD69 double-positive staining.

FIG. 5A reports mRNA expression data from publicly available datasets (CCLE Cancer cell line encyclopedia) in transcripts per million (TPM). FIG. 5B demonstrates reactivity of the TCRs transduced either into CD3+ or CD8+ T-cells to cancer cell lines as measured by secretion of the indicated cytokines (IFNg, TNFa, and Granzyme B). Plotted is the mean±standard deviation (n=3). FIG. 5C provides a summary depiction of TCR 41 CD3 data from FIG. 5B.

FIG. 6A shows that TCR 32-39 and 32-41 kill cancer cell lines expressing high to medium levels of MAGEA1 (TPM is indicated for each cell line). FIG. 6B shows that TCR 32-41 does not kill cell lines with low to zero MAGEA1 expression. Indicated cell lines were transduced with Incucyte® NucLight™ Red and either co-cultured with TCR 32-39 (triangle), TCR 32-41 (circle) with non-transduced donor T cells (diamond) or with no T-cells (square). T cells were added at the indicated E:T ratios at the start of the assay. Red fluorescence was measured over time with an Incucyte® instrument and displayed as total red integrated intensity per well normalized to timepoint 0. Summary data presented as bar graph are shown below each cell survival plot and indicate the mean level of cell survival at 72 h with error bars representing 0.5 of the range (n=2). FIG. 6C provides a simplified depiction of data from FIGS. 6A and 6B but only showing TCR 41 data at an E:T of 1:1.

FIG. 9A shows that co-culture of T cells expressing 32-41 with C*07:02 HEK reporter cells that express the indicated full length proteins show no activation of the reporter, measured as % IFP, except for LAMB4-IR. When challenged with dilutions of the cross-reactive peptide from LAMB4-IR, FIG. 9B shows poor reactivity of TCR 32-41 to the LAMB4-IR peptide below 2,000 ng/mL. A table is shown summarizing the results obtained for evaluating predicted off-targets from the genome-wide SafetyScan screen.

Figure 1:
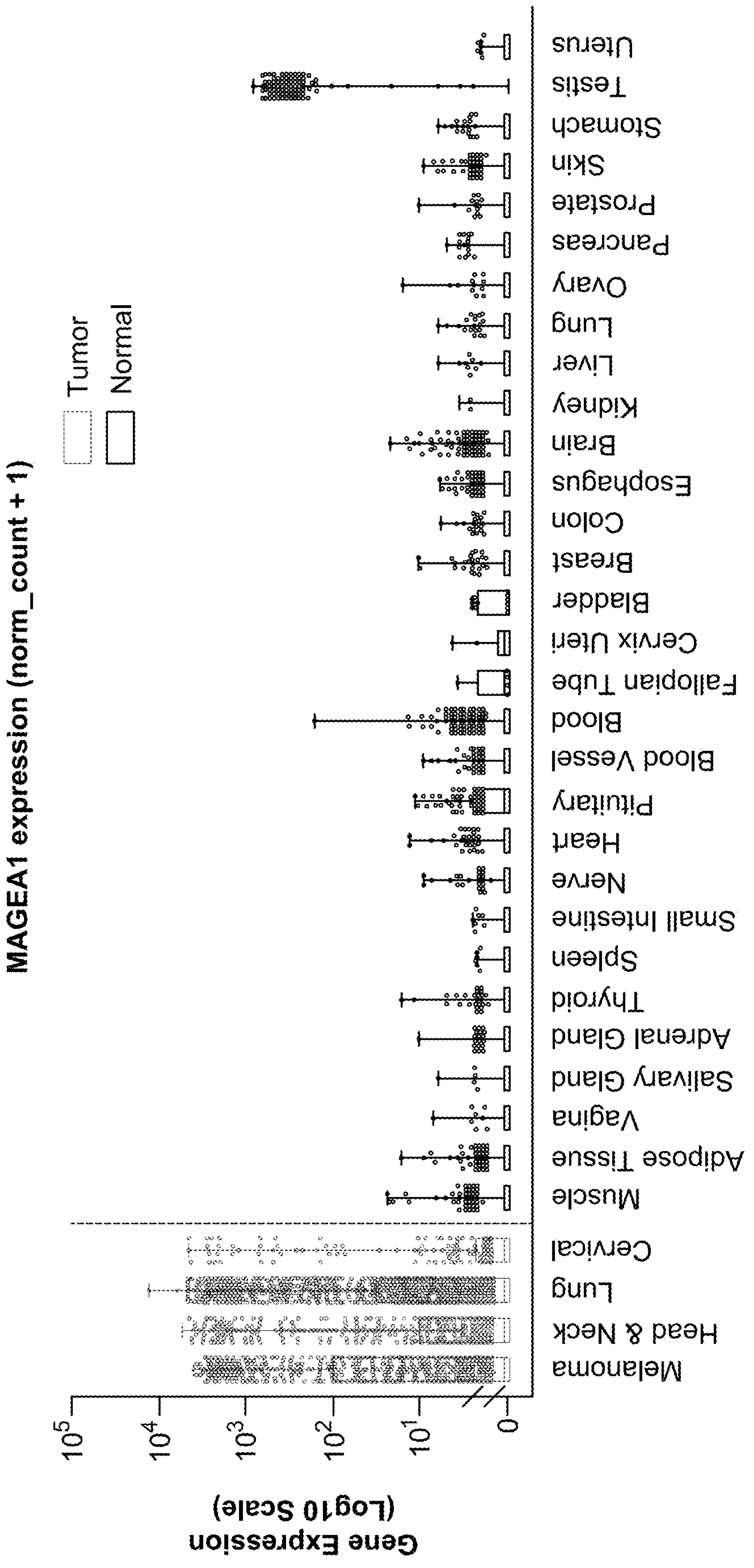
FIG. 1 shows nucleic acid gene expression of MAGEA1 in a wide panel of tumor types and normal tissues and further demonstrates that MAGEA1 is frequently expressed in several target indications, which enables multiplexed TCR-T therapy.
Figure 1:
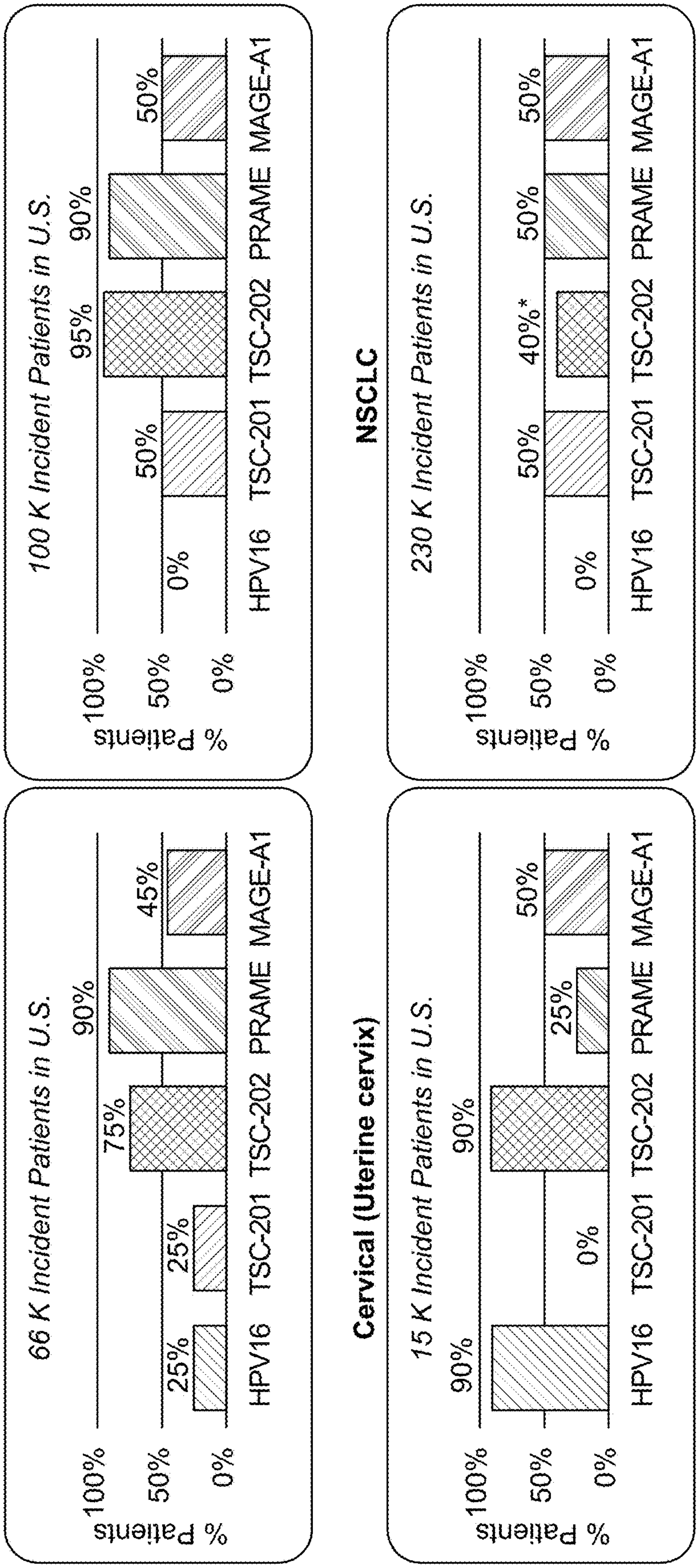

For any figure showing a bar histogram, curve, or other data associated with a legend, the bars, cruve, or other data presented from left to right for each indication correspond directly and in order to the boxes from top to bottom, or from left to right, of the legend unless indicated otherwise.

DETAILED DESCRIPTION OF THE INVENTION

The present invention is based, at least in part, on the discovery of MAGEA1 immunogenic peptides (e.g., those comprising or consisting of sequences listed in Table 1), binding proteins (e.g., those having sequences listed in Table 2) that recognize MAGEA1 antigens, and uses thereof. A systematic, comprehensive survey was carried out to map the precise T cell targets recognized by an initial pool of T cells of interest.

Accordingly, the present invention relates, in part, to the identified epitopes (immunodominant peptides) of therapeutically relevant MAGEA1 protein and related compositions (e.g., immunodominant peptides, vaccines, and the like), compositions comprising immunogenic peptides alone or with MHC molecules, stable MHC-peptide complexes, methods of diagnosing, prognosing, and monitoring immune responses to disorders characterized by MAGEA1 expression, and methods for preventing and/or treating disorders characterized by MAGEA1 expression. The present invention also relates, in part, to identified binding proteins (e.g., TCRs), host cells expressing binding proteins (e.g., TCRs), compositions comprising binding proteins (e.g., TCRs) and host cells expressing binding proteins (e.g., TCRs), methods of diagnosing, prognosing, and monitoring T cell response to cells expressing MAGEA1, and methods for preventing and/or treating disorders characterized by MAGEA1 expression.

I. Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element. In addition, references to a table provided herein encompass all sub-tables of the table unless otherwise indicated.

The term "administering" means providing a pharmaceutical agent or composition to a subject, and includes, but is not limited to, administering by a medical professional and self-administering. This involves the physical introduction of a composition comprising a therapeutic agent to a subject, using any of the various methods and delivery systems known to those skilled in the art. In some embodiments, routes of administration for binding proteins described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a binding protein described herein may be administered via a non-parenteral route, such as a topical, epidermal or mucosal route of administration, for example, intranasally, orally, vaginally, rectally, sublingually or topically. Administering may also be performed, for example, once, a plurality of times, and/or over one or more extended periods.

As used herein, the term "antigen" refers to any natural or synthetic immunogenic substance, such as a protein, peptide, or hapten. An antigen may be a MAGEA1 antigen, or a fragment thereof, against which protective or therapeutic immune responses are desired. An "epitope" is the part of the antigen bound by a natural or synthetic substance.

The term "adjuvant" as used herein refers to substances, which when administered prior, together or after administration of an antigen accelerates, prolong and/or enhances the quality and/or strength of an immune response to the antigen in comparison to the administration of the antigen alone. Adjuvants can increase the magnitude and duration of the immune response induced by vaccination.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions may be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, P1(3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen presenting cell" or "APC" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "antigen-binding portion" of a binding protein, such as a TCR, as used herein, refers to one or more portions of a TCR that retain the ability to bind (e.g., specifically and/or selectively) to an antigen (e.g., a MAGEA1 antigen). Such portions are, for example, between about 8 and about 1,500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of a TCR can be performed by fragments of a full-length TCR. Examples of binding portions encompassed within the term "antigen-binding portion" of a TCR, include (i) a Fv fragment consisting of the $V_\alpha$ and VB domains of a TCR, (ii) an isolated complementarity determining region (CDR) or (iii) a combination of two or more isolated CDRs which may optionally be joined by a synthetic linker. Furthermore, although $V_\alpha$ and $V_\beta$, are coded by separate genes, they may be joined, using recombinant methods, by a synthetic linker that enables them to be made as a single protein chain in which the $V_\alpha$ and VB regions pair to form monovalent molecules (known as single chain TCR (scTCR)). Such single chain TCRs are also intended to be encompassed within the term "antigen-binding portion" of a TCR. These TCR fragments can be obtained using conventional techniques known to those with skill in the art, and the fragments are screened for utility in the same manner as are complete binding proteins. Antigen-binding portions may be produced by recombinant DNA techniques, or by enzymatic or chemical cleavage of intact immunoglobulins.

The terms "complementarity determining region" and "CDR" are synonymous with "hypervariable region" or "HVR" and are known in the art to refer to non-contiguous sequences of amino acids within certain binding proteins, such as TCR variable regions, which confer antigen specificity and/or binding affinity. For TCRs, in general, there are three CDRs in each α-chain variable region (αCDR1, αCDR2, and αCDR3) and three CDRs in each β-chain variable region (βCDR1, βCDR2, and βCDR3). CDR3 is believed to be the main CDR responsible for recognizing processed antigen. CDR1 and CDR2 mainly interact with the MHC.

The term "body fluid" refers to fluids that are excreted or secreted from the body as well as fluids that are normally not excreted or secreted from the body (e g, amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In some embodiments, the body fluid comprises immune cells, optionally wherein the immune cells are cytotoxic lymphocytes such as cytotoxic T cells and/or NK cells, CD4+ T cells, and the like.

The term "coding region" refers to regions of a nucleotide sequence comprising codons that are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and, in other embodiments, at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or any range in between, inclusive, such as at least about 80%-100%, of the nucleotide residues of the first portion are capable of base pairing with nucleotide residues in the second portion. In some embodiments, all nucleotide residues of the first portion are capable of base pairing with nucleotide residues in the second portion.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal may result in cytokine secretion, e.g., in a T cell that has received a T cell-receptor-mediated signal. Immune cells that have received a cell-receptor mediated signal, e.g., via an activating receptor are referred to herein as "activated immune cells."

"CD3" is known in the art as a multi-protein complex of six chains (see, Abbas and Lichtman, Cellular and Molecular Immunology (9th Edition) (2018); Janeway et al. (Immunobiology) (9th Edition) (2016)). In mammals, the complex comprises a CD3γ chain, a CD3δ chain, two CD3ε chains, and a homodimer of CD3ξ chains. The CD3γ, CD3δ, and CD3ε chains are related cell surface proteins of the immunoglobulin superfamily containing a single immunoglobulin domain. The transmembrane regions of the CD3γ, CD3δ, and CD3ε chains are negatively charged, which is a characteristic that is believed to allow these chains to associate with positively charged regions or residues of T cell receptor chains. The intracellular tails of the CD3γ, CD3δ, and CD3ε chains each contain a single conserved motif known as an immunoreceptor tyrosine-based activation motif or IT AM, whereas each CD3ξ chain has three ITAMs. Without wishing to be bound by theory, it is believed that the IT AMs are important for the signaling capacity of a TCR complex. CD3 used in accordance with the present invention may be from various animal species, including human, mouse, rat, or other mammals.

A "component of a TCR complex," as used herein, refers to a TCR chain (i.e. TCRα, TCRβ, TCRγ or TCRδ), a CD3 chain (i.e., CD3γ, CD3δ, CD3ε or CD3ξ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

The term "chimeric antigen receptor" or "CAR" refers to a fusion protein that is engineered to contain two or more amino acid sequences linked together in a way that does not occur naturally or does not occur naturally in a host cell, which fusion protein can function as a receptor when present on a surface of a cell. CARs encompassed by the present invention include an extracellular portion comprising an antigen-binding domain (i.e., obtained or derived from an immunoglobulin or immunoglobulin-like molecule, such as a TCR specific for a MAGEA1 antigen, a single chain TCR-derived binding protein, an scFv derived from an antibody, an antigen binding domain derived or obtained from a killer immunoreceptor from an NK cell, and the like) linked to a transmembrane domain and one or more intracellular signaling domains (such as an effector domain, optionally containing co-stimulatory domain(s)) (see, e.g., Sadelain et al. (2013) *Cancer Discov.* 3:388; see also Harris and Kranz (2016) *Trends Pharmacol. Sci.* 37: 220; Stone et al. (2014) *Cancer Immunol. Immunother.* 63:1163).

As used herein, the term "cytotoxic T lymphocyte (CTL) response" refers to an immune response induced by cytotoxic T cells. CTL responses are mediated primarily by $CD8^+$ T cells.

The term "consisting essentially of is not equivalent to "comprising" and refers to the specified materials or steps of a claim, or to those that do not materially affect the basic characteristics of a claimed subject matter. For example, a protein domain, region, or module (e.g., a binding domain, hinge region, linker module) or a protein (which may have one or more domains, regions, or modules) "consists essentially of a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

The term "determining a suitable treatment regimen for the subject" is taken to mean the determination of a treatment regimen (i.e., a single therapy or a combination of different therapies that are used for the prevention and/or treatment of the viral infection in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "dominant negative TGFβ receptor" or "DN-TGFβR" refers to a transforming growth factor (TGF) beta receptor variant or mutant that provides resistance to TGFβ signaling. There are five type II receptors (activation receptors) and seven type I receptors (signaling propagation receptors). The active TGFβ receptor is a heterotetramer consisting of two TGF β receptors I (TGFβRI) and two TGF β receptors II (TGFβRII). In some embodiments, the DN-TGFβR is a DN-TGFβRII (i.e., a TGF beta receptor II variant or mutant). In some embodiments, resistance is to the suppressive effect of TGFβ signaling on an immune cell, such as a T cell, which TGFβ may be produced by cancer cells or by other immune cells within a cellular environment, such as by stromal cells, macrophages, myeloid cells, epithelial cells, natural killer cells, and the like. TGFβ signaling inhibitors are well-known in the art and include, without limitation, mutant TGFβ that sequesters receptors and thereby inhibits signaling, antibodies that bind to TGFβ and/or TGFβ receptors (e.g., lerdelimumab, metlimumab, fressolimumab, and the like), soluble TGFβ-binding proteins such as portions of TGFβ receptors that sequester TGFβ (e.g., TGFβRII-Fc fusion proteins) or other binders, such as beta-glycans. Any and all known TGFβ signaling inhibitors may be used instead of or in addition to DN-TGFβR (e.g., DN-TGFβRII) described herein. In some embodiments, a DN-TGFβR lacks an intracellular portion required for TGFβ-mediated signaling, such as the entire intracellular domain, a kinase signaling domain, etc. DN-TGFβR constructs are well-known in the art (see representative, non-limiting embodiments at Brand et al. (1993) *J. Biol. Chem.* 268:11500-11503; Weiser et al. (1993) *Mol. Cell Biol.* 13:7239-7247; Bollard et al. (2002) *Blood* 99:: 3179-3187; PCT Publ. WO 2009/152610; PCT Publ. WO 2017/156484; Kloss et al. (2018) *Mol. Ther.* 26:1855-1866; PCT Publ. WO. 2019/089884; PCT Publ. WO 2020/042647; and PCT Publ. WO 2020/042648.

In some embodiments, immune cell products (e.g., engineered T cells) comprising one or more binding proteins (e.g., TCRs) described herein are resistant to β-mediated immunosuppression. As described above and further herein, TGFβ is an immunosuppressive cytokine produced by tumor cells and cells in the tumor microenvironment. TGFβ inhibits the function and expansion of cytotoxic and Th1 helper T cells resulting in suppression of the tumor-specific T cell responses (Dahmani and Delisle (2018) Cancers 10:194). TGFβ signaling in T cells can be abrogated by expression of a dominant negative TGFβ type II receptor (DN-TGFβRII) (Wieser et al. (1993) *Mol. Cell. Biol.* 13:7239-7247; Bollard et al. (2002) *Blood* 99:3179-3187). Upon binding to TGFβ, wild-type TGFβRII phosphorylates and thereby activates the TGFβRI and initiating intracellular signal transmission. This signaling cascade is interrupted in cells that express truncated TGFβRII lacking the intracellular kinase domain (DN-TGFβRII), thereby rendering the cells resistant to inhibition by TGFβ. DN-TGFβRII blocks TGFβ signaling in engineered T cells (both CAR-T and TCR-T cells) (Bollard et al. (2002) *Blood* 99:3179-3187; Foster et al. (2008) *J. Immunother.* 31:500-505; Kloss et al. (2018) *Mol. Ther.* 26:1855-1866; Alabanza et al. (2022) *Front. Immunol.* 13:832645; Silk et al. (2022) *J. Immunol.* 208:169-180; Li et al. (2020) *Front. Oncol.* 10:1117). In a representative study, evaluation of EBV-specific T cells equipped with DN-TGFβRII for the treatment of Hodgkin lymphoma showed that T cells engineered with DN-TGFβRII are both safe and efficacious (Bollard et al. (2018) *J. Clin. Oncol.* 36:1128-1139).

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}$ Lin−$CD117^{+}$ phenotype or those found in the thymus (referred to as progenitor thymocytes).

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. In some embodiments, the first region comprises a first portion and the second region comprises a second portion, whereby, at least about 50%, and, in other embodiments, at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or any range in between, inclusive, such as at least about 80%-100%, of the nucleotide residue positions of each of the portions are occupied by the same nucleotide residue. In some embodiments, all nucleotide residue positions of each of the portions are occupied by the same nucleotide residue.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

An increased ability to stimulate an immune response or the immune system, can result from an enhanced agonist activity of T cell costimulatory receptors and/or an enhanced antagonist activity of inhibitory receptors. An increased ability to stimulate an immune response or the immune system may be reflected by a fold increase of the $EC_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity may be enhanced by at least 10%, 20%, 30%, 40%, 50%, 60%, 70%, 80%, 90%, 100%, 110%, 120%, 130%, 140%, 150%, 160%, 170%, 180%, 190%, 200%, 250%, 300%, 350%, 400%, 500%, or more.

The term "immunotherapeutic agent" may include any molecule, peptide, antibody or other agent which can stimulate a host immune system to generate an immune response to a viral infection in the subject. Various immunotherapeutic agents are useful in the compositions and methods described herein.

The term "immune cell" refers to any cell of the immune system that originates from a hematopoietic stem cell in the bone marrow, which gives rise to two major lineages: a myeloid progenitor cell (which give rise to myeloid cells such as monocytes, macrophages, dendritic cells, megakaryocytes and granulocytes); and a lymphoid progenitor cell (which give rise to lymphoid cells such as T cells, B cells and natural killer (NK) cells). Exemplary immune system cells include a $CD4^{+}$ T cell, a $CD8^{+}$ T cell, a CD4 CD8 double negative T cell, a gd T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the binding protein, antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), or, in some embodiments, less than about 25%, 20%, 15%, 10%, 5%, 1%, or less, or any range in between inclusive, such as less than about 1% to 5%, of non-biomarker protein. When binding protein, antibody, polypeptide, peptide or fusion protein or fragment thereof, e.g., a biologically active fragment thereof, is recombinantly produced, it may be substantially free of culture medium, i.e., culture medium represents less than about 20%, 15%, 10%, 5%, 1%, or less, or any range in between inclusive, such as less than about 1% to 5%, of the volume of the protein preparation.

As used herein, the term "isotype" refers to the antibody class (e.g., IgM, IgG1, IgG2C, and the like) that is encoded by heavy chain constant region genes.

As used herein, the term "$K_D$" is intended to refer to the dissociation equilibrium constant of a particular binding protein-antigen interaction. The binding affinity of binding proteins encompassed by the present invention may be measured or determined by standard binding protein-target binding assays, for example, competitive assays, saturation assays, or standard immunoassays, such as ELISA or RIA. A relatively lower Kd value indicates a relatively higher binding affinity (e.g., Kd values of less than or equal to about $5\times10^{-4}$ M (500 uM) include a Kd value of $1\times10^{-4}$ M (100 uM) and a 100 uM Kd indicates a relatively higher binding affinity as compared to a 500 uM Kd).

A "kit" is any manufacture (e.g., a package or container) comprising at least one reagent, e.g., a probe or small molecule, for detecting and/or affecting the expression of a marker encompassed by the present invention. The kit may be promoted, distributed, or sold as a unit for performing the methods encompassed by the present invention. The kit may comprise one or more reagents necessary to express a composition useful in the methods encompassed by the present invention. In some embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous house-keeping proteins. Reagents in the kit may be provided in individual containers or as mixtures of two or more reagents in a single container. In addition, instructional materials which describe the use of the compositions within the kit may be included.

As used herein, the term "linked" refers to the association of two or more molecules. The linkage may be covalent or non-covalent. The linkage also may be genetic (i.e., recombinantly fused). Such linkages may be achieved using a wide variety of art recognized techniques, such as chemical conjugation and recombinant protein production.

A "linker," in some embodiments, may refer to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In some embodiments, a linker is comprised of about two to about 35 amino acids, for instance, or about four to about 20 amino acids or about eight to about 15 amino acids or about 15 to about 25 amino acids.

The term "MAGEA1" refers to a particular member of the melanoma antigen gene family clustered on human chromosome Xq28 (e.g., chromosome X: 153,179,284-153,183, 880 forward strand. GRCh38:CM000685.2) that is also known as cancer/testis antigen 1.1 (CT1.1); melanoma-associated antigen 1; MAGE1; melanoma antigen family A, 1 (directs expression of antigen MZ2-E); cancer/testis antigen family 1, member 1; melanoma-associated antigen MZ2-E; melanoma antigen family A1; cancer/testis antigen 1.1; melanoma antigen MAGE-1; MAGE-1 antigen; antigen Z2-E, MGC9326; and MAGE1A (Mao et al. (2019) *J. Hematol. Oncol.* 12:106; Fanipakdel et al. (2019) *J. Cell Physiol.* 234:12080-12086; Gu et al. (2018) *Thorac. Cancer* 9:431-438; Mecklenburg et al. (2017) *Clin. Cancer Res.* 23:1213-1219; Wang et al. (2016) *Biochem. Biophys. Res. Commun.* 473:959-965; Kozakova et al. (2015) *Cell Cycle* 14:920-930; Cannuyer et al. (2013) *PLoS One* 8:e5874; Pereira et al. (2012) *Oncol. Rep.* 27:1843-1848; Ogata et al. (2011) *Ann. Surg. Oncol.* 18:1195-1203; Roch et al. (2010) *Anticancer Res.* 30:1617-1623; Dango et al. (2010) *Lung Cancer* 67:290-295; van der Bruggen et al. (1991) *Science* 254:1643-1647). MAGEA1 is a melanoma antigen recognized by cytolytic T lymphocytes and is believed to be involved in transcriptional regulation through interaction with SNW1 and recruiting histone deactelyase HDAC1, as well as in inhibiting notch intracellular domain (NICD) transactivation, embryonal development, association with some herediatyr disorders (e.g., dyskeratosis congenital), and/or tumor transformation or aspects of tumor progression (e.g., gastric carcinomas, hepatocellular carcinomas, etc.). MAGEA1 is not highly expressed in normal tissues, except for testis, and is expressed in tumors of various histological types, such as melanoma, head & neck cancer, lung cancer, cervical cancer, hepatocellular carcinoma, colorectal cancer, gastrointestinal cancer, colorectal cancer, gastrointestinal cancer, breast invasive carcinoma, and bladder urothelial carcinoma.

The term "MAGEA1" is intended to include fragments, variants (e.g., allelic variants), and derivatives thereof. Representative human MAGEA1 cDNA and human MAGEA1 protein sequences are well-known in the art and are publicly available from the National Center for Biotechnology Information (NCBI) (see, for example, ncbi.nlm.nih.gov/gene/4100). For example, human MAGEA1 (NP_004979.3) is encodable by the transcript (NM_004988.5). Nucleic acid and polypeptide sequences of MAGEA1 orthologs in organisms other than humans are well-known and include, for example, chimpanzee MAGEA1 (XM_529226.2 and XP_529226.2) and mouse MAGEA1 (Chromosome X:155088686-155089793; Ensembl *Mus musculus* version 104.39 (GRCm39)). Representative sequences of MAGEA1 sequences are also presented below in Table 3.

Anti-MAGEA1 antibodies suitable for detecting MAGEA1 protein are well-known in the art and include, for example, antibodies AM32863PU, AM50138PU, AP06212PU, AP13128PU-TA312178, TA39275, TA339275, TA339276, and TA347677 (OriGene, Rockville, MD); antibodies orb167376 and orb11016 (Biorbyt, Cambridge, United Kingdom); antibodies A03570 and A03570-1 (Boster Bio, Pleasanton, CA); antibodies E22-11B2-E9 and N1C3 (GeneTex, Irvince, CA); antibodies AFLGC-MAGEA1, MM-37821, and MA1-91067 (Invitrogen, Waltham, MA); antibodies ABIN2782493 and ABIN2782494 (Antibodies-online, Limerick, PA); and antibodies MA454 and 6C1 (Santa Cruz Biotechnology, Dallas, TX). In addition, reagents are well-known for detecting MAGEA1 expression. Moreover, multiple siRNA, shRNA, CRISPR constructs for modulating MAGEA1 expression can be found in the commercial product lists of a variety of companies, such as open reading frame (ORF) clones MG212171, MR212171, MR212171L3, MR212171L3V, MR212171L4, MR212171L4V, RC202134, RC202134L3, RC202134L3V, RC202134L4, RC202134L4V, and RG202134 (OriGene, Rockville, MD), CRISPR knockouts GA102785, GA202555, KN202134, KN202134BN, KN202134LP, KN202134RB, KN402134, and KN509652 (OriGene, Rockville, MD), and RNA interference (RNAi) clones, such as siRNA and shRNA clones, including SR302776, TL311617, SR410578, TL311617V, TTL516288, TL516288V, TL704467, TL04467V, TR311617, TR516288, and TR704467 (OriGene, Rockville, MD). It is to be noted that the term can further be used to refer to any combination of features described herein regarding MAGEA1 molecules. For example, any combination of sequence composition, percentage identify, sequence length, domain structure, functional activity, etc. can be used to describe a MAGEA1 molecule encompassed by the present invention.

The term "MAGEA1 antigen" or "MAGEA1 peptide antigen" or "MAGEA1-containing peptide antigen" or "MAGEA1 epitope" or "MAGEA1 peptide epitope" or "MAGEA1 peptide" refers to a naturally or synthetically produced immunogenic portion of MAGEA1. In sonic embodiments, MAGEA1 antigen protein can range in length from about 7, 8, 9, 10, 11, 12, 13, 14, 15, 16, 17, 18, 19, 20, 21, 22, 23, 24, 25 amino acids, or any range in between, inclusive, such as 8-15 amino acids. In some embodiments, MAGEA1 antigen protein can form a complex with an MHC (e.g., HLA) molecule such that a binding protein of this disclosure that recognizes a MAGEA1 peptide:MHC (e.g., HLA) complex can bind (e.g., specifically and/or selectively) to such a complex. Representative MAGEA1 peptide antigen sequences are shown in Table 1.

The term "major histocompatibility complex" (MHC) refers to glycoproteins that deliver peptide antigens to a cell surface. MHC class I molecules are heterodimers having a membrane spanning a chain (with three a domains) and a non-covalently associated b2 microglobulin. MHC class II molecules are composed of two transmembrane glycoproteins, a and b, both of which span the membrane. Each chain has two domains. MHC class I molecules deliver peptides originating in the cytosol to the cell surface, where a peptide antigen-MHC (pMHC) complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "prognosis" includes a prediction of the probable course and outcome of a viral infection or the likelihood of recovery from the disease. In some embodiments, the use of statistical algorithms provides a prognosis of a viral infection in an individual. For example, the prognosis may be surgery, development of a clinical subtype of a viral infection, development of one or more clinical factors, or recovery from the disease.

As used herein, "percent identity" between amino acid sequences is synonymous with "percent homology," which can be determined using the algorithm of Karlin and Altschul (1990) *Proc. Natl. Acad. Sci. USA* 87:2264-2268, modified by Karlin and Altschul (1993) *Proc. Natl. Acad. Sci. USA* 90:5873-5877. The noted algorithm is incorporated into the NBLAST and XBLAST programs of Altschul et al. (1990) *J. Mol. Biol.* 215:403-410. BLAST nucleotide searches are performed with the NBLAST program, score=100, wordlength=12, to obtain nucleotide sequences homologous to a polynucleotide described herein. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (1997) *Nuc. Acids Res.* 25:3389-3402. When utilizing BLAST and Gapped BLAST programs, the default parameters of the respective programs (e.g., XBLAST and NBLAST) may be used.

The phrase "pharmaceutically-acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body.

The term "ratio" refers to a relationship between two numbers (e.g., scores, summations, and the like). Although, ratios may be expressed in a particular order (e.g., a to b or a:b), one of ordinary skill in the art will recognize that the underlying relationship between the numbers may be expressed in any order without losing the significance of the underlying relationship, although observation and correlation of trends based on the ratio may be reversed.

The term "recombinant host cell" (or simply "host cell") refers to a cell that comprises a nucleic acid that is not naturally present in the cell, such as a cell into which a recombinant expression vector has been introduced. It should be understood that cells according to the present invention is intended to refer not only to the particular subject cell, but also encompasses progeny of such a cell. Because certain modifications may occur in succeeding generations due to either mutation or environmental influences, such progeny may not, in fact, be identical to the parent cell, but are still included within the scope of the term cell according to the present invention.

The term "cancer response," "response to immunotherapy," or "response to modulators of T-cell mediated cytotoxicity/immunotherapy combination therapy" relates to any response of the hyperproliferative disorder (e.g., cancer) to a cancer agent, such as a modulator of T-cell mediated cytotoxicity, and an immunotherapy, preferably to a change in tumor mass and/or volume after initiation of neoadjuvant or adjuvant therapy. The term "neoadjuvant therapy" refers to a treatment given before the primary treatment. Examples of neoadjuvant therapy may include chemotherapy, radiation therapy, and hormone therapy. Hyperproliferative disorder response may be assessed, for example for efficacy or in a neoadjuvant or adjuvant situation, where the size of a tumor after systemic intervention may be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment may be expanded to include response to chemotherapy, probability of survival, probability of metastasis within a given time period, and probability of tumor recurrence. For example, in order to determine appropriate threshold values, a particular cancer therapeutic regimen may be administered to a population of subjects and the outcome may be correlated to biomarker measurements that were determined prior to administration of any cancer therapy. The outcome measurement may be pathologic response to therapy given in the neoadjuvant setting. Alternatively, outcome measures, such as overall survival and disease-free survival may be monitored over a period of time for subjects following cancer therapy for which biomarker measurement values are known. In certain embodiments, the doses administered are standard doses known in the art for cancer therapeutic agents. The period of time for which subjects are monitored may vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy may be determined using well-known methods in the art, such as those described in the Examples section.

As indicated, the terms may also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 5%, 10%, 15%, 20%, 25%, 30%, 35%, 40%, 45%, 50%, 55%, 60%, 65%, 70%, 75%, 80%, 85%, 90%, 95%, 100%, or more, such 2-fold, 3-fold, 4-fold, 5-fold, 10-fold, 15-fold, 20-fold or more, or any range in between, inclusive. The reduction in response may be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance may be mediated by P-glycoprotein or may be mediated by other mechanisms, or it may occur when a mammal is infected with a multi-drug-resistant microorganism or a combination of microorganisms. The determination of resistance to a therapeutic treatment is routine in the art and within the skill of an ordinarily skilled clinician, for example, may be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing logarithmically.

The term "sample" used for detecting or determining the absence, presence, or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a skin, colon sample, or surgical resection tissue. In some embodiments, methods encompassed by the present invention further comprises obtaining the sample from the individual prior to detecting or determining the absence, presence, or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa et al. (1982) *Cancer Res.* 42:2159-2164) and cell death assays (Weisenthal et al. (1984) *Cancer Res.* 94:161-173; Weisenthal et al. (1985) *Cancer Treat Rep.* 69:615-632; Weisenthal et al., In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993:415-432; Weisenthal (1994) *Contrib. Gynecol. Obstet.* 19:82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 5%, 10%, 15%, 20%, 25%, 30%, 35%, 40%, 45%, 50%, 55%, 60%, 65%, 70%, 75%, 80%, 85%, 90%, 95%, 100%, or more, such 2-fold, 3-fold, 4-fold, 5-fold, 10-fold, 15-fold, 20-fold or more, or any range in between, inclusive, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy may be equally applied to methods for sensitizing hyperproliferative or otherwise cancerous cells (e.g., resistant cells) to the cancer therapy.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which may be screened for activity include, but are not limited to, peptides, peptidomimetics, nucleic acids, carbohydrates, small organic molecules (e.g., polyketides) (Cane et al. (1998) *Science* 282:63-68), and natural product extract libraries. In another embodiment, the compounds are small, organic non-peptidic compounds. In a further embodiment, a small molecule is not biosynthetic.

The term "specific binding" refers to binding protein binding to a predetermined antigen. Typically, the binding protein binds with an affinity ($K_D$) of approximately less than or equal to about $5\times10^{-4}$ M, less than or equal to about $1\times10^{-4}$ M, less than or equal to about $5\times10^{-5}$ M, less than or equal to about $1\times10^{-5}$ M, less than or equal to about $5\times10^{-6}$ M, less than or equal to about $1\times10^{-6}$ M, less than or equal to about $5\times10^{-7}$ M, less than or equal to about $1\times10^{-7}$ M, less than or equal to about $5\times10^{-8}$ M, less than or equal to about $1\times10^{-8}$ M, less than or equal to about $5\times10^{-9}$ M, less than or equal to about $1\times10^{-9}$ M, less than or equal to about $5\times10^{-10}$ M, less than or equal to about $1\times10^{-10}$ M, less than or equal to about $5\times10^{-11}$ M, less than or equal to about $1\times10^{-11}$ M, less than or equal to about $5\times10^{-12}$ M, less than or equal to about $1\times10^{-12}$ M, or even lower, or any range in between, inclusive, such as between about 1-50 micromolar, 1-100 micromolar, 0.1-500 micromolar, and the like, when determined by a binding assay, such as surface plasmon resonance (SPR) technology in a BIAcore™ assay instrument using an antigen of interest as the analyte and the binding protein as the ligand. In some embodiments, the binding protein binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "a binding protein recognizing an antigen" and "a binding protein specific for an antigen" are used interchangeably herein with the term "a binding protein which binds specifically to an antigen." Selective binding is a relative term referring to the ability of a binding protein to discriminate the binding of one antigen over another, such as a particular family member or antigen target over a related family member or antigen target. For example, analytical data provided in the Examples section demonstrates that binding proteins described herein specifically bind MAGEA1 immunogenic epitopes and/or selectively bind a number of related epitopes (e.g., MAGEA1 immunogenic epitopes and closely related sequences) discriminating such targets from the vast majority of other possible epitopes available in the human genome.

The term "subject" refers to any healthy animal, mammal or human, or any animal, mammal or human afflicted with a disorder characterized by MAGEA1 expression. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment may be expanded to include response to chemotherapy, probability of survival, probability of metastasis within a given time period, and probability of tumor recurrence.

The term "synergistic effect" refers to the combined effect of two or more agents (e.g., a MAGEA1-related agent described herein and another therapy for treating a disorder associated with MAGEA1 expression) that is greater than the sum of the separate effects of the cancer agents/therapies alone.

As used herein, the term "T cell-mediated response" refers to a response mediated by T cells, including effector T cells (e.g., $CD8^+$ cells) and helper T cells (e.g., $CD4^+$ cells). T cell mediated responses include, for example, T cell cytotoxicity and proliferation.

A "transcribed polynucleotide" or "nucleotide transcript" is a polynucleotide (e.g., an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g., splicing), if any, of the RNA transcript, and reverse transcription of the RNA transcript.

A "T cell" is an immune system cell that matures in the thymus and produces T cell receptors (TCRs). T cells may be naive (not exposed to antigen; increased expression of CD62L, CCR7, CD28, CD3, CD 127, and CD45RA, and decreased expression of CD45RO as compared to $T_{CM}$), memory T cells ($T_M$) (antigen-experienced and long-lived), and effector cells (antigen-experienced, cytotoxic). $T_M$ may be further divided into subsets of central memory T cells ($T_{CM}$, increased expression of CD62L, CCR7, CD28, CD127, CD45RO, and CD95, and decreased expression of CD54RA as compared to naive T cells) and effector memory T cells (TEM, decreased expression of CD62L, CCR7, CD28, CD45RA, and increased expression of CD127 as compared to naive T cells or $T_{CM}$). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as $CD4^+$ $CD25^+$ ($Foxp3^+$) regulatory T cells and Treg17 cells, as well as Trl, Th3, $CD8^+$CD28, and Qa-1 restricted T cells.

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naive T cells, activated T cells, memory T cells, resting Tcons, or Tcons that have differentiated toward, for example, the Th1 or Th2 lineages. In some embodiments, Teffs are a subset of non-Treg T cells. In some embodiments, Teffs are CD4+ Teffs or CD8+ Teffs, such as CD4+ helper T lymphocytes (e.g., Th0, Th1, Tfh, or Th17) and CD8+ cytotoxic T lymphocytes. As described further herein, cytotoxic T cells are CD8+ T lymphocytes. "Naive Tcons" are $CD4^+$ T cells that have differentiated in bone marrow, and successfully underwent a positive and negative processes of central selection in a thymus, but have not yet been activated by exposure to an antigen. Naive Tcons are commonly characterized by surface expression of L-selectin (CD62L), absence of activation markers such as CD25, CD44 or CD69, and absence of memory markers such as CD45RO. Naive Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) *Philos. Trans. R. Soc. Lond. Biol. Sci.* 356:625-637).

"T effector" ("$T_{eff}$" or "$T_E$") cells refers to T cells (e.g., CD4+ and CD8+ T cells) with cytolytic activities as well as T helper (Th) cells, which secrete cytokines and activate and direct other immune cells, but does not include regulatory T cells (Treg cells).

"T cell receptor" or "TCR" refers to an immunoglobulin superfamily member (having a variable binding domain, a constant domain, a transmembrane region, and a short cytoplasmic tail; see, e.g., Janeway et al. (1997) *Curr. Biol. Publ.* 4:33) that is capable of binding (e.g., e.g., specifically and/or selectively) to an antigen peptide bound to an MHC receptor. A TCR can be found on the surface of a cell or in soluble form and generally is comprised of a heterodimer having alpha and beta chains (also known as TCRα and TCRβ, respectively), or γ and δ chains (also known as TCRγ and TCRδ, respectively). Like immunoglobulins (e.g., antibodies), the extracellular portion of TCR chains (e.g., α-chain and β-chain) contain two immunoglobulin domains: a variable domain (e.g., α-chain variable domain or $V_\alpha$ and β-chain variable domain or $V_\beta$; typically amino acids 1 to 116 based on Kabat numbering (Kabat et al. (1991) "Sequences of Proteins of Immunological Interest, US Dept. Health and Human Services, Public Health Service National Institutes of Health, 5th ed.) at the N-terminal end, and one constant domain (e.g., α-chain constant domain or $C_\alpha$, typically amino acids 117 to 259 based on Kabat, β-chain constant domain or $C_\beta$, typically amino acids 117 to 295 based on Kabat) at the C-terminal end and adjacent to the cell membrane. Also like immunoglobulins, the variable domains contain complementary determining regions ("CDRs", also called hypervariable regions or "HVBs") separated by framework regions ("FRs") (see, e.g., Fores et al. (1990) *Proc. Natl. Acad Sci. U.S.A.* 87:9138; Chothia et al. (1988) *EMBO J.* 7:3745; Lefranc et al. (2003) *Dev. Comp. Immunol.* 27:55). In some embodiments, a TCR is found on the surface of a T cell (or T lymphocyte) and associates with the CD3 complex. The source of a TCR encompassed by the present invention may be from various animal species, such as a human, mouse, rat, rabbit or other mammal.

The term "T cell receptor" or "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR may contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

Nomenclature established by the International Immunogenetics Information System (IMGT) (see also Scaviner and Lefranc (2000) *Exp. Clin. Immunogenet.* 17:83-96 and 97-106; Folch and Lefranc (2000) *Exp. Clin. Immunogenet,* 17:107-114; T Cell Receptor Factsbook", (2001) LeFranc and LeFranc, Academic Press, ISBN 0-12-441352-8). The IMGT provides unique sequences used to describe a TCR, and sequences described herein may be identified by reference to such unique sequences provided herein. TCR sequences are publicly available at the IMGT database at imgt.org.

As described above, native alpha/beta heterodimeric TCRs have an alpha chain and a beta chain. Broadly, each chain comprises variable, joining and constant regions, and the beta chain also usually contains a short diversity region between the variable and joining regions, but this diversity region is often considered as part of the joining region. Each variable region comprises three hypervariable CDRs (Complementarity Determining Regions) embedded in a framework sequence. CDR3 is well-known to be the main mediator of antigen recognition. There are several types of alpha chain variable ($V_\alpha$) regions and several types of beta chain variable (Vβ) regions distinguished by their framework, CDR1 and CDR2 sequences, and by a partly defined CDR3 sequence. The Vα types are referred to in IMGT nomenclature by a unique TRAY number. For example, "TRAV4" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV2" defines a TCR Vβ region having unique framework and CDR1 and CDR2 sequences, but with only a partly defined CDR3 sequence. It is known that there are 54 alpha variable genes, of which 44 are functional, and 67 beta variable genes, of which 42 are functional, within the alpha and beta loci, respectively.

The joining regions of the TCR are similarly defined by the unique IMGT TRAJ and TRBJ nomenclature, and the constant regions by the IMGT TRAC and TRBC nomenclature. The beta chain diversity region is referred to in IMGT nomenclature by the abbreviation TRBD, and, as mentioned, the concatenated TRBD/TRBJ regions are often considered together as the joining region.

The gene pools that encode the TCR alpha and beta chains are located on different chromosomes and contain separate V, (D), J and C gene segments, which are brought together by rearrangement during T cell development. This leads to a very high diversity of T cell alpha and beta chains due to the large number of potential recombination events that occur between the 54 TCR alpha variable genes and 61 alpha J genes or between the 67 beta variable genes, two beta D genes and 13 beta J genes. The recombination process is not precise and introduces further diversity within the CDR3 region. Each alpha and beta variable gene may also comprise allelic variants, designated in IMGT nomenclature as TRAVxx*01 and *02, or TRBVx-x*01 and *02 respectively, thus further increasing the amount of variation. In the same way, some of the TRBJ sequences have two known variations. (Note that the absence of a "*" qualifier means that only one allele is known for the relevant sequence). The natural repertoire of human TCRs resulting from recombination and thymic selection has been estimated to comprise approximately $10^6$ unique beta chain sequences, determined from CDR3 diversity (Arstila et al. (1999) *Science* 286:958-961) and could be even higher (Robins et al. (2009) *Blood* 114:4099-4107). Each beta chain is estimated to pair with at least 25 different alpha chains, thus generating further diversity (Arstila et al. (1999) *Science* 286:958-961).

The term "TCR alpha variable domain" therefore refers to the concatenation of TRAY and TRAJ regions; a TRAY region only; or TRAY and a partial TRAJ region, and the term TCR alpha constant domain refers to the extracellular TRAC region, or to a C-terminal truncated or full length TRAC sequence. Likewise the term "TCR beta variable domain" refers to the concatenation of TRBV and TRBD/TRBJ regions; to the TRBV and TRBD regions only; to the TRBV and TRBJ regions only; or to the TRBV and partial TRBD and/or TRBJ regions, and the term TCR beta constant domain refers to the extracellular TRBC region, or to a C-terminal truncated or full length TRBC sequence. These TCR alpha variable domain and TCR beta variable domain nomenclature similarly applies to the variable domains of TCR gamma and TCR delta chains, respectively, for gamma/delta TCRs. An ordinarily skilled artisan can obtain TRAY, TRAJ, TRAC, TRBV, TRBJ, and TRBC gene sequences, such as through the publicly available IMGT database.

The term "TCR complex" refers to a complex formed by the association of CD3 with TCR. For example, a TCR complex may be composed of a CD3γ chain, a CD3δ chain, two CD3ε chains, a homodimer of CD3ξ chains, a TCRα chain, and a TCRβ chain. Alternatively, a TCR complex may be composed of a CD3γ chain, a CD3δ chain, two CD3ε chains, a homodimer of CD3ξ chains, a TCRγ chain, and a TCRδ chain.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human.

The terms "therapeutically effective amount" and "effective amount" means that amount of a substance that produces some desired effect, such as a desired local or systemic therapeutic effect, in at least a sub-population of cells in an animal at a reasonable benefit/risk ratio applicable to any treatment. In some embodiments, a therapeutically effective amount of a substance will depend on the substance's therapeutic index, solubility, pharmacokinetics, half-life, and the like. Toxicity and therapeutic efficacy of subject compounds may be determined by standard pharmaceutical procedures in cell cultures or experimental animals, e.g., for determining the $LD_{50}$ and the $ED_{50}$. In some embodiments, compositions that exhibit large therapeutic indices are used. In some embodiments, the $LD_{50}$ (lethal dosage) may be measured and may be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) may be measured and may be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ may be measured and may be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, T cell immune response in an assay may be increased by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a viral load may be achieved.

The term "treat" refers to the therapeutic management or improvement of a condition (e.g., a disease or disorder) of interest. Treatment may include, but is not limited to, administering an agent or composition (e.g., a pharmaceutical composition) to a subject. Treatment is typically undertaken in an effort to alter the course of a disease (which term is used to indicate any disease, disorder, syndrome or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. A therapeutic agent may be administered to a subject who has a disease or is at increased risk of developing a disease relative to a member of the general population. In some embodiments, a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease.

The term "unresponsiveness" includes refractivity of cancer cells to therapy or refractivity of therapeutic cells, such as immune cells, to stimulation, e.g., stimulation via an activating receptor or a cytokine. Unresponsiveness may occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells may, however, proliferate if cultured with cytokines (e.g., IL-2). For example, T cell anergy may also be observed by the lack of IL-2 production by T lymphocytes as measured by ELISA or by a proliferation assay using an indicator cell line. Alternatively, a reporter gene construct may be used. For example, anergic T cells fail to initiate IL-2 gene transcription induced by a heterologous promoter under the control of the 5' IL-2 gene enhancer or by a multimer of the AP1 sequence that may be found within the enhancer (Kang et al. (1992) *Science* 257:1134).

The term "vaccine" refers to a pharmaceutical composition that elicits an immune response to an antigen of interest. The vaccine may also confer protective immunity upon a subject.

The term "variable region" or "variable domain" refers to the domain of an immunoglobulin superfamily binding protein (e.g., a TCR α-chain or β-chain (or γ chain and δ chain for γδ TCRs)) that is involved in binding of the immunoglobulin superfamily binding protein (e.g., TCR) to antigen. The variable domains of the α-chain and β-chain ($V_\alpha$ and $V_\beta$, respectively) of a native TCR generally have similar structures, with each domain comprising four conserved framework regions (FRs) and three CDRs. The $V_\alpha$ domain is encoded by two separate DNA segments, the variable gene segment and the joining gene segment (V-J); the $V_\beta$ domain is encoded by three separate DNA segments, the variable gene segment, the diversity gene segment, and the joining gene segment (V-D-J). A single $V_\alpha$ or $V_\beta$ domain may be sufficient to confer antigen-binding specificity. Furthermore, TCRs that bind a particular antigen may be isolated using a $V_\alpha$ or $V_\beta$ domain from a TCR that binds the antigen to screen a library of complementary $V_\alpha$ or $V_\beta$ domains, respectively.

The term "vector" refers to a nucleic acid molecule capable of transporting another nucleic acid to which it has been linked. In some embodiments, a vector is an episome, i.e., a nucleic acid capable of extra-chromosomal replication. In some embodiments, vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is the most commonly used form of vector. However, as will be appreciated by those skilled in the art, the present invention is intended to include such other forms of expression vectors that serve equivalent functions and which become subsequently known in the art.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |

-continued

| GENETIC CODE | |
|---|---|
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) may be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

II. Peptides

In certain aspects, provided herein are methods and compositions for the treatment and/or prevention of disorders associated with MAGEA1 expression through the induction of an immune response against MAGEA1 or cells expressing MAGEA1 relating to administration of MAGEA1 immunogenic peptides, nucleic acids encoding same, and/or cells expressing same, described herein.

In certain embodiments, the MAGEA1 immunogenic peptide comprises (e.g., consists of) a peptide epitope selected from peptide sequences listed in Table 1, such as Table 1A. Peptide epitopes described herein may be combined with MHC molecules, such as particular HLA molecules having particular HLA alpha chain alleles. For example, Table 1A peptides were identified in association with an MHC whose alpha chain had an HLA-C*07 serotype, such as that encoded by an HLA-C*0702 allele, as described further in the Examples section. In some embodiments, MAGEA1 immunogenic peptides may be combined with an MHC molecule, wherein the MHC molecule comprises an MHC alpha chain that is an HLA serotype selected from the group consisting of HLA-A*02, HLA-A*03, HLA-A*01, HLA-A*11, HLA-A*24, HLA-B*07, HLA-C*07, HLA-C*01, HLA-C*02, HLA-C*03, HLA-C*04, HLA-C*05, HLA-C*06, HLA-C*08, HLA-C*12, HLA-C*14, HLA-C*15, HLA-C*16, HLA-C*17, and HLA-C*18, optionally wherein the HLA allele is selected from the group consisting of HLA-A*0201, HLA-A*0202, HLA-A*0203, HLA-A*0204, HLA-A*0205, HLA-A*0206, HLA-A*0207, HLA-A*0210, HLA-A*0211, HLA-A*0212, HLA-A*0213, HLA-A*0214, HLA-A*0216, HLA-A*0217, HLA-A*0219, HLA-A*0220, HLA-A*0222, HLA-A*0224, HLA-A*0230, HLA-A*0242, HLA-A*0253, HLA-A*0260, HLA-A*0274 allele, HLA-A*0301, HLA-A*0302, HLA-A*0305, HLA-A*0307, HLA-A*0101, HLA-A*0102, HLA-A*0103, HLA-A*0116 allele, HLA-A*1101, HLA-A*1102, HLA-A*1103, HLA-A*1104, HLA-A*1105, HLA-A*1119 allele, HLA-A*2402, HLA-A*2403, HLA-A*2405, HLA-A*2407, HLA-A*2408, HLA-A*2410, HLA-A*2414, HLA-A*2417, HLA-A*2420, HLA-A*2422, HLA-A*2425, HLA-A*2426, HLA-A*2458 allele, HLA-B*0702, HLA-B*0704, HLA-B*0705, HLA-B*0709, HLA-B*0710, HLA-B*0715, HLA-B*0721, HLA-C*0702, HLA-C*0701, HLA-C*0401, HLA-C*0602, HLA-C*0304, HLA-C*0501, HLA-C*1601, HLA-C*0202, HLA-C*0303, HLA-C*1203, HLA-C*0802, HLA-C*0102, HLA-C*1701, HLA-C*1502, HLA-C*1402, HLA-C*1202, HLA-C*0704, HLA-C*0801, HLA-C*0302, HLA-C*1801, HLA-C*1505, HLA-C*1602, HLA-C*0804, HLA-C*0305, and HLA-C*1403 allele. In some embodiments, the MAGEA1 immunogenic peptides are derived from a human MAGEA1 protein and/or a MAGEA1 protein shown in Table 3. In some embodiments, one or more MAGEA1 immunogenic peptides are administered alone or in combination with an adjuvant.

In certain aspects, provided herein are compositions comprising one or more MAGEA1 immunogenic peptides described herein and an adjuvant.

TABLE 1

MAGEA1 epitopes
Table 1A
MAGEA1 epitopes presented by HLA serotype HLA-C*07 (bold epitopes highlight reactivity described herein)

| Peptide Epitopes | SEQ ID NO: |
|---|---|
| **VRFFFPSL** | 1 |
| FFFPSLREA | 2 |
| ARVRFFFPSL | 3 |
| VRFFFPSLR | 4 |
| **RVRFFFPSL** | 5 |
| **RVRFFFPSLR** | 6 |
| FFPSLREA | 7 |
| ARVRFFFPSLR | 8 |
| SARVRFFF | 9 |
| VRFFFPSLREA | 10 |
| RFFFPSLREA | 11 |

*Included in Table 1, such as Table 1A are peptide epitopes, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any sequence listed in Table 1, such as Table 1A, or a portion thereof. Such polypeptides may have a function of the full-length peptide or polypeptide as described further herein.

In some embodiments, provided herein are MAGEA1 polypeptides and/or nucleic acids encoding MAGEA1 polypeptides. In some embodiments, MAGEA1 polypeptides are polypeptides that include an amino acid sequence of sufficient length to elicit a MAGEA1-specific immune response. In certain embodiments, the MAGEA1 polypeptide also includes amino acids that do not correspond to the amino acid sequence (e.g., a fusion protein comprising a MAGEA1 amino acid sequence and an amino acid sequence corresponding to a non-MAGEA1 protein or polypeptide). In some embodiments, the MAGEA1 polypeptide only includes amino acid sequence corresponding to a MAGEA1 protein or fragment thereof.

In some embodiments, the MAGEA1 polypeptide has an amino acid sequence that comprises, consists essentially of, or consists of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 373, or more, or any range in between inclusive (e.g., 7-25, 8-22, 9-22, etc.) consecutive amino acids of a MAGEA1 protein amino acid sequence, such as those set forth in Table 3. In some embodiments, the consecutive amino acids are identical to an amino acid sequence of MAGEA1 set forth in Table 3. In some embodiments, MAGEA1 polypeptides comprise, consist essentially of, or consist of one or more peptide epitopes selected from the group consisting of MAGEA1 peptide epitopes listed in Table 1, such as Table 1A.

As is well-known to those skilled in the art, polypeptides having substantial sequence similarities can cause identical or very similar immune reaction in a host animal. Accordingly, in some embodiments, a derivative, equivalent, variant, fragment, or mutant of a MAGEA1 immunogenic peptide described herein or fragment thereof may also suitable for the methods and compositions provided herein.

In some embodiments, variations or derivatives of the MAGEA1 immunogenic polypeptides are provided herein. The altered polypeptide may have an altered amino acid sequence, for example by conservative substitution, yet still elicits immune responses which react with the unaltered protein antigen, and are considered functional equivalents. As used herein, the term "conservative substitution" denotes the replacement of an amino acid residue by another, biologically similar residue. It is well-known in the art that the amino acids within the same conservative group may typically substitute for one another without substantially affecting the function of a protein. According to certain embodiments, the derivative, equivalents, variants, or mutants of the ligand-binding domain of a MAGEA1 immunogenic peptide are polypeptides that are at least 85% homologous to the sequence of a MAGEA1 immunogenic peptide described herein or fragment thereof. In some embodiments, the homology is at least 90%, at least 95%, at least 98%, or more.

Immunogenic peptides encompassed by the present invention may comprise a peptide epitope derived from a MAGEA1 protein, such as those listed in Table 1, such as Table A. In some embodiments, the immunogenic peptide is 8, 9, 10, 11, 12, 13, 14, or 15 amino acids in length. In some embodiments, the peptide amino acid sequences is modified, which may include conservative or non-conservative mutations. A peptide may comprise at most 1, 2, 3, 4, or more mutations. In some embodiments, a peptide may comprise at least 1, 2, 3, 4, or more mutations.

In some embodiments, a peptide may be chemically modified. For example, a peptide can be mutated to modify peptide properties such as detectability, stability, biodistribution, pharmacokinetics, half-life, surface charge, hydrophobicity, conjugation sites, pH, function, and the like. N-methylation is one example of methylation that can occur in a peptide of the disclosure. In some embodiments, a peptide may be modified by methylation on free amines such as by reductive methylation with formaldehyde and sodium cyanoborohydride.

A chemical modification may comprise a polymer, a polyether, polyethylene glycol, a biopolymer, a zwitterionic polymer, a polyamino acid, a fatty acid, a dendrimer, an Fc region, a simple saturated carbon chain such as palmitate or myristolate, or albumin. The chemical modification of a peptide with an Fc region may be a fusion Fc-peptide. A polyamino acid may include, for example, a poly amino acid sequence with repeated single amino acids (e.g., poly glycine), and a poly amino acid sequence with mixed poly amino acid sequences that may or may not follow a pattern, or any combination of the foregoing. In some embodiments, the peptides encompassed by the present disclosure may be modified such that the modification increases the stability and/or the half-life of the peptides. In some embodiments, the attachment of a hydrophobic moiety, such as to the N-terminus, the C-terminus, or an internal amino acid, can be used to extend half-life of a peptide encompassed by the present disclosure. In other embodiments, a peptide may include post-translational modifications (e.g., methylation and/or amidation), which can affect, for example, serum half-life. In some embodiments, simple carbon chains (e.g., by myristoylation and/or palmitylation) can be conjugated to the fusion proteins or peptides. In some embodiments, the simple carbon chains may render the fusion proteins or peptides easily separable from the unconjugated material. For example, methods that may be used to separate the fusion proteins or peptides from the unconjugated material include, but are not limited to, solvent extraction and reverse phase chromatography. The lipophilic moieties can extend half-life through reversible binding to serum albumin. The conjugated moieties may be lipophilic moieties that extend half-life of the peptides through reversible binding to serum albumin. In some embodiments, the lipophilic moiety may be cholesterol or a cholesterol derivative, including cholestenes, cholestanes, cholestadienes and oxysterols. In some embodiments, the peptides may be conjugated to myristic acid (tetradecanoic acid) or a derivative thereof. In other embodiments, a peptide may be coupled (e.g., conjugated) to a half-life modifying agent. Examples of half-life modifying agents include but are not limited to: a polymer, a polyethylene glycol (PEG), a hydroxyethyl starch, polyvinyl alcohol, a water soluble polymer, a zwitterionic water soluble polymer, a water soluble poly(amino acid), a water soluble polymer of proline, alanine and serine, a water soluble polymer containing glycine, glutamic acid, and serine, an Fc region, a fatty acid, palmitic acid, or a molecule that binds to albumin. In some embodiments, a spacer or linker may be coupled to a peptide, such as 1, 2, 3, 4, or more amino acid residues that serve as a spacer or linker in order to facilitate conjugation or fusion to another molecule, as well as to facilitate cleavage of the peptide from such conjugated or fused molecules. In some embodiments, fusion proteins or peptides may be conjugated to other moieties that, for example, can modify or effect changes to the properties of the peptides.

A peptide may, in some embodiments, be covalently linked to a moiety. In some embodiments, the covalently linked moiety comprises an affinity tag or a label. The affinity tag may be selected from the group consisting of glutathione-S-transferase (GST), calmodulin binding protein (CBP), protein C tag, Myc tag, HaloTag, HA tag, Flag® tag, His tag, biotin tag, and V5 tag. The label may be a fluorescent protein. In some embodiments, the covalently linked moiety is selected from the group consisting of an inflammatory agent, an anti-inflammatory agent, a cytokine, a toxin, a cytotoxic molecule, a radioactive isotope, or an antibody such as a single-chain Fv.

A peptide may be conjugated to an agent used in imaging, research, therapeutics, theranostics, pharmaceuticals, chemotherapy, chelation therapy, targeted drug delivery, and radiotherapy. In some embodiments, a peptide may be conjugated to or fused with detectable agents, such as a fluorophore, a near-infrared dye, a contrast agent, a nanoparticle, a metal-containing nanoparticle, a metal chelate, an X-ray contrast agent, a PET agent, a metal, a radioisotope, a dye, radionuclide chelator, or another suitable material that can be used in imaging. In some embodiments, 1, 2, 3, 4, 5, 6, 7, 8, 9, 10, or more detectable moieties may be linked to a peptide. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium- 225 or lead-212. In some embodiments, the near-infrared dyes are not easily quenched by biological tissues and fluids. In some embodiments, the fluorophore is a fluorescent agent emitting electromagnetic radiation at a wavelength between 650 nm and 4000 nm, such emissions being used to detect such agent. Non-limiting examples of fluorescent dyes that may be used as a conjugating molecule include DyLight®-680, DyLight®-750, VivoTag®-750, DyLight®-800, IRDye®-800, VivoTag®-680, Cy5.5, ZQ800, or indocyanine green (ICG). In some embodiments, near infrared dyes often include cyanine dyes (e.g., Cy7, Cy5.5, and Cy5). Additional non-limiting examples of fluorescent dyes for use as a conjugating molecule in the present disclosure include acradine orange or yellow, Alexa Fluors® (e.g., Alexa Fluor® 790, 750, 700, 680, 660, and 647) and any derivative thereof, 7-actinomycin D, 8-anilinonaphthalene-1-sulfonic acid, ATTO dye and any derivative thereof, auramine-rhodamine stain and any derivative thereof, bensantrhone, bimane, 9-10-bis(phenylethynyl)anthracene, 5,12-bis(phenylethynyl)naththacene, bisbenzimide, brainbow, calcein, carbodyfluorescein and any derivative thereof, 1-chloro-9,10-bis(phenylethynyl)anthracene and any derivative thereof, DAPI, DiOC6, DyLight Fluors and any derivative thereof, epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, fluorescent proteins and any derivative thereof, m isoform proteins and any derivative thereof such as for example mCherry, hetamethine dye and any derivative thereof, hoeschst stain, iminocoumarin, indian yellow, indo-1 and any derivative thereof, laurdan, lucifer yellow and any derivative thereof, luciferin and any derivative thereof, luciferase and any derivative thereof, mercocyanine and any derivative thereof, nile dyes and any derivative thereof, perylene, phloxine, phyco dye and any derivative thereof, propium iodide, pyranine, rhodamine and any derivative thereof, ribogreen, RoGFP, rubrene, stilbene and any derivative thereof, sulforhodamine and any derivative thereof, SYBR™ and any derivative thereof, synapto-pHluorin, tetraphenyl butadiene, tetrasodium tris, Texas Red, Titan Yellow, TSQ, umbelliferone, violanthrone, yellow fluorescent protein and YOYO-1. Other Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green® Dyes (e.g., Oregon Green® 488, Oregon Green® 500, Oregon Green® 514., etc.), Texas Red, Texas Red-X, SPECTRUM RED, SPECTRUM GREEN, cyanine dyes (e.g., CY-3, Cy-5, CY-3.5, CY-5.5, etc.), ALEXA FLUOR® dyes (e.g., ALEXA FLUOR® 350, ALEXA FLUOR® 488, ALEXA FLUOR® 532, ALEXA FLUOR® 546, ALEXA FLUOR® 568, ALEXA FLUOR® 594, ALEXA FLUOR® 633, ALEXA FLUOR® 660, ALEXA FLUOR® 680, etc.), BODIPY® dyes (e.g., BODIPY® FL, BODIPY® R6G, BODIPY® TMR, BODIPY® TR, BODIPY® 530/550, BODIPY® 558/568, BODIPY® 564/570, BODIPY® 576/589, BODIPY® 581/591, BODIPY® 630/650, BODIPY® 650/665, etc.), IRDyes (e.g., IRD40, IRD 700, IRD 800, etc.), and the like. Additional suitable detectable agents are described in PCT/US14/56177. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212.

A peptide may be conjugated to a radiosensitizer or photosensitizer. Examples of radiosensitizers include but are not limited to: ABT-263, ABT-199, WEHI-539, paclitaxel, carboplatin, cisplatin, oxaliplatin, gemcitabine, etanidazole, misonidazole, tirapazamine, and nucleic acid base derivatives (e.g., halogenated purines or pyrimidines, such as 5-fluorodeoxyuridine). Examples of photosensitizers include but are not limited to: fluorescent molecules or beads that generate heat when illuminated, nanoparticles, porphyrins and porphyrin derivatives (e.g., chlorins, bacteriochlorins, isobacteriochlorins, phthalocyanines, and naphthalocyanines), metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid. Advantageously, this approach allows for highly specific targeting of cells of interest (e g, immune cells) using both a therapeutic agent (e.g., drug) and electromagnetic energy (e.g., radiation or light) concurrently. In some embodiments, the peptide is fused with, or covalently or non-covalently linked to the agent, for example, directly or via a linker.

In some embodiments, the binding protein may be chemically modified. For example, a binding protein may be mutated to modify peptide properties such as detectability, stability, biodistribution, pharmacokinetics, half-life, surface charge, hydrophobicity, conjugation sites, pH, function, and the like. N-methylation is one example of methylation that can occur in a binding protein encompassed by the present invention. In some embodiments, a binding protein may be modified by methylation on free amines such as by reductive methylation with formaldehyde and sodium cyanoborohydride.

A chemical modification may comprise a polymer, a polyether, polyethylene glycol, a biopolymer, a zwitterionic polymer, a polyamino acid, a fatty acid, a dendrimer, an Fc region, a simple saturated carbon chain such as palmitate or myristolate, or albumin. The chemical modification of a binding protein with an Fc region may be a fusion Fc-protein. A polyamino acid may include, for example, a poly amino acid sequence with repeated single amino acids (e.g., poly glycine), and a poly amino acid sequence with mixed poly amino acid sequences that may or may not follow a pattern, or any combination of the foregoing.

In some embodiments, the binding proteins encompassed by the present invention may be modified. In some embodiments, the modifications having substantial or significant sequence identity to a parent binding protein to generate a functional variant that maintains one or more biophysical and/or biological activities of the parent binding protein (e.g., maintain pMHC binding specificity). In some embodiments, the mutation is a conservative amino acid substitution.

In some embodiments, binding proteins encompassed by the present invention may comprise synthetic amino acids in place of one or more naturally-occurring amino acids. Such synthetic amino acids are well-known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, oc-aminocyclohexane carboxylic acid, α-aminocycloheptane carboxylic acid, a-(2-amino-2-norbornane)-carboxylic acid, α,γ-diaminobutyric acid, β-diaminopropionic acid, homophenylalanine, and oc-tert-butylglycine.

Binding proteins encompassed by the present invention may be glycosylated, amidated, carboxylated, phosphorylated, esterified, N-acylated, cyclized (e.g., via a disulfide bridge), or converted into an acid addition salt and/or optionally dimerized or polymerized, or conjugated.

In some embodiments, the attachment of a hydrophobic moiety, such as to the N-terminus, the C-terminus, or an internal amino acid, may be used to extend half-life of a peptide encompassed by the present invention. In other embodiments, a binding protein may include post-translational modifications (e.g., methylation and/or amidation), which can affect, for example, serum half-life. In some embodiments, simple carbon chains (e.g., by myristoylation and/or palmitylation) may be conjugated to the binding proteins. In some embodiments, the simple carbon chains may render the binding proteins easily separable from the unconjugated material. For example, methods that may be used to separate the binding proteins from the unconjugated material include, but are not limited to, solvent extraction and reverse phase chromatography. The lipophilic moieties can extend half-life through reversible binding to serum albumin. The conjugated moieties may be lipophilic moieties that extend half-life of the peptides through reversible binding to serum albumin. In some embodiments, the lipophilic moiety may be cholesterol or a cholesterol derivative, including cholestenes, cholestanes, cholestadienes and oxysterols. In some embodiments, the binding proteins may be conjugated to myristic acid (tetradecanoic acid) or a derivative thereof. In other embodiments, a binding protein may be coupled (e.g., conjugated) to a half-life modifying agent. Examples of half-life modifying agents include but are not limited to: a polymer, a polyethylene glycol (PEG), a hydroxyethyl starch, polyvinyl alcohol, a water soluble polymer, a zwitterionic water soluble polymer, a water soluble poly(amino acid), a water soluble polymer of proline, alanine and serine, a water soluble polymer containing glycine, glutamic acid, and serine, an Fc region, a fatty acid, palmitic acid, or a molecule that binds to albumin. In some embodiments, a spacer or linker may be coupled to a binding protein, such as 1, 2, 3, 4, or more amino acid residues that serve as a spacer or linker in order to facilitate conjugation or fusion to another molecule, as well as to facilitate cleavage of the peptide from such conjugated or fused molecules. In some embodiments, binding proteins may be conjugated to other moieties that, for example, can modify or effect changes to the properties of the binding proteins.

A protein such as a peptide may be produced recombinantly or synthetically, such as by solid-phase peptide synthesis or solution-phase peptide synthesis. Protein synthesis may be performed by known synthetic methods, such as using fluorenylmethyloxycarbonyl (Fmoc) chemistry or by butyloxycarbonyl (Boc) chemistry. Protein fragments may be joined together enzymatically or synthetically.

In an aspect encompassed by the present invention, provided herein are methods of producing a protein described herein, comprising the steps of: (i) culturing a transformed host cell which has been transformed by a nucleic acid comprising a sequence encoding a binding protein described herein under conditions suitable to allow expression of said binding protein; and (ii) recovering the expressed binding protein.

Methods useful for isolating and purifying recombinantly produced binding protein, by way of example, may include obtaining supernatants from suitable host cell/vector systems that secrete the binding protein into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of binding proteins described herein include batch cell culture, which is monitored and controlled to maintain appropriate culture conditions. Purification of the binding protein may be performed according to methods described herein and known in the art.

In some embodiments, provided herein is a nucleic acid encoding a MAGEA1 immunogenic peptide described herein or fragment thereof, such as a DNA molecule encoding a MAGEA1 immunogenic peptide. In some embodiments, the composition comprises an expression vector comprising an open reading frame encoding a MAGEA1 immunogenic peptide described herein or fragment thereof. In some embodiments, the nucleic acid includes regulatory elements necessary for expression of the open reading frame. Such elements may include, for example, a promoter, an initiation codon, a stop codon, and a polyadenylation signal. In addition, enhancers may be included. These elements may be operably linked to a sequence that encodes the MAGEA1 immunogenic polypeptide or fragment thereof. Representative vectors, promoters, regulatory elements, and the like useful for expressing proteins such as peptide are described further below.

III. MHC-Peptide Complexes

In certain aspects, provided herein are compositions comprising a MAGEA1 immunogenic peptide described herein and a MHC molecule. In some embodiments, the MAGEA1 immunogenic peptide forms a stable complex with the MHC molecule.

MHC proteins may be conjugated to an agent, such as a detection moiety, readiosensitizer, photosensitizer, and the like, and/or may be chemically modified as described above regarding peptides.

The MHC proteins provided and used in the compositions and methods encompassed by the present disclosure may be any suitable MHC molecules known in the art. Generally, they have the formula $(\alpha\text{-}\beta\text{-}P)_n$, where n is at least 2, for example between 2-10, e.g., 4. α is an α chain of a class I or class II MHC protein. β is a β chain, herein defined as the β chain of a class II MHC protein or $\beta_2$ microglobulin for a MHC class I protein. P is a peptide antigen.

In some embodiments, the MHC proteins are MHC class I complexes, such as HLA I complexes.

The MHC proteins may be from any mammalian or avian species, e.g., primate sp., particularly humans; rodents, including mice, rats and hamsters; rabbits; equines, bovines, canines, felines; etc. For instance, the MHC protein may be derived the human HLA proteins or the murine H-2 proteins. HLA proteins include the class II subunits HLA-DPα, HLA-DPβ, HLA-DQα, HLA-DQβ, HLA-DRα and HLA-DRβ, and the class I proteins HLA-A, HLA-B, HLA-C, and β2-microglobulin. H-2 proteins include the class I subunits H-2K, H-2D, H-2L, and the class II subunits I-Aα, I-Aβ, I-Eα and I-Eβ, and β2-microglobulin. Sequences of some representative MHC proteins may be found in Kabat et al. Sequences of Proteins of Immunological Interest, NIH Publication No. 91-3242, pp 724-815. MHC protein subunits suitable for use in the present invention are a soluble form of the normally membrane-bound protein, which is prepared as known in the art, for instance by deletion of the transmembrane domain and the cytoplasmic domain.

For class I proteins, the soluble form may include the α1, α2 and α3 domain. Soluble class II subunits may include the α1 and α2 domains for the a subunit, and the β1 and β2 domains for the β subunit.

The α and β subunits may be separately produced and allowed to associate in vitro to form a stable heteroduplex complex, or both of the subunits may be expressed in a single cell. Methods for producing MHC subunits are known in the art.

In certain embodiments, the MHC-peptide complex comprises a peptide epitope selected from Table 1 and an MHC. In some embodiments, the MHC molecule comprises an MHC alpha chain that is an HLA serotype selected from the group consisting of HLA-A*02, HLA-A*03, HLA-A*01, HLA-A*11, HLA-A*24, HLA-B*07, HLA-C*07, HLA-C*01, HLA-C*02, HLA-C*03, HLA-C*04, HLA-C*05, HLA-C*06, HLA-C*08, HLA-C*12, HLA-C*14, HLA-C*15, HLA-C*16, HLA-C*17, and HLA-C*18, optionally wherein the HLA allele is selected from the group consisting of HLA-A*0201, HLA-A*0202, HLA-A*0203, HLA-A*0204, HLA-A*0205, HLA-A*0206, HLA-A*0207, HLA-A*0210, HLA-A*0211, HLA-A*0212, HLA-A*0213, HLA-A*0214, HLA-A*0216, HLA-A*0217, HLA-A*0219, HLA-A*0220, HLA-A*0222, HLA-A*0224, HLA-A*0230, HLA-A*0242, HLA-A*0253, HLA-A*0260, HLA-A*0274 allele, HLA-A*0301, HLA-A*0302, HLA-A*0305, HLA-A*0307, HLA-A*0101, HLA-A*0102, HLA-A*0103, HLA-A*0116 allele, HLA-A*1101, HLA-A*1102, HLA-A*1103, HLA-A*1104, HLA-A*1105, HLA-A*1119 allele, HLA-A*2402, HLA-A*2403, HLA-A*2405, HLA-A*2407, HLA-A*2408, HLA-A*2410, HLA-A*2414, HLA-A*2417, HLA-A*2420, HLA-A*2422, HLA-A*2425, HLA-A*2426, HLA-A*2458 allele, HLA-B*0702, HLA-B*0704, HLA-B*0705, HLA-B*0709, HLA-B*0710, HLA-B*0715, HLA-B*0721, HLA-C*0702, HLA-C*0701, HLA-C*0401, HLA-C*0602, HLA-C*0304, HLA-C*0501, HLA-C*1601, HLA-C*0202, HLA-C*0303, HLA-C*1203, HLA-C*0802, HLA-C*0102, HLA-C*1701, HLA-C*1502, HLA-C*1402, HLA-C*1202, HLA-C*0704, HLA-C*0801, HLA-C*0302, HLA-C*1801, HLA-C*1505, HLA-C*1602, HLA-C*0804, HLA-C*0305, and HLA-C*1403 allele. In some embodiments, the MHC-peptide complex comprises a peptide epitope selected from Table 1A and an MHC whose alpha chain has an HLA-C*07 serotype, such as that encoded by an HLA-C*0702, HLA-C*0701, and/or HLA-C*0704 allele.

To prepare the MHC-peptide complex, the subunits may be combined with an antigenic peptide and allowed to fold in vitro to form a stable heterodimer complex with intrachain disulfide bonded domains. The peptide may be included in the initial folding reaction, or may be added to the empty heterodimer in a later step. In the compositions and methods encompassed by the present invention, this is a MAGEA1 immunogenic peptide or fragment thereof. Conditions that permit folding and association of the subunits and peptide are known in the art. As one example, roughly equimolar amounts of solubilized a and (3 subunits may be mixed in a solution of urea. Refolding is initiated by dilution or dialysis into a buffered solution without urea. Peptides may be loaded into empty class II heterodimers at about pH 5 to 5.5 for about 1 to 3 days, followed by neutralization, concentration and buffer exchange. However, the specific folding conditions are not critical for the practice of the invention.

The monomeric complex (α-β-P) (herein monomer) may be multimerized, for example, for a MHC tetramer. The resulting multimer is stable over long periods of time. Preferably, the multimer may be formed by binding the monomers to a multivalent entity through specific attachment sites on the α or β subunit, as known in the art (e.g., as described in U.S. Pat. No. 5,635,363). The MHC proteins, in either their monomeric or multimeric forms, may also be conjugated to beads or any other support.

The multimeric complex may be labeled, so as to be directly detectable when used in immunostaining or other methods known in the art, or may be used in conjunction with secondary labeled immunoreagents which specifically and/or selectively bind the complex (e.g., bind to a MHC protein subunit) as known in the art. For example, the detectable label may be a fluorophore, such as fluorescein isothiocyanate (FITC), rhodamine, Texas Red, phycoerythrin (PE), allophycocyanin (APC), Brilliant Violet™ 421, Brilliant UV™ 395, Brilliant Violet™ 480, Brilliant Violet™ 421 (BV421), Brilliant Blue™ 515, APC-R700, or APC-Fire750. In some embodiments, the multimeric complex is labeled by a moiety that is capable of specifically and/or selectively binding another moiety. For instance, the label may be biotin, streptavidin, an oligonucleotide, or a ligand. Other labels of interest may include fluorochromes, dyes, enzymes, chemiluminescers, particles, radioisotopes, or other directly or indirectly detectable agent.

In some embodiments, a cell presenting an immunogenic peptides in context of an MHC molecule on the cell surface is generated by transfecting or transducing the cell with a vector (e.g., a viral vector) that comprising nucleic acid that encodes a recombinant or heterologous antigen into a cell. In some embodiments, the vector is introduced into the cell under conditions in which one or more peptide antigens, including, in some cases, one or more peptide antigens of the expressed heterologous protein, are expressed by the cell, processed and presented on the surface of the cell in the context of a major histocompatibility complex (MHC) molecule.

Generally, the cell to which the vector is contacted is a cell that expresses MHC, i.e., MHC-expressing cells. The cell may be one that normally expresses an MHC on the cell surface, that is induced to express and/or upregulate expression of MHC on the cell surface or that is engineered to express an MHC molecule on the cell surface. In some embodiments, the MHC contains a polymorphic peptide binding site or binding groove that can, in some cases, complex with peptide antigens of polypeptides, including peptide antigens processed by the cell machinery. In some cases, MHC molecules may be displayed or expressed on the cell surface, including as a complex with peptide, i.e., MHC-peptide complex, for presentation of an antigen in a conformation recognizable by TCRs on T cells, or other peptide binding molecules.

In some embodiments, the cell is a nucleated cell. In some embodiments, the cell is an antigen-presenting cell. In some embodiments, the cell is a macrophage, dendritic cell, B cell, endothelial cell or fibroblast. In some embodiments, the cell is an endothelial cell, such as an endothelial cell line or primary endothelial cell. In some embodiments, the cell is a fibroblast, such as a fibroblast cell line or a primary fibroblast cell.

In some embodiments, the cell is an artificial antigen presenting cell (aAPC). Typically, aAPCs include features of natural APCs, including expression of an MHC molecule, stimulatory and costimulatory molecule(s), Fc receptor, adhesion molecule(s) and/or the ability to produce or secrete cytokines (e.g., IL-2). Normally, an aAPC is a cell line that lacks expression of one or more of the above, and is generated by introduction (e.g., by transfection or transduction) of one or more of the missing elements from among an MHC molecule, a low affinity Fc receptor (CD32), a high affinity Fc receptor (CD64), one or more of a co-stimulatory signal (e.g., CD7, B7-1 (CD80), B7-2 (CD86), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6 or a ligand of B7-H3; or an antibody that specifically binds to CD27, CD28, 4-1BB, OX40, CD30, CD40, PD-1, ICOS, LFA-1, CD2, CD7, LIGHT, NKG2C, B7-H3, Toll ligand receptor or a ligand of CD83), a cell adhesion molecule (e.g., ICAM-1 or LFA-3) and/or a cytokine (e.g., IL-2, IL-4, IL-6, IL-7, IL-10, IL-12, IL-15, IL-21, interferon-alpha (IFN.alpha.), interferon-beta (IFN.beta.), interferon-gamma (IFN.gamma.), tumor necrosis factor-alpha (TNF.alpha.), tumor necrosis factor-beta (TNF.beta.), granulocyte macrophage colony stimulating factor (GM-CSF), and granulocyte colony stimulating factor (GCSF)). In some cases, an aAPC does not normally express an MHC molecule, but may be engineered to express an MHC molecule or, in some cases, is or may be induced to express an MHC molecule, such as by stimulation with cytokines. In some cases, aAPCs also may be loaded with a stimulatory ligand, which may include, for example, an anti-CD3 antibody, an anti-CD28 antibody or an anti-CD2 antibody. An exemplary cell line that may be used as a backbone for generating an aAPC is a K562 cell line or a fibroblast cell line. Various aAPCs are known in the art, see e.g., U.S. Pat. No. 8,722,400, published application No. US2014/0212446; Butler and Hirano (2014) *Immunol Rev.* 257:10. 1111/imr.12129; Suhoshki et al. (2007) *Mol. Ther.* 15:981-988).

It is well within the level of a skilled artisan to determine or identify the particular MHC or allele expressed by a cell. In some embodiments, prior to contacting cells with a vector, expression of a particular MHC molecule may be assessed or confirmed, such as by using an antibody specific for the particular MHC molecule. Antibodies to MHC molecules are known in the art, such as any described below.

In some embodiments, the cells may be chosen to express an MHC allele of a desired MHC restriction. In some embodiments, the MHC typing of cells, such as cell lines, are well-known in the art. In some embodiments, the MHC typing of cells, such as primary cells obtained from a subject, may be determined using procedures well-known in the art, such as by performing tissue typing using molecular haplotype assays (BioTest ABC SSPtray, BioTest Diagnostics Corp., Denville, N.J.; SeCore Kits, Life Technologies, Grand Island, N.Y.). In some cases, it is well within the level of a skilled artisan to perform standard typing of cells to determine the HLA genotype, such as by using sequence-based typing (SBT) (Adams et al. (2004) J. Transl. Med., 2:30; Smith (2012) Methods Mol Biol., 882:67-86). In some cases, the HLA typing of cells, such as fibroblast cells, are known. For example, the human fetal lung fibroblast cell line MRC-5 is HLA-A*0201, A29, B13, B44 Cw7 (C*0702); the human foreskin fibroblast cell line Hs68 is HLA-A1, A29, B8, B44, Cw7, Cw16; and the WI-38 cell line is A*6801, B*0801, (Solache et al. (1999) J Immunol, 163:5512-5518; Ameres et al. (2013) PloS Pathog. 9:e1003383). The human transfectant fibroblast cell line M1DR1/Ii/DM express HLA-DR and HLA-DM (Karakikes et al. (2012) FASEB J., 26:4886-96).

In some embodiments, the cells to which the vector is contacted or introduced are cells that are engineered or transfected to express an MHC molecule. In some embodiments, cell lines may be prepared by genetically modifying a parental cells line. In some embodiments, the cells are normally deficient in the particular MHC molecule and are engineered to express such particular MHC molecule. In some embodiments, the cells are genetically engineered using recombinant DNA techniques.

In some embodiments, the stable MHC-peptide complexes described herein are used to detect T cells that bind a stable MHC-peptide complex. In some embodiments, the stable MHC-peptide complexes described herein are used to monitor T cell response in a subject, for example, by detecting the amount and/or percentage of T cells (e.g., CD8+ T cells) that specifically and/or selectively bind to the MHC-peptide complexes that are fluorescently labeled. Methods of generating, labeling, and using MHC-peptide complexes (e.g., MHC-peptide tetramers) for detecting MHC-peptide complex-specific T cells are well-known in the art. Additional description can be found in, for example, U.S. Pat. Nos. 7,776,562; 8,268,964; and U.S. Pat. Publ. 2019/0085048.

IV Immunogenic Compositions

In some aspects, provided herein are pharmaceutical compositions (e.g., a vaccine composition) comprising a MAGEA1 immunogenic peptide and/or a nucleic acid encoding a MAGEA1 immunogenic peptide and an adjuvant. In some aspects, provided herein are pharmaceutical compositions (e.g., a vaccine composition) comprising a stable MHC-peptide complex comprising a MAGEA1 immunogenic peptide in the context of a MHC molecule and an adjuvant. In some embodiments, the composition includes a combination of multiple (e.g., two or more) MAGEA1 immunogenic peptides or nucleic acids and an adjuvant. In some embodiments, the composition includes a combination of multiple (e.g., two or more) stable MHC-peptide complexes comprising a MAGEA1 immunogenic peptide in the context of a MHC molecule and an adjuvant. In some embodiments, the compositions described above further comprises a pharmaceutically acceptable carrier.

The pharmaceutical compositions disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Methods of preparing these formulations or compositions include the step of bringing into association a MAGEA1 immunogenic peptide and/or nucleic acid described herein with the adjuvant, carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions suitable for parenteral administration comprise MAGEA1 immunogenic peptides and/or nucleic acids described herein in combination with a adjuvant, as well as one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Regardless of the route of administration selected, the agents provided herein, which may be used in a suitable hydrated form, and/or the pharmaceutical compositions disclosed herein, are formulated into pharmaceutically-acceptable dosage forms by conventional methods known to those of skill in the art.

In some embodiments, the pharmaceutical composition described, when administered to a subject, can elicit an immune response against a cell that is infected by MAGEA1. Such pharmaceutical compositions may be useful as vaccine compositions for prophylactic and/or therapeutic treatment of disorders characterized by MAGEA1 expression.

In some embodiments, the pharmaceutical composition further comprises a physiologically acceptable adjuvant. In some embodiments, the adjuvant employed provides for increased immunogenicity of the pharmaceutical composition. Such a further immune response stimulating compound or adjuvant may be (i) admixed to the pharmaceutical composition according to the invention after reconstitution of the peptides and optional emulsification with an oil-based adjuvant as defined above, (ii) may be part of the reconstitution composition of the invention defined above, (iii) may be physically linked to the peptide(s) to be reconstituted or (iv) may be administered separately to the subject, mammal or human, to be treated. The adjuvant may be one that provides for slow release of antigen (e.g., the adjuvant may be a liposome), or it may be an adjuvant that is immunogenic in its own right thereby functioning synergistically with antigens (i.e., antigens present in the MAGEA1 immunogenic peptide). For example, the adjuvant may be a known adjuvant or other substance that promotes antigen uptake, recruits immune system cells to the site of administration, or facilitates the immune activation of responding lymphoid cells. Adjuvants include, but are not limited to, immunomodulatory molecules (e.g., cytokines), oil and water emulsions, aluminum hydroxide, glucan, dextran sulfate, iron oxide, sodium alginate, Bacto-Adjuvant, synthetic polymers such as poly amino acids and co-polymers of amino acids, saponin, paraffin oil, and muramyl dipeptide. In some embodiments, the adjuvant is Adjuvant 65, α-GalCer, aluminum phosphate, aluminum hydroxide, calcium phosphate, β-Glucan Peptide, CpG DNA, GM-CSF, GPI-0100, IFA, IFN-γ, IL-17, lipid A, lipopolysaccharide, Lipovant, Montanide, N-acetyl-muramyl-L-alanyl-D-isoglutamine, Pam3CSK4, quil A, trehalose dimycolate or zymosan.

In some embodiments, the adjuvant is an immunomodulatory molecule. For example, the immunomodulatory molecule may be a recombinant protein cytokine, chemokine, or immunostimulatory agent or nucleic acid encoding cytokines, chemokines, or immunostimulatory agents designed to enhance the immunologic response.

Examples of immunomodulatory cytokines include interferons (e.g., IFNα, IFNβ and IFNγ), interleukins (e.g., IL-1, IL-2, IL-3, IL-4, IL-5, IL-6, IL-7, IL-8, IL-9, IL-10, IL-12, IL-17 and IL-20), tumor necrosis factors (e.g., TNFα and TNFβ), erythropoietin (EPO), FLT-3 ligand, gIp10, TCA-3, MCP-1, MIF, MIP-1.alpha., MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing.

In some embodiments, an immunomodulatory chemokine that binds to a chemokine receptor, i.e., a CXC, CC, C, or CX3C chemokine receptor, also may be included in the compositions provided here. Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, 1309, IL-8, Gcp-2 Gro-α, Gro-β, Gro-γ, Nap-2, Ena-78, Gcp-2, Ip-10, Mig, I-Tac, Sdf-1, and Bca-1 (Blc), as well as functional fragments of any of the foregoing.

In some embodiments, the composition comprises a nucleic acid encoding an MAGEA1 immunogenic polypeptide described herein, such as a DNA molecule encoding a MAGEA1 immunogenic peptide. In some embodiments the composition comprises an expression vector comprising an open reading frame encoding a MAGEA1 immunogenic peptide.

When taken up by a cell (e.g., host cell, an antigen-presenting cell (APC) such as a dendritic cell, macrophage, etc.), a DNA molecule may be present in the cell as an extrachromosomal molecule and/or may integrate into the chromosome. DNA may be introduced into cells in the form of a plasmid which may remain as separate genetic material. Alternatively, linear DNAs that may integrate into the chromosome may be introduced into the cell. Optionally, when introducing DNA into a cell, reagents which promote DNA integration into chromosomes may be added.

V. Binding Proteins

In some aspects, a binding moiety that binds a peptide described herein and/or a stable MHC-peptide complex described herein, are provided. For example, binding proteins like T cell receptors (TCRs), antibodies, and the like that specifically and/or selectively bind to the peptide and/or the stable MHC-peptide complex, such as with a $K_d$ less than or equal to about $10^{-4}$ M (e.g., about $10^{-4}$, $10^{-5}$, $10^{-6}$, $10^{-7}$, about $10^{-8}$, about $10^{-9}$, about $10^{10}$, about $10^{-11}$, about $10^{-12}$, about $10^{-13}$, about $10^{-14}$, etc.), are provided.

In an aspect encompassed by the present invention, provided herein are binding proteins that bind (e.g., specifically and/or selectively) to a peptide-MHC (pMHC) complex comprising a MAGEA1 immunogenic peptide in the context of an MHC molecule (e.g., an MHC class I molecule). In some embodiments, the binding protein is capable of binding (e.g., specifically and/or selectively) to a MAGEA1 peptide-MHC (pMHC) complex with a $K_d$ less than or equal to about $5\times10^{-4}$ M, less than or equal to about $1\times10^{-4}$ M, less than or equal to about $5\times10^{-5}$ M, less than or equal to about $1\times10^{-5}$ M, less than or equal to about $5\times10^{-6}$ M, less than or equal to about $1\times10^{-6}$ M, less than or equal to about $5\times10^{-7}$ M, less than or equal to about $1\times10^{-7}$ M, less than or equal to about $5\times10^{-8}$ M, less than or equal to about $1\times10^{-8}$ M, less than or equal to about $5\times10^{-9}$ M, less than or equal to about $1\times10^{-9}$ M, less than or equal to about $5\times10^{-10}$ M, less than or equal to about $1\times10^{-10}$ M, less than or equal to about $5\times10^{-11}$ M, less than or equal to about $1\times10^{-11}$ M, less than or equal to about $5\times10^{-12}$ M, less than or equal to about $1\times10^{-12}$ M, or any range in between, inclusive, such as between about 1-50 micromolar, 1-100 micromolar, 0.1-500 micromolar, and the like. In some embodiments, the MHC molecule comprises an MHC alpha chain that is an HLA serotype selected from the group consisting of HLA-A*02, HLA-A*03, HLA-A*01, HLA-A*11, HLA-A*24, HLA-B*07, HLA-C*07, HLA-C*01, HLA-C*02, HLA-C*03, HLA-C*04, HLA-C*05, HLA-C*06, HLA-C*08, HLA-C*12, HLA-C*14, HLA-C*15, HLA-C*16, HLA-C*17, and HLA-C*18, optionally wherein the HLA allele is selected from the group consisting of HLA-A*0201, HLA-A*0202, HLA-A*0203, HLA-A*0204, HLA-A*0205, HLA-A*0206, HLA-A*0207, HLA-A*0210, HLA-A*0211, HLA-A*0212, HLA-A*0213, HLA-A*0214, HLA-A*0216, HLA-A*0217, HLA-A*0219, HLA-A*0220, HLA-A*0222, HLA-A*0224, HLA-A*0230, HLA-A*0242, HLA-A*0253, HLA-A*0260, HLA-A*0274 allele, HLA-A*0301, HLA-A*0302, HLA-A*0305, HLA-A*0307, HLA-A*0101, HLA-A*0102, HLA-A*0103, HLA-A*0116 allele, HLA-A*1101, HLA-A*1102, HLA-A*1103, HLA-A*1104, HLA-A*1105, HLA-A*1119 allele, HLA-A*2402, HLA-A*2403, HLA-A*2405, HLA-A*2407, HLA-A*2408, HLA-A*2410, HLA-A*2414, HLA-A*2417, HLA-A*2420, HLA-A*2422, HLA-A*2425, HLA-A*2426, HLA-A*2458 allele, HLA-B*0702, HLA-B*0704, HLA-B*0705, HLA-B*0709, HLA-B*0710, HLA-B*0715, HLA-B*0721, HLA-C*0702, HLA-C*0701, HLA-C*0401, HLA-C*0602, HLA-C*0304, HLA-C*0501, HLA-C*1601, HLA-C*0202, HLA-C*0303, HLA-C*1203, HLA-C*0802, HLA-C*0102, HLA-C*1701, HLA-C*1502, HLA-C*1402, HLA-C*1202, HLA-C*0704, HLA-C*0801, HLA-C*0302, HLA-C*1801, HLA-C*1505, HLA-C*1602, HLA-C*0804, HLA-C*0305, and HLA-C*1403 allele. In some embodiments, the HLA serotype is HLA-C*07 and/or the HLA allele is selected from the group consisting of HLA-C*0702, HLA-C*0701, and HLA-C*0704 alleles. In a specific embodiment, the HLA allele is HLA-C*0702. In some embodiments, the binding proteins provided herein are genetically engineered, isolated, and/or purified.

In some embodiments, the binding proteins have a higher binding affinity to the MAGEA1 peptide-MHC (pMHC) than does a known T-cell receptor (e.g., a TCR from van Kunert et al. (2016) *J. Immunol.* 197:2541-2552 or others described herein). For example, the binding proteins may have at least 1.2 fold, 1.5 fold, 1.8 fold, 2.0 fold, 2.2 fold, 2.5 fold, 2.8 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 25 fold, 30 fold, 35 fold, 40 fold, 45 fold, 50 fold, 60 fold, 70 fold, 80 fold, 90 fold, 100 fold, 1000 fold, 5000 fold, 10000 fold, 50000 fold, 100000 fold, 500000 fold, 1000000 fold, or more, or any range in between, inclusive, such as 1.2 fold to 2 fold, higher binding affinity to the MAGEA1 peptide-MHC (pMHC) than does a known T-cell receptor.

In some embodiments, the binding protein induces higher T cell expansion, cytokine release, and/or cytotoxic killing than does a known T-cell receptor when contacted with target cells with expression of MAGEA1 at a certain level or below (e.g., see the Examples section for representative cell lines expressing MAGEA1 at varying levels). For example, in some embodiments of any aspect described herein, MAGEA1 level can be expressed in terms of transcripts per million and may be, for example, less than or equal to about 1,000 transcript per million transcripts (TPM), 950 TPM, 900 TPM, 850 TPM, 800 TPM, 750 TPM, 700 TPM, 650 TPM, 600 TPM, 550 TPM, 500 TPM, 450 TPM, 400 TPM, 350 TPM, 300 TPM, 250 TPM, 200 TPM, 150 TPM, 100 TPM, 95 TPM, 90 TPM, 85 TPM, 80 TPM, 75 TPM, 70 TPM, 65 TPM, 60 TPM, 55 TPM, 50 TPM, 45 TPM, 40 TPM, 35 TPM, 34 TPM, 33 TPM, 32 TPM, 31 TPM, 30 TPM, 29 TPM, 28 TPM, 27 TPM, 26 TPM, 25 TPM, 24 TPM, 23 TPM, 22 TPM, 21 TPM, 20 TPM, 19 TPM, 18 TPM, 17 TPM, 16 TPM, 15 TPM, 14 TPM, 13 TPM, 12 TPM, 11 TPM, 10 TPM, 9 TPM, 8 TPM, 7 TPM, 6 TPM, 5 TPM, 4 TPM, 3 TPM, 2 TPM, and 1 TPM, or any range in between, inclusive, such as less than or equal to about 1,000 TPM to less than or equal to about 73 TPM). As described further herein, TPM is measured according to well-known techniques, such as RNA-Seq, and gene expression TPM data are well-known in the art for a variety of cell lines, tissue types, and the like (see, for example, the Broad Institute Cancer Cell Line Encyclopedia (CCLE) on the World Wide Web at portals.broadinstitute.org). In some embodiment, the binding protein induces at least 1.2 fold, 1.5 fold, 1.8 fold, 2.0 fold, 2.2 fold, 2.5 fold, 2.8 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 25 fold, 30 fold, 35 fold, 40 fold, 45 fold, 50 fold, 60 fold, 70 fold, 80 fold, 90 fold, 100 fold, 1000 fold, or more, or any range in between, inclusive, such as 1.2 fold to 2 fold, increase in T cell expansion, cytokine release, and/or cytotoxic killing than does a known T-cell receptor when contacted with target cells with heterozygous expression of MAGEA1.

In some embodiments, the expression of MAGEA1 is detected using RNA-sequencing (RNA-seq). RNA-seq generally comprises the following steps: obtaining a sample containing genetic material, isolating total RNA from the sample obtained, preparing an amplified cDNA library from the total RNA, sequencing the amplified cDNA library, and analyzing and profiling the amplified cDNA to assess the expression level of different transcripts. The sample can be a population of cells, a tissue sample, a biopsy sample, a cell culture, or a single cell. Total RNA can be isolated from the biological sample using any method known in the art. In certain embodiments, total RNA is extracted from plasma.

Plasma RNA extraction is described in Enders et al., "The Concentration of Circulating Corticotropin-Releasing Homer mRNA in Material Plasma Is Inclined in Preclampsia," Clinr. As described therein, the plasma collected after the centrifugation step is mixed with Trizol LS reagent (Invitrogen) and chloroform. The mixture is centrifuged and the aqueous layer is transferred to a new tube. Ethanol is added to this aqueous layer. The mixture is then placed in an RNeasy mini column (Qiagen) and processed according to the manufacturer's recommendations.

In some embodiments, RNA-seq described herein includes the step of preparing amplified cDNA from total RNA. For example, cDNA is prepared and the isolated RNA sample is randomly amplified without dilution, or the mixture of genetic material in the isolated RNA is dispersed into individual reaction samples. In certain embodiments, amplification is initiated randomly at the 3' end and throughout the entire transcriptome in the sample to amplify both mRNA and non-polyadenylated transcripts. In this way, double-stranded cDNA amplification products are optimized for the generation of sequencing libraries for next generation sequencing platforms. A kit suitable for amplification of cDNA by the method encompassed by the present invention includes, for example, Ovation® RNA-Seq System.

In some embodiments, RNA-seq described herein includes the step of sequencing the amplified cDNA. Any known sequencing method can be used to sequence the amplified cDNA mixture including the single molecule sequencing method. In certain embodiments, the amplified cDNA is sequenced by whole transcriptome shotgun sequencing. Whole transcriptome shotgun sequencing can be performed using various next generation sequencing platforms such as Illumina® Genome Analyzer platform, ABI SOLiD™ Sequencing platform, or Life Science's 454 Sequencing platform.

In some embodiments, RNA-seq described herein further comprises performing digital counting and analysis on the cDNA. The number of amplified sequences for each transcript in the amplified sample can be quantified by sequence reading (one reading per amplified strand). In some embodiments, transcript per million (TPM) is used to quantify the expression level of a particular transcript. TPM may be calculated as shown in Wagner et al. (2012) *Theory in Biosciences* 131:281-285, the content of which is incorporated by reference herein in its entirety.

In certain embodiments, the binding proteins recognize a MAGEA1 immunogenic peptide in a complex with MHC molecules, such as particular HLA molecules having particular HLA alpha chain alleles. For example, binding proteins listed in Table 2A were identified as binders of MAGEA1 immunogenic peptides in association with an MHC whose alpha chain had an HLA-C*07 serotype, such as that encoded by an HLA-B*0702, HLA-C*0701, and/or HLA-C*0704 allele, as described further in the Examples section. In some embodiments, the binding proteins recognize a complex of MAGEA1 immunogenic peptide and an MHC molecule, wherein the MHC molecule comprises an MHC alpha chain that is an HLA serotype selected from the group consisting of HLA-A*02, HLA-A*03, HLA-A*01, HLA-A*11, HLA-A*24, HLA-B*07, HLA-C*07, HLA-C*01, HLA-C*02, HLA-C*03, HLA-C*04, HLA-C*05, HLA-C*06, HLA-C*08, HLA-C*12, HLA-C*14, HLA-C*15, HLA-C*16, HLA-C*17, and HLA-C*18, optionally wherein the HLA allele is selected from the group consisting of HLA-A*0201, HLA-A*0202, HLA-A*0203, HLA-A*0204, HLA-A*0205, HLA-A*0206, HLA-A*0207, HLA-A*0210, HLA-A*0211, HLA-A*0212, HLA-A*0213, HLA-A*0214, HLA-A*0216, HLA-A*0217, HLA-A*0219, HLA-A*0220, HLA-A*0222, HLA-A*0224, HLA-A*0230, HLA-A*0242, HLA-A*0253, HLA-A*0260, HLA-A*0274 allele, HLA-A*0301, HLA-A*0302, HLA-A*0305, HLA-A*0307, HLA-A*0101, HLA-A*0102, HLA-A*0103, HLA-A*0116 allele, HLA-A*1101, HLA-A*1102, HLA-A*1103, HLA-A*1104, HLA-A*1105, HLA-A*1119 allele, HLA-A*2402, HLA-A*2403, HLA-A*2405, HLA-A*2407, HLA-A*2408, HLA-A*2410, HLA-A*2414, HLA-A*2417, HLA-A*2420, HLA-A*2422, HLA-A*2425, HLA-A*2426, HLA-A*2458 allele, HLA-B*0702, HLA-B*0704, HLA-B*0705, HLA-B*0709, HLA-B*0710, HLA-B*0715, HLA-B*0721, HLA-C*0702, HLA-C*0701, HLA-C*0401, HLA-C*0602, HLA-C*0304, HLA-C*0501, HLA-C*1601, HLA-C*0202, HLA-C*0303, HLA-C*1203, HLA-C*0802, HLA-C*0102, HLA-C*1701, HLA-C*1502, HLA-C*1402, HLA-C*1202, HLA-C*0704, HLA-C*0801, HLA-C*0302, HLA-C*1801, HLA-C*1505, HLA-C*1602, HLA-C*0804, HLA-C*0305, and HLA-C*1403 allele. In some embodiments, the MAGEA1 immunogenic peptides are derived from a human MAGEA1 protein and/or a MAGEA1 protein shown in Table 3. In some embodiments, one or more MAGEA1 immunogenic peptides are administered alone or in combination with an adjuvant.

In some embodiments, the binding proteins provided herein include (e.g., comprise, consist essentially of, or consist of): a) a TCR alpha chain sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR alpha chain sequence selected from the group consisting of the TCR alpha sequences listed in Table 2; and/or b) a TCR beta chain sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR beta chain sequence selected from the group consisting of the TCR beta chain sequences listed in Table 2.

In some embodiments, the binding proteins provided herein include (e.g., comprise, consist essentially of, or consist of): a) a TCR alpha chain sequence selected from the group consisting of the TCR alpha chain sequences listed in Table 2; and/or b) a TCR beta chain sequence selected from the group consisting of the TCR beta chain sequences listed in Table 2.

In some embodiments, the binding proteins provided herein include (e.g., comprise, consist essentially of, or consist of): a) a TCR alpha chain variable ($V_\alpha$) domain sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR alpha chain variable ($V_\alpha$) domain sequence selected from the group consisting of the TCR $V_\alpha$ domain sequences listed in Table 2; and/or b) a TCR beta chain variable ($V_\beta$) domain sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR beta chain variable ($V_\beta$) domain sequence selected from the group consisting of the TCR $V_\beta$ domain sequences listed in Table 2.

In some embodiments, the binding proteins provided herein include (e.g., comprise, consist essentially of, or consist of): a) a TCR alpha chain variable ($V_\alpha$) domain sequence selected from the group consisting of the TCR $V_\alpha$ domain sequences listed in Table 2; and/or b) a TCR beta chain variable ($V_\beta$) domain sequence selected from the group consisting of the TCR $V_\beta$ domain sequences listed in Table 2.

In some embodiments, the binding proteins provided herein include (e.g., comprise, consist essentially of, or consist of at least one (e.g., one, two or three, such as CDR3 alone or in combination with a CDR1 and CDR2)) TCR alpha chain complementarity determining region (CDR) sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR alpha chain CDR sequence selected from the group consisting of the TCR alpha chain CDR sequences listed in Table 2. CDR3 is believed to be the main CDR responsible for recognizing processed antigen and CDR1 and CDR2 mainly interact with the MHC, so, in some embodiments, binding protein comprising a CDR3 alone from a TCR alpha chain and/or a CDR3 alone from a TCR beta chain listed in Table 2, each CDR3 having a sequence homology as recited in this paragraph, are provided.

In some embodiments, the binding proteins provided herein may also include (e.g., comprise, consist essentially of, or consist of at least one (e.g., one, two or three, such as CDR3 alone or in combination with a CDR1 and CDR2)) TCR beta chain complementarity determining region (CDR) sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR beta chain CDR sequence selected from the group consisting of the TCR beta chain CDR sequences listed in Table 2. As described above, CDR3 is believed to be the main CDR responsible for recognizing processed antigen and CDR1 and CDR2 mainly interact with the MHC, so, in some embodiments, binding protein comprising a CDR3 alone from a TCR beta chain and/or a CDR3 alone from a TCR alpha chain listed in Table 2, each CDR3 having a sequence homology as recited in this paragraph, are provided.

In some embodiments, the binding proteins provided herein include (e.g., comprise, consist essentially of, or consist of at least one (e.g., one, two or three)) TCR alpha chain complementarity determining region (CDR) listed in Table 2.

In some embodiments, the binding proteins provided herein may also include (e.g., comprise, consist essentially of, or consist of at least one (e.g., one, two or three)) TCR beta chain complementarity determining region (CDR) listed in Table 2.

In some embodiments, the binding proteins provided herein include (e.g., comprise, consist essentially of, or consist of) a TCR alpha chain constant region (Ca) sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR Ca sequence listed in Table 2.

In some embodiments, the binding proteins provided herein may also include (e.g., comprise, consist essentially of, or consist of) a TCR beta chain constant region ($C_\beta$) sequence with at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR $C_\beta$ sequence listed in Table 2.

In some embodiments, the binding proteins provided herein include (e.g., comprise, consist essentially of, or consist of) a TCR alpha chain constant region ($C_\alpha$) sequence selected from the group consisting of the TCR $C_\alpha$ sequences listed in Table 2.

In some embodiments, the binding proteins provided herein may also include (e.g., comprise, consist essentially of, or consist of) a TCR beta chain constant region ($C_\beta$) sequence selected from the group consisting of the TCR $C_\beta$ sequences listed in Table 2.

TABLE 2

TCR sequences recognizing a MAGEA1 antigen

Table 2A
TCR sequences recognizing a MAGEA1 antigen presented by HLA serotype HLA-C*07

MAGEA1 TCR 32-39 wild type sequence
Alpha chain:
TRAV29-DV5/TRAJ43/TRAC

Alpha chain DNA sequence
ATGGCCATGCTCCTGGGGGCATCAGTGCTGATTCTGTGGCTTCAGCCAGACTGG
GTTAACAGTCAACAGAAGAATGATGACCAGCAAGTTAAGCAAAATTCACCATC
CCTGAGCGTCCAGGAAGGAAGAATTTCTATTCTGAACTGTGACTATACTAACA
GCATGTTTGATTATTTCCTTTGGTACAAGAAATACCCTGCTGAAGGTCCTACAT
TCCTGATTTCTATTAGTTCCATTAAGGATAAAAATGAAGATGGAAGATTCACT
GTTTTCCTTAACAAAAGTGCCAAGCACCTCTCTCTGCACATTGTGCCCTCCCAG
CCTGGAGACTCTGCAGTGTACTTCTGTGCAGCAAGCGCTCAGAACAATGACA
TGCGCTTTGGAGCAGGGACCAGACTGACAGTTAAACCAAatatccagaaccctgaccctgc
cgtgtaccagctgagagactctaaatccagtgacaagtctgtctgcctattcaccgattttgattctcaaacaaatgtgtcacaaagtaa
ggattctgatgtgtatatcacagacaaaactgtgctagacatgaggtctatggacttcaagagcaacagtgctgtggcctggagcaa
caaatctgactttgcatgtgcaaacgccttcaacaacagcattattccagaagacaccttcttccccagcccagaaagttcctgtgatg
tcaagctggtcgagaaaagctttgaaacagatacgaacctaaactttcaaaacctgtcagtgattgggttccgaatcctcctcctgaaa
gtggccgggtttaatctgctcatgacgctgcggctgtggtccagc (SEQ ID NO: 12)

Alpha chain protein sequence
MAMLLGASVLILWLQPDWVNSQQKNDDQQVKQNSPSLSVQEGRISILNCDYTNS
MFDYFLWYKKYPAEGPTFLISISSIKDKNEDGRFTVFLNKSAKHLSLHIVPSQPGDS
AVYFCAASAQNNDMRFGAGTRLTVKPNiqnpdpavyqlrdskssdksvclftdfdsqtnvsqskdsdv
yitdktvldmrsmdfksnsavawsnksdfacanafnnsiipedtffpspesscdvklveksfetdtnlnfqnlsvigfrilllkva
gfnllmtlrlwss (SEQ ID NO: 13)

TABLE 2-continued

TCR sequences recognizing a MAGEA1 antigen

Beta chain:
TRBV18/TRBJ2-7/TRBC1

Beta chain DNA sequence
ATGGACACCAGACTTCTCTGCTGTGCTGTCATCTGTCTCCTGGGGGCAGGCCTC
TCAAATGCCGGCGTCATGCAGAACCCAAGACACCTGGTCAGGAGGAGGGGACA
GGAGGCAAGACTGAGATGCAGCCCAATGAAAGGACACAGTCATGTTTACTGG
TATCGGCAGCTCCCAGAGGAAGGTCTGAAATTCATGGTTTATCTCCAGAAAGA
AAATATCATTGATGAGTCAGGAATGCCAAAGGAACGCTTTTCTGCTGAATTTCC
CAAAGAGGGCCCCAGCATCCTGAGGATCCAGCAGGTTGTGCGCGGAGATTCTG
CAGCTTATTTCTGTGCCAGCTCACCCTCCTACGAGCAGTACTTCGGGCCTGG
CACCAGGCTCACTGTCACAGaggacctgaacaaggtgttcccacccgaggtcgctgtgtttgagccatcagaag
cagagatctcccacacccaaaaggccacactggtgtgcctggccacaggcttcttccctgaccacgtggagctgagctggtgggt
gaatgggaaggaggtgcacagtggggtcagcacggacccgcagcccctcaaggagcagcccgccctcaatgactccagatact
gcctgagcagccgcctgagggtctcggccaccttctggcagaacccccgcaaccacttccgctgtcaatccagttctacgggctc
tcggagaatgacgagtgacccaggatagggccaaacccgtcacccagatcgtcagcgccgaggcctggggtagagcagactg
tggctttacctcggtgtcctaccagcaaggggtcctgtctgccaccatcctctatgagatcctgctagggaaggccaccctgtatgct
gtgctggtcagcgcccttgtgttgatggccatggtcaagagaaaggatttc (SEQ ID NO: 14)

Beta chain protein sequence
MDTRLLCCAVICLLGAGLSNAGVMQNPRHLVRRRGQEARLRCSPMKGHSHVYW
YRQLPEEGLKFMVYLQKENIIDESGMPKERFSAEFPKEGPSILRIQQVVRGDSAAYF
CASSPSYEQYFGPGTRLTVTEdlnkvfppevavfepseaeishtqkatlvclatgffpdhvelswwvngkevh
yqqgvlsatilyeillgkatlyavlvsalvlmamvkrkdf (SEQ ID NO: 15)

MAGEA1 TCR 32-41 wild type sequence
Alpha chain:
TRAV27/TRAJ52/TRAC

Alpha chain DNA sequence
ATGGTCCTGAAATTCTCCGTGTCCATTCTTTGGATTCAGTTGGCATGGGTGAGC
ACCCAGCTGCTGGAGCAGAGCCCTCAGTTTCTTAGCATCCAAGAGGGAGAAAA
TCTCACTGTGTACTGCAACTCCTCAAGTGTTTTCTCCAGCCTTCAATGGTACAG
ACAGGAGCCTGGGGAAGGTCCTGTCCTCCTGGTGACAGTTGTTACTGGTGGA
GAAGTGAAGAAGCTGAAGAGACTTACCTTTCAGTTTGGTGATGCAAGAAAGGA
CAGTTCTCTCCACATCACTGCAGCCCAGCCTGGTGATACAGGCCTCTACCTCTG
TGCAGGAGATGAAAGTATTAGCTATGGAAAGCTGACATTTGGACAAGGGAC
CATCTTGACTGTCCATCCAAatatccagaaccctgaccctgccgtgtaccagctgagagactctaaatccagtga
caagtctgtctgcctattcaccgattttgattctcaaacaaatgtgtcacaaagtaaggattctgatgtgtatatcacagacaaaactgtg
ctagacatgaggtctatggacttcaagagcaacagtgctgtggcctggagcaacaaatctgactttgcatgtgcaaacgccttcaac
aacagcattattccagaagacaccttcttccccagcccagaaagttcctgtgatgtcaagctggtcgagaaaagctttgaaacagata
cgaacctaaactttcaaaacctgtcagtgattgggttccgaatcctcctcctgaaagtggccgggtttaatctgctcatgacgctgcgg
ctgtggtccagc (SEQ ID NO: 16)

Alpha chain protein sequence
MVLKFSVSILWIQLAWVSTQLLEQSPQFLSIQEGENLTVYCNSSSVFSSLQWYRQEP
GEGPVLLVTVVTGGEVKKLKRLTFQFGDARKDSSLHITAAQPGDTGLYLCAGDES
ISYGKLTFGQGTILTVHPNiqnpdpavyqlrdskssdksvelftdfdsqtnvsqskdsdvyitdktvldmrsmdf
ksnsavawsnksdfacanafinnsiipedtffpspesscdvklveksfetdtnlnfqnlsvigfrillllkvagfnllmtlrlwss
(SEQ ID NO: 17)

Beta chain:
TRBV12-4/TRBJ1-4/TRBC1

Beta chain DNA sequence
ATGGGCTCCTGGACCCTCTGCTGTGTGTCCCTTTGCATCCTGGTTGCAAAGCAC
ACAGATGCTGGAGTTATCCAGTCACCCCGGCACGAGGTGACAGAGATGGGACA
AGAAGTGACTCTGAGATGTAAACCAATTTCAGGACATGACTACCTTTTCTGGT
ACAGACAGACCATGATGCGGGGACTGGAGTTGCTCATTTACTTTAACAACAAC
GTTCCTATTGATGATTCAGGGATGCCCGAGGATCGCTTCTCAGCTAAGATGCCT
AATGCATCATTCTCCACTCTGAAGATCCAGCCCTCAGAACCCAGGGACTCAGCT
GTGTACTTCTGTGCCAGCAGTTTTCTCGGCTGGAATGAAAAACTGTTCTTTG
GCAGTGGAACCCAGCTCTCTGTCTTGGaggacctgaacaaggtgttcccacccgaggtcgctgtgtttga
gccatcagaagcagagatctcccacacccaaaaggccacactggtgtgcctggccacaggcttcttccctgaccacgtggagctg
agctggtgggtgaatgggaaggaggtgcacagtggggtcagcacggacccgcagcccctcaaggagcagcccgccctcaatg
actccagatactgcctgagcagccgcctgagggtctcggccaccttctggcagaacccccgcaaccacttccgctgtcaagtccag
ttctacgggctctcggagaatgacgagtggacccaggatagggccaaacccgtcacccagatcgtcagcgccgaggcctggggt
agagcagactgtggctttacctcggtgtcctaccagcaaggggtcctgtctgccaccatcctctatgagatcctgctagggaaggcc
accctgtatgctgtgctggtcagcgcccttgtgttgatggccatggtcaagagaaaggatttc (SEQ ID NO: 18)

Beta chain protein sequence
MGSWTLCCVSLCILVAKHTDAGVIQSPRHEVTEMGQEVTLRCKPISGHDYLFWYR
QTMMRGLELLIYFNNNVPIDDSGMPEDRFSAKMPNASFSTLKIQPSEPRDSAVYFC
ASSFLGWNEKLFFGSGTQLSVLEdlnkvfppevavfepseaeishtqkatlvclatgffpdhvelswwvng
kevhsgvstdpqplkeqpalndsryclssrlrvsatfwqnprnhfreqvqfyglsendewtqdrakpvtqivsaeawgradcg
ftsvsyqqgvlsatilyeillgkatlyavlvsalvlmamvkrkdf (SEQ ID NO: 19)

TABLE 2-continued

TCR sequences recognizing a MAGEA1 antigen

MAGEA1 TCR 32-39 HM codon optimized sequence
Alpha chain:
TRAV29-DV5/TRAJ43/codon optimized mouse TRAC Alpha chain DNA sequence
ATGGCCATGCTCCTGGGGGCATCAGTGCTGATTCTGTGGCTTCAGCCAGACTGG
GTTAACAGTCAACAGAAGAATGATGACCAGCAAGTTAAGCAAAATTCACCATC
CCTGAGCGTCCAGGAAGGAAGAATTTCTATTCTGAACTGTGACTATACTAACA
GCATGTTTGATTATTTCCTTTGGTACAAGAAATACCCTGCTGAAGGTCCTACAT
TCCTGATTTCTATTAGTTCCATTAAGGATAAAAATGAAGATGGAAGATTCACT
GTTTTCCTTAACAAAAGTGCCAAGCACCTCTCTCTGCACATTGTGCCCTCCCAG
CCTGGAGACTCTGCAGTGTACTTCTGTGCAGCAAGCGCTCAGAACAATGACA
TGCGCTTTGGAGCAGGGACCAGACTGACAGTTAAACCAAacattcaaaacccagaacccgc
cgtctaccagctgaaagacccgaggtctcaagactctacgttgtgcttgttcaccgatttcgacagtcagataaatgtgcctaagacc
atggagagtggcactttcatcactgacaaatgtgtgttggacatgaaggctatggacagcaagtcaaacggcgcgattgcttggtcc
aaccaaacttctttcacgtgccaggacatcttcaaggagacaaacgccacctatccatcctctgatgttccgtgcgatgcgactcttac
cgagaaaagcttcgagacggacatgaacttgaacttccaaaacctgcttgtgatggtactgcgaatacttcttcttaaggtggcgggc
ttcaatttgctcatgacactcagactttggtctagc (SEQ ID NO: 20)

Alpha chain protein sequence
MAMLLGASVLILWLQPDWVNSQQKNDDQQVKQNSPSLSVQEGRISILNCDYTNS
MFDYFLWYKKYPAEGPTFLISISSIKDKNEDGRFTVFLNKSAKHLSLHIVPSQPGDS
AVYFCAASAQNNDMRFGAGTRLTVKPNiqnpepavyqlkdprsqdstlclftdfdsqinvpktmesgtf
itdkcvldmkamdsksngaiawsnqtsftcqdifketnatypssdvpcdatlteksfetdmnlnfqnllvmvlrilllkvagfnll
mtlrlwss (SEQ ID NO: 21)

Beta chain:
TRBV18/TRBJ2-7/codon optimized mouse TRBC

Beta chain DNA sequence
ATGGACACCAGACTTCTCTGCTGTGCTGTCATCTGTCTCCTGGGGGCAGGCCTC
TCAAATGCCGGCGTCATGCAGAACCCAAGACACCTGGTCAGGAGGAGGGGACA
GGAGGCAAGACTGAGATGCAGCCCAATGAAAGGACACAGTCATGTTTACTGG
TATCGGCAGCTCCCAGAGGAAGGTCTGAAATTCATGGTTTATCTCCAGAAAGA
AAATATCATTGATGAGTCAGGAATGCCAAAGGAACGCTTTTCTGCTGAATTTCC
CAAAGAGGGCCCCAGCATCCTGAGGATCCAGCAGGTTGTGCGCGGAGATTCTG
CAGCTTATTTCTGTGCCAGCTCACCCTCCTACGAGCAGTACTTCGGGCCTGG
CACCAGGCTCACTGTCACAGaagatcttcgaaacgtaacccctccaaaagtgagtctctttgaaccgagtaaggc
tgagatcgcgaacaaacaaaaggcgaccctcgtctgtcttgcgcgaggatttttcccgaccacgtggagttgtcttggtgggtaaac
ggtaaggaagtacacagcggtgtttgcaccgaccctcaagcctacaaggaatctaactattcatactgcctttcatcccgacttaggg
tttctgctaccttttggcacaatccgaggaatcactttaggtgtcaagtacagttccacggattgtcagaggaggataaatggccggag
ggtaaggaagtacacagcggtgtttgcaccgaccctcaagcctacaaggaatctaactattcatactgcctttcatcccgacttaggg
tttctgctaccttttggcacaatccgaggaatcactttaggtgtcaagtacagttccacggattgtcagaggaggataaatggccggag
ggctccccgaagccggttacgcagaacattagtgcggaagcctggggacgagcagactgcggtatcacgtctgccagctatcag
caaggcgttctgtcagcgacaattctgtacgaaatacttttgggtaaggctacattgtatgcggtattggtgtctacgctggtagtcatg
gccatggtgaaacgaaaaaactca (SEQ ID NO: 22)

Beta chain protein sequence
MDTRLLCCAVICLLGAGLSNAGVMQNPRHLVRRRGQEARLRCSPMKGHSHVYW
YRQLPEEGLKFMVYLQKENIIDESGMPKERFSAEFPKEGPSILRIQQVVRGDSAAYF
CASSPSYEQYFGPGTRLTVTEdlrnvtppkvslfepskaeiankqkatlvclargffpdhvelswwvngkevh
sgvctdpqaykesnysyclssrlrvsatfwhnprnhfrcqvqfhglseedkwpegspkpvtqnisaeawgradcgitsasyqq
gvlsatilyeillgkatlyavlvstlvvmamvkrkns (SEQ ID NO: 23)

Complete Beta and Alpha ORF DNA Sequence (The underlined italic region in the "Furin-P2A" site encodes a sequence allowing for expression of two polypeptide chains in a single cassette")
ATGGACACCAGACTTCTCTGCTGTGCTGTCATCTGTCTCCTGGGGGCAGGCCTC
TCAAATGCCGGCGTCATGCAGAACCCAAGACACCTGGTCAGGAGGAGGGGACA
GGAGGCAAGACTGAGATGCAGCCCAATGAAAGGACACAGTCATGTTTACTGG
TATCGGCAGCTCCCAGAGGAAGGTCTGAAATTCATGGTTTATCTCCAGAAAGA
AAATATCATTGATGAGTCAGGAATGCCAAAGGAACGCTTTTCTGCTGAATTTCC
CAAAGAGGGCCCCAGCATCCTGAGGATCCAGCAGGTTGTGCGCGGAGATTCTG
CAGCTTATTTCTGTGCCAGCTCACCCTCCTACGAGCAGTACTTCGGGCCTGG
CACCAGGCTCACTGTCACAGaagatcttcgaaacgtaacccctccaaaagtgagtctctttgaaccgagtaaggc
tgagatcgcgaacaaacaaaaggcgaccctcgtctgtcttgcgcgaggatttttcccgaccacgtggagttgtcttggtgggtaaac
ggtaaggaagtacacagcggtgtttgcaccgaccctcaagcctacaaggaatctaactattcatactgcctttcatcccgacttaggg
tttctgctaccttttggcacaatccgaggaatcactttaggtgtcaagtacagttccacggattgtcagaggaggataaatggccggag
ggtccccgaagccggttacgcagaacattagtgcggaagcctggggacgagcagactgcggtatcacgtctgccagctatcag
caaggcgttctgtcagcgacaattctgtacgaaatacttttgggtaaggctacattgtatgcggtattggtgtctacgctggtagtcatg
gccatggtgaaacgaaaaaactca*AGAGCCAAAAGAAGCGGGAGCGGTGCGACAAACTTTAGCC*
*TGTTGAAACAAGCCGGCGACGTTGAAGAGAACCCCGGACCT*ATGGCCATGCTCCTG
GGGGCATCAGTGCTGATTCTGTGGCTTCAGCCAGACTGGGTTAACAGTCAACAG
AAGAATGATGACCAGCAAGTTAAGCAAAATTCACCATCCCTGAGCGTCCAGGA
AGGAAGAATTTCTATTCTGAACTGTGACTATACTAACAGCATGTTTGATTATT
TCCTTTGGTACAAGAAATACCCTGCTGAAGGTCCTACATTCCTGATTTCTATTA
GTTCCATTAAGGATAAAAATGAAGATGGAAGATTCACTGTTTTCCTTAACAAA
AGTGCCAAGCACCTCTCTCTGCACATTGTGCCCTCCCAGCCTGGAGACTCTGCA TABLE 2-continued TCR sequences recognizing a MAGEA1 antigen GTGTACTTCTGTGCAGCAAGCGCTCAGAACAATGACATGCGCTTTGGAGCA
GGGACCAGACTGACAGTTAAACCAAacattcaaaacccagaacccgccgtctaccagctgaaagacccg
aggtctcaagactctacgttgtgcttgttcaccgatttcgacagtcagataaatgtgcctaagaccatggagagtggcactttcatcact
gacaaatgtgtgttggacatgaaggctatggacagcaagtcaaacggcgcgattgcttggtccaaccaaacttctttcacgtgccag
gacatcttcaaggagacaaacgccacctatccatcctctgatgttccgtgcgatgcgactcttaccgagaaaagcttcgagacggac
atgaacttgaacttccaaaacctgcttgtgatggtactgcgaatacttcttcttaaggtggcgggcttcaatttgctcatgacactcagac
tttggtctagc (SEQ ID NO: 24)

Complete Beta and Alpha ORF Protein Sequence (The underlined italic region in the
"Furin-P2A" site allows expression of two polypeptide chains in a single cassette")")
MDTRLLCCAVICLLGAGLSNAGVMQNPRHLVRRRGQEARLRCSPMKGHSHVYW
YRQLPEEGLKFMVYLQKENIIDESGMPKERFSAEFPKEGPSILRIQQVVRGDSAAYF
CASSPSYEQYFGPGTRLTVTEdlrnvtppkvslfepskaeiankqkatlvclargffpdhvelswwvngkevh
sgvctdpqaykesnysyclssrlrvsatfwhnprnhfrcqvqfhglseedkwpegspkpvtqnisaeawgradcgitsasyqq
gvlsatilyeillgkatlyavlvstlvvmamvkrkns*RAKRSGSGATNFSLLKQAGDVEENPGP*MAMLL
GASVLILWLQPDWVNSQQKNDDQQVKQNSPSLSVQEGRISILNCDYTNSMFDYFL
WYKKYPAEGPTFLISISSIKDKNEDGRFTVFLNKSAKHLSLHIVPSQPGDSAVYF**CA
ASAQNNDMRF**GAGTRLTVKPNiqnpepavyqlkdprsqdstlclftdfdsqinvpktmesgtfitdkcvldm
kamdsksngaiawsnqtsftcqdifketnatypssdvpcdatlteksfetdmnlnfqnllvmvlrillllkvagfnllmtlrlwss
(SEQ ID NO: 25)

MAGEA1 TCR 32-41 Human/Mouse hybrid (HM) sequence (same CDRs as
"MAGEA1 TCR32-41 MGTM".". In some embodiments, the codon optimized alpha
chain and beta chain DNA sequences encoding the TCR can be used as shown in a vector
provided in Table 3, such as vector pNVVD142.)

Alpha chain:
TRAV27/TRAJ52/codon optimized mouse TRAC

Alpha chain DNA sequence
ATGGTCCTGAAATTCTCCGTGTCCATTCTTTGGATTCAGTTGGCATGGGTGAGC
ACCCAGCTGCTGGAGCAGAGCCCTCAGTTTCTTAGCATCCAAGAGGGAGAAAA
TCTCACTGTGTACTGCAACTCCTCAAGTGTTTTCTCCAGCCTTCAATGGTACAG
ACAGGAGCCTGGGGAAGGTCCTGTCCTCCTGGTGACA**GTTGTTACTGGTGGA
GAA**GTGAAGAAGCTGAAGAGACTTACCTTTCAGTTTGGTGATGCAAGAAAGGA
CAGTTCTCTCCACATCACTGCAGCCCAGCCTGGTGATACAGGCCTCTACCTC**TG
TGCAGGAGATGAAAGTATTAGCTATGGAAAGCTGACATTT**GGACAAGGGAC
CATCTTGACTGTCCATCCAAacattcaaaacccagaacccgccgtctaccagctgaaagacccgaggtctcaag
actctacgttgtgcttgttcaccgatttcgacagtcagataaatgtgcctaagaccatggagagtggcactttcatcactgacaaatgtg
tgttggacatgaaggctatggacagcaagtcaaacggcgcgattgcttggtccaaccaaacttctttcacgtgccaggacatcttcaa
ggagacaaacgccacctatccatcctctgatgttccgtgcgatgcgactcttaccgagaaaagcttcgagacggacatgaacttgaa
cttccaaaacctgcttgtgatggtactgcgaatacttcttcttaaggtggcgggcttcaatttgctcatgacactcagactttggtctagc
(SEQ ID NO: 26)

Alpha chain protein sequence
MVLKFSVSILWIQLAWVSTQLLEQSPQFLSIQEGENLTVYCNSSSVFSSLQWYRQEP
GEGPVLLVTVVTGGEVKKLKRLTFQFGDARKDSSLHITAAQPGDTGLYL**CAGDES
ISYGKLTF**GQGTILTVHPNiqnpepavyqlkdprsqdstlclftdfdsqinvpktmesgtfitdkcvldmkamds
ksngaiawsnqtsftcqdifketnatypssdvpcdatlteksfetdmnlnfqnllvmvlrillikvagfnllmtlrlwss (SEQ
ID NO: 27)

Beta chain:
TRBV12-4/TRBJ1-4/codon optimized mouse TRBC

Beta chain DNA sequence
ATGGGCTCCTGGACCCTCTGCTGTGTGTCCCTTTGCATCCTGGTTGCAAAGCAC
ACAGATGCTGGAGTTATCCAGTCACCCCGGCACGAGGTGACAGAGATGGGACA
AGAAGTGACTCTGAGATGTAAACCAATTTCAGGACATGACTACCTTTTCTGGT
ACAGACAGACCATGATGCGGGGACTGGAGTTGCTCATTTAC**TTTAACAACAAC
GTTCCT**ATTGATGATTCAGGGATGCCCGAGGATCGCTTCTCAGCTAAGATGCCT
AATGCATCATTCTCCACTCTGAAGATCCAGCCCTCAGAACCCAGGGACTCAGCT
GTGTACTTCTGTGCCAGCAGTTTTCTCGGCTGGAATGAAAAACTGTTCTTTG
GCAGTGGAACCCAGCTCTCTGTCTTGGaagatettegaaacgtaacccctccaaaagtgagtctctttgaac
cgagtaaggctgagatcgcgaacaaacaaaaggcgaccctcgtctgtcttgcgcgaggatttttcccgaccacgtggagttgtctt
ggtgggtaaacggtaaggaagtacacagcggtgtttgcaccgaccctcaagcctacaaggaatctaactattcatactgcctttcatc
ccgacttagggtttctgctaccttttggcacaatccgaggaatcactttaggtgtcaagtacagttccacggattgtcagaggaggata
aatggccggagggctccccgaagccggttacgcagaacattagtgcggaagcctggggacgagcagactgcggtatcacgtctg
ccagctatcagcaaggcgttctgtcagcgacaattctgtacgaaatacttttgggtaaggctacattgtatgcggtattggtgtctacgc
tggtagtcatggccatggtgaaacgaaaaaactca (SEQ ID NO: 28)

TABLE 2-continued

TCR sequences recognizing a MAGEA1 antigen

Beta chain protein sequence
MGSWTLCCVSLCILVAKHTDAGVIQSPRHEVTEMGQEVTLRCKPISGHDYLFWYR
QTMMRGLELLIYFNNNVPIDDSGMPEDRFSAKMPNASFSTLKIQPSEPRDSAVYFC
ASSFLGWNEKLFFGSGTQLSVLEdlrnvtppkvslfepskaeiankqkatlvclargffpdhvelswwvng
kevhsgvctdpqaykesnysyclssrlrvsatfwhnprnhfreqvqfhglseedkwpegspkpvtqnisaeawgradcgitsa
syqqgvlsatilyeillgkatlyavlvstlvvmamvkrkns (SEQ ID NO: 29)

Complete Beta and Alpha ORF DNA Sequence (The underlined italic region in the "Furin-P2A" site encodes a sequence allowing for expression of two polypeptide chains in a single cassette")
ATGGGCTCCTGGACCCTCTGCTGTGTGTCCCTTTGCATCCTGGTTGCAAAGCAC
ACAGATGCTGGAGTTATCCAGTCACCCCGGCACGAGGTGACAGAGATGGGACA
AGAAGTGACTCTGAGATGTAAACCAATTTCAGGACATGACTACCTTTTCTGGT
ACAGACAGACCATGATGCGGGGACTGGAGTTGCTCATTTACTTTAACAACAAC
GTTCCTATTGATGATTCAGGGATGCCCGAGGATCGCTTCTCAGCTAAGATGCCT
AATGCATCATTCTCCACTCTGAAGATCCAGCCCTCAGAACCCAGGGACTCAGCT
GTGTACTTCTGTGCCAGCAGTTTTCTCGGCTGGAATGAAAAACTGTTCTTTG
GCAGTGGAACCCAGCTCTCTGTCTTGGaagatcttcgaaacgtaacccctccaaaagtgagtctctttgaac
cgagtaaggctgagatcgcgaacaaacaaaaggcgaccctcgtctgtcttgcgcgaggatttttcccgaccacgtggagttgtctt
ggtgggtaaacggtaaggaagtacacagcggtgtttgcaccgaccctcaagcctacaaggaatctaactattcatactgcctttcatc
ccgacttagggtttctgctaccttttggcacaatccgaggaatcactttaggtgtcaagtacagttccacggattgtcagaggaggata
aatggccggagggctccccgaagccggttacgcagaacattagtgcggaagcctggggacgagcagactgcggtatcacgtctg
ccagctatcagcaaggcgttctgtcagcgacaattctgtacgaaatacttttgggtaaggctacattgtatgcggtattggtgtctacgc
tggtagtcatggccatggtgaaacgaaaaaactca*AGAGCCAAAAGAAGCGGGAGCGGTGCGACAAAC*
*TTTAGCCTGTTGAAACAAGCCGGCGACGTTGAAGAGAACCCCGGACCT*ATGGTCCT
GAAATTCTCCGTGTCCATTCTTTGGATTCAGTTGGCATGGGTGAGCACCCAGCT
GCTGGAGCAGAGCCCTCAGTTTCTTAGCATCCAAGAGGGAGAAAATCTCACTG
TGTACTGCAACTCCTCAAGTGTTTTCTCCAGCCTTCAATGGTACAGACAGGAG
CCTGGGGAAGGTCCTGTCCTCCTGGTGACAGTTGTTACTGGTGGAGAAGTGA
AGAAGCTGAAGAGACTTACCTTTCAGTTTGGTGATGCAAGAAAGGACAGTTCT
CTCCACATCACTGCAGCCCAGCCTGGTGATACAGGCCTCTACCTCTGTGCAGG
AGATGAAAGTATTAGCTATGGAAAGCTGACATTTGGACAAGGGACCATCTTG
ACTGTCCATCCAAacattcaaaacccagaacccgccgtctaccagctgaaagacccgaggtctcaagactctacgttgt
gcttgttcaccgatttcgacagtcagataaatgtgcctaagaccatggagagtggcactttcatcactgacaaatgtgtgttggacatg
aaggctatggacagcaagtcaaacggcgcgattgcttggtccaaccaaacttctttcacgtgccaggacatcttcaaggagacaaa
cgccacctatccatcctctgatgttccgtgcgatgcgactcttaccgagaaaagcttcgagacggacatgaacttgaacttccaaaac
ctgcttgtgatggtactgcgaatacttcttcttaaggtgggggcttcaatttgctcatgacactcagactttggtctagc (SEQ ID NO: 30)

Complete Beta and Alpha ORF Protein Sequence (The underlined italic region in the "Furin-P2A" site allows expression of two polypeptide chains in a single cassette")")
MGSWTLCCVSLCILVAKHTDAGVIQSPRHEVTEMGQEVTLRCKPISGHDYLFWYR
QTMMRGLELLIYFNNNVPIDDSGMPEDRFSAKMPNASFSTLKIQPSEPRDSAVYFC
ASSFLGWNEKLFFGSGTQLSVLEdlrnvtppkvslfepskaeiankqkatlvclargffpdhvelswwvng
kevhsgvctdpqaykesnysyclssrlrvsatfwhnprnhfrcqvqfhglseedkwpegspkpvtqnisaeawgradcgitsa
syqqgvlsatilyeillgkatlyavlvstlvvmamvkrkns*RAKRSGSGATNFSLLKQAGDVEENPGP*MVL
KFSVSILWIQLAWVSTQLLEQSPQFLSIQEGENLTVYCNSSSVFSSLQWYRQEPGEG
PVLLVTVVTGGEVKKLKRLTFQFGDARKDSSLHITAAQPGDTGLYLCAGDESISY
GKLTFGQGTILTVHPNiqnpepavyqlkdprsqdstlclftdfdsqinvpktmesgtfitdkcvldmkamdsksn
gaiawsnqtsftcqdifketnatypssdvpcdatlteksfetdmnlnfqnllvmvlrillllkvagfnllmtlrlwss (SEQ ID NO: 31)

Note: CDR1 and CDR2 sequences for each clone below are redundant for the corresponding base clone name listed above MAGEA1 TCR 32-39 MGTM codon optimized sequence
Alpha chain:
TRAV29-DV5/TRAJ43/MGTM modified TRAC
Alpha chain DNA sequence
ATGGCCATGCTCCTGGGGGCATCAGTGCTGATTCTGTGGCTTCAGCCAGACTGG
GTTAACAGTCAACAGAAGAATGATGACCAGCAAGTTAAGCAAAATTCACCATC
CCTGAGCGTCCAGGAAGGAAGAATTTCTATTCTGAACTGTGACTATACTAACA
GCATGTTTGATTATTTCCTTTGGTACAAGAAATACCCTGCTGAAGGTCCTACAT
TCCTGATTTCTATTAGTTCCATTAAGGATAAAAATGAAGATGGAAGATTCACT
GTTTTCCTTAACAAAAGTGCCAAGCACCTCTCTCTGCACATTGTGCCCTCCCAG
CCTGGAGACTCTGCAGTGTACTTCTGTGCAGCAAGCGCTCAGAACAATGACA
TGCGCTTTGGAGCAGGGACCAGACTGACAGTTAAACCAaacatccagaaccccgaccccgc
cgtgtaccagctgagggactccaagtccagcgacaagagcgtgtgtctgtttacggacttcgacagccagaccaacgtgagtcaaa
gcaaggacagcgacgtctacataacggataagaccgtgctggacatgcggagcatggacttcaagagcaacagcgccgtggcct
ggtccaacaagagcgacttcgcctgcgccaacgccttcaacaacagcatcatccccgaggacaccttcttccccagcagcgacgt
gccctgcgacgtgaaactggtggagaagtccttcgagacagacaccaatctgaactttcagaacctgctggtgatcgtgctgcggat
tctgctgctgaaagtggccggcttcaatctgctgatgaccctgcggctgtggagc (SEQ ID NO: 32)

TABLE 2-continued

TCR sequences recognizing a MAGEA1 antigen

Alpha chain protein sequence
MAMLLGASVLILWLQPDWVNSQQKNDDQQVKQNSPSLSVQEGRISILNCDYTNS
MFDYFLWYKKYPAEGPTFLISISSIKDKNEDGRFTVFLNKSAKHLSLHIVPSQPGDS
AVYFCAASAQNNDMRFGAGTRLTVKPNiqnpdpavyqlrdskssdksvclftdfdsqtnvsqskdsdv
yitdktvldmrsmdfksnsavawsnksdfacanafnnsiipedtffpssdvpcdvklveksfetdtnlnfqnllvivlrilllkva
gfnllmtlrlws (SEQ ID NO: 33)

Beta chain:
TRBV18/TRBJ2-7/MGTM modified TRBC1
Beta chain DNA sequence
ATGGACACCAGACTTCTCTGCTGTGCTGTCATCTGTCTCCTGGGGGCAGGCCTC
TCAAATGCCGGCGTCATGCAGAACCCAAGACACCTGGTCAGGAGGAGGGGACA
GGAGGCAAGACTGAGATGCAGCCCAATGAAAGGACACAGTCATGTTTACTGG
TATCGGCAGCTCCCAGAGGAAGGTCTGAAATTCATGGTTTATCTCCAGAAAGA
AAATATCATTGATGAGTCAGGAATGCCAAAGGAACGCTTTTCTGCTGAATTTCC
CAAAGAGGGCCCCAGCATCCTGAGGATCCAGCAGGTTGTGCGCGGAGATTCTG
CAGCTTATTTCTGTGCCAGCTCACCCTCCTACGAGCAGTACTTCGGGCCTGG
CACCAGGCTCACTGTCACAgaagatctgaacaaggtgttccctccagaggtggccgtgttcgagccttctaaggc
cgagatcgcccacacacaaaaagccaccctcgtgtgcctggccaccggcttttccccgaccacgtggaactgtcttggtgggtca
acggcaaagaggtgcactccggcgtgtcaacggatccccagcctctgaaagaacagcctgccctgaacgacagccggtactgcc
tgagctccagactgagagtgtccgccaccttctggcagaaccccggaaccacttcagatgccaggtgcagttttacggcctgagc
gagaacgacgagtggacccaggacagagccaagcccgtgacacaaatcgtgtctgccgaagcctggggaagagccgattgcg
gcatcaccagcgcctcctatcaccagggcgtgctgagcgccacaatcctgtacgaaatcctgctgggcaaggccaccctgtacgc
cgtgctggtgtctgctctggtgctgatggccatggtcaagcggaaggacttt (SEQ ID NO: 34)

Beta chain protein sequence
MDTRLLCCAVICLLGAGLSNAGVMQNPRHLVRRRGQEARLRCSPMKGHSHVYW
YRQLPEEGLKFMVYLQKENIIDESGMPKERFSAEFPKEGPSILRIQQVVRGDSAAYF
CASSPSYEQYFGPGTRLTVTEdlnkvfppevavfepskaeiahtqkatlvclatgffpdhvelswwvngkevh
yhqgvlsatilyeillgkatlyavlvsalvlmamvkrkdf (SEQ ID NO: 35)

Complete Beta and Alpha ORF DNA Sequence
ATGGACACCAGACTTCTCTGCTGTGCTGTCATCTGTCTCCTGGGGGCAGGCCTC
TCAAATGCCGGCGTCATGCAGAACCCAAGACACCTGGTCAGGAGGAGGGGACA
GGAGGCAAGACTGAGATGCAGCCCAATGAAAGGACACAGTCATGTTTACTGG
TATCGGCAGCTCCCAGAGGAAGGTCTGAAATTCATGGTTTATCTCCAGAAAGA
AAATATCATTGATGAGTCAGGAATGCCAAAGGAACGCTTTTCTGCTGAATTTCC
CAAAGAGGGCCCCAGCATCCTGAGGATCCAGCAGGTTGTGCGCGGAGATTCTG
CAGCTTATTTCTGTGCCAGCTCACCCTCCTACGAGCAGTACTTCGGGCCTGG
CACCAGGCTCACTGTCACAgaagatctgaacaaggtgttccctccagaggtggccgtgttcgagccttctaaggc
cgagatcgcccacacacaaaaagccaccctcgtgtgcctggccaccggcttttccccgaccacgtggaactgtcttggtgggtca
acggcaaagaggtgcactccggcgtgtcaacggatccccagcctctgaaagaacagcctgccctgaacgacagccggtactgcc
tgagctccagactgagagtgtccgccaccttctggcagaaccccggaaccacttcagatgccaggtgcagttttacggcctgagc
gagaacgacgagtggacccaggacagagccaagcccgtgacacaaatcgtgtctgccgaagcctggggaagagccgattgcg
gcatcaccagcgcctcctatcaccagggcgtgctgagcgccacaatcctgtacgaaatcctgctgggcaaggccaccctgtacgc
cgtgctggtgtctgctctggtgctgatggccatggtcaagcggaaggacttt*GGCAGCGGCAGAGCCAAAAGGT*
*CCGGGAGCGGTGCGACAAACTTTAGCCTGTTGAAACAAGCCGGCGACGTTGAAGAG*
*AACCCCGGACCT*ATGGCCATGCTCCTGGGGGCATCAGTGCTGATTCTGTGGCTTC
AGCCAGACTGGGTTAACAGTCAACAGAAGAATGATGACCAGCAAGTTAAGCAA
AATTCACCATCCCTGAGCGTCCAGGAAGGAAGAATTTCTATTCTGAACTGTGAC
TATACTAACAGCATGTTTGATTATTTCCTTTGGTACAAGAAATACCCTGCTGA
AGGTCCTACATTCCTGATTTCTATTAGTTCCATTAAGGATAAAAATGAAGATG
GAAGATTCACTGTTTTCCTTAACAAAAGTGCCAAGCACCTCTCTCTGCACATTG
TGCCCTCCCAGCCTGGAGACTCTGCAGTGTACTTCTGTGCAGCAAGCGCTCAG
AACAATGACATGCGCTTTGGAGCAGGGACCAGACTGACAGTTAAACCAaacatcc
agaaccccgaccccgccgtgtaccagctgagggactccaagtccagcgacaagagcgtgtgtctgtttacggacttcgacagcca
gaccaacgtgagtcaaagcaaggacagcgacgtctacataacggataagaccgtgctggacatgcggagcatggacttcaagag
caacagcgccgtggcctggtccaacaagagcgacttcgcctgcgccaacgccttcaacaacagcatcatccccgaggacaccttc
ttccccagcagcgacgtgccctgcgacgtgaaactggtggagaagtccttcgagacagacaccaatctgaactttcagaacctgct
ggtgatcgtgctgcggattctgctgctgaaagtggccggcttcaatctgctgatgaccctgcggctgtggagc (SEQ ID NO:
36)

Complete Beta and Alpha ORF Protein Sequence
MDTRLLCCAVICLLGAGLSNAGVMQNPRHLVRRRGQEARLRCSPMKGHSHVYW
YRQLPEEGLKFMVYLQKENIIDESGMPKERFSAEFPKEGPSILRIQQVVRGDSAAYF
CASSPSYEQYFGPGTRLTVTEdlnkvfppevavfepskaeiahtqkatlvclatgffpdhvelswwvngkevh
sgvstdpqplkeqpalndsryclssrlrvsatfwqnprnhfrcqvqfyglsendewtqdrakpvtqivsaeawgradcgitsas
yhqgvlsatilyeillgkatlyavlvsalvlmamvkrkdf*GSGRAKRSGSGATNFSLLKQAGDVEENPGP*M
AMLLGASVLILWLQPDWVNSQQKNDDQQVKQNSPSLSVQEGRISILNCDYTNSMF
DYFLWYKKYPAEGPTFLISISSIKDKNEDGRFTVFLNKSAKHLSLHIVPSQPGDSAV
YFCAASAQNNDMRFGAGTRLTVKPNiqnpdpavyqlrdskssdksvclftdfdsqtnvsqskdsdvyitd
ktvldmrsmdfksnsavawsnksdfacanafnnsiipedtffpssdvpcdvklveksfetdtnlnfqnllvivlrilllkvagfnll
mtlrlws (SEQ ID NO: 37)

TABLE 2-continued

TCR sequences recognizing a MAGEA1 antigen

MAGEA1 TCR 32-41 MGTM codon optimized sequence (also known as “TCR41” or “41” or “TCR-204-C07”. In some embodiments, the codon optimized alpha chain and beta chain DNA sequences encoding the TCR can be used as shown in a vector provided in Table 3, such as vector pNVVD142.)

Alpha chain:
TRAV27/TRAJ52/MGTM modified TRAC
Alpha chain DNA sequence
ATGGTCCTGAAATTCTCCGTGTCCATTCTTTGGATTCAGTTGGCATGGGTGAGC
ACCCAGCTGCTGGAGCAGAGCCCTCAGTTTCTTAGCATCCAAGAGGGAGAAAA
TCTCACTGTGTACTGCAACTCCTCAAGTGTTTTCTCCAGCCTTCAATGGTACAG
ACAGGAGCCTGGGGAAGGTCCTGTCCTCCTGGTGACAGTTGTTACTGGTGGA
GAAGTGAAGAAGCTGAAGAGACTTACCTTTCAGTTTGGTGATGCAAGAAAGGA
CAGTTCTCTCCACATCACTGCAGCCCAGCCTGGTGATACAGGCCTCTACCTCTG
TGCAGGAGATGAAAGTATTAGCTATGGAAAGCTGACATTTGGACAAGGGAC
CATCTTGACTGTCCATCCAaacatccagaaccccgaccccgccgtgtaccagctgagggactccaagtccagcg
acaagagcgtgtgtctgtttacggacttcgacagccagaccaacgtgagtcaaagcaaggacagcgacgtctacataacggataa
gaccgtgctggacatgcggagcatggacttcaagagcaacagcgccgtggcctggtccaacaagagcgacttcgcctgcgccaa
cgccttcaacaacagcatcatccccgaggacaccttcttccccagcagcgacgtgccctgcgacgtgaaactggtggagaagtcct
tcgagacagacaccaatctgaactttcagaacctgctggtgatcgtgctgcggattctgctgctgaaagtggccggcttcaatctgct
gatgaccctgcggctgtggagc (SEQ ID NO: 38)

Alpha chain protein sequence
MVLKFSVSILWIQLAWVSTQLLEQSPQFLSIQEGENLTVYCNSSSVFSSLQWYRQEP
GEGPVLLVTVVTGGEVKKLKRLTFQFGDARKDSSLHITAAQPGDTGLYLCAGDES
ISYGKLTFGQGTILTVHPNiqnpdpavyqlrdskssdksvclftdfdsqtnvsqskdsdvyitdktvldmrsmdf
ksnsavawsnksdfacanafnnsiipedtffpssdvpcdvklveksfetdtnlnfqnllvivlrilllkvagfnllmtlrlws
(SEQ ID NO: 39)

Beta chain:
TRBV12-4/TRBJ1-4/MGTM modified TRBC1
Beta chain DNA sequence
ATGGGCTCCTGGACCCTCTGCTGTGTGTCCCTTTGCATCCTGGTTGCAAAGCAC
ACAGATGCTGGAGTTATCCAGTCACCCCGGCACGAGGTGACAGAGATGGGACA
AGAAGTGACTCTGAGATGTAAACCAATTTCAGGACATGACTACCTTTTCTGGT
ACAGACAGACCATGATGCGGGGACTGGAGTTGCTCATTTACTTTAACAACAAC
GTTCCTATTGATGATTCAGGGATGCCCGAGGATCGCTTCTCAGCTAAGATGCCT
AATGCATCATTCTCCACTCTGAAGATCCAGCCCTCAGAACCCAGGGACTCAGCT
GTGTACTTCTGTGCCAGCAGTTTTCTCGGCTGGAATGAAAAACTGTTCTTTG
GCAGTGGAACCCAGCTCTCTGTCTTGgaagatctgaacaaggtgttccctccagaggtggccgtgttcgag
ccttctaaggccgagatcgcccacacacaaaaagccaccctcgtgtgcctggccaccggctttttccccgaccacgtggaactgtct
tggtgggtcaacggcaaagaggtgcactccggcgtgtcaacggatccccagcctctgaaagaacagcctgccctgaacgacagc
cggtactgcctgagctccagactgagagtgtccgccaccttctggcagaacccccggaaccacttcagatgccaggtgcagttttac
ggcctgagcgagaacgacgagtggacccaggacagagccaagcccgtgacacaaatcgtgtctgccgaagcctggggaagag
ccgattgcggcatcaccagcgcctcctatcaccagggcgtgctgagcgccacaatcctgtacgaaatcctgctgggcaaggccac
cctgtacgccgtgctggtgtctgctctggtgctgatggccatggtcaagcggaaggacttt (SEQ ID NO: 40)

Beta chain protein sequence
MGSWTLCCVSLCILVAKHTDAGVIQSPRHEVTEMGQEVTLRCKPISGHDYLFWYR
QTMMRGLELLIYFNNNVPIDDSGMPEDRFSAKMPNASFSTLKIQPSEPRDSAVYFC
ASSFLGWNEKLFFGSGTQLSVLEdlnkvfppevavfepskaeiahtqkatlvclatgffpdhvelswwvng
kevhsgvstdpqplkeqpalndsryclssrlrvsatfwqnprnhfrcqvqfyglsendewtqdrakpvtqivsaeawgradcgi
tsasyhqgvlsatilyeillgkatlyavlvsalvlmamvkrkdf (SEQ ID NO: 41)

Complete Beta and Alpha ORF DNA Sequence
ATGGGCTCCTGGACCCTCTGCTGTGTGTCCCTTTGCATCCTGGTTGCAAAGCAC
ACAGATGCTGGAGTTATCCAGTCACCCCGGCACGAGGTGACAGAGATGGGACA
AGAAGTGACTCTGAGATGTAAACCAATTTCAGGACATGACTACCTTTTCTGGT
ACAGACAGACCATGATGCGGGGACTGGAGTTGCTCATTTACTTTAACAACAAC
GTTCCTATTGATGATTCAGGGATGCCCGAGGATCGCTTCTCAGCTAAGATGCCT
AATGCATCATTCTCCACTCTGAAGATCCAGCCCTCAGAACCCAGGGACTCAGCT
GTGTACTTCTGTGCCAGCAGTTTTCTCGGCTGGAATGAAAAACTGTTCTTTG
GCAGTGGAACCCAGCTCTCTGTCTTGgaagatctgaacaaggtgttccctccagaggtggccgtgttcgag
ccttctaaggccgagatcgcccacacacaaaaagccaccctcgtgtgcctggccaccggctttttccccgaccacgtggaactgtct
tggtgggtcaacggcaaagaggtgcactccggcgtgtcaacggatccccagcctctgaaagaacagcctgccctgaacgacagc
cggtactgcctgagctccagactgagagtgtccgccaccttetggcagaacccccggaaccacttcagatgccaggtgcagttttac
ggcctgagegagaacgacgagtggacccaggacagagccaagcccgtgacacaaatcgtgtctgccgaagcctggggaagag
ccgattgcggcatcaccagcgcctcctatcaccagggcgtgctgagcgccacaatcctgtacgaaatcctgctgggcaaggccac
cctgtacgccgtgctggtgtctgctctggtgctgatggccatggtcaagcggaaggacttt*GGCAGCGGCAGAGCCAA*
*AAGGTCCGGGAGCGGTGCGACAAACTTTAGCCTGTTGAAACAAGCCGGCGACGTTG*
*AAGAGAACCCCGGACCTATGGTCCT*GAAATTCTCCGTGTCCATTCTTTGGATTCA
GTTGGCATGGGTGAGCACCCAGCTGCTGGAGCAGAGCCCTCAGTTTCTTAGCAT
CCAAGAGGGAGAAAATCTCACTGTGTACTGCAACTCCTCAAGTGTTTTCTCCA
GCCTTCAATGGTACAGACAGGAGCCTGGGGAAGGTCCTGTCCTCCTGGTGACA
GTTGTTACTGGTGGAGAAGTGAAGAAGCTGAAGAGACTTACCTTTCAGTTTG
GTGATGCAAGAAAGGACAGTTCTCTCCACATCACTGCAGCCCAGCCTGGTGAT
ACAGGCCTCTACCTCTGTGCAGGAGATGAAAGTATTAGCTATGGAAAGCTG
ACATTTGGACAAGGGACCATCTTGACTGTCCATCCAaacatccagaaccccgaccccgccgtgt TABLE 2-continued

| TCR sequences recognizing a MAGEA1 antigen |
|---|
| accagctgagggactccaagtccagcgacaagagcgtgtgtctgtttacggacttcgacagccagaccaacgtgagtcaaagcaa |
| ggacagcgacgtctacataacggataagaccgtgctggacatgcggagcatggacttcaagagcaacagcgccgtggcctggtc |
| caacaagagcgacttcgcctgcgccaacgccttcaacaacagcatcatccccgaggacaccttcttccccagcagcgacgtgccc |
| tgcgacgtgaaactggtggagaagtccttcgagacagacaccaatctgaactttcagaacctgctggtgatcgtgctgcggattctg |
| ctgctgaaagtggccggcttcaatctgctgatgaccctgcggctgtggagc (SEQ ID NO: 42) |
| |
| Complete Beta and Alpha ORF Protein Sequence |
| MGSWTLCCVSLCILVAKHTDAGVIQSPRHEVTEMGQEVTLRCKPI**SGHDY**LFWYR |
| QTMMRGLELLIY**FNNNVP**IDDSGMPEDRFSAKMPNASFSTLKIQPSEPRDSAVYF**C** |
| **ASSFLGWNEKLFF**GSGTQLSVLEdlnkvfppevavfepskaeiahtqkatlvclatgffpdhvelswwvng |
| kevhsgvstdpqplkeqpalndsryclssrlrvsatfwqnprnhfreqvqfyglsendewtqdrakpvtqivsaeawgradcgi |
| tsasyhqgvlsatilyeillgkatlyavlvsalvlmamvkrkdf*GSGRAKRSGSGATNFSLLKQAGDVEENPG* |
| *P*MVLKFSVSILWIQLAWVSTQLLEQSPQFLSIQEGENLTVYCNSS**SVFSS**LQWYRQE |
| PGEGPVLLVT**VVTGGEV**KKLKRLTFQFGDARKDSSLHITAAQPGDTGLYL**CAGDE** |
| **SISYGKLTF**GQGTILTVHPNiqnpdpavyqlrdskssdksvclftdfdsqtnvsqskdsdvyitdktvldmrsm |
| dfksnsavawsnksdfacanafnnsiipedtffpssdvpcdvklveksfetdtnlnfqnllvivlrilllkvagfnllmtlrlws |
| (SEQ ID NO: 43) |

*Table 2 provides, in part, representative TCR sequences are grouped according to MHC serotype presentation and sub-grouped according to different peptides presented by the MHC serotype and bound by the sub-grouped TCRs. Individual TCRs, such as those representatively exemplified in the tables, are described and claimed, as well as the genus of binding proteins that bind a peptide epitope sequence described herein either alone or in a complex with an MHC, such as those grouped in the tables provided herein. In addition, TRAY, TRAJ, and TRAC genes for each TCR alpha chain described herein, and TRBV, TRBJ, and TRBC genes for each TCR beta chain described herein, are provided. Sequences for each TCR described herein are provided as pairs of cognate alpha chain and beta chains for each named TCR. TCR sequences described herein are annotated. Variable domain sequences are capitalized. Constant domain sequences are in lower case. CDR1, CDR2, and CDR3 sequences are annotated using bold and underlined text. CDR1, CDR2, and CDR3 are shown in standard order of appearance from left (N-terminus) to right (C-terminus). TRAY, TRAJ, and TRAC genes for each TCR alpha chain described herein, and TRBV, TRBJ, and TRBC genes for each TCR beta chain described herein, are annotated according to well-known IMGT nomenclature described herein. Similarly, CDR1 and CDR2 of TRAY and TRBV are well-known in the art since they are based on well-known and annotated TRAY and TRBV sequences (e.g., as annotated in databases like IMGT available at imt.org and IEDB available at iedb.org).

TABLE 3

| |
|---|
| Representative Human MAGEA1 cDNA sequence |
| atgtctcttgagcagaggagtctgcactgcaagcctgaggaagcccttgaggcccaacaagaggccctgggcctggtgtgtgtgc |
| aggctgccacctcctcctcctctcctctggtcctgggcaccctggaggaggtgcccactgctgggtcaacagatcctccccagagtc |
| ctcagggagcctccgcctttcccactaccatcaacttcactcgacagaggcaacccagtgagggttccagcagccgtgaagagga |
| ggggccaagcacctcttgtatcctggagtccttgttccgagcagtaatcactaagaaggtggctgatttggttggttttctgctcctcaa |
| atatcgagccagggagccagtcacaaaggcagaaatgctggagagtgtcatcaaaaattacaagcactgttttcctgagatcttcgg |
| caaagcctctgagtccttgcagctggtctttggcattgacgtgaaggaagcagaccccaccggccactcctatgtccttgtcacctgc |
| ctaggtctctcctatgatggcctgctgggtgataatcagatcatgcccaagacaggcttcctgataattgtcctggtcatgattgcaatg |
| gagggcggccatgctcctgaggaggaaatctgggaggagctgagtgtgatggaggtgtatgatgggagggagcacagtgcctat |
| ggggagcccaggaagctgctcacccaagatttggtgcaggaaaagtacctggagtaccggcaggtgccggacagtgatcccgc |
| acgctatgagttcctgtggggtccaagggccctcgctgaaaccagctatgtgaaagtccttgagtatgtgatcaaggtcagtgca**ag** |
| **agttcgcttttcttcccatccctgcgtgaagca**gctttgagagaggaggaagagggagtctga (SEQ ID NO: 44) |
| |
| Representative Human MAGEA1 protein sequence |
| MSLEQRSLHCKPEEALEAQQEALGLVCVQAATSSSSPLVLGTLEEVPTAGSTDPPQS |
| PQGASAFPTTINFTRORQPSEGSSSREEEGPSTSCILESLFRAVITKKVADLVGFLLLK |
| YRAREPVTKAEMLESVIKNYKHCFPEIFGKASESLQLVFGIDVKEADPTGHSYVLVT |
| CLGLSYDGLLGDNQIMPKTGFLIIVLVMIAMEGGHAPEEEIWEELSVMEVYDGREH |
| SAYGEPRKLLTQDLVQEKYLEYRQVPDSDPARYEFLWGPRALAETSYVKVLEYVI |
| KVSAR**VRFFFPSL**REA |
| ALREEEEGV* (SEQ ID NO: 45) |
| |
| Representative Human HLA-C*07:02 DNA sequence |
| atgcgcgtcatggctccacgcgccctcctcctgctgctctcaggggggcctggccctgaccgagacctgggcctgctcccactccat |
| gcgctatttcgacaccgccgtgtcccgcccaggccgcggtgagccacgcttcatctcagtgggctacgtggacgacactcagttcg |
| tgcgcttcgacagcgacgccgccagtcctcgcggggagccacgcgcaccatgggtggagcaggaggggcctgagtattgggac |
| cgcgagacacagaagtacaagcgccaggcacaggctgaccgcgtgagcctgcgcaacctgcgcggctactacaaccagagcg |
| aggacgggtctcacaccctccagcgcatgtctggctgcgacctggggcctgacgggcgcctcctccgcgggtatgaccagtccg |
| cctacgacggcaaggattacatcgccctgaacgaggacctgcgctcctggaccgccgctgacaccgccgctcagatcacccagc |
| gcaagttggaggctgcccgcgccgctgagcagctgcgcgcctacctggagggcacatgcgtggagtggctccgccgctacctg |
| gagaacgggaaggagaccctgcagcgcgcagaaccaccaaagacacacgtgacccaccaccctctctctgaccatgaggccac |
| cctgcgctgctgggccctgggcttctaccctgctgagatcacactgacctggcagcgcgatggggaggaccagacccaggacac |
| cgagcttgtggagacccgcccagcaggtgatggcaccttccagaagtgggcagctgtggtggtgccttctgggcaagagcagcg |
| ctacacatgccatatgcagcacgaggggctgcaagagccactcaccctgagctgggagccatcttcccagccaaccatcccaatc |

TABLE 3-continued atgggcatcgttgctggcctggctgtcctggttgtcctggctgtccttggtgctgtggtcaccgctatgatgtgtcgccgcaagagctc
aggtgggaaaggtgggagctgctctcaggctgcatgcagcaacagtgcccagggctctgatgagtctctcatcacttgtaaagcct
ga (SEQ ID NO: 46)

Representative Human HLA-C*07:02 protein sequence
MRVMAPRALLLLLSGGLALTETWACSHSMRYFDTAVSRPGRGEPRFISVGYVDDT
QFVRFDSDAASPRGEPRAPWVEQEGPEYWDRETQKYKRQAQADRVSLRNLRGYY
NQSEDGSHTLQRMSGCDLGPDGRLLRGYDQSAYDGKDYIALNEDLRSWTAADTA
AQITQRKLEAARAAEQLRAYLEGTCVEWLRRYLENGKETLQRAEPPKTHVTHHPL
SDHEATLRCWALGFYPAEITLTWORDGEDQTQDTELVETRPAGDGTFQKWAAVV
VPSGQEQRYTCHMQHEGLQEPLTLSWEPSSQPTIPIMGIVAGLAVLVVLAVLGAVV
TAMMCRRKSSGGKGGSCSQAACSNSAQGSDESLITCKA* (SEQ ID NO: 47)

Representative Human LAMB4-intron retained DNA sequence (coding sequence; CDS)
(intron retention shown in uppercase text)
atgcaatttcaactgacccttttttgcaccttgggtggctcagttactcaaaagctcaagatgactgcaacaggggtgcctgtcatccc
accactggtgatctcctggtgggcaggaacacgcagcttatggcttcttctacctgtgggctgagcagagcccagaaatactgcatc
ctcagttacctggagggggaacaaaaatgcttcatctgtgactctagatttccatatgatccgtatgaccaacccaacagccacacca
ttgagaatgtcattgtaagttttgaaccagacagagaaaagaaatggtggcaatctgaaaatggtcttgatcatgtcagcatcagactg
gacttagaggcattatttcggttcagccaccttatcctgacctttaagacttttcggcctgctgcaatgttagttgaacgttccacagacta
tggacacaactggaaagtgttcaaatatttgcaaaagactgtgccacttcctttcctaacatcacatctggccaggcccagggagtg
ggagacattgtttgtgactccaaatactcggatattgaaccctcaacaggtggagaggttgttttaaaagttttggatcccagttttgaaa
ttgaaaacccttatagcccctacatccaagaccttgtgacattgacaaacctgaggataaactttaccaagctccacacccttggggat
gctttgcttggaaggaggcaaaatgattcccttgataaatactactatgctctgtacgagatgattgttcggggaagctgcttttgcaat
ggccatgctagcgaatgtcgccctatgcagaagatgcggggagatgttttcagccctcctggaatggttcacggtcagtgtgtgtgtc
agcacaatacagatggtccgaactgtgagagatgcaaggacttcttccaggatgctccttggaggccagctgcagacctccaggac
aacgcttgcagatcgtgcagctgtaatagccactccagccgctgtcactttgacatgactacgtacctggcaagcggtggcctcagc
gggggcgtgtgtgaagactgccagcacaacactgaggggcagcactgcgaccgctgcagacccctcttctacagggacccgctc
aagaccatctcagatccctacgcgtgcattccttgtgaatgtgaccccgatgggaccatatctggtggcatttgtgtgagccactctga
tcctgccttagggtctgtggccggccagtgcctttgtaaagagaacgtggaaggagccaaatgcgaccagtgcaaacccaaccact
acggactaagcgccaccgacccctgggctgccagccctgcgactgtaaccccttgggagtctgccattcttgacctgtgatgtg
gatacaggccaatgcttgtgcctgtcatatgtcaccggagcacactgcgaagaatgcactgttggatactggggcctgggaaatcat
ctccatgggtgttctccctgtgactgtgatattggaggtgcttattctaacgtgtgctcacccaagaatgggcagtgtgaatgccgccc
acatgtcactggccgtagctgctctgaaccagcccctggctacttctttgctcctttgaatttctatctctacgaggcagaggaagccac
aacactccaaggactggcgcctttgggctcggagacgtttggccagagtcctgctgttcacgttgttttaggagagccagttcctggg
aaccctgttacatggactggacctggatttgccagggttctccctggggctggcttgagatttgctgtcaacaacattccctttcctgtg
gacttcaccattgccattcactatgaaacccagtctgcagctgactggactgtccagattgtggtgaacccccctggagggagtgag
cactgcatacccaagactctacagtcaaagcctcagtcttttgccttaccagcggctacgagaatcatgctgcttcccacacccatctg
tttagaaccagatgtacaatattccatagatgtctatttttctcagcctttgcaaggagagtcccacgctcattcacatgtcctggtggact
ctcttggccttattccccaaatcaattcattggagaatttctgcagcaagcaggacttagatgagtatcagcttcacaactgtgttgaaat
tgcctcagcaatgggacctcaagtgctcccgggtgcctgtgaaaggctgatcatcagcatgtctgccaagctgcatgatggggctgt
ggcctgcaagtgtcacccccagggctcagtcggatccagctgcagccgacttggaggccagtgccagtgtaaacctcttgtggtcg
ggcgctgctgtgacaggtgctcaactggaagctatgatttggggcatcacggctgtcacccatgtcactgccatcctcaaggatcaa
aggacactgtatgtgaccaagtaacaggacagtgcccctgccatggagaggtgtctggccgccgctgtgatcgctgcctggcagg
ctactttggatttcccagctgccacccttgcccttgtaataggtttgctgaactttgtgatcctgagacagggtcatgcttcaattgtgga
ggctttacaactggcagaaactgtgaaaggtgtattgatggttactatggaaatccttcttcaggacagccctgtcgtccttgcctgtgt
ccagatgatccctcaagcaatcagtatttgcccattcctgttatcagaatctgtggagctcagatgtaatctgcaattgtcttcaaggtta
tacgggtactcagtgtggagaatgctctactggtttctatggaaatccaagaatttcaggagcaccttgccaaccatgtgcctgcaaca
acaacatagatgtaaccgatccagagtcctgcagccgggtaacaggggagtgccttcgatgtttgcacaacactcagggcgcaaa
ctgccagctctgcaaaccaggtcactatggatcagccctcaatcagacctgcagaagatgctcctgccatgcttccggcgtgagtcc
catggagtgtcccccctggtgggggagcttgcctctgtgaccctgtcactggtgcatgtccttgtctgccgaatgtcacaggcctggcc
tgtgaccgttgtgctgatggatactggaatctggtccctggcagaggatgtcagtcatgtgactgtgaccctaggacctctcaaagta
gccactgtgaccagcttacaggccagtgtccgtgtaaattaggttacggcgggaaacgttgcagtgagtgccaggaaaattattatg
gtgatccacctgggcgatgcattccatgtgattgtaacagggcaggtacccagaagcccatctgtgatccagacacaggcatgtgc
cgctgccgggagggtgtcagcggccagagatgtgatcgctgtgcccggggacacagccaggaattccctacttgtcttcaatgtca
cttgtgctttgatcagtgggaccacaccatttcttccctctccaaagcggtgcaagggttaatgagactggctgctaacatggaagata
aaagagagaccctgcctgtctgtgaggcagacttcaaagacctcagagggaacgtgtctgaaatagaaaggattttgaaacatcct
gttttcccatctgggaaattcttaaaagtcaaggattatcatgactctgttagaagacaaatcatgcagctaaatgaacaactgaaagca
gtgtatgaatttcaagatctgaaagatacaatagaaagagcaaagaatgaagcagacctcttacttgaagaccttcaggaagaaattg
atttgcaatccagtgtccttaatgcaagcattgcggactcctcagaaaacatcaagaaatattatcacatatcatcatctgctgaaaaga
aaattaatgaaactagttccaccattaatacctctgcaaatacaaggaatgacttacttaccatcttagatacactaacctcaaaaggaa
acttgtcattggaaagattaaagcagattaagataccagatatccaaatattgaatgaaaaggtgtgcggagatccaggaaatgtgcc
atgtgtgcccttgccctgtggcggtgctctctgcacgggccggaaggggcacaggaagtgtaggggtcccggctgtcacggctcc
ctgaccctctcaacgaatgccctccaaaaagcccaggaagcaaaatccattattcgtaatttggacaaacaggttcgtgggttgaaaa
atcagatcgaaagtataagtgaacaggcagaagtctccaaaaacaatgccttacagctgagggaaaaactgggaaatataagaaa
ccaaagtgactctgaagaagaaaacatcaatcttttcatcaaaaaagtgaaaaacttttgttagGTAATTTAAAAATAT
ATATTAGGACTAGTTTTTGTTTTTTTCCCTTTTTAATGTATAGTCAAACATCATA
CGTGAACCCAGGAGGCGGAGCTTGCAGTGAGCCGAGATCGCGCCACTGCACTC
CAGCCTGGGCGACAGAGCGAGACTCCGTCTCAAAAAAAAAAAAAAAAAAAAA
AAAAAAAAAAAAAAAAAAAAAAAAAAAAAAAACATCATAGCCAGTTCCAAATT
ATATTAATTGGAAATGACAAGCCTAAATCAGAAAAAA (SEQ ID NO: 48)

Representative Human LAMB4-intron retained protein sequence (coding sequence; CDS)
(intron retention shown in bold text; putative cross-reactive epitope underlined)
MQFQLTLFLHLGWLSYSKAQDDCNRGACHPTTGDLLVGRNTQLMASSTCGLSRA
QKYCILSYLEGEQKCFICDSRFPYDPYDQPNSHTIENVIVSFEPDREKKWWQSENGL
DHVSIRLDLEALFRESHLILTFKTFRPAAMLVERSTDYGHNWKVFKYFAKDCATSF
PNITSGQAQGVGDIVCDSKYSDIEPSTGGEVVLKVLDPSFEIENPYSPYIQDLVTLTN
LRINFTKLHTLGDALLGRRQNDSLDKYYYALYEMIVRGSCFCNGHASECRPMQKM
RGDVFSPPGMVHGQCVCQHNTDGPNCERCKDFFQDAPWRPAADLQDNACRSCSC TABLE 3-continued NSHSSRCHFDMTTYLASGGLSGGVCEDCQHNTEGQHCDRCRPLFYRDPLKTISDPY
ACIPCECDPDGTISGGICVSHSDPALGSVAGQCLCKENVEGAKCDQCKPNHYGLSA
TDPLGCQPCDCNPLGSLPFLTCDVDTGQCLCLSYVTGAHCEECTVGYWGLGNHLH
GCSPCDCDIGGAYSNVCSPKNGQCECRPHVTGRSCSEPAPGYFFAPLNFYLYEAEE
ATTLQGLAPLGSETFGQSPAVHVVLGEPVPGNPVTWTGPGFARVLPGAGLRFAVN
NIPFPVDFTIAIHYETQSAADWTVQIVVNPPGGSEHCIPKTLQSKPQSFALPAATRIM
LLPTPICLEPDVQYSIDVYFSQPLQGESHAHSHVLVDSLGLIPQINSLENFCSKQDLD
EYQLHNCVEIASAMGPQVLPGACERLIISMSAKLHDGAVACKCHPQGSVGSSCSRL
GGQCQCKPLVVGRCCDRCSTGSYDLGHHGCHPCHCHPQGSKDTVCDQVTGQCPC
HGEVSGRRCDRCLAGYFGFPSCHPCPCNRFAELCDPETGSCFNCGGFTTGRNCERCI
DGYYGNPSSGQPCRPCLCPDDPSSNQYFAHSCYQNLWSSDVICNCLQGYTGTQCG
ECSTGFYGNPRISGAPCQPCACNNNIDVTDPESCSRVTGECLRCLHNTQGANCQLC
KPGHYGSALNQTCRRCSCHASGVSPMECPPGGGACLCDPVTGACPCLPNVTGLAC
DRCADGYWNLVPGRGCQSCDCDPRTSQSSHCDQLTGQCPCKLGYGGKRCSECQE
NYYGDPPGRCIPCDCNRAGTQKPICDPDTGMCRCREGVSGQRCDRCARGHSQEFP
TCLQCHLCFDQWDHTISSLSKAVQGLMRLAANMEDKRETLPVCEADFKDLRGNVS
EIERILKHPVFPSGKFLKVKDYHDSVRRQIMQLNEQLKAVYEFQDLKDTIERAKNE
ADLLLEDLQEEIDLQSSVLNASIADSSENIKKYYHISSSAEKKINETSSTINTSANTRN
DLLTILDTLTSKGNLSLERLKQIKIPDIQILNEKVCGDPGNVPCVPLPCGGALCTGRK
GHRKCRGPGCHGSLTLSTNALQKAQEAKSIIRNLDKQVRGLKNQIESISEQAEVSKN
NALQLREKLGNIRNQSDSEEENINLFIKKVKNFLLGNLKIYIRTSFCFFPFLMYSQT
SYVNPGGGACSEPRSRHCTPAWATERDSVSKKKKKKKKKKKKKKKKKHHSQ
FQIILIGNDKPKSEK (SEQ ID NO: 49)

Representative Vector (the TCR-encoding protein of which can be interchanged with
any TCR sequence of interest): pTSLV102-MSCV-HA1-10-30-MGTM-Q-CD8
tggaagggctaattcactcccaaagaagacaagatatccttgatctgtggatctaccacacacaaggctacttccctgattagcagaa
ctacacaccagggccaggggtcagatatccactgacctttggatggtgctacaagctagtaccagttgagccagataaggtagaag
aggccaataaaggagagaacaccagcttgttacaccctgtgagcctgcatgggatggatgacccggagagagaagtgttagagtg
gaggtttgacagccgcctagcatttcatcacgtggcccgagagctgcatccggagtacttcaagaactgctgatatcgagcttgctac
aagggactttccgctggggactttccagggaggcgtggcctgggcgggactggggagtggcgagccctcagatcctgcatataa
gcagctgctttttgcctgtactgggtctctctggttagaccagatctgagcctgggagctctctggctaactagggaacccactgctta
agcctcaataaagcttgccttgagtgcttcaagtagtgtgtgcccgtctgttgtgtgactctggtaactagagatccctcagaccctttta
gtcagtgtggaaaatctctagcagtggcgcccgaacagggacttgaaagcgaaagggaaaccagaggagctctctcgacgcagg
actcggcttgctgaagcgcgcacggcaagaggcgaggggcggcgactggtgagtacgccaaaaattttgactagcggaggcta
gaaggagagagatgggtgcgagagcgtcagtattaagcgggggagaattagatcgcgatgggaaaaaattcggttaaggccagg
gggaaagaaaaaatataaattaaaacatatagtatgggcaagcagggagctagaacgattcgcagttaatcctggcctgttagaaac
atcagaaggctgtagacaaatactgggacagctacaaccatcccttcagacaggatcagaagaacttagatcattatataatacagta
gcaaccctctattgtgtgcatcaaaggatagagataaaagacaccaaggaagctttagacaagatagaggaagagcaaaacaaaa
gtaagaccaccgcacagcaagcggccggccgctgatcttcagacctggaggaggagatatgagggacaattggagaagtgaatt
atataaatataaagtagtaaaaattgaaccattaggagtagcacccaccaaggcaaagagaagagtggtgcagagagaaaaaaga
gcagtgggaataggagctttgttccttgggttcttgggagcagcaggaagcactatgggcgcagcgtcaatgacgctgacggtaca
ggccagacaattattgtctggtatagtgcagcagcagaacaatttgctgagggctattgaggcgcaacagcatctgttgcaactcaca
gtctggggcatcaagcagctccaggcaagaatcctggctgtggaaagatacctaaaggatcaacagctcctggggatttggggttg
ctctggaaaactcatttgcaccactgctgtgccttggaatgctagttggagtaataaatctctggaacagatttggaatcacacgacct
ggatggagtgggacagagaaattaacaattacacaagcttaatacactccttaattgaagaatcgcaaaaccagcaagaaaagaat
gaacaagaattattggaattagataaatgggcaagtttgtggaattggtttaacataacaaattggctgtggtatataaaattattcataat
gatagtaggaggcttggtaggtttaagaatagtttttgctgtactttctatagtgaatagagttaggcagggatattcaccattatcgtttc
agacccacctcccaaccccgaggggacccgacaggcccgaaggaatagaagaagaaggtggagagagagacagagacagat
ccattcgattagtgaacggatctcgacggtatcgccgaattaattcacaaatggcagtattcatccacaattttaaaagaaaagggggg
gattggggggtacagtgcaggggaaagaatagtagacataatagcaacagacatacaaactaaagaattacaaaaacaaattaca
aaaattcaaaattttcgggtttattacaggCGcGCcagagatccagtttggacCTgcAGGTGAAAGACCCCAC
CTGTAGGTTTGGCAAGtTAGCTTAAGTAACGCCATTTTGCAAGGCATGGAA
AATACATAACTGAGAATAGAGAAGTTCAGATCAAGGTTAGGAACAGAGAG
ACAGCAGAATATGGGCCAAACAGGATATCTGTGGTAAGCAGTTCCTGCCC
CGGCTCAGGGCCAAGAACAGATGGTCCCCAGATGCGGTCCCGCCCTCAGC
AGTTTCTAGCGAACCATCAGATGTTTCCAGGGTGCCCCAAGGACCTGAAAT
GACCCTGTGCCTTATTTGAACTAACCAATCAGTTtGCTTCTtGCTTCTGTTtGt
GtGCTTCTGCTCCCtGAGCTCAATAAAAGAGCCCACAACCCCTCACTtGGtGg
GCCAGTCCTCtGATAGACTGtGTCcCCtGGaTACCCGTAcggtaccgctagcgccacc*ATGGG*
*CACCAGCCTCCTCTGCTGGATGGCCCTGTGTCTCCTGGGGGCAGATCACGCAGAT*
*ACTGGAGTCTCCCAGGACCCCAGACACAAGATC ACAAAGAGGGGACAGAATGTT*
*ACTTTCAGGTGTGATCCAATTTCTGAACACAACCGCCTTTATTGGTACCGCCAGA*
*CCCTGGGGCAGGGCCCAGAGTTTCTGACTTACTTCCAGAATGAAGCTCAACTTGA*
*AAAATCAAGCTGCTCAGTGATCGGTTCTCTGCAGAGAGGCCTAAGGATCTTTC*
*TCCACCTTGGAGATCCAGCGCACAGAGCAGGGGGACTCTGCCATGTATCTCTGTG*
*CCAGCAGCCGCACTGCTGGAGATACTCAGTATTTTGGCCCAGGCACCCGGCTGA*
*CAGTGCTCGAAGATCTGAACAAGGTGTTCCCTCCAGAGGTGGCCGTGTTCGAGC*
*CTTCTaAGGCCGAGATCgccCACACaCAaAAAGCCACCCTCGTGTGCCTGGCCACC*
*GGCTTTTTCCCCGACCACGTGGAACTGTCTTGGTGGGTCAACGGCAAAGAGGTG*
*CACTCCGGCGTGtcAACgGATCCCCAGCCTCTGAAAGAACAGCCTGCCCTGAACGA*
*CAGCCGGTACTGCCTGAGCTCCAGACTGAGAGTGTCCGCCACCTTCTGGCAGAA*
*CCCCCGAACCACTTCAGATGCCAGGTGCAGTTTTACGGCCTGAGCGAGAACGA*
*CGAGTGGACCCAGGACAGAGCCAAGCCCGTGACACAAATCGTGTCTGCCGAAGC*
*CTGGGGAAG AGCCGATTGCGGCATCACCAGCGCCTCCTATCACCAGGGCGTGCT*
*GAGCGCCACAATCCTGTACGAAATCCTGCTGGGCAAGGCCACCCTGTACGCCGT*
*GCTGGTGTCTGCTCTGGTGCTGATGGCCATGGTCAAGCGGAAGGACTTTGGCAG*
*CGGC*AGAGCCAAAAGGTCCGGGAGCGGTGCGACAAACTTTAGCCTGTTGAAAC
AAGCCGGCGACGTTGAAGAGAACCCCGGACCTATGGAAACCCTCTTGGGCCT
GCTTATCCTTTGGCTGCAGCTGCAATGGGTGAGCAGCAAACAGGAGGTGA

TABLE 3-continued

CTCAGATTCCTGCAGCTCTGAGTGTCCCAGAAGGAGAAAACTTGGTTCTCA
ACTGCAGTTTCACTGATAGCGCTATTTACAACCTCCAGTGGTTTAGGCAGG
ACCCTGGGAAAGGCCTCACATCTCTGTTGCTTATTCAGTCAAGTCAGAGAG
AGCAAACAAGTGGACGCCTTAATGCCTCTCTGGATAAATCATCAGGACGCA
GTACTCTTTACATTGCAGCTTCTCAGCCTGGTGATTCAGCCACCTACCTGT
GCGCTGTGAGGGGTGGTACCTCAGGAACCTACAAATACATCTTTGGAACA
GGCACCAGGCTGAAGGTTCTTGCAAACATCCAGAACCCCGACCCCGCCGT
GTACCAGCTGAGGGACTCCAAGTCCAGCGACAAGAGCGTGTGTCTGTTTA
CGGACTTCGACAGCCAGACCAACGTGAGTCAAAGCAAGGACAGCGACGTC
TACATAACGGATAAGACCGTGCTGGACATGCGGAGCATGGACTTCAAGAG
CAACAGCGCCGTGGCCTGGTCCAACAAGAGCGACTTCGCCTGCGCCAACG
CCTTCAACAACAGCATCATCCCCGAGGACACCTTCTTCCCCAGCAGCGACG
TGCCCTGCGACGTGAAACTGGTGGAGAAGTCCTTCGAGACAGACACCAAT
CTGAACTTTCAGAACCTGCTGGTGATCGTGCTGCGGATTCTGCTGCTGAAA
GTGGCCGGCTTCAATCTGCTGATGACCCTGCGGCTGTGGAGCAGCAGGGC
TAAGAGGTCCGGCAGCGGAGCCACCAATTTTTCCCTGCTGAAACAGGCTGGTG
ACGTGGAAGAAAACCCTGGCCCCATGGCGCTGCCCGTCACCGCGCTGCTGCTG
CCCCTGGCGCTGCTGTTACACGCCGCTCGGCCA*GAGCTTCCCACCCAGGGCACAT*
*TCTCCAACGTGTCCACCAATGTGTCGGGAGGCGGCGGATCGTCCCAGTTCAGAGTG*
*TCCCCTCTGGACCGCACCTGGAACCTGGGCGAGACCGTGGAGCTGAAATGTCAGGT*
*CCTGCTGAGCAACCCGACCTCCGGGTGCAGTTGGCTGTTCCAGCCGCGTGGTGCTG*
*CCGCAAGCCCTACGTTCCTGCTTTACCTGAGCCAGAACAAGCCCAAGGCGGCCGAG*
*GGCCTGGACACCCAGAGATTCTCCGGCAAGCGCCTGGGGGACACATTCGTGCTTAC*
*TTTGAGCGATTTCCGCAGAGAGAACGAGGGCTACTATTTCTGTTCGGCGCTGAGCAA*
*TTCCATCATGTATTTCAGCCACTTTGTGCCAGTGTTCCTGCCTGCCAAGCCTACCACA*
*ACACCAGCTCCCCGTCCCCCGACTCCGGCGCCTACCATCGCGAGTCAACCGTTGAG*
*CCTGAGGCCTGAGGCTTGTCGGCCCGCTGCGGGGGGTGCCGTCCACACCAGGGGC*
*CTCGACTTTGCGTGCGACATCTATATTTGGGCGCCTCTGGCGGGTACCTGCGGGGT*
*GCTGCTGCTGTCATTGGTGATTACCCTGTACTGCAATCACCGCAACCGCCGGCGGGT*
*CTGTAAGTGCCCACGGCCTGTGGTCAAGTCCGGTGACAAACCGTCGCTCTCGGCTC*
*GCTACGTG*CGCGCTAAGCGCAGCGGTTCCGGGGCCACCAACTTTTCATTGCTGA
AGCAGGCCGGTGATGTGGAGGAGAATCCAGGGCCCATGCGCCCCAGGCTTTGG
CTCCTTCTTGCTGCTCAGCTCACTGTCTTGCATGGCAACTCCGTTCTGCAGCAGA
CTCCCGCCTACATCAAGGTGCAGACGAACAAGATGGTGATGCTGTCATGCGAG
GCCAAGATCTCTCTTTCAAATATGAGAATTTATTGGCTACGACAGCGCCAGGCC
CCCTCCAGCGACAGCCACCACGAGTTCCTGGCGCTTTGGGATTCTGCTAAAGGC
ACCATCCATGGAGAGGAGGTGGAACAGGAGAAGATAGCTGTCTTCCGCGACGC
ATCCCGCTTCATCCTGAACCTGACCAGCGTGAAGCCGGAGGACAGCGGCATCT
ACTTCTGTATGATCGTTGGCTCCCCCGAGCTGACCTTCGGCAAAGGCACCCAGC
TGTCCGTGGTGGACTTCCTGCCCACCACAGCCCAGCCAACCAAGAAATCCACCC
TCAAGAAGCGCGTGTGCCGACTGCCCCGCCCTGAAACCCAGAAGGGCCCTCTG
TGCTCCCCCATCACCCTTGGACTGCTGGTGGCGGGAGTCCTGGTGCTGCTCGTA
TCTCTGGGTGTCGCCATCCACCTGTGCTGCCGCCGCCGCCGCGCCCGCCTGAGG
TTTATGAAACAGTTTTACAAGTGATAAatcgatagatcctaatcaacctctggattacaaaatttgtgaaag
attgactggtattcttaactatgttgctccttttacgctatgtggatacgctgctttaatgcctttgtatcatgctattgcttcccgtatggcttt
cattttctcctccttgtataaatcctggttgctgtctctttatgaggagttgtggcccgttgtcaggcaacgtggcgtggtgtgcactgtgt
ttgctgacgcaacccccactggttggggcattgccaccacctgtcagctcctttccgggactttcgctttccccctccctattgccacg
gcggaactcatcgccgcctgccttgcccgctgctggacaggggctcggctgttgggcactgacaattccgtggtgttgtcggggaa
atcatcgtcctttccttggctgctcgcctgtgttgccacctggattctgcgcgggacgtccttctgctacgtcccttcggccctcaatcca
gcggaccttccttcccgcggcctgctgccggctctgcggcctcttccgcgtcttcgccttcgccctcagacgagtcggatctcccttt
gggccgcctccccgcctgagatcctttaagaccaatgacttacaaggcagctgtagatcttagccactttttaaaagaaaagggggg
actggaagggctaattcactcccaacgaagacaagatctgctttttgcttgtactgggtctctctggttagaccagatctgagcctggg
agctctctggctaactagggaacccactgcttaagcctcaataaagcttgccttgagtgcttcaagtagtgtgtgcccgtctgttgtgtg
actctggtaactagagatccctcagacccttttagtcagtgtggaaaatctctagcagtagtagttcatgtcatcttattattcagtatttat
aacttgcaaagaaatgaatatcagagagtgagaggcccgggttaattaaggaaagggctagatcattcttgaagacgaaagggcct
cgtgatacgcctatttttataggttaatgtcatgataataatggtttcttagacgtcaggtggcacttttcggggaaatgtgcgcggaacc
cctatttgtttatttttctaaatacattcaaatatgtatccgctcatgagacaataaccctgataaatgcttcaataatattgaaaaaggaag
agtatgagtattcaacatttccgtgtcgcccttattcccttttttgcggcattttgccttcctgtttttgctcacccagaaacgctggtgaaa
gtaaaagatgctgaagatcagttgggtgcacgagtgggttacatcgaactggatctcaacagcggtaagatccttgagagttttcgcc
ccgaagaacgttttccaatgatgagcacttttaaagttctgctatgtggcgcggtattatcccgtgttgacgccgggcaagagcaactc
ggtcgccgcatacactattctcagaatgacttggttgagtactcaccagtcacagaaaagcatcttacggatggcatgacagtaaga
gaattatgcagtgctgccataaccatgagtgataacactgcggccaacttacttctgacaacgatcggaggaccgaaggagctaac
cgcttttttgcacaacatgggggatcatgtaactcgccttgatcgttgggaaccggagctgaatgaagccataccaaacgacgagcg
tgacaccacgatgcctgtagcaatggcaacaacgttgcgcaaactattaactggcgaactacttactctagcttcccggcaacaatta
atagactggatggaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacgggg
agtcaggcaactatggatgaacgaaatagacagatcgctgagataggtgcctcactgattaagcattggtaactgtcagaccaagttt
actcatatatactttagattgatttaaaacttcatttttaatttaaaaggatctaggtgaagatcctttttgataatctcatgaccaaaatccctt
aacgtgagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactggcttca
gcagagcgcagataccaaatactgttcttctagtgtagccgtagttaggccaccacttcaagaactctgtagcaccgcctacatacct
cgctctgctaatcctgttaccagtggctgctgccagtggcgataagtcgtgtcttaccgggttggactcaagacgatagttaccggat
aaggcgcagcggtcgggctgaacggggggttcgtgcacacagcccagcttggagcgaacgacctacaccgaactgagatacct
acagcgtgagctatgagaaagcgccacgcttcccgaagggagaaaggcggacaggtatccggtaagcggcagggtcggaaca
ggagagcgcacgagggagcttccagggggaaacgcctggtatctttatagtcctgtcgggtttcgccacctctgacttgagcgtcg
atttttgtgatgctcgtcaggggggcggagcctatggaaaaacgccagcaacgcggcctttttacggttcctggccttttgctggcctt
ttgctcacatgttctttcctgcgttatccCCTGATTCTGTGGATAACCGTATTACCGCCTTTGAGTG
AGCTGATACCGCTCGCCGCAGCCGAACGACCGAGCGCAGCGAGTCAGTGAGCG
AGGAAGCGGAAGAGCGCCCAATACGCAAACCGCCTCTCCCCGCGCGTTGGCCG
ATTCATTAATGCAGCAAGCTCATGGCTGACTAATTTTTTTTATTTATGCAGAGGC TABLE 3-continued CGAGGCCGCCTCGGCCTCTGAGCTATTCCAGAAGTAGTGAGGAGGCTTTTTTGG
AGGCCTAGGCTTTTGCAAAAAGCTCCCCGTGGCACGACAGGTTTCCCGACTGGA
AAGCGGGCAGTGAGCGCAACGCAATTAATGTGAGTTAGCTCACTCATTAGGCA
CCCCAGGCTTTACACTTTATGCTTCCGGCTCGTATGTTGTGTGGAATTGTGAGCG
GATAACAATTTCACACAGGAAACAGCTATGACATGATTACGAATTTCACAAAT
AAAGCATTTTTTTCACTGCATTCTAGTTGTGGTTTGTCCAAACTCATCAATGTAT
CTTATCATGTCTGGATCAACTGGATAACTCAAGCTAACCAAAATCATCCCAAAC
TTCCCACCCCATACCCTATTACCACTGCCAATTACCTGTGGTTTCATTTACTCTA
AACCTGTGATTCCTCTGAATTATTTTCATTTTAAAGAAATTGTATTTGTTAAATA
TGTACTACAAACTtagtagt (SEQ ID NO: 50)

Representative Vector (the TCR-encoding protein of which can be interchanged with any TCR sequence of interest): pHAGE-MSCV-HN-P32-41-P2A-dnTGFbRII (with dnTGFbRII highlighted in bold text)

tggaagggctaattcactcccaaagaagacaagatatccttgatctgtggatctaccacacacaaggctacttccctgattagcagaa
ctacacaccagggccaggggtcagatatccactgacctttggatggtgctacaagctagtaccagttgagccagataaggtagaag
aggccaataaaggagagaacaccagcttgttacaccctgtgagcctgcatgggatggatgacccggagagagaagtgttagagtg
gaggtttgacagccgcctagcatttcatcacgtggcccgagagctgcatccggagtacttcaagaactgctgatatcgagcttgctac
aagggactttccgctggggactttccagggaggcgtggcctgggcgggactggggagtggcgagccctcagatcctgcatataa
gcagctgctttttgcctgtactgggtctctctggttagaccagatctgagcctgggagctctctggctaactagggaacccactgctta
agcctcaataaagcttgccttgagtgcttcaagtagtgtgtgcccgtctgttgtgtgactctggtaactagagatccctcagacccttta
gtcagtgtggaaaatctctagcagtggcgcccgaacagggacttgaaagcgaaagggaaaccagaggagctctctcgacgcagg
actcggcttgctgaagcgcgcacggcaagaggcgaggggcggcgactggtgagtacgccaaaaattttgactagcggaggcta
gaaggagagagatgggtgcgagagcgtcagtattaagcgggggagaattagatcgcgatgggaaaaaattcggttaaggccagg
gggaaagaaaaaatataaattaaaacatatagtatgggcaagcagggagctagaacgattcgcagttaatcctggcctgttagaaac
atcagaaggctgtagacaaatactgggacagctacaaccatcccttcagacaggatcagaagaacttagatcattatataatacagta
gcaaccctctattgtgtgcatcaaaggatagagataaaagacaccaaggaagctttagacaagatagaggaagagcaaaacaaaa
gtaagaccaccgcacagcaagcggccggccgctgatcttcagacctggaggaggagatatgagggacaattggagaagtgaatt
atataaatataaagtagtaaaaattgaaccattaggagtagcacccaccaaggcaaagagaagagtggtgcagagagaaaaaaga
gcagtgggaataggagctttgttccttgggttcttgggagcagcaggaagcactatgggcgcagcgtcaatgacgctgacggtaca
ggccagacaattattgtctggtatagtgcagcagcagaacaatttgctgagggctattgaggcgcaacagcatctgttgcaactcaca
gtctggggcatcaagcagctccaggcaagaatcctggctgtggaaagatacctaaaggatcaacagctcctggggatttggggttg
ctctggaaaactcatttgcaccactgctgtgccttggaatgctagttggagtaataaatctctggaacagatttggaatcacacgacct
ggatggagtgggacagagaaattaacaattacacaagcttaatacactccttaattgaagaatcgcaaaaccagcaagaaaagaat
gaacaagaattattggaattagataaatgggcaagtttgtggaattggtttaacataacaaattggctgtggtatataaaattattcataat
gatagtaggaggcttggtaggtttaagaatagtttttgctgtactttctatagtgaatagagttaggcagggatattcaccattatcgtttc
agacccacctcccaaccccgaggggacccgacaggcccgaaggaatagaagaagaaggtggagagagagacagagacagat
ccattcgattagtgaacggatctcgacggtatcgccgaattaattcacaaatggcagtattcatccacaattttaaaagaaaagggg
gattggggggtacagtgcaggggaaagaatagtagacataatagcaacagacatacaaactaaagaattacaaaaacaaattaca
aaaattcaaaattttcgggtttattacaggCGcGCcagagatccagtttggacCTgcAGGTGAAAGACCCCACC
TGTAGGTTTGGCAAGtTAGCTTAAGTAACGCCATTTTGCAAGGCATGGAAAATA
CATAACTGAGAATAGAGAAGTTCAGATCAAGGTTAGGAACAGAGAGACAGCA
GAATATGGGCCAAACAGGATATCTGTGGTAAGCAGTTCCTGCCCCGGCTCAGG
GCCAAGAACAGATGGTCCCCAGATGCGGTCCCGCCCTCAGCAGTTTCTAGCGA
ACCATCAGATGTTTCCAGGGTGCCCCAAGGACCTGAAATGACCCTGTGCCTTAT
TTGAACTAACCAATCAGTTtGCTTCTtGCTTCTGTTtGtGtGCTTCTGCTCCCtGAGC
TCAATAAAAGAGCCCACAACCCCTCACTtGGtGgGCCAGTCCTCtGATAGACTGtG
TCcCCtGGaTACCCGTAcggtaccgctagcgccaccATGGGCTCCTGGACCCTCTGCTGTGT
GTCCCTTTGCATCCTGGTTGCAAAGCACACAGATGCTGGAGTTATCCAGTCACC
CCGGCACGAGGTGACAGAGATGGGACAAGAAGTGACTCTGAGATGTAAACCA
ATTTCAGGACATGACTACCTTTTCTGGTACAGACAGACCATGATGCGGGGACTG
GAGTTGCTCATTTACTTTAACAACAACGTTCCTATTGATGATTCAGGGATGCCC
GAGGATCGCTTCTCAGCTAAGATGCCTAATGCATCATTCTCCACTCTGAAGATC
CAGCCCTCAGAACCCAGGGACTCAGCTGTGTACTTCTGTGCCAGCAGTTTTCTC
GGCTGGAATGAAAAACTGTTCTTTGGCAGTGGAACCCAGCTCTCTGTCTTGGAA
GATCTGAACAAGGTGTTCCCTCCAGAGGTGGCCGTGTTCGAGCCTTCTaAGGCC
GAGATCgccCACACaCAaAAAGCCACCCTCGTGTGCCTGGCCACCGGCTTTTTCCC
CGACCACGTGGAACTGTCTTGGTGGGTCAACGGCAAAGAGGTGCACTCCGGCG
TGtcAACgGATCCCCAGCCTCTGAAAGAACAGCCTGCCCTGAACGACAGCCGGT
ACTGCCTGAGCTCCAGACTGAGAGTGTCCGCCACCTTCTGGCAGAACCCCCGGA
ACCACTTCAGATGCCAGGTGCAGTTTTACGGCCTGAGCGAGAACGACGAGTGG
ACCCAGGACAGAGCCAAGCCCGTGACACAAATCGTGTCTGCCGAAGCCTGGGG
AAGAGCCGATTGCGGCATCACCAGCGCCTCCTATCACCAGGGCGTGCTGAGCG
CCACAATCCTGTACGAAATCCTGCTGGGCAAGGCCACCCTGTACGCCGTGCTGG
TGTCTGCTCTGGTGCTGATGGCCATGGTCAAGCGGAAGGACTTTGGCAGCGGCA
GAGCCAAAAGGTCCGGGAGCGGTGCGACAAACTTTAGCCTGTTGAAACAAGCC
GGCGACGTTGAAGAGAACCCCGGACCTATGGTCCTGAAATTCTCCGTGTCCATT
CTTTGGATTCAGTTGGCATGGGTGAGCACCCAGCTGCTGGAGCAGAGCCCTCAG
TTTCTTAGCATCCAAGAGGGAGAAAATCTCACTGTGTACTGCAACTCCTCAAGT
GTTTTCTCCAGCCTTCAATGGTACAGACAGGAGCCTGGGGAAGGTCCTGTCCTC
CTGGTGACAGTTGTTACTGGTGGAGAAGTGAAGAAGCTGAAGAGACTTACCTT
TCAGTTTGGTGATGCAAGAAAGGACAGTTCTCTCCACATCACTGCAGCCCAGCC
TGGTGATACAGGCCTCTACCTCTGTGCAGGAGATGAAAGTATTAGCTATGGAA
AGCTGACATTTGGACAAGGGACCATCTTGACTGTCCATCCAAacatccagaaccccgacc
ccgccgtgtaccagctgagggactccaagtccagcgacaagagcgtgtgtctgtttacggacttcgacagccagaccaacgtgag
tcaaagcaaggacagcgacgtctacataacggataagaccgtgctggacatgcggagcatggacttcaagagcaacagcgccgt
ggcctggtccaacaagagcgacttcgcctgcgccaacgccttcaacaacagcatcatccccgaggacaccttcttccccagcagc
gacgtgccctgcgacgtgaaactggtggagaagtccttcgagacagacaccaatctgaactttcagaacctgctggtgatcgtgctg
cggattctgctgCTGAAAGTGGCCGGCTTCAATCTGCTGATGACCCTGCGGCTGTGGA
GCAGCAGGGCTAAGAGGTCCGGCAGCGGAGCCACCAATTTTTCCCTGCTGAAA TABLE 3-continued CAGGCTGGTGACGTGGAAGAAAACCCTGGCCCCATGGGTCGGGGGCTGCTCA
GGGGCCTGTGGCCGCTGCACATCGTCCTGTGGACGCGTATCGCCAGCACG
ATCCCACCGCACGTTCAGAAGTCGGTTAATAACGACATGATAGTCACTGAC
AACAACGGTGCAGTCAAGTTTCCACAACTGTGTAAATTTTGTGATGTGAGA
TTTTCCACCTGTGACAACCAGAAATCCTGCATGAGCAACTGCAGCATCACC
TCCATCTGTGAGAAGCCACAGGAAGTCTGTGTGGCTGTATGGAGAAAGAA
TGACGAGAACATAACACTAGAGACAGTTTGCCATGACCCCAAGCTCCCCTA
CCATGACTTTATTCTGGAAGATGCTGCTTCTCCAAAGTGCATTATGAAGGA
AAAAAAAAAGCCTGGTGAGACTTTCTTCATGTGTTCCTGTAGCTCTGATGA
GTGCAATGACAACATCATCTTCTCAGAAGAATATAACACCAGCAATCCTGA
CTTGTTGCTAGTCATATTTCAAGTGACAGGCATCAGCCTCCTGCCACCACT
GGGAGTTGCCATATCTGTCATCATCATCTTCTACTGCTACCGCGTTaaccggca
gcagaagTAGTGATAAatcgatagatcctaatcaacctctggattacaaaatttgtgaaagattgactggtattcttaactatgt
tgctccttttacgctatgtggatacgctgctttaatgcctttgtatcatgctattgcttcccgtatggctttcattttctcctccttgtataaatc
ctggttgctgtctctttatgaggagttgtggcccgttgtcaggcaacgtggcgtggtgtgcactgtgtttgctgacgcaacccccactg
gttggggcattgccaccacctgtcagctcctttccgggactttcgctttccccctccctattgccacggcggaactcatcgccgcctgc
cttgcccgctgctggacaggggctcggctgttgggcactgacaattccgtggtgttgtcggggaaatcatcgtcctttccttggctgct
cgcctgtgttgccacctggattctgcgcgggacgtccttctgctacgtcccttcggccctcaatccagcggaccttccttcccgcggc
ctgctgccggctctgcggcctcttccgcgtcttcgccttcgccctcagacgagtcggatctccctttgggccgcctccccgcctgaga
tcctttaagaccaatgacttacaaggcagctgtagatcttagccactttttaaaagaaaaggggggactggaagggctaattcactcc
caacgaagacaagatctgctttttgcttgtactgggtctctctggttagaccagatctgagcctgggagctctctggctaactagggaa
cccactgcttaagcctcaataaagcttgccttgagtgcttcaagtagtgtgtgcccgtctgttgtgtgactctggtaactagagatccct
cagacccttttagtcagtgtggaaaatctctagcagtagtagttcatgtcatcttattattcagtatttataacttgcaaagaaatgaatatc
agagagtgagaggcccgggttaattaaggaaagggctagatcattcttgaagacgaaagggcctcgtgatacgcctatttttatagg
ttaatgtcatgataataatggtttcttagacgtcaggtggcacttttcggggaaatgtgcgcggaacccctatttgtttatttttctaaatac
attcaaatatgtatccgctcatgagacaataaccctgataaatgcttcaataatattgaaaaaggaagagtatgagtattcaacatttccg
tgtcgcccttattcccttttttgcggcattttgccttcctgtttttgctcacccagaaacgctggtgaaagtaaaagatgctgaagatcagtt
gggtgcacgagtgggttacatcgaactggatctcaacagcggtaagatccttgagagttttcgccccgaagaacgttttccaatgatg
agcacttttaaagttctgctatgtggcgcggtattatcccgtgttgacgccgggcaagagcaactcggtcgccgcatacactattctca
gaatgacttggttgagtactcaccagtcacagaaaagcatcttacggatggcatgacagtaagagaattatgcagtgctgccataac
catgagtgataacactgcggccaacttacttctgacaacgatcggaggaccgaaggagctaaccgcttttttgcacaacatggggg
atcatgtaactcgccttgatcgttgggaaccggagctgaatgaagccataccaaacgacgagcgtgacaccacgatgcctgtagca
atggcaacaacgttgcgcaaactattaactggcgaactacttactctagcttcccggcaacaattaatagactggatggaggcggata
aagttgcaggaccacttctgcgctcggcccttccggctggctggtttattgctgataaatctggagccggtgagcgtgggtctcgcg
gtatcattgcagcactggggccagatggtaagccctcccgtatcgtagttatctacacgacggggagtcaggcaactatggatgaac
gaaatagacagatcgctgagataggtgcctcactgattaagcattggtaactgtcagaccaagtttactcatatatactttagattgattt
aaaacttcatttttaatttaaaaggatctaggtgaagatcctttttgataatctcatgaccaaaatcccttaacgtgagttttcgttccactga
gcgtcagaccccgtagaaaagatcaaaggatcttcttgagatcctttttttctgcgcgtaatctgctgcttgcaaacaaaaaaaccacc
gctaccagcggtggtttgtttgccggatcaagagctaccaactctttttccgaaggtaactggcttcagcagagcgcagataccaaat
actgttcttctagtgtagccgtagttaggccaccacttcaagaactctgtagcaccgcctacatacctcgctctgctaatcctgttacca
gtggctgctgccagtggcgataagtcgtgtcttaccgggttggactcaagacgatagttaccggataaggcgcagcggtcgggctg
aacggggggttcgtgcacacagcccagcttggagcgaacgacctacaccgaactgagatacctacagcgtgagctatgagaaag
cgccacgcttcccgaagggagaaaggcggacaggtatccggtaagcggcagggtcggaacaggagagcgcacgagggagct
tccagggggaaacgcctggtatctttatagtcctgtcgggtttcgccacctctgacttgagcgtcgatttttgtgatgctcgtcaggggg
gcggagcctatggaaaaacgccagcaacgcggcctttttacggttcctggccttttgctggccttttgctcacatgttctttcctgcgtta
tccCCTGATTCTGTGGATAACCGTATTACCGCCTTTGAGTGAGCTGATACCGCTCG
CCGCAGCCGAACGACCGAGCGCAGCGAGTCAGTGAGCGAGGAAGCGGAAGAG
CGCCCAATACGCAAACCGCCTCTCCCCGCGCGTTGGCCGATTCATTAATGCAGC
AAGCTCATGGCTGACTAATTTTTTTTATTTATGCAGAGGCCGAGGCCGCCTCGG
CCTCTGAGCTATTCCAGAAGTAGTGAGGAGGCTTTTTTGGAGGCCTAGGCTTTT
GCAAAAAGCTCCCCGTGGCACGACAGGTTTCCCGACTGGAAAGCGGGCAGTGA
GCGCAACGCAATTAATGTGAGTTAGCTCACTCATTAGGCACCCCAGGCTTTACA
CTTTATGCTTCCGGCTCGTATGTTGTGTGGAATTGTGAGCGGATAACAATTTCA
CACAGGAAACAGCTATGACATGATTACGAATTTCACAAATAAAGCATTTTTTTC
ACTGCATTCTAGTTGTGGTTTGTCCAAACTCATCAATGTATCTTATCATGTCTGG
ATCAACTGGATAACTCAAGCTAACCAAAATCATCCCAAACTTCCCACCCCATAC
CCTATTACCACTGCCAATTACCTGTGGTTTCATTTACTCTAAACCTGTGATTCCT
CTGAATTATTTTCATTTTAAAGAAATTGTATTTGTTAAATATGTACTACAAACTta
gtagt (SEQ ID NO: 51)

Representative Vector (the TCR-encoding protein of which can be interchanged with any TCR sequence of interest): pNVVD142_TSC-204-C07_TCR-41_MSCV-TCR41-CD8-EF1a-TGFR-DHFR GAATTCGTCGACGCTAGCTGGCTTGTTGTCCACAACCATTAAACCTTAAAAGCT
TTAAAAGCCTTATATATTCTTTTTTTTCTTATAAAACTTAAAACCTTAGAGGCTA
TTTAAGTTGCTGATTTATATTAATTTTATTGTTCAAACATGAGAGCTTAGTACGT
GAAACATGAGAGCTTAGTACATTAGCCATGAGAGCTTAGTACATTAGCCATGA
GGGTTTAGTTCATTAAACATGAGAGCTTAGTACATTAAACATGAGAGCTTAGTA
CATACTATCAACAGGTTGAACTGCTGATCTGTACAGTAGAATTGGTAAAGAGA
GTTGTGTAAAATATTGAGTTCGCACATCTTGTTGTCTGATTATTGATTTTTGGCG
AAACCATTTGATCATATGACAAGATGTGTATCTACCTTAACTTAATGATTTTGA
TAAAAATCATTAGGTACCAATTACATTGCTTGCAATTAACCCTTTAACGGTTAT
AAGGATCTAGATGAGATAGAAAGATTTGGTTTTCGGATTTGTGTTACATAAGAT
GCCTAAAATAAAAATTGAGATTCAATTTTTTTTAAACTTTTTTTTAATTGGTGGT
AAGAATATTCCCTCTACCTGTTTGAGAGTAATGAAATTGTAGTATGATTTTTCA
ACAAACTAAAAAAACAACATAAATCTCACATAATAACTTTATTTCAATCACACA
ATTGAATACCAATAGGTTGACAGTACTTACCAGCCTGCAGGTGAAAGACCCCA
CCTGTAGGTTTGGCAAGTTAGCTTAAGTAACGCCATTTTGCAAGGCATGGA
AAATACATAACTGAGAATAGAGAAGTTCAGATCAAGGTTAGGAACAGAGA
GACAGCAGAATATGGGCCAAACAGGATATCTGTGGTAAGCAGTTCCTGCC

TABLE 3-continued

CCGGCTCAGGGCCAAGAACAGATGGTCCCCAGATGCGGTCCCGCCCTCAG
CAGTTTCTAGCGAACCATCAGATGTTTCCAGGGTGCCCCAAGGACCTGAAA
TGACCCTGTGCCTTATTTGAACTAACCAATCAGTTTGCTTCTTGCTTCTGTT
TGTGTGCTTCTGCTCCCTGAGCTCAATAAAAGAGCCCACAACCCCTCACTT
GGTGGGCCAGTCCTCTGATAGACTGTGTCCCCTGGATACCCGTACGGTACC
GCTAGCGCCACCATGGGCTCCTGGACCCTCTGCTGTGTGTCCCTTTGCATCCTGG
TTGCAAAGCACACAGATGCTGGAGTTATCCAGTCACCCCGGCACGAGGTGACAG
AGATGGGACAAGAAGTGATCTGAGATGTAAACCAATTTCAGGACATGACTACCT
TTTCTGGTACAGACAGACCATGATGCGGGACTGGAGTTGCTCATTTACTTCAAC
AACAACGTTCCTATTGATGATTCAGGGATGCCCGAGGATCGCTTCTCAGCTAAGA
TGCCTAATGCATCATTCTCCACTCTGAAGATCCAGCCCTCAGAACCCAGGGACTC
AGCTGTGTACTTCTGTGCCAGCAGTTTTCTCGGCTGGAATGAAAAACTGTTCTTT
GGCAGTGGAACCCAGCTCT CTGTCTTGGAAGATCTGAACAAGGTGTTCCCTCCAG
AGGTGGCCGTGTTCGAGCCTTCTAAGGCCGAGATCGCCCACACACAAAAAGCCA
CCCTCGTGTGCCTGGCCACCGGCTTTTTCCCCGACCACGTGGAACTGTCTTGGTG
GGTCAACGGCAAAGAGGTGCACTCCGGCGTGTCAACGGATCCCCAGCCTCTGAA
AGAACAGCCTGCCCTGAACGACAGCCGGTACTGCCTGAGCTCCAGACTGAGAGT
GTCCGCCACCTTCTGGCAGAACCCCCGGAACCACTTCAGATGCCAGGTGCAGTTT
TACGGCCTGAGCGAGAACGACGAGTGGACCCAGGACAGAGCCAAGCCCGTGACA
CAAATCGTGTCTGCCGAAGCCTGGGGAAGAGCCGATTGCGGCATCAGCAGCGCC
TCCTATCACCAGGGCGTGCTGAGCGCCACAATCCTGTACGAAATCCTGCTGGGCA
AGGCCACCCTGTACGCCGTGCTGGTGTCTGCTCTGGTGCTGATGGCCATGGTCAA
GCGGAAGGACTTTGGCAGCGGC AGAGCCAAAAGGTCCGGGAGCGGTGCGACAA
ACTTTAGCCTGTTGAAACAAGCCGGCGACGTTGAAGAGAACCCCGGACCTATG
GTCCTGAAATTCTCCGTGTCCATTCTTTGGATTCAGTTGGCATGGGTGAGC
ACCCAGCTGCTGGAGCAGAGCCCTCAGTTTCTTAGCATCCAAGAGGGAGA
AAATCTCACTGTGTACTGCAACTCCTCAAGTGTTTTCTCCAGCCTTCAATG
GTACAGACAGGAGCCTGGGGAAGGTCCTGTCCTCCTGGTGACAGTTGTTA
CTGGTGGAGAAGTGAAGAAGCTGAAGAGACTTACCTTTCAGTTTGGTGAT
GCAAGAAAGGACAGTTCTCTCCACATCACTGCAGCCCAGCCTGGTGATAC
AGGCCTCTACCTCTGTGCAGGAGATGAAAGTATTAGCTATGGAAAGCTGA
CATTTGGACAAGGGACCATCTTGACTGTCCATCCAAACATCCAGAACCCCG
ACCCCGCCGTGTACCAGCTGAGGGACTCCAAGTCCAGCGACAAGAGCGTG
TGTCTGTTTACGGACTTCGACAGCCAGACCAACGTGAGTCAAAGCAAGGA
CAGCGACGTCTACATAACGGATAAGACCGTGCTGGACATGCGGAGCATGG
ACTTCAAGAGCAACAGCGCCGTGGCCTGGTCCAACAAGAGCGACTTCGCC
TGCGCCAACGCCTTCAACAACAGCATCATCCCCGAGGACACCTTCTTCCCC
AGCAGCGACGTGCCCTGCGACGTGAAACTGGTGGAGAAGTCCTTCGAGAC
AGACACCAATCTGAACTTTCAGAACCTGCTGGTGATCGTGCTGCGGATTCT
GCTGCTGAAAGTGGCCGGCTTCAATCTGCTGATGACCCTGCGGCTGTGGA
GCAGCAGGGCTAAGAGGTCCGGCAGCGGAGCCACCAATTTTTCCCTGCTGAAA
CAGGCTGGTGACGTGGAAGAAAACCCTGGCCCCATGGCGCTGCCCGTCACCGCG
CTGCTGCTGCCCCTGGCGCTGCTGTTACACGCCGCTCGGCCAGAGCTTCCCACCCA
GGGCACATTCTCCAACGTGTCCACCAATGTGTCGGGAGGCGGCGGATCGTCCCAGT
TCAGAGTGTCCCCTCTGGACCGCACCTGGAACCTGGGCGAGACCGTGGAGCTGAAA
TGTCAGGTCCTGCTGAGCAACCCGACCTCCGGGTGCAGTTGGCTGTTCCAGCCGCG
TGGTGCTGCCGCAAGCCCTACGTTCCTGCTTTACCTGAGCCAGAACAAGCCCAAGGC
GGCCGAGGGCCTGGACACCCAGAGATTCTCCGGCAAGCGCCTGGGGGACACATTC
GTGCTTACTTTGAGCGATTTCCGCAGAGAGAACGAGGGCTACTATTTCTGTTCGGCG
CTGAGCAATTCCATCATGTATTTCAGCCACTTTGTGCCAGTGTTCCTGCCTGCCAAGC
CTACCACAACACCAGCTCCCCGTCCCCCGACTCCGGCGCCTACCATCGCGAGTCAA
CCGTTGAGCCTGAGGCCTGAGGCTTGTCGGCCCGCTGCGGGGGGTGCCGTCCACA
CCAGGGGCCTCGACTTTGCGTGCGACATCTATATTTGGGCGCCTCTGGCGGGTACC
TGCGGGGTGCTGCTGCTGTCATTGGTGATTACCCTGTACTGCAATCACCGCAACCGC
CGGCGGGTCTGTAAGTGCCCACGGCCTGTGGTCAAGTCCGGTGACAAACCGTCGCT
CTCGGCTCGCTACGTGCGCGCTAAGCGCAGCGGTTCCGGGGCCACCAACTTTTC
ATTGCTGAAGCAGGCCGGTGATGTGGAGGAGAATCCAGGGCCCATGCGCCCCA
GGCTTTGGCTCCTTCTTGCTGCTCAGCTCACTGTCTTGCATGGCAACTCCGTTCT
GCAGCAGACTCCCGCCTACATCAAGGTGCAGACGAACAAGATGGTGATGCTGT
CATGCGAGGCCAAGATCTCTCTTTCAAATATGAGAATTTATTGGCTACGACAGC
GCCAGGCCCCCTCCAGCGACAGCCACCACGAGTTCCTGGCGCTTTGGGATTCTG
CTAAAGGCACCATCCATGGAGAGGAGGTGGAACAGGAGAAGATAGCTGTCTTC
CGCGACGCATCCCGCTTCATCCTGAACCTGACCAGCGTGAAGCCGGAGGACAG
CGGCATCTACTTCTGTATGATCGTTGGCTCCCCCGAGCTGACCTTCGGCAAAGG
CACCCAGCTGTCCGTGGTGGACTTCCTGCCCACCACAGCCCAGCCAACCAAGA
AATCCACCCTCAAGAAGCGCGTGTGCCGACTGCCCCGCCCTGAAACCCAGAAG
GGCCCTCTGTGCTCCCCCATCACCCTTGGACTGCTGGTGGCGGGAGTCCTGGTG
CTGCTCGTATCTCTGGGTGTCGCCATCCACCTGTGCTGCCGCCGCCGCCGCGCC
CGCCTGAGGTTTATGAAACAGTTTTACAAGTGATAAATCGATGGAAGGGTGGC
ATCCCTGTGACCCCTCCCCAGTGCCTCTCCTGGCCCTGGAAGTTGCCACTCCAG
TGCCCACCAGCCTTGTCCTAATAAAATTAAGTTGCATCATTTTGTCTGACTAGGT
GTCCTTCTATAATATTATGGGGTGGAGGGGGGTGGTATGGAGCAAGGGGCAAG
TTGGGAAGACAACCTGTAGGGCCTGCGGGGTCTATTGGGAACCAAGCTGGAGT
GCAGTGGCACAATCTTGGCTCACTGCAATCTCCGCCTCCTGGGTTCAAGCGATT
CTCCTGCCTCAGCCTCCCGAGTTGTTGGGATTCCAGGCATGCATGACCAGGCTC
AGCTAATTTTTGTTTTTTTGGTAGAGACGGGGTTTCACCATATTGGCCAGGCTG
GTCTCCAACTCCTAATCTCAGGTGATCTACCCACCTTGGCCTCCCAAATTGCTG
GGATTACAGGCGTGAACCACTGCTCCCTTCCCTGTCCTTCTGATTACTAGTGGCT
CCGGTGCCCGTCAGTGGGCAGAGCGCACATCGCCCACAGTCCCCGAGAAGTTG
TGGGGAGGGGTCGGCAATTGAACCGGTGCCTAGAGAAGGTGGCGCGGGGTAA

TABLE 3-continued

| |
|---|
| ACTGGGAAAGTGATGTCGTGTACTGGCTCCGCCTTTTTCCCGAGGGTGGGGGAG |
| AACCGTATATAAGTGCAGTAGTCGCCGTGAACGTTCTTTTTCGCAACGGGTTTG |
| CCGCCAGAACACAGGTAAGTGCCGTGTGTGGTTCCCGCGGGCCTGGCCTCTTTA |
| CGGGTTATGGCCCTTGCGTGCCTTGAATTACTTCCACCTGGCTGCAGTACGTGA |
| TTCTTGATCCCGAGCTTCGGGTTGGAAGTGGGTGGGAGAGTTCGAGGCCTTGCG |
| CTTAAGGAGCCCCTTCGCCTCGTGCTTGAGTTGAGGCCTGGCCTGGGCGCTGGG |
| GCCGCCGCGTGCGAATCTGGTGGCACCTTCGCGCCTGTCTCGCTGCTTTCGATA |
| AGTCTCTAGCCATTTAAAATTTTTGATGACCTGCTGCGACGCTTTTTTTCTGGCA |
| AGATAGTCTTGTAAATGCGGGCCAAGATCTGCACACTGGTATTTCGGTTTTTGG |
| GGCCGCGGGCGGCGACGGGGCCCGTGCGTCCCAGCGCACATGTTCGGCGAGGC |
| GGGGCCTGCGAGCGCGGCCACCGAGAATCGGACGGGGGTAGTCTCAAGCTGGC |
| CGGCCTGCTCTGGTGCCTGGCCTCGCGCCGCCGTGTATCGCCCCGCCCTGGGCG |
| GCAAGGCTGGCCCGGTCGGCACCAGTTGCGTGAGCGGAAAGATGGCCGCTTCC |
| CGGCCCTGCTGCAGGGAGCTCAAAATGGAGGACGCGGCGCTCGGGAGAGCGG |
| GCGGGTGAGTCACCCACACAAAGGAAAAGGGCCTTTCCGTCCTCAGCCGTCGC |
| TTCATGTGACTCCACGGAGTACCGGGCGCCGTCCAGGCACCTCGATTAGTTCTC |
| GAGCTTTTGGAGTACGTCGTCTTTAGGTTGGGGGGAGGGGTTTTATGCGATGGA |
| GTTTCCCCACACTGAGTGGGTGGAGACTGAAGTTAGGCCAGCTTGGCACTTGAT |
| GTAATTCTCCTTGGAATTTGCCCTTTTTGAGTTTGGATCTTGGTTCATTCTCAAG |
| CCTCAGACAGTGGTTCAAAGTTTTTTTCTTCCATTTCAGGTGTCGTGAACTAGTC |
| CAGTGTGGTGGAATTCTGCAGATATCACGGCTAGCGCCACCATGGGTCGGGGG |
| CTGCTCAGGGGCCTGTGGCCGCTGCACATCGTCCTGTGGACGCGTATCGCCAGC |
| ACGATCCCACCGCACGTTCAGAAGTCGGTGAATAACGACATGATAGTCACTGA |
| CAACAACGGTGCAGTCAAGTTTCCACAACTGTGTAAATTTTGTGATGTGAGATT |
| TTCCACCTGTGACAACCAGAAATCCTGCATGAGCAACTGCAGCATCACCTCCAT |
| CTGTGAGAAGCCACAGGAAGTCTGTGTGGCTGTATGGAGAAAGAATGACGAGA |
| ACATAACACTAGAGACAGTTTGCCATGACCCCAAGCTCCCCTACCATGACTTTA |
| TTCTGGAAGATGCTGCTTCTCCAAAGTGCATTATGAAGGAGAAGAAAAAGCCT |
| GGTGAGACTTTCTTCATGTGTTCCTGTAGCTCTGATGAGTGCAATGACAACATC |
| ATCTTCTCAGAAGAATATAACACCAGCAATCCTGACTTGTTGCTAGTCATATTT |
| CAAGTGACAGGCATCAGCCTCCTGCCACCACTGGGAGTTGCCATATCTGTCATC |
| ATCATCTTCTACTGCTACCGCGTGAACCGGCAGCAGAAGGCTAGTGGTTCAGGC |
| GCAACGAATTTCTCTTTGCTGAAGCAGGCTGGGGATGTCGAAGAAAATCCGGG |
| TCCAATGGTGGGCTCGCTCAACTGCATCGTAGCAGTCTCCCAGAATATGGGCAT |
| CGGGAAGAACGGTGATTTCCCGTGGCCCCCACTTCGCAACGAGAGCCGTTATTT |
| CCAAAGAATGACTACAACCTCCTCCGTGGAGGGTAAGCAGAACCTGGTCATCA |
| TGGGGAAGAAGACCTGGTTCTCTATCCCTGAAAAAAACCGCCCCCTGAAGGGC |
| CGCATCAACCTGGTGCTGAGCAGGGAACTCAAGGAGCCTCCTCAGGGCGCGCA |
| TTTTCTGAGCCGCTCATTGGATGACGCTCTCAAACTGACCGAACAGCCGGAGCT |
| AGCCAACAAGGTGGACATGGTGTGGATCGTCGGAGGCTCCTCCGTGTACAAGG |
| AGGCCATGAATCACCCCGGCCACTTGAAGCTGTTCGTCACCCGGATCATGCAGG |
| ACTTCGAGTCGGACACGTTCTTTCCAGAGATTGACCTGGAGAAGTACAAGCTGC |
| TGCCCGAGTACCCGGGAGTTCTTAGTGATGTGCAGGAGGAGAAAGGCATCAAG |
| TACAAATTTGAGGTGTACGAGAAGAACGACTAACGGTCCGTCCTGACCAATGC |
| TGGAGTTCTTCGCCCACCCCAACTTGTTTATTGCAGCTTATAATGGTTACAAATA |
| AAGCAATAGCATCACAAATTTCACAAATAAAGCATTTTTTTCACTGCATTCTAG |
| TTGTGGTTTGTCCAAACTCATCAATGTATCTTATCATGTCTGTATACAGGTTACC |
| TCAGTCTCCTAGGTACGTCTTATATCTATGAAAAAACATTCAAAAGCACAACAT |
| CTAGAAGAACTTACCTTTTTTCACCACTCTATTGCAAAGATATGTACCGATTTCT |
| CTCGAAGTACAAAAAACCGCTAGTTTTCAAATTCACCTCAAGACTTTGAAAAAA |
| AATTGAATCTGTCAATGTCAAATAAAATCAGAAACAAATGTCATAATGTTACGT |
| TAATGTTGTCAGGTCGAAAAATAAAATTGCAAATAGAAATTTTGTTCCTTTTTT |
| ATTGGTTTTTATTGGTGGAAAAATATTCCCTCTAACTGCAAAAGGGTTAATTA |
| TGTTAGAGGTAGAGTCGACAAGCTT (SEQ ID NO: 52) |

*For certain depicted vectors, MSCV promoter is in bold. Beta chain is annotated using bold and italic text. Alpha chain is annotated using bold and underlined text. CD34-enrichment tag (Q tag) is annotated using italic and underlined text. CD8-alpha is in italic. CD8-beta is underlined.

*Included in Tables 1-3 are peptide epitopes, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any sequences listed in Table 1, or a portion thereof. Such polypeptides may have a function of the full-length peptide or polypeptide as described further herein.

*Included in Tables 2 and 3 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any sequence listed in Tables 2 or 3, or a portion thereof. Such nucleic acid molecules can have a function of the full-length nucleic acid as described further herein.

In some embodiments, the binding proteins provided herein comprise a constant region that is chimeric, humanized, human, primate, or rodent (e.g., rat or mouse). For example, a human variable region may be chimerized with a murine constant region or a murine variable region may be humanized with a human constant region and/or human framework regions. In some embodiments, the constant regions may be mutated to modify functionality (e.g., introduction of non-naturally occurring cysteine substitutions in opposing residue locations in TCR alpha and beta chains to provide disulfide bonds useful for increasing affinity between the TCR alpha and beta chains). Similarly, mutations may be made in the transmembrane domain of the constant region to modify functionality (e.g., to increase hydrophobicity by introducing a non-naturally occurring substitution of a residue with a hydrophobic amino acid). In some embodiments, each CDR of the binding protein has up to five amino acid substitutions, insertions, deletions, or a combination thereof as compared to a reference CDR sequence. In some embodiments, mutations may be made to the constant region to increase cell surface expression.

In some embodiments, the binding proteins disclosed herein may be engineered protein scaffolds, an antibody or an antigen-binding fragment thereof, TCR-mimic antibodies, and the like. Such binding moieties may be designed and/or generated against peptides and/or MHC-peptide complexes described herein using routine immunological methods, such as immunizing a host, obtaining antibody-producing cells and/or antibodies thereof, and generating hybridomas useful for producing monoclonal antibodies (e.g., Watt et al. (2006) *Nat. Biotechnol.* 24:177-183; Gebauer and Skerra (2009) *Curr. Opin. Chem Biol.* 13:245-255; Skerra et al. (2008) *FEBS J.* 275:2677-2683; Nygren et al. (2008) *FEBS J.* 275:2668-2676; Dana et al. (2012) *Exp. Rev. Mol. Med.* 14:e6; Sergeva et al. (2011) *Blood* 117:4262-4272; PCT Publ. Nos. WO 2007/143104, PCT/US86/02269, and WO 86/01533; U.S. Pat. No. 4,816,567; Better et al. (1988) *Science* 240:1041-1043; Liu et al. (1987) *Proc. Natl. Acad. Sci. U.S.A.* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060. If desired, binding moieties may be isolated or purified using conventional procedures such as, for example, protein A-Sepharose, hydroxylapatite chromatography, gel electrophoresis, dialysis, affinity chromatography, ammonium sulfate or ethanol precipitation, acid extraction, anion or cation exchange chromatography, phosphocellulose chromatography, hydrophobic interaction chromatography, hydroxylapatite chromatography, lectin chromatography, and high performance liquid chromatography (HPLC) (e.g., Current Protocols in Immunology, or *Current Protocols in Protein Science*, John Wiley & Sons, NY, N.Y.).

The terms “antibody” and “antibodies” broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin $V_L$ domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publ. Nos. WO 08/020079, WO 94/02610, WO 95/22618, and WO 03/014960; U.S. Pat. No. 7,004,940; Cattaneo and Biocca (1997) *Intracellular Antibodies: Development and Applications* (*Landes and* Springer-Verlag pubis.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term “antibody” as used herein also includes an “antigen-binding portion” of an antibody (or simply “antibody portion”). The term “antigen-binding portion”, as used herein, refers to one or more fragments of an antibody that retain the ability to specifically and/or selectively bind to an antigen (e.g., a peptide and/or an MHC-peptide complex described herein). It has been shown that the antigen-binding function of an antibody can be performed by fragments of a full-length antibody. Examples of binding fragments encompassed within the term “antigen-binding portion” of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term “antigen-binding portion” of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, protein subunit peptide and a C-terminal polyhistidine tag to make bivalent and biotinylated scFv polypeptides (Kipriyanov et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically and/or selectively or substantially specifically and/or selectively to a peptide and/or an MHC-peptide complex described herein. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Similar to other binding moieties described herein, antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitrolex vivo or by somatic mutation in vivo), for example in the CDRs. The term "humanized antibody", as used herein, also includes antibodies in which CDR sequences derived from the germline of another mammalian species, have been grafted onto human framework sequences.

In some embodiments, the binding proteins disclosed herein may comprise a T cell receptor (TCR), an antigen-binding fragment of a TCR, or a chimeric antigen receptor (CAR). In some embodiments, the binding protein disclosed herein may comprise two polypeptide chains, each of which comprises a variable region comprising a CDR3 of a TCR alpha chain and a CDR3 of a TCR beta chain, or a CDR1, CDR2, and CDR3 of both a TCR alpha chain and a TCR beta chain. In some embodiments, a binding protein comprises a single chain TCR (scTCR), which comprises both the TCR $V_\alpha$ and TCR $V_\beta$ domains, but only a single TCR constant domain ($C_\alpha$ or $C_\beta$). The term "chimeric antigen receptor" (CAR) refers to a fusion protein that is engineered to contain two or more naturally-occurring amino acid sequences linked together in a way that does not occur naturally or does not occur naturally in a host cell, which fusion protein can function as a receptor when present on a surface of a cell. CARs encompassed by the present invention may include an extracellular portion comprising an antigen-binding domain (i.e., obtained or derived from an immunoglobulin or immunoglobulin-like molecule, such as an antibody or TCR, or an antigen binding domain derived or obtained from a killer immunoreceptor from an NK cell) linked to a transmembrane domain and one or more intracellular signaling domains (optionally containing co-stimulatory domain(s)) (see, e.g., Sadelain et al. (2013) *Cancer Discov.* 3:388, Harris and Kranz (2016) *Trends Pharmacol. Sci.* 37:220, and Stone et al. (2014) *Cancer Immunol. Immunother.* 63:1163).

In some embodiments, 1) the TCR alpha chain CDR, TCR $V_\alpha$ domain, and/or TCR alpha chain is encoded by a TRAY, TRAJ, and/or TRAC gene or fragment thereof selected from the group of TRAY, TRAJ, and TRAC genes listed in Table 2, and/or 2) the TCR beta chain CDR, TCR $V_\beta$ domain, and/or TCR beta chain is encoded by a TRBV, TRBJ, and/or TRBC gene or fragment thereof selected from the group of TRBV, TRBJ, and TRBC genes listed in Table 2, and/or 3) each CDR of the binding protein has up to five amino acid substitutions, insertions, deletions, or a combination thereof as compared to the cognate reference CDR sequence listed in Table 2.

In some embodiments, the binding proteins (e.g., the TCR, antigen-binding fragment of a TCR, or chimeric antigen receptor (CAR)) disclosed herein is chimeric (e.g., comprises amino acid residues or motifs from more than one donor or species), humanized (e.g., comprises residues from a non-human organism that are altered or substituted so as to reduce the risk of immunogenicity in a human), or human.

Methods for producing engineered binding proteins, such as TCRs, CARs, and antigen-binding fragments thereof, are well-known in the art (e.g., Bowerman et al. (2009) *Mol. Immunol.* 5:3000; U.S. Pat. Nos. 6,410,319; 7,446,191; U.S. Pat. Publ. No. 2010/065818; U.S. Pat. No. 8,822,647; PCT Publ. No. WO 2014/031687; U.S. Pat. No. 7,514,537; and Brentjens et al. (2007) *Clin. Cancer Res.* 73:5426).

In some embodiments, the binding protein described herein is a TCR, or antigen-binding fragment thereof, expressed on a cell surface, wherein the cell surface-expressed TCR is capable of more efficiently associating with a CD3 protein as compared to endogenous TCR. A binding protein encompassed by the present invention, such as a TCR, when expressed on the surface of a cell like a T cell, may also have higher surface expression on the cell as compared to an endogenous binding protein, such as an endogenous TCR. In some embodiments, provided herein is a CAR, wherein the binding domain of the CAR comprises an antigen-specific TCR binding domain (see, e.g., Walseng et al. (2017) *Scientific Reports* 7:10713).

Also provided are modified binding proteins (e.g., TCRs, antigen-binding fragments of TCRs, or CARs) that may be prepared according to well-known methods using a binding protein having one or more of the $V_\alpha$ and/or $V_\beta$ sequences disclosed herein as starting material to engineer a modified binding protein that may have altered properties from the starting binding protein. A binding protein may be engineered by modifying one or more residues within one or both variable regions (i.e., $V_\alpha$ and/or $V_\beta$), for example within one or more CDR regions and/or within one or more framework regions. Additionally or alternatively, a binding protein may be engineered by modifying residues within the constant region(s).

Another type of variable region modification is to mutate amino acid residues within the $V_\alpha$ and/or $V_\beta$ CDR1, CDR2 and/or CDR3 regions to thereby improve one or more binding properties (e.g., affinity) of the binding protein of interest. Site-directed mutagenesis or PCR-mediated mutagenesis may be performed to introduce the mutation(s) and the effect on protein binding, or other functional property of interest, may be evaluated in in vitro, ex vivo, or in vivo assays as described herein and provided in the Examples. In some embodiments, conservative modifications (as discussed above) may be introduced. The mutations may be amino acid substitutions, additions or deletions. In some embodiments, the mutations are substitutions. Moreover, typically no more than one, two, three, four or five residues within a CDR region are modified.

In some embodiments, binding proteins (e.g., TCRs, antigen-binding fragments of TCRs, or CARs) described herein may possess one or more amino acid substitutions, deletions, or additions relative to a naturally occurring TCR. In some embodiments, each CDR of the binding protein has up to five amino acid substitutions, insertions, deletions, or a combination thereof as compared to the cognate reference CDR sequence listed in Table 2. Conservative substitutions of amino acids are well-known and may occur naturally or may be introduced when the binding protein is recombinantly produced Amino acid substitutions, deletions, and additions may be introduced into a protein using mutagenesis methods known in the art (see, e.g., Sambrook et al. (2001) *Molecular Cloning: A Laboratory Manual,* 3d ed., Cold Spring Harbor Laboratory Press, NY). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al. supra).

A variety of criteria known to the ordinarily skilled artisan indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In some embodiments, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS™, Align, the BLAST algorithm, or other algorithms described herein and practiced in the art).

In some embodiments, an encoded binding protein (e.g., TCR, antigen-binding fragment of a TCR, or CAR) may comprise a "signal peptide" (also known as a leader sequence, leader peptide, or transit peptide). Signal peptides target newly synthesized polypeptides to their appropriate location inside or outside the cell. A signal peptide may be removed from the polypeptide during or once localization or secretion is completed. Polypeptides that have a signal peptide are referred to herein as a "pre-protein" and polypeptides having their signal peptide removed are referred to herein as "mature" proteins or polypeptides. In some embodiments, a binding protein (e.g., TCR, antigen-binding fragment of a TCR, or CAR) described herein comprises a mature $V_\alpha$ domain, a mature $V_\beta$ domain, or both. In some embodiments, a binding protein (e.g., TCR, antigen-binding fragment of a TCR, or CAR) described herein comprises a mature TCR β-chain, a mature TCR α-chain, or both.

In some embodiments, the binding proteins are fusion proteins comprising: (a) an extracellular component comprising a TCR or antigen-binding fragment thereof; (b) an intracellular component comprising an effector domain or a functional portion thereof; and (c) a transmembrane domain connecting the extracellular and intracellular components. In some embodiments, the fusion protein is capable of binding (e.g., specifically and/or selectively) to a peptide-MHC (pMHC) complex comprising a MAGEA1 immunogenic peptide in the context of an MHC molecule (e.g., an MHC class I molecule).

As used herein, an "effector domain" or "immune effector domain" is an intracellular portion or domain of a fusion protein or receptor that can directly or indirectly promote an immune response in a cell when receiving an appropriate signal. In some embodiments, an effector domain is from an immune cell protein or portion thereof or immune cell protein complex that receives a signal when bound (e.g., CD3ξ), or when the immune cell protein or portion thereof or immune cell protein complex binds directly to a target molecule and triggers signal transduction from the effector domain in an immune cell.

An effector domain may directly promote a cellular response when it contains one or more signaling domains or motifs, such as an intracellular tyrosine-based activation motif (ITAM), such as those found in costimulatory molecules. Without wishing to be bound by theory, it is believed that ITAMs are useful for T cell activation following ligand engagement by a T cell receptor or by a fusion protein comprising a T cell effector domain. In some embodiments, the intracellular component or functional portion thereof comprises an ITAM. Exemplary immune effector domains include but are not limited to those from, CD3ε, CD3δ, CD3ξ, CD25, CD79A, CD79B, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, Wnt, ROR2, Ryk, SLAMF1, Slp76, pTα, TCRα, TCRβ, TRIM, Zap70, PTCH2, or any combination thereof. In some embodiments, an effector domain comprises a lymphocyte receptor signaling domain (e.g., CD3ξ or a functional portion or variant thereof).

In further embodiments, the intracellular component of the fusion protein comprises a costimulatory domain or a functional portion thereof selected from CD27, CD28, 4-1BB (CD137), OX40 (CD134), CD2, CD5, ICAM-1 (CD54), LFA-1 (CD11a/CD18), ICOS (CD278), GITR, CD30, CD40, BAFF-R, HVEM, LIGHT, MKG2C, SLAMF7, NKp80, CD160, B7-H3, a ligand that binds (e.g., specifically and/or selectively) with CD83, or a functional variant thereof, or any combination thereof. In some embodiments, the intracellular component comprises a CD28 costimulatory domain or a functional portion or variant thereof (which may optionally include a LL-GG mutation at positions 186-187 of the native CD28 protein (e.g., Nguyen et al. (2003) *Blood* 702:4320), a 4-1BB costimulatory domain or a functional portion or variant thereof, or both.

In some embodiments, an effector domain comprises a CD3ε endodomain or a functional (e.g., signaling) portion thereof, or a functional variant thereof. In further embodiments, an effector domain comprises a CD27 endodomain or a functional (e.g., signaling) portion thereof, or a functional variant thereof. In further embodiments, an effector domain comprises a CD28 endodomain or a functional (e.g., signaling) portion thereof, or a functional variant thereof. In still further embodiments, an effector domain comprises a 4-1BB endodomain or a functional (e.g., signaling) portion thereof, or a functional variant thereof. In further embodiments, an effector domain comprises an OX40 endodomain or a functional (e.g., signaling) portion thereof, or a functional variant thereof. In further embodiments, an effector domain comprises a CD2 endodomain or a functional (e.g., signaling) portion thereof, or a functional variant thereof. In further embodiments, an effector domain comprises a CD5 endodomain or a functional (e.g., signaling) portion thereof, or a functional variant thereof. In further embodiments, an effector domain comprises an ICAM-1 endodomain or a functional (e.g., signaling) portion thereof, or a functional variant thereof. In further embodiments, an effector domain comprises a LFA-1 endodomain or a functional (e.g., signaling) portion thereof, or a functional variant thereof. In further embodiments, an effector domain comprises an ICOS endodomain or a functional (e.g., signaling) portion thereof, or a functional variant thereof.

An extracellular component and an intracellular component encompassed by the present invention are connected by a transmembrane domain. A "transmembrane domain," as used herein, is a portion of a transmembrane protein that can insert into or span a cell membrane. Transmembrane domains have a three-dimensional structure that is thermodynamically stable in a cell membrane and generally range in length from about 15 amino acids to about 30 amino acids. The structure of a transmembrane domain may comprise an alpha helix, a beta barrel, a beta sheet, a beta helix, or any combination thereof. In some embodiments, the transmembrane domain comprises or is derived from a known transmembrane protein (e.g., a CD4 transmembrane domain, a CD8 transmembrane domain, a CD27 transmembrane domain, a CD28 transmembrane domain, or any combination thereof).

In some embodiments, the extracellular component of the fusion protein further comprises a linker disposed between the binding domain and the transmembrane domain. As used herein when referring to a component of a fusion protein that connects the binding and transmembrane domains, a "linker" may be an amino acid sequence having from about two amino acids to about 500 amino acids, which can provide flexibility and room for conformational movement between two regions, domains, motifs, fragments, or modules connected by the linker. For example, a linker encompassed by the present invention can position the binding domain away from the surface of a host cell expressing the fusion protein to enable proper contact between the host cell and a target cell, antigen binding, and activation (Patel et al. (1999) *Gene Therapy* 6:412-419). Linker length may be varied to maximize antigen recognition based on the selected target molecule, selected binding epitope, or antigen binding domain seize and affinity (see, e.g., Guest et al. (2005) *Immunother.* 28:203-11 and PCT Publ. No. WO 2014/031687). Exemplary linkers include those having a glycine-serine amino acid chain having from one to about ten repeats of $Gly_xSer_y$, wherein x and y are each independently an integer from 0 to 10 (SEQ ID NO: 53), provided that x and y are not both 0 (e.g., $(Gly_4Ser)_2$ (SEQ ID NO: 54), $(Gly_3Ser)_2$ (SEQ ID NO: 55), $Gly_2Ser$, or a combination thereof, such as $((Gly_3Ser)_2Gly_2Ser$ (SEQ ID NO: 56))).

A binding protein may be conjugated to an agent, such as a detection moiety, readiosensitizer, photosensitizer, and the like, and/or may be chemically modified as described above regarding peptides.

In any of the herein disclosed embodiments, the encoded binding protein is capable of bind to a peptide-MHC (pMHC) complex comprising a MAGEA1 immunogenic peptide in the context of an MHC molecule (e.g., an MHC class I molecule).

A variety of assays are well-known for assessing binding affinity and/or determining whether a binding molecule binds (e.g., specifically and/or selectively) to a particular ligand (e.g., peptide antigen-MHC complex). It is within the level of a skilled artisan to determine the binding affinity of a binding protein for a target, such as a T cell peptide epitope of a target polypeptide, such as by using any of a number of binding assays that are well-known in the art. For example, in some embodiments, a Biacore™ machine may be used to determine the binding constant of a complex between two proteins. The dissociation constant ($K_D$) for the complex may be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy and surface plasmon resonance (Biacore™) analysis (see, e.g., Scatchard et al. (1949) *Ann. N.Y. Acad. Sci.* 51:660, Wilson (2002) *Science* 295:2103, Wolff et al. (1993) *Cancer Res.* 53:2560, and U.S. Pat. Nos. 5,283,173 and 5,468,614), flow cytometry, sequencing and other methods for detection of expressed nucleic acids. In one example, apparent affinity for a target is measured by assessing binding to various concentrations of tetramers, for example, by flow cytometry using labeled multimers, such as MHC-antigen tetramers. In one representative example, apparent $K_D$ of a binding protein is measured using 2-fold dilutions of labeled tetramers at a range of concentrations, followed by determination of binding curves by non-linear regression, apparent $K_D$ being determined as the concentration of ligand that yielded half-maximal binding.

VI. Nucleic Acids and Vectors

In an aspect encompassed by the present invention, provided herein are nucleic acid molecules that encode proteins described herein, such as MAGEA1 immunogenic peptides and fragments thereof, MHC molecules, binding proteins (e.g., TCRs, antigen-binding fragments of the TCRs, CARs, and the like), and the like.

In some embodiments, the nucleic acid molecule hybridizes, under stringent conditions, with the complement of a sequence with at least about at least about 80%, 81%, 82%, 83%, 84%, 85%, 86%, 87%, 88%, 89%, 90%, 91%, 92%, 93%, 94%, 95%, 96%, 97%, 98%, 99%, or more identity, such as over the full length, to a nucleic acid encoding a polypeptide selected from the group consisting of the polypeptide sequences listed in Tables 1-3.

In some embodiments, the nucleic acid molecule hybridizes, under stringent conditions, with the complement of a nucleic acid encoding a polypeptide selected from the group consisting of polypeptide sequences listed in Tables 1-3.

In some embodiments, the nucleic acid molecule comprises (e.g., comprises, consists essentially of, or consists of) a nucleotide sequence encoding a polypeptide selected from the group consisting of polypeptide sequences listed in Tables 1-3.

In some embodiments, the nucleic acid sequence encodes a MAGEA1 immunogenic peptides described herein.

In some embodiments, the nucleic acids comprise (e.g., comprise, consist essentially of, or consist of) a nucleotide sequence encoding at least one (e.g., one, two, or three) TCR α-chain CDR set forth in Table 2. In some embodiments, the nucleic acids comprise (e.g., comprise, consist essentially of, or consist of) a nucleotide sequence encoding a TCR $V_{\alpha}$ domain having an amino acid sequence that is at least about at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR $V_{\alpha}$ domain sequence set forth in Table 2. In some embodiments, the nucleic acids comprise (e.g., comprise, consist essentially of, or consist of) a nucleotide sequence encoding a TCR α-chain having an amino acid sequence that is at least about at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR α-chain sequence set forth in Table 2.

In some embodiments, the nucleic acids comprise (e.g., comprise, consist essentially of, or consist of) a nucleotide sequence encoding at least one (e.g., one, two, or three) TCR β-chain CDR set forth in Table 2. In some embodiments, the nucleic acids comprise (e.g., comprise, consist essentially of, or consist of) a nucleotide sequence encoding a TCR $V_{\beta}$ domain having an amino acid sequence that is at least about at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR $V_{\beta}$ domain sequence set forth in Table 2. In some embodiments, the nucleic acids comprise (e.g., comprise, consist essentially of, or consist of) a nucleotide sequence encoding a TCR β-chain having an amino acid sequence that is at least about at least about 80%, 81%, 82%, 83%, 84%, 85%, 86%, 87%, 88%, 89%, 90%, 91%, 92%, 93%, 94%, 95%, 96%, 97%, 98%, 99%, or more identity to a TCR β-chain sequence set forth in Table 2.

The term "nucleic acid" includes "polynucleotide," "oligonucleotide," and "nucleic acid molecule," and generally means a polymer of DNA or RNA, which may be single-stranded or double-stranded, synthesized or obtained (e.g., isolated and/or purified) from natural sources, which may contain natural, non-natural or altered nucleotides, and which may contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA).

In some embodiments, the nucleic acids encompassed by the present invention are recombinant. As used herein, the term "recombinant" refers to (i) molecules that are constructed outside living cells by joining natural or synthetic nucleic acid segments to nucleic acid molecules that may replicate in a living cell, or (ii) molecules that result from the replication of those described in (i) above. For purposes herein, the replication may be in vitro, ex vivo, or in vivo replication.

The nucleic acids can be constructed based on chemical synthesis and/or enzymatic ligation reactions using procedures known in the art. See, for example, Green and Sambrook et al. supra. For example, a nucleic acid may be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that may be used to generate the nucleic acids include, but are not limited to, 5-fiuorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids encompassed by the present invention can be purchased from companies, such as Integrated DNA Technologies (Coralville, IA).

In one embodiment, the nucleic acid comprises a codon-optimized nucleotide sequence. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In some embodiments, the nucleotide sequences described herein are codon-optimized for expression in a host cell (e.g., an immune cell, such as a T cell).

The present invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically and/or selectively hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions may be rendered more stringent by the addition of increasing amounts of formamide The present invention also provides a nucleic acid comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, or more identical to any of the nucleic acids described herein.

Typically, said nucleic acid is a DNA or RNA molecule, which may be included in a suitable vector, such as a plasmid, cosmid, episome, artificial chromosome, phage or a viral vector.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Thus, a further object encompassed by the present invention relates to a vector comprising a nucleic acid encompassed by the present invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell may be used. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other representative examples of plasmids include replicating plasmids comprising an origin of replication, or integrative plasmids, such as for instance pUC, pcDNA, pBR, and the like. Representative examples of viral vector include adenoviral, retroviral, lentiviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv-positive cells, 293 cells, etc. Detailed protocols for producing such replication-defective recombinant viruses are well-known in the art and may be found, for instance, in PCT Publ. WO 95/14785, PCT. Publ. WO 96/22378, U.S. Pat. Nos. 5,882,877, 6,013,516, 4,861,719, 5,278,056, and PCT Publ. WO 94/19478.

In some embodiments, the expression vector is a nanoplasmid. The term "nanoplasmid" used herein refers to a circular DNA sequence having a reduced bacterial sequence that provides a smaller plasmid with a desired cargo insert. The reduced size of the vector is associated with limited DNA-induced toxicity upon transfection, potentially longer duration in cells, potentially better viability after transfection, and potentially higher transposition efficiency. In some embodiments, the nanoplasmid is an antibiotic resistance marker-free nanoplasmid. In some embodiments, the nanoplasmid comprises a selection marker and/or nonsense suppressor marker. Due to the small backbone size, <500 by backbone, such nanoplasmids maximize the size of the desired cargo insert. The desired cargo insert (e.g., a eukaryotic transgene) can be any size that can be delivered into target cells, e.g., up to 50 kb, 45 kb, 40 kb, 35 kb, 30 kb, 25 kb, 20 kb, 18 kb, 15 kb, 12 kb, 10 kb, 5.0 kb, 4.5 kb, 4.0 kb, 3.5 kb, 3.0 kb, 2.8 kb, 2.5 kb, 2.2 kb, 2 kb, 1.8 kb, 1.5 kb, 1.2 kb, 1 kb, or any range in between, inclusive, such as 8-12 kb. They also provide high transgene expression and reduce transgene silencing, with a tunable integration efficiency of the cargo associated with random integration of the cargo in the genome of engineered cells.

In some embodiments, the nanoplasmid may comprise elements shown in vectors provided in Table 3 R6K and RNA-OUT). For example, in some embodiments, a nanoplasmid comprises a minimized bacterial ColE1 or R6K origin of replication (which provides for such nanoplasmids to be replicable in a bacterial host strain), a selectable marker (e.g., a bacterial RNA-selectable marker), and a eukaryotic gene region. An RNA selectable marker is a vector-borne expressed non-translated RNA that regulates a chromosomally expressed target gene to afford selection of the vector. This may be a plasmid borne nonsense suppressing tRNA that regulates a nonsense suppressible selectable chromosomal target, such as described in U.S. Pat. No. 6,977,174 and incorporated herein by reference. 'This may also be a plasmid-borne antisense repressor RNA, an RNA-OUT gene that represses RNA-IN regulated targets, pMB1 plasmid origin encoded RNAI that represses RNAII regulated targets, IncB plasmid pMU720 origin encoded RNAI that represses RNA II regulated targets, ParB locus Sok. of plasmid RI that represses Hok regulated targets, Elm locus FlmB of F plasmid that represses flmA regulated targets, an natural antisense repressor RNA such as those described in e.g., Wagner et al. (2002) *Adv. Genet.* 46:361 and Franch and Gerdes (2000) *Current Opin. Microbiol.* 3:159, or an engineered repressor RNA, such as a small synthetic small RNA like the SgrS, MicC, or MicF scaffolds as described in Park el al. (2013) *Nature Biotechnology* 31:170-174.

Exemplary nanoplasmids produced by an antibiotic free RNA-OUT selection system and methods of making such nanoplasmids are described in e.g., PCT Publ. No. WO 2008153733, U.S. Pat. No. 9,737,620, U.S. Pat. Publ. No. 2010/0303859, and U.S. Pat. No. 9,109,012, which are hereby incorporated by reference in their entirety. Additional exemplary nanoplasmids are described in e.g., PCT Appl. Nos. PCT/US2013/0002'59, PCT/US2013/00067 and PCT/US2013/00068, and U.S. Pat. Publ. No. 2015/0275221, each of which is hereby incorporated by reference in their entirety.

Nanoplasmids are commercially available. For example, Nature Technology Corporation, a subsidiary of Aldevron, provides nanoplasmid vectors combining an RNA selectable marker with a R6K, ColE2, or ColE2-related replication origin. These nanoplasmid vectors include, e.g., NTC9385C, NTC9685C, NTC9385R, NTC9685R vectors, as well as modifications thereof, such as those disclosed in PCT Appl. No. PCT/US2013/00068; NTC9385R-BE, NTC9385Ra-01 and NTC9385Ra-O2 vectors, such as described in U.S. Pat. No. 10,144,935; and NTC9385C2, NTC9385C2a, NTC9385R2, NTC9385R2a, NTC9385R2b, NTC9385Ra, NTC9385RaF and NTC9385RbF replicative minicircle vectors such as described in U.S. Pat. Publ. No. 2021/0189407, each of which is hereby incorporated by reference in their entirety.

In some embodiments, the composition comprises an expression vector comprising an open reading frame encoding a binding protein or a polypeptide described herein or a fragment thereof. In some embodiments, the nucleic acid includes regulatory elements necessary for expression of the open reading frame. Such elements may include, for example, a promoter, an initiation codon, a stop codon, and a polyadenylation signal. In addition, enhancers may be included. These elements may be operably linked to a sequence that encodes the binding protein, polypeptide or fragment thereof.

In some embodiments, the vector further comprises nucleic acid sequence encoding CD8α, CD8β, a dominant negative TGFβ receptor (e.g., a DN-TGFβRII), selectable protein marker, optionally wherein the selectable protein marker is dihydrofolate reductase (DHFR). In certain embodiments, the nucleic acid sequence encoding CD8α, CD8β, the DN-TGFβR, and/or the selectable protein marker is operably linked to a nucleic acid encoding a tag (e.g., a CD34 enrichment tag). In specific embodiments, a nucleic acid sequence described herein, such as a nucleic acid sequence encoding a TCRα, TCRβ. CD8α, CD8β, DN-TGFβR, and/or selectable protein marker are interconnected with an internal ribosome entry site or a nucleic acid sequence encoding a self-cleaving peptide, such as P2A, E2A, F2A or T2A, etc.

In some embodiments, the expression vector provided herein comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, or more identical to any of the nucleic acids set forth in Tables 1-3.

As described above, representative examples of promoters include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein. Examples of suitable polyadenylation signals include but are not limited to SV40 polyadenylation signals and LTR polyadenylation signals.

In addition to the regulatory elements required for expression, other elements may also be included in the nucleic acid molecule. Such additional elements include enhancers. Enhancers include the promoters described herein. In some embodiments, enhancers/promoters include, for example, human actin, human myosin, human hemoglobin, human muscle creatine and viral enhancers such as those from CMV, RSV and EBV.

In some embodiments, the nucleic acid may be operably incorporated in a carrier or delivery vector as described further below. Useful delivery vectors include but are not limited to biodegradable microcapsules, immuno-stimulating complexes (ISCOMs) or liposomes, and genetically engineered attenuated live carriers such as viruses or bacteria.

In some embodiments, the vector is a viral vector, such as lentiviruses, retroviruses, herpes viruses, adenoviruses, adeno-associated viruses, vaccinia viruses, baculoviruses, Fowl pox, AV-pox, modified vaccinia Ankara (MVA) and other recombinant viruses. For example, a lentivirus vector may be used to infect T cells.

In some embodiments, the recombinant expression vector is capable of delivering a polynucleotide to an appropriate host cell, for example, a T cell or an antigen-presenting cell, i.e., a cell that displays a peptide/MHC complex on its cell surface (e.g., a dendritic cell) and lacks CD8. In some embodiments, the host cell is a hematopoietic progenitor cell or a human immune system cell. For example, the immune system cell may be a CD4+ T cell, a CD8+ T cell, a CD4/CD8 double negative T cell, a gd T cell, a natural killer cell, a dendritic cell, or any combination thereof. In some embodiments, wherein a T cell is the host, the T cell may be naive, a central memory T cell, an effector memory T cell, or any combination thereof. The recombinant expression vectors may therefore also include, for example, lymphoid tissue-specific transcriptional regulatory elements (TREs), such as a B lymphocyte, T lymphocyte, or dendritic cell specific TREs. Lymphoid tissue specific TREs are known in the art (see, e.g., Thompson et al. (1992) *Mol. Cell. Biol.* 72:1043, Todd et al. (1993) *J. Exp. Med.* 777:1663, and Penix et al. (1993) *J. Exp. Med.* 775:1483).

In some embodiments, a recombinant expression vector comprises a nucleotide sequence encoding a TCR α chain, a TCR β chain, and/or a linker peptide. For example, in some embodiments, the recombinant expression vector comprises a nucleotide sequence encoding the full-length TCR alpha and TCR beta chains of the binding protein with a linker positioned between them, wherein the nucleotide sequence encoding the beta chain is positioned 5' of the nucleotide sequence encoding the alpha chain. In some embodiments, the nucleotide sequence encodes the full-length TCR alpha and TCR beta chains with a linker positioned between them, wherein the nucleotide sequence encoding the TCR beta chain is positioned 3' of the nucleotide sequence encoding the TCR alpha chain. In some embodiments, the full-length TCR alpha and/or TCR beta chains are replaced with fragments thereof.

As described further below, another aspect encompassed by the present invention relates to a cell which has been transfected, infected or transformed by a nucleic acid and/or a vector in accordance with the present invention. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods (see, e.g., Sambrook el al. (1989) *Molecular Cloning: A Laboratory Manual* 2d ed. (Cold Spring Harbor Laboratory)). The term "transformation" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed."

For example, in some embodiments, engineered immune cells (e.g., T cells) may comprise pan T cells (both $CD4^+$ and $CD8^+$ T cells) engineered by transposon/transposase-mediated gene delivery to express a genetic cargo coding for elements such as the alpha and beta chains of a recombinant T cell receptor (TCR) specific to a given target antigen presented on a particular MHC (e.g., class I HLA). Additional elements can be expressed by the vector, such as one or more elements selected from the group consisting of a) CD8a and CD8β co-receptors to enable engagement of CD4+ T cells; b) a CD34-derived QBEND/10 epitope tag fused to the amino-terminus of CD8a to enable tracking of engineered cells in vitro and in vivo; c) a dominant-negative type II TGFβ receptor (DN-TGFβRII) to overcome tumor-mediated immune suppression; and d) a selection marker, such as a mutated form of dihydrofolate reductase (DHFRdm) to facilitate enrichment of engineered cells during the manufacturing process. The α and β chains of the exogenous TCR and the α and β chains of CD8 may be encoded by a single mRNA molecule under control of a single promoter, such as a murine stem cell virus (MSCV) promoter. Post-translational processing at self-cleaving peptide elements, such as P2A sites, can result in independent polypeptides, such as to produce the individual four polypeptides corresponding to each element in the vector. Similarly, DN-TGFβRII and DHFRdm may be encoded by a single mRNA molecule driven by a single promoter, such as the human elongation factor 1a (EF1a) promoter. Post-translational processing at self-cleaving peptide elements, such as P2A sites, can result in independent polypeptides, corresponding to each individual element in the vector.

The nucleic acids encompassed by the present invention may be used to produce a recombinant polypeptide encompassed by the present invention in a suitable expression system. The term "expression system" means a host cell and compatible vector under suitable conditions, e.g., for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al (1980), rat YB2/3HL.P2.G11.16Ag.20 cell (ATCC CRL 1662, hereinafter referred to as "YB2/0 cell"), and the like. In some embodiments, the YB2/0 cell is used since ADCC activity of chimeric or humanized binding proteins is enhanced when expressed in this cell.

The present invention also encompasses methods of producing a recombinant host cell expressing binding proteins, peptides and fragments thereof encompassed by the present invention, said method comprising the steps consisting of (i) introducing in vitro or ex vivo a recombinant nucleic acid or a vector as described above into a competent host cell, (ii) culturing in vitro or ex vivo the recombinant host cell obtained and (iii), optionally, selecting the cells which express said binding proteins, peptides and fragments thereof. Such recombinant host cells may be used for the diagnostic, prognostic, and/or therapeutic method encompassed by the present invention.

In another aspect, as described above, the present invention provides isolated nucleic acids that hybridize under selective hybridization conditions to a polynucleotide disclosed herein. Thus, the polynucleotides of this embodiment may be used for isolating, detecting, and/or quantifying nucleic acids comprising such polynucleotides. For example, polynucleotides encompassed by the present invention may be used to identify, isolate, or amplify partial or full-length clones in a deposited library. In some embodiments, the polynucleotides are genomic or cDNA sequences isolated, or otherwise complementary to, a cDNA from a human or mammalian nucleic acid library. In some embodiments, the cDNA library comprises at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or any range in between, inclusive, such as at least about 80%-100%, full-length sequences. The cDNA libraries may be normalized to increase the representation of rare sequences. Low or moderate stringency hybridization conditions are typically, but not exclusively, employed with sequences having a reduced sequence identity relative to complementary sequences. Moderate and high stringency conditions may optionally be employed for sequences of greater identity. Low stringency conditions allow selective hybridization of sequences having about 70% sequence identity and may be employed to identify orthologous or paralogous sequences. Optionally, polynucleotides encompassed by the present invention will encode at least a portion of a binding protein encoded by the polynucleotides described herein. The polynucleotides encompassed by the present invention embrace nucleic acid sequences that may be employed for selective hybridization to a polynucleotide encoding a binding protein encompassed by the present invention (see, e.g., Ausubel, supra and Colligan, supra).

VII. Engineered Cells

In an aspect encompassed by the present invention, provided herein are host cells that express proteins described herein, such as MAGEA1 immunogenic peptides, MAGEA1 immunogenic peptide-MHC (pMHC) complexes, MAGEA1 binding proteins (e.g., TCRs, antigen-binding fragments of TCRs, CARs, or fusion proteins comprising a TCR and an effector domain), and the like described herein. In some embodiments, the host cells comprise the nucleic acids or vectors described herein.

In some embodiments, a polynucleotide encoding a binding protein is used to transform, transfect, or transduce a host cell (e.g., a T cell) for use in adoptive transfer therapy. Advances in nucleic acid sequencing and particular TCR sequencing have been described (e.g., Robins et al. (2009) *Blood* 114:4099; Robins et al. (2010) *Sci. Translat. Med.* 2:47ra64, Robins et al. (2011) *J. Imm. Meth.*, and Warren et al. (2011) *Genome Res.* 21:790) and may be employed in the course of practicing embodiments encompassed by the present invention. Similarly, methods for transfecting or transducing T cells with desired nucleic acids are well-known in the art (e.g., U.S. Pat. Publ. No. US 2004/0087025) as have adoptive transfer procedures using T cells of desired antigen-specificity (e.g., Schmitt et al. (2009) *Hum. Gen.* 20:1240, Dossett et al. (2009) *Mol. Ther.* 77:742, Till et al. (2008) *Blood* 772:2261, Wang et al. (2007) *Hum. Gene Ther.* 18:112, Kuball et al. (2007) *Blood* 709:2331, U.S. Pat. Publ. 2011/0243972, U.S. Pat. Publ. 2011/0189141, and Leen et al. (2007) *Ann. Rev. Immunol.* 25:243).

Any suitable immune cell may be modified to include a heterologous polynucleotide encompassed by the present invention, including, for example, a T cell, a NK cell, or a NK-T cell. In some embodiments, the cell may be a primary cell or a cell of a cell line. In some embodiments, a modified immune cell comprises a CD4+ T cell, a CD8+ T cell, or both. For purposes herein, the T cell may be any T cell, such as a cultured T cell, e.g., a primary T cell, or a T cell from a cultured T cell line, e.g., Jurkat, SupTl, etc., or a T cell obtained from a mammal. If obtained from a mammal, the T cell may be obtained from numerous sources, including but not limited to blood, bone marrow, lymph node, the thymus, or other tissues or fluids. T cells may also be enriched for or purified. In some embodiments, the T cell is a human T cell. In some embodiments, the T cell is a T cell isolated from a human. The T cell may be any type of T cell and may be of any developmental stage, including but not limited to, cytotoxic lymphocyte, cytotoxic lymphocyte precursor cell, cytotoxic lymphocyte progenitor cell, cytotoxic lymphocyte stem cell, $CD4^+/CD8^+$ double positive T cells, $CD4^+$ helper T cells, e.g., Th1 and Th2 cells, $CD4^+$ T cells, $CD8^+$ T cells (e.g., cytotoxic T cells), tumor infiltrating lymphocytes (TILs), memory T cells (e.g., central memory T cells and effector memory T cells), naive T cells, and the like.

Any appropriate method may be used to transfect or transduce the cells (e.g., T cells), or to administer the nucleotide sequences or compositions encompassed by methods described herein. Methods for delivering polynucleotides to host cells include, for example, use of cationic polymers, lipid-like molecules, and certain commercial products such as, for example, in vivo-jetPEI®. Other methods include ex vivo transduction, injection, electroporation, DEAE-dextran, sonication loading, liposome-mediated transfection, receptor-mediated transduction, microprojectile bombardment, transposon-mediated transfer, and the like. Still further methods of transfecting or transducing host cells employ vectors, described in further detail herein.

Modified immune cells as described herein may be functionally characterized using methodologies for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting 51Cr release from pre-loaded target cells), changes in T cell phenotypic marker expression, and other measures of T-cell functions.

Procedures for performing these and similar assays may be found, for example, in Lefkovits (Immunology Methods Manual: Hie Comprehensive Sourcebook of Techniques, 1998), as well as *Current Protocols in Immunology*, Weir, (1986) *Handbook of Experimental Immunology*, Blackwell Scientific, Boston, MA; Mishell and Shigii (eds.) (1979) Selected Methods in Cellular Immunology, Freeman Publishing, *San Francisco, CA; Green and Reed* (1998) *Science* 281:1309, and references cited therein.

In some embodiments, apparent affinity for a binding protein, such as a TCR or antigen-binding portion thereof, may be measured by assessing binding to various concentrations of MHC multimers. "MHC-peptide multimer staining" refers to an assay used to detect antigen-specific T cells, which, in some embodiments, features a tetramer of MHC molecules, each comprising an identical peptide having an amino acid sequence that is cognate (e.g., identical or related to) at least one antigen (e.g., a MAGEA1 immunogenic peptide), wherein the complex is capable of binding to a binding protein, such as a TCR or antigen-binding portion thereof, that recognizes the cognate antigen. Each of the MHC molecules may be tagged with a biotin molecule. Biotinylated MHC/peptides may be multimerized (e.g., tetramerized) by the addition of streptavidin, which may be fluorescently labeled.

The multimer may be detected by flow cytometry via the fluorescent label. In some embodiments, a pMHC multimer assay is used to detect or select enhanced affinity binding protein, such as a TCR or antigen-binding portion thereof, encompassed by the present invention. In some examples, apparent $K_D$ of a binding protein, such as a TCR or antigen-binding portion thereof, is measured using 2-fold dilutions of labeled multimers at a range of concentrations, followed by determination of binding curves by non-linear regression, apparent $K_D$ being determined as the concentration of ligand that yielded half-maximal binding.

Levels of cytokines may be determined using methods described herein, such as ELISA, ELISPOT, intracellular cytokine staining, and flow cytometry and combinations thereof (e.g., intracellular cytokine staining and flow cytometry).

Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-g, IL-12, IL-2, and TNF-b, and Type 2 cytokines, such as IL-4, IL-5, IL-9, IL-10, and IL-13.

A host cell encompassed by the present invention may comprise a single polynucleotide that encodes a binding protein as described herein, or the binding protein may be encoded by more than one polynucleotide. In other words, components or portions of a binding protein may be encoded by two or more polynucleotides, which may be contained on a single nucleic acid molecule or may be contained on two or more nucleic acid molecules.

Moreover, as described further below and in the working examples, a host ell encompassed by the present invention may encode and/or express useful accessory proteins in addition to a binding protein as described herein, either on the same polynucleotide or a different polynucleotide as the binding protein or components thereof. For example, the host cell may encode and/or express CD8α, CD8β, a DN-TGFβR (e.g., a DN-TGFβRII), and/or a selectable protein marker, optionally wherein the selectable protein marker is DHFR.

In some embodiments, a polynucleotide encoding two or more components or portions of a binding protein encompassed by the present invention comprises the two or more coding sequences operatively associated in a single open reading frame. Such an arrangement can advantageously allow coordinated expression of desired gene products, such as, for example, contemporaneous expression of alpha- and beta-chains of a TCR, such that they are produced in about a 1:1 ratio. In some embodiments, two or more substituent gene products of a binding protein encompassed by the present invention, such as a TCR (e.g., alpha- and beta-chains) or CAR, are expressed as separate molecules and associate post-translationally. In further embodiments, two or more substituent gene products of a binding protein encompassed by the present invention are expressed as a single peptide with the parts separated by a cleavable or removable segment. For instance, self-cleaving peptides useful for expression of separable polypeptides encoded by a single polynucleotide or vector are known in the art and include, for example, a porcine teschovirus-1 2 A (P2A) peptide, a thoseaasigna virus 2A (T2A) peptide, an equine rhinitis A virus (ERAV) 2A (E2A) peptide, and a foot-and-mouth disease vims 2A (F2A) peptide.

In some embodiments, a binding protein encompassed by the present invention comprises one or more junction amino acids. "Junction amino acids" or "junction amino acid residues" refer to one or more (e.g., 2 to about 10) amino acid residues between two adjacent motifs, regions or domains of a polypeptide, such as between a binding domain and an adjacent constant domain or between a TCR chain and an adjacent self-cleaving peptide. Junction amino acids can result from the design of a construct that encodes a fusion protein (e g, amino acid residues resulting from the use of a restriction enzyme site during the construction of a nucleic acid molecule encoding a fusion protein), or from cleavage of, for example, a self-cleaving peptide adjacent one or more domains of an encoded binding protein encompassed by the present invention (e.g., a P2A peptide disposed between a TCR α-chain and a TCR β-chain, the self-cleavage of which can leave one or more junction amino acids in the α-chain, the TCR (3-chain, or both).

Engineered immune cells encompassed by the present invention may be administered as therapies for, e.g., a disorder characterized by MAGEA1 expression. In some circumstances, it may be desirable to reduce or stop the activity associated with a cellular immunotherapy. Thus, in some embodiments, an engineered immune cell encompassed by the present invention comprises a heterologous polynucleotide encoding a binding protein and an accessory protein, such as a safety switch protein, which can be targeted using a cognate drug or other compound to selectively modulate the activity (e.g., lessen or ablate) of such cells when desirable. Safety switch proteins used in this regard include, for example, a truncated EGF receptor polypeptide (huEGFRt) that is devoid of extracellular N-terminal ligand binding domains and intracellular receptor tyrosine kinase activity but retains the native amino acid sequence, type I transmembrane cell surface localization, and a conformationally intact binding epitope for pharmaceutical-grade anti-EGFR monoclonal antibody, cetuximab (Erbitux) tEGF receptor (tEGFr; Wang et al. (2011) *Blood* 118:1255-1263), a caspase polypeptide (e.g., iCasp9; Straathof et al. (2005) *Blood* 105:4247-4254, Di Stasi et al. (2011) *N. Engl. J. Med.* 365:1673-1683, Zhou and Brenner (2016) Hematol. pii:S0301-472X:30513-30516), RQR8 (Philip et al. (2014) *Blood* 124:1277-1287), and a human c-myc protein tag (Kieback et al. (2008) *Proc. Natl. Acad. Sci. USA* 105:623-628).

Other accessory components useful for therapeutic cells comprise a tag or selection marker (e.g., a CD34 enrichment tag) that allows the cells to be identified, sorted, isolated, enriched, or tracked. For example, marked immune cells having desired characteristics (e.g., an antigen-specific TCR and a safety switch protein) may be sorted away from unmarked cells in a sample and more efficiently activated and expanded for inclusion in a therapeutic product of desired purity.

As used herein, the term "selection marker" comprises a nucleic acid construct that confers an identifiable change to a cell permitting detection and positive selection of immune cells transduced with a polynucleotide comprising a selection marker. For example, RQR is a selection marker that comprises a major extracellular loop of CD20 and two minimal CD34 binding sites. In some embodiments, an RQR-encoding polynucleotide comprises a polynucleotide that encodes the 16 amino acid CD34 minimal epitope. In some embodiments, such as certain embodiments provided in the examples herein, the CD34 minimal epitope is incorporated at the amino terminal position of the CD8 stalk domain (Q8). In further embodiments, the CD34 minimal binding site sequence may be combined with a target epitope for CD20 to form a compact marker/suicide gene for T cells (RQR8) (Philip et al. 2014). This construct allows for the selection of immune cells expressing the construct, with for example, CD34-specific antibody bound to magnetic beads (Miltenyi) and that utilizes clinically accepted pharmaceutical antibody, rituximab, that allows for the selective deletion of a transgene expressing engineered T cell (e.g., Philip et al. (2014) *Blood* 124:1277-1287, U.S. Pat. Publ. 2015-0093401, and U.S. Pat. Publ. 2018-0051089).

Further exemplary selection markers include several truncated type I transmembrane proteins normally not expressed on T cells: the truncated low-affinity nerve growth factor, truncated CD19, and truncated CD34 (e.g., Di Stasi et al. (2011) *N. Engl. J. Med.* 365:1673-1683, Mavilio et al. (1994) *Blood* 83:1988-1997, and Fehse et al. (2000) *Mol. Ther.* 7:448-456). A particularly attractive feature of CD19 and CD34 is the availability of the off-the-shelf Miltenyi CliniMACs™ selection system that can target these markers for clinical-grade sorting. However, CD19 and CD34 are relatively large surface proteins that may tax the vector packaging capacity and transcriptional efficiency of an integrating vector. Surface markers containing the extracellular, non-signaling domains or various proteins (e.g., CD19, CD34, LNGFR, etc.) also may be employed. Any selection marker may be employed and should be acceptable for good manufacturing practices. In some embodiments, selection markers are expressed with a polynucleotide that encodes a gene product of interest (e.g., a binding protein encompassed by the present invention, such as a TCR or CAR, or antigen-binding fragment thereof). Further examples of selection markers include, for example, reporters such as GFP, EGFP, β-gal or chloramphenicol acetyltransferase (CAT). In some embodiments, a selection marker, such as, for example, CD34 is expressed by a cell and the CD34 may be used to select enrich for, or isolate (e.g., by immunomagnetic selection) the transduced cells of interest for use in the methods described herein. As used herein, a CD34 marker is distinguished from an anti-CD34 antibody, or, for example, a scFv, TCR, or other antigen recognition moiety that binds to CD34.

In some embodiments, a selection marker comprises an RQR polypeptide, a truncated low-affinity nerve growth factor (tNGFR), a truncated CD19 (tCD19), a truncated CD34 (tCD34), or any combination thereof.

By way of background, inclusion of $CD4^+$ T cells in an immunotherapy cell product can provide antigen-induced IL-2 secretion and augment persistence and function of transferred cytotoxic $CD8^+$ T cells (e.g., Kennedy et al. (2008) *Immunol. Rev.* 222:129 and Nakanishi et al. *Nature* (2009) 52:510). In some embodiments, a class I-restricted TCR in $CD4^+$ T cells may require the transfer of a CD8 co-receptor to enhance sensitivity of the TCR to class I HLA peptide complexes. CD4 co-receptors differ in structure to CD8 and cannot effectively substitute for CD8 co-receptors (e.g., Stone & Kranz (2013) *Front. Immunol.* 4:244 and Cole et al. (2012) *Immunology* 737:139). Thus, another accessory protein for use in the compositions and methods encompassed by the present invention comprises a CD8 co-receptor or component thereof. Engineered immune cells comprising a heterologous polynucleotide encoding a binding protein encompassed by the present invention may, in some embodiments, further comprise a heterologous polynucleotide encoding a CD8 co-receptor protein, or a beta-chain or alpha-chain component thereof.

A host cell may be efficiently transduced to contain, and may efficiently express, a single polynucleotide that encodes the binding protein, safety switch protein, selection marker, and CD8 co-receptor protein.

In one embodiment, the host cell encompassed by the present invention further includes a nucleic acid encoding a co-stimulatory molecule, such that the modified T cell expresses the co-stimulatory molecule. In some embodiments, the co-stimulatory domain is selected from CD3, CD27, CD28, CD83, CD86, CD127, 4-1BB, 4-1BBL, PD1 and PD1L.

In any of the foregoing embodiments, a host cell that express the binding protein described herein may be a universal immune cell. A "universal immune cell" comprises an immune cell that has been modified to reduce or eliminate expression of one or more endogenous genes that encode a polypeptide product selected from PD-1, LAG-3, CTLA4, TIM3, TIGIT, an HLA molecule, a TCR molecule, or any combination thereof. Without wishing to be bound by theory, certain endogenously expressed immune cell proteins may downregulate the immune activity of the modified immune cells (e.g., PD-1, LAG-3, CTLA4, TIGIT), or may interfere with the binding activity of a heterologously expressed binding protein encompassed by the present invention (e.g., an endogenous TCR that binds a non-MAGEA1 antigen and interferes with the modified immune cell binding to a target cell that expresses a MAGEA1 antigen such as a MAGEA1 immunogenic peptide in the context of an MHC molecule. Further, endogenous proteins (e g, immune cell proteins, such as an HLA allele) expressed on a donor immune cell may be recognized as foreign by an allogeneic host, which may result in elimination or suppression of the modified donor immune cell by the allogeneic host.

Accordingly, decreasing or eliminating expression or activity of such endogenous genes or proteins can improve the activity, tolerance, or persistence of the modified immune cells in an autologous or allogeneic host setting, and allows universal administration of the cells (e.g., to any recipient regardless of HLA type). In some embodiments, cells in accordance with the present invention are syngeneic, meaning that they are genetically identical or sufficiently identical and immunologically compatible as to allow for transplantation. In some embodiments, a universal immune cell is a donor cell (e.g., allogeneic) or an autologous cell. In some embodiments, a modified immune cell (e.g., a universal immune cell) encompassed by the present invention comprises a chromosomal gene knockout of one or more of a gene that encodes PD-1, LAG-3, CTLA4, TIM3, TIGIT, an HLA component (e.g., a gene that encodes an cd macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai el al. (2016) *Nature Sci. Rep.* 6:21757; Torikai et al. (2012) *Blood* 179:5697; and Torikai et al. (2013) *Blood* 722:1341, which also provide representative, exemplary gene editing techniques, compositions, and adoptive cell therapies useful according to the present invention).

As used herein, the term "chromosomal gene knockout" refers to a genetic alteration or introduced inhibitory agent in a host cell that prevents (e.g., reduces, delays, suppresses, or abrogates) production, by the host cell, of a functionally active endogenous polypeptide product. Alterations resulting in a chromosomal gene knockout may include, for example, introduced nonsense mutations (including the formation of premature stop codons), missense mutations, gene deletion, and strand breaks, as well as the heterologous expression of inhibitory nucleic acid molecules that inhibit endogenous gene expression in the host cell.

In some embodiments, a chromosomal gene knock-out or gene knock-in may be made by chromosomal editing of a host cell. Chromosomal editing may be performed using, for example, endonucleases. As used herein "endonuclease" refers to an enzyme capable of catalyzing cleavage of a phosphodiester bond within a polynucleotide chain. In some embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for a donor gene "knock-in", for target gene "knock-out", and optionally to inactivate a target gene through a donor gene knock in or target gene knock out event. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases include zinc finger nucleases, TALE-nucleases, CRISPR-Cas nucleases, meganucleases, and megaTALs.

As used herein, a "zinc finger nuclease" (ZFN) refers to a fusion protein comprising a zinc finger DNA-binding domain fused to a non-specific DNA cleavage domain, such as a Fold endonuclease. Each zinc finger motif of about 30 amino acids binds to about 3 base pairs of DNA, and amino acids at certain residues may be changed to alter triplet sequence specificity (e.g., Desjarlais et al. (1993) *Proc. Natl. Acad. Sci.* 90:2256-2260 and Wolfe et al. (1999) *J. Mol. Biol.* 255:1917-1934). Multiple zinc finger motifs may be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In some embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a Fok1 endonuclease. A "TALE DNA binding domain" or "TALE" is composed of one or more TALE repeat domains/units, each generally having a highly conserved 33-35 amino acid sequence with divergent 12th and 13th amino acids. The TALE repeat domains are involved in binding of the TALE to a target DNA sequence. The divergent amino acid residues, referred to as the repeat variable diresidue (RVD), correlate with specific nucleotide recognition. The natural (canonical) code for DNA recognition of these TALEs has been determined such that an HD (histine-aspartic acid) sequence at positions 12 and 13 of the TALE leads to the TALE binding to cytosine (C), NG (asparagine-glycine) binds to a T nucleotide, NI (asparagine-isoleucine) to A, NN (asparagine-asparagine) binds to a G or A nucleotide, and NG (asparagine-glycine) binds to a T nucleotide. Non-canonical (atypical) RVDs are also well-known in the art (e.g., U.S. Pat. Publ. No. US 2011/0301073, which atypical RVDs are incorporated by reference herein in their entirety). TALENs may be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In some embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences may be introduced at the site of DSB via homology directed repair. The crRNA and tracrRNA may be engineered into a single guide RNA (sgRNA or gRNA) (e.g., Jinek et al. (2012) *Science* 337:816-821). Further, the region of the guide RNA complementary to the target site may be altered or programed to target a desired sequence (Xie et al. (2014) *PLOS One* 9:e100448, U.S. Pat. Publ. No. US 2014/0068797, U.S. Pat. Publ. No. US 2014/0186843, U.S. Pat. No. 8,697,359, and PCT Publ. No. WO 2015/071474). In some embodiments, a gene knockout comprises an insertion, a deletion, a mutation or a combination thereof, and made using a CRISPR/Cas nuclease system.

Exemplary gRNA sequences and methods of using the same to knock out endogenous genes that encode immune cell proteins include those described in Ren et al. (2017) *Clin. Cancer Res.* 23:2255-2266, which provides representative, exemplary gRNAs, CAS9 DNAs, vectors, and gene knockout techniques.

As used herein, a "meganuclease," also referred to as a "homing endonuclease," refers to an endodeoxyribonuclease characterized by a large recognition site (double stranded DNA sequences of about 12 to about 40 base pairs). Meganucleases may be divided into five families based on sequence and structure motifs: LAGLIDADG (SEQ ID NO: 57), GIY-YIG, HNH, His-Cys box, and PD-(D/E)XK. Exemplary meganucleases include I-SceI, I-CeuI, PI-PspI, RI-Sce, I-SceIV, I-CsmI, I-PanI, I-SceII, I-PpoI, I-SceIII, I-CreI, I-TevI, I-TevII and I-TevIII, whose recognition sequences are well-known (e.g., U.S. Pat. Nos. 5,420,032 and 6,833,252, Belfort et al. (1997) *Nucl. Acids Res.* 25:3379-3388, Dujon et al. (1989) *Gene* 52:115-118, Perler et al. (1994) *Nucl. Acids Res.* 22:1125-1127, Jasin (1996) *Trends Genet.* 72:224-228, Gimble et al. (1996) *J. Mol. Biol.* 263:163-180, and Argast et al. (1998) *J. Mol. Biol.* 280:345-353).

In some embodiments, naturally-occurring meganucleases may be used to promote site-specific genome modification of a target of interest, such as an immune checkpoint, an HLA-encoding gene, or a TCR component-encoding gene.

In other embodiments, an engineered meganuclease having a novel binding specificity for a target gene is used for site-specific genome modification (see, e.g., Porteus et al. (2005) *Nat. Biotechnol.* 23:967-73, Sussman et al. (2004) *J. Mol. Biol.* 342:31-41, Epinat et al. (2003) *Nucl. Acids Res.* 37:2952-2962, Chevalier et al. (2002) *Mol. Cell* 70:895-905, Ashworth et al. (2006) *Nature* 441:656-659, Paques et al. (2007) *Curr. Gene Ther.* 7:49-66, and U.S. Pat. Publ. Nos. US 2007/0117128, US 2006/0206949, US 2006/0153826, US 2006/0078552, and US 2004/0002092). In further embodiments, a chromosomal gene knockout is generated using a homing endonuclease that has been modified with modular DNA binding domains of TALENs to make a fusion protein known as a megaTAL. MegaTALs may be utilized to not only knock-out one or more target genes, but to also introduce (knock in) heterologous or exogenous polynucleotides when used in combination with an exogenous donor template encoding a polypeptide of interest.

In some embodiments, a chromosomal gene knockout comprises an inhibitory nucleic acid molecule that is introduced into a host cell (e.g., an immune cell) comprising a heterologous polynucleotide encoding an antigen-specific receptor that binds (e.g., specifically and/or selectively) to a MAGEA1 antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, TIGIT, an HLA component, or a TCR component, or any combination thereof) in the host immune cell.

A chromosomal gene knockout may be confirmed directly by DNA sequencing of the host immune cell following use of the knockout procedure or agent.

Chromosomal gene knockouts may also be inferred from the absence of gene expression (e.g., the absence of an mRNA or polypeptide product encoded by the gene) following the knockout.

In some embodiments, a host cell encompassed by the present invention is capable of specifically and/or selectively killing 50% or more of target cells that comprise a peptide-MHC (pMHC) complex comprising a MAGEA1 immunogenic peptide in the context of an MHC molecule.

In some embodiments, the modified immune cell is capable of producing a cytokine when contacted with target cells that comprise a peptide-MHC (pMHC) complex comprising a MAGEA1 immunogenic peptide in the context of an MHC molecule.

In some embodiments, the cytokine comprises IFN-γ or IL2. In some embodiments, the cytokine comprises TNF-α.

In some embodiments, the host cell is capable of producing a higher level of cytokine or a cytotoxic molecule when contacted with a target cell with expression of MAGEA1 at a level of less than or equal to about 1,000 transcript per million transcripts (TPM), 950 TPM, 900 TPM, 850 TPM, 800 TPM, 750 TPM, 700 TPM, 650 TPM, 600 TPM, 550 TPM, 500 TPM, 450 TPM, 400 TPM, 350 TPM, 300 TPM, 250 TPM, 200 TPM, 150 TPM, 100 TPM, 95 TPM, 90 TPM, 85 TPM, 80 TPM, 75 TPM, 70 TPM, 65 TPM, 60 TPM, 55 TPM, 50 TPM, 45 TPM, 40 TPM, 35 TPM, 34 TPM, 33 TPM, 32 TPM, 31 TPM, 30 TPM, 29 TPM, 28 TPM, 27 TPM, 26 TPM, 25 TPM, 24 TPM, 23 TPM, 22 TPM, 21 TPM, 20 TPM, 19 TPM, 18 TPM, 17 TPM, 16 TPM, 15 TPM, 14 TPM, 13 TPM, 12 TPM, 11 TPM, 10 TPM, 9 TPM, 8 TPM, 7 TPM, 6 TPM, 5 TPM, 4 TPM, 3 TPM, 2 TPM, and 1 TPM, or any range in between, inclusive, such as less than or equal to about 1,000 TPM to less than or equal to about 35 TPM). In some embodiments, the low MAGEA1 expression level is termed "heterozygous expression" meaning between about 1 TPM and about 35 TPM, or any range in between, inclusive, such as 1-32 TPM. For example, the host cell is capable of producing an at least 1.2 fold, 1.5 fold, 1.8 fold, 2.0 fold, 2.2 fold, 2.5 fold, 2.8 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 25 fold, 30 fold, 35 fold, 40 fold, 45 fold, 50 fold, 60 fold, 70 fold, 80 fold, 90 fold, 100 fold, 1000 fold, or more, or any range in between, inclusive, such as 1.2 fold to 2 fold, higher level of cytokine or a cytotoxic molecule.

In some embodiments, the host cell is capable of specifically and/or selectively killing a taget cell expressing MAGEA1 (e.g., a hyperproliferative cell expressing MAGEA1). In certain embodiments, the target cell expresses a MAGEA1 immunogenic peptide in the context of an MHC molecule (e.g., a matched MHC molecule).

In some embodiments, host cells do not express MAGEA1 antigen, are not recognized by a binding protein described herein, are not of serotype HLA-C*07, and/or do not express an HLA-C*07 allele, such as HLA-C*0702, HLA-C*0701, and/or HLA-C*0704 alleles. For example, a patient may receive host cells from a healthy donor who is MAGEA1-negative or HLA-C*07:02-negative, or even autologous cells that have selected and/or engineered. Cells isolated from that donor may be used as the source of transplant material. In parallel, T cells isolated from the same donor may be genetically engineered to recognize MAGEA1, such as by expressing a MAGEA1 binding protein described herein. Donor cells may be used to engraft cell populations into the patient (e.g., hematopoietic stem cells used to reconstitute an immune system) and host cells may be infused into the patient with the goal of eliciting a highly specific anti-tumor effect. The engineered donor T cells may be designed to recognize and eliminate the patient's MAGEA1-positive, thereby preventing relapse and promoting complete cures of disorders characterized by MAGEA1 expression. Because the transplanted cells are derived from the donor and are therefore either MAGEA1-negative, HLA-C*07 serotype negative, and/or or HLA-C*07 allele-negative (e.g., negative for HLA-C*0702, HLA-C*0701, and/or HLA-C*0704 alleles), engineered cells described herein may have minimal toxic side effects. Such patient-matched host cells and treatment methods may be used according to therapeutic methods described further below.

In some embodiments, the killing is determined by a killing assay. In some embodiment, the killing assay is carried out by coculturing the host cell and the target cell at a ratio from 20:1 to 0.625:1, for example, from 15:1 to 1.25:1, from 10:1 to 1.5:1, from 8:1 to 3:1, from 6:1 to 5:1, 20:1 to 5:1, 10:1 to 2.5:1 etc. In some embodiments, the target cell is pulsed with 1 μg/mL to 50 pg/mL of MAGEA1 peptide, for example, from 1 ug/mL to 10 ng/mL, 500 ng/mL to 0.5 ng/mL, from 10 ng/mL to 10 pg/mL from 250 ng/mL to 1 ng/mL, from 50 ng/mL to 5 ng/mL, from 20 ng/mL to 10 ng/mL, etc.

In some embodiments, the host cell is capable of killing a higher number of target cells when contacted with target cells with a level of MAGEA1 less than or equal to about 1,000 transcript per million transcripts (TPM), 950 TPM, 900 TPM, 850 TPM, 800 TPM, 750 TPM, 700 TPM, 650 TPM, 600 TPM, 550 TPM, 500 TPM, 450 TPM, 400 TPM, 350 TPM, 300 TPM, 250 TPM, 200 TPM, 150 TPM, 100 TPM, 95 TPM, 90 TPM, 85 TPM, 80 TPM, 75 TPM, 70 TPM, 65 TPM, 60 TPM, 55 TPM, 50 TPM, 45 TPM, 40 TPM, 35 TPM, 34 TPM, 33 TPM, 32 TPM, 31 TPM, 30 TPM, 29 TPM, 28 TPM, 27 TPM, 26 TPM, 25 TPM, 24 TPM, 23 TPM, 22 TPM, 21 TPM, 20 TPM, 19 TPM, 18 TPM, 17 TPM, 16 TPM, 15 TPM, 14 TPM, 13 TPM, 12 TPM, 11 TPM, 10 TPM, 9 TPM, 8 TPM, 7 TPM, 6 TPM, 5 TPM, 4 TPM, 3 TPM, 2 TPM, and 1 TPM, or any range in between, inclusive, such as less than or equal to about 1,000 TPM to less than or equal to about 73 TPM). For example, the host cell may be capable of killing an at least 1.2 fold, 1.5 fold, 1.8 fold, 2.0 fold, 2.2 fold, 2.5 fold, 2.8 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 25 fold, 30 fold, 35 fold, 40 fold, 45 fold, 50 fold, 60 fold, 70 fold, 80 fold, 90 fold, 100 fold, 1000 fold, or more, or any range in between, inclusive, such as 1.2 fold to 2 fold, higher number of target cells.

The present invention further provides a population of cells comprising at least one host cell described herein. The population of cells may be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells may be a substantially homogeneous population, in which the population comprises mainly of host cells (e.g., consisting essentially of) comprising the recombinant expression vector. The population also may be a clonal population of cells, in which all cells of the population are clones of a single host cell comprising a recombinant expression vector, such that all cells of the population comprise the recombinant expression vector. In one embodiment encompassed by the present invention, the population of cells is a clonal population comprising host cells comprising a recombinant expression vector as described herein.

In an embodiment encompassed by the present invention, the numbers of cells in the population may be rapidly expanded. Expansion of the numbers of T cells may be accomplished by any of a number of methods as are well-known in the art (e.g., U.S. Pat. Nos. 8,034,334 and 8,383,099, U.S. Pat. Publ. No. 2012/0244133, Dudley et al. (2003) *J. Immunother.* 26:332-242, and Riddell et al. (1990) *J. Immunol. Methods* 128:189-201). For example, expansion of the numbers of T cells may be carried out by culturing the T cells with OKT3 antibody, IL-2, and feeder PBMC (e.g., irradiated allogeneic PBMC).

VIII. Pharmaceutical Compositions

In another aspect encompassed by the present invention, pharmaceutical compositions are provided herein comprising compositions described herein (e.g., binding proteins, nucleic acids, cells, and the like) and a pharmaceutically acceptable carrier, diluent, or excipient.

The term "pharmaceutically acceptable" refers to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Agents and other compositions encompassed by the present invention may be specially formulated for administration in solid or liquid form, including those adapted for various routes of administration, such as (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound. Any appropriate form factor for an agent or composition described herein, such as, but not limited to, tablets, capsules, liquid syrups, soft gels, suppositories, and enemas, is contemplated.

Pharmaceutical compositions encompassed by the present invention may be presented as discrete dosage forms, such as capsules, sachets, or tablets, or liquids or aerosol sprays each containing a pre-determined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms may be prepared by any of the methods of pharmacy.

Suitable excipients include water, saline, dextrose, glycerol, or the like and combinations thereof. In some embodiments, compositions comprising host cells, binding proteins, or fusion proteins as disclosed herein further comprise a suitable infusion media. Suitable infusion media may be any isotonic medium formulation, typically normal saline, Normosol™-R (Abbott) or Plasma-Lyte™ A (Baxter), 5% dextrose in water, Ringer's lactate may be utilized. An infusion medium may be supplemented with human serum albumin or other human serum components. Unit doses comprising an effective amount of a host cell, or composition are also contemplated.

Also provided herein are unit doses that comprise an effective amount of a host cell or of a composition comprising the host cell. As described herein, host cells include immune cells, T cells ($CD4^+$ T cells and/or CD8+ T cells), cytotoxic lymphocytes (e.g., cytotoxic T cells and/or natural killer (NK) cells), and the like. For example, in some embodiments, a unit dose comprises a composition comprising at least about 30%, at least about 40%, at least about 50%, at least about 60%), at least about 70%, at least about 80%, at least about 85%, at least about 90%, or at least about 95% engineered cells, either alone or in combination with other cells, such as comprising at least about 30%, at least about 40%, at least about 50%, at least about 60%), at least about 70%, at least about 80%, at least about 85%, at least about 90%, or at least about 95% other cells. In some embodiments, undesired cells are present at a reduced amount or substantially not present, such as less than about 50%, less than about 40%, less than about 30%, less than about 20%, less than about 10%, less than about 5%, or less then about 1% the population of cells in the composition.

The amount of cells in a composition or unit dose is at least one cell (for example, at least one engineered $CD8^+$ T cell, engineered $CD4^+$ T cell, and/or NK cell) or is more typically greater than $10^2$ cells, for example, up to $10^6$, up to $10^7$, up to $10^8$ cells, up to $10^9$ cells, or more than $10^{10}$ cells. In some embodiments, the cells are administered in a range from about 106 to about $10^{10}$ cells/$m^2$, such as in a range of about $10^5$ to about $10^9$ cells/$m^2$. The number of cells will depend upon the ultimate use for which the composition is intended as well the type of cells included therein. For example, cells modified to contain a binding protein specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 ml or less, 250 ml or less, or 100 ml or less. In embodiments, the density of the desired cells is typically greater than $10^4$ cells/ml and generally is greater than $10^7$ cells/ml, generally $10^8$ cells/ml or greater. The cells may be administered as a single infusion or in multiple infusions over a range of time. A clinically relevant number of immune cells may be apportioned into multiple infusions that cumulatively equal or exceed $10^6$, $10^7$, $10^8$, $10^9$, $10^{10}$, or $10^{11}$ cells. In some embodiments, a unit dose of the engineered immune cells may be co-administered with (e.g., simultaneously or contemporaneously) hematopoietic stem cells from an allogeneic donor.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity).

An effective amount of a pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutically effective amount" may be used in reference to treatment, whereas "prophylactically effective amount" may be used to describe administrating an effective amount to a subject that is susceptible or at risk of developing a disease or disease-state (e.g., recurrence) as a preventative course.

The pharmaceutical compositions described herein may be presented in unit-dose or multi-dose containers, such as sealed ampoules or vials. Such containers may be frozen to preserve the stability of the formulation until infusion into the patient. In some embodiments, a unit dose comprises a host cell as described herein at a dose of about $10^7$ cells/$m^2$ to about $10^{11}$ cells/$m^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of engineered immune cells or active compound calculated to produce the desired effect in association with an appropriate pharmaceutical carrier.

In some embodiments, the pharmaceutical composition described herein and as described above for immunogenic compositions representatively exemplified for peptides, when administered to a subject, can elicit an immune response against a cell of interest that expresses MAGEA1. Such pharmaceutical compositions may be useful as vaccines for prophylactic and/or therapeutic treatment of a disorder characterized by MAGEA1 expression.

IX. Uses and Methods

The compositions described herein may be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

In some uses and methods encompassed by the present invention, subjects or subject samples are utilized. In some embodiments, the subject is an animal. The animal may be of either sex and may be at any stage of development. In some embodiments, the animals is a vertebrate, such as a mammal. In some embodiments, the subject is a non-human mammal. In some embodiments, the subject is a domesticated animal, such as a dog, cat, cow, pig, horse, sheep, or goat. In some embodiments, the subject is a companion animal, such as a dog or cat. In some embodiments, the subject is a livestock animal, such as a cow, pig, horse, sheep, or goat. In some embodiments, the subject is a zoo animal. In some embodiments, the subject is a research animal, such as a rodent (e.g., mouse or rat), dog, pig, or non-human primate. In some embodiments, the animal is a genetically engineered animal. In some embodiments, the animal is a transgenic animal (e.g., transgenic mice and transgenic pigs). In some embodiments, the subject is a fish or reptile.

In some embodiments, the subject is a rodent, such as a mouse. In some such embodiments, the mouse is a transgenic mouse, such as a mouse expressing human MHC (i.e., HLA) molecules, such as HLA-B72 (e.g., Nicholson et al. (2012) *Adv. Hematol.* 2012:404081). In some embodiments, the subject is a transgenic mouse expressing human TCRs or is an antigen-negative mouse (e.g., Li et al. (2010) *Nat. Med.* 16:1029-1034 and Obenaus et al. (2015) *Nat. Biotechnol.* 33:402-407). In some embodiments, the subject is a transgenic mouse expressing human HLA molecules and human TCRs. In some embodiments, such as where the subject is a transgenic HLA mouse, the identified TCRs are modified, e.g., to be chimeric or humanized. In some embodiments, the TCR scaffold is modified, such as analogous to known binding protein humanizing methods.

In some embodiments, the subject is a human. In some embodiments, the subject is an animal model of a disorder characterized by MAGEA1 expression, such as a cancer. For example, the animal model may be an orthotopic xenograft animal model of a human-derived cancer.

In some embodiments, the subject is a human, such as a human with a disorder characterized by MAGEA1 expression.

The methods described herein may be used to treat a subject in need thereof. As used herein, a "subject in need thereof" includes any subject who has a disorder characterized by MAGEA1 expression, a relapse of a disorder characterized by MAGEA1 expression, and/or who is predisposed to a disorder characterized by MAGEA1 expression.

In some embodiments of the methods encompassed by the present invention, the subject has not undergone treatment for a disorder characterized by MAGEA1 expression, such as chemotherapy, radiation therapy, targeted therapy, and/or immunotherapies. In some embodiments, the subject has undergone treatment for a disorder characterized by MAGEA1 expression, such as chemotherapy, radiation therapy, targeted therapy, and/or immunotherapies.

In some embodiments, the subject has had surgery to remove cancerous or precancerous tissue. In some embodiments, the cancerous tissue has not been removed, e.g., the cancerous tissue may be located in an inoperable region of the body, such as in a tissue that is essential for life, or in a region where a surgical procedure would cause considerable risk of harm to the patient.

In some embodiments, the subject or cells thereof are resistant to a therapy of relevance, such as resistant to standard of care therapy, immune checkpoint inhibitor therapy, and the like. For example, modulating one or more biomarkers encompassed by the present invention may overcome resistance to immune checkpoint inhibitor therapy.

In some embodiments, the subjects are in need of modulation according to compositions and methods described herein, such as having been identified as having an unwanted absence, presence, or aberrant MAGEA1 expression.

a. Diagnostic Methods

In an aspect encompassed by the present invention, provided herein are diagnostic methods for detecting the presence or absence of a MAGEA1 antigen, a MAGEA1 antigen-MHC complex, a cell of interest expressing MAGEA1, and/or a cell having had exposure to MAGEA1, comprising detecting the presence or absence of said MAGEA1 antigen in a sample by use of at least one binding protein, or at least one host cell described herein. In some embodiments, the method further comprising obtaining the sample (e.g., from a subject). In some embodiments, the at least one binding protein or the at least one host cell, forms a complex with a MAGEA1 peptide epitope in the context of an MHC molecule, and the complex is detected in the form of fluorescence activated cell sorting (FACS), enzyme linked immunosorbent assay (ELISA), radioimmune assay (RIA), immunochemically, Western blot, or intracellular flow assay.

In an aspect encompassed by the present invention, provided herein are diagnostic methods for detecting the level of MAGEA1 or a disorder characterized by MAGEA1 expression in a subject, comprising: a) contacting a sample obtained from the subject with at least one agent (e.g., a MAGEA1 immunogenic peptide, MAGEA1 immunogenic peptide-MHC complex (pMHC), binding protein, host cell, or a population of host cells described herein); and b) detecting the level of reactivity, wherein a higher level of reactivity compared to a control level indicates the level of a disorder characterized by MAGEA1 expression in the subject.

In some embodiments, the level of reactivity is indicated by T cell activation or effector function, such as, but not limited to, T cell proliferation, killing, or cytokine release. The control level may be a reference number or a level of a healthy subject who has no exposure to a disorder characterized by MAGEA1 expression.

A biological sample may be obtained from a subject for determining the presence and level of an immune response to the agent as described herein. A "biological sample" as used herein may be a blood sample (from which serum or plasma may be prepared), biopsy specimen, body fluids (e.g., blood, isolated PBMCs, isolated T cells, lung lavage, ascites, mucosal washings, synovial fluid, etc.), bone marrow, lymph nodes, tissue explant, organ culture, or any other tissue or cell preparation from the subject or a biological source. Biological samples may also be obtained from the subject prior to receiving any pharmaceutical composition, which biological sample is useful as a control for establishing baseline data.

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

The level of an immune response, such as a cytotoxic T lymphocyte (CTL), may be determined by any one of numerous immunological methods described herein and routinely practiced in the art. For example, the level of a CTL immune response may be determined prior to and following administration of any one of the herein described binding proteins expressed by, for example, a T cell. Cytotoxicity assays for determining CTL activity may be performed using any one of several techniques and methods routinely practiced in the art (e.g., Henkart el al., "Cytotoxic T-Lymphocytes" in Fundamental Immunology, Paul (ed.) (2003 Lippincott Williams & Wilkins, Philadelphia, PA), pages 1127-50, and references cited therein).

The present invention provides, in part, methods, systems, and code for accurately classifying whether a biological sample is associated with an output of interest, such as expression of a target of interest, such as MAGEA1. In some embodiments, the present invention is useful for classifying a sample (e.g., from a subject) as associated with or at risk for responding to or not responding to therapy for a disorder associated with MAGEA1 expression using a statistical algorithm and/or empirical data.

An exemplary method for detecting the amount or activity of MAGEA1, and thus useful for classifying whether a sample is likely or unlikely to respond to a therapy for a disorder associated with MAGEA1 expression involves contacting a biological sample with an agent, such as a MAGEA1 immunogenic peptide or binding agent described herein, capable of detecting the amount or activity of MAGEA1 in the biological sample. In some embodiments, the method further comprise obtaining a biological sample, such as from a test subject. In some embodiments, at least one agent is used, wherein two, three, four, five, six, seven, eight, nine, ten, or more such agents may be used in combination (e.g., in sandwich ELISAs) or in serial. In certain instances, the statistical algorithm is a single learning statistical classifier system. For example, a single learning statistical classifier system may be used to classify a sample as a based upon a prediction or probability value and the presence or level of the biomarker. The use of a single learning statistical classifier system typically classifies the sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method encompassed by the present invention further comprises sending the sample classification results to a clinician, e.g., an oncologist.

In some embodiments, the diagnosis of a subject (e.g., including HLA typing and/or loss of heterozygosity (LOH) to determine compatibility with TCR-HLA complex binding by TCRs of interest) is followed by administering to the individual a therapeutically effective amount of a defined treatment based upon the diagnosis.

In some embodiments, the methods further involve obtaining a control biological sample (e.g., biological sample from a subject who does not have a disorder associated with MAGEA1 expression, a subject who is in remission, a subject whose disorder is susceptible to therapy, a subject whose disorder is progressing, or other subjects of interest).

In some embodiments of analytical methods described herein, MAGEA1 expression (e.g., in a sample from a subject) is compared to a pre-determined control (standard) sample. The sample from the subject is typically from a diseased tissue, such as cancer cells or tissues. The control sample may be from the same subject or from a different subject. The control sample is typically a normal, non-diseased sample. However, in some embodiments, such as for staging of disease or for evaluating the efficacy of treatment, the control sample may be from a diseased tissue. The control sample may be a combination of samples from several different subjects. In some embodiments, the MAGEA1 expression measurement(s) from a subject is compared to a pre-determined level. This pre-determined level is typically obtained from normal samples. As described herein, a "pre-determined" expression may be used to, by way of example only, evaluate a subject that may be selected for treatment, evaluate a response to cancer, and/or evaluate a response to a combination cancer therapy. A pre-determined biomarker amount and/or activity measurement(s) may be determined in populations of patients with or without a disorder associated with MAGEA1 expression. The pre-determined biomarker amount and/or activity measurement(s) may be a single number, equally applicable to every patient, or the pre-determined biomarker amount and/or activity measurement(s) may vary according to specific sub-populations of patients. Age, weight, height, and other factors of a subject may affect the pre-determined biomarker amount and/or activity measurement(s) of the individual. Furthermore, the pre-determined biomarker amount and/or activity may be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis may be based on the ratio of pre-treatment biomarker measurement as compared to post-treatment biomarker measurement. Pre-treatment biomarker measurement may be made at any time prior to initiation of a therapy. Post-treatment biomarker measurement may be made at any time after initiation of therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of therapy, and even longer toward indefinitely for continued monitoring. Treatment may comprise therapy to treat the disorder characterized by MAGEA1 expression, either alone or in combination with other agents, such as anti-cancer agents like chemotherapy or immune checkpoint inhibitors.

The pre-determined MAGEA1 expression may be any suitable standard. For example, the pre-determined MAGEA1 expression may be obtained from the same or a different subject for whom a subject selection is being assessed. In one embodiment, the pre-determined biomarker amount and/or activity measurement(s) may be obtained from a previous assessment of the same patient. In such a manner, the progress of the selection of the patient may be monitored over time. In addition, the control may be obtained from an assessment of another human or multiple humans, e.g., selected groups of humans, if the subject is a human. In such a manner, the extent of the selection of the human for whom selection is being assessed may be compared to suitable other humans, e.g., other humans who are in a similar situation to the human of interest, such as those suffering from similar or the same condition(s) and/or of the same ethnic group.

In some embodiments encompassed by the present invention the change of MAGEA1 expression from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cut-off values apply equally when the measurement is based on relative changes, such as based on the ratio of pre-treatment biomarker measurement as compared to post-treatment biomarker measurement.

In some embodiments, MAGEA1 expression may be detected and/or quantified by detecting or quantifying MAGEA1 polypeptide or antigen thereof, such as by using a composition described herein. The polypeptide may be detected and quantified by any of a number of means well-known to those of skill in the art, such as by immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991).

b. Therapeutic Methods

In an aspect encompassed by the present invention, provided herein are methods for preventing and/or treating a disorder characterized by MAGEA1 expression and/or for inducing an immune response against a cell of interest, such as a hyperproliferative cell, expressing MAGEA1. In some embodiments, the method comprises administering to a subject a therapeutically effective amount of a composition described herein, such as an immunogenic composition, cells expressing at least one binding protein, and the like. The methods encompassed by the present invention also may be used to determine the responsiveness to cancer therapy of many different cancers in subjects such as those described herein.

In some embodiments, the disorder characterized by MAGEA1 expression is a cancer. The terms "cancer" or "tumor" or "hyperproliferative" refer to the presence of cells possessing characteristics typical of cancer-causing cells, such as uncontrolled proliferation, immortality, invasive or metastatic potential, rapid growth, and certain characteristic morphological features. In some embodiments, such cells exhibit such characteristics in part or in full due to the expression and activity of immune checkpoint proteins, such as PD-1, PD-L1, PD-L2, and/or CTLA-4.

Cancer cells are often in the form of a tumor, but such cells may exist alone within an animal, or may be a non-tumorigenic cancer cell, such as in a hematologic cancer like leukemia. As used herein, the term "cancer" includes premalignant as well as malignant cancers. Cancers include, but are not limited to, a variety of cancers, carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, head and neck cancer, gastric cancer, germ cell tumor, bone cancer, bone tumors, adult malignant fibrous histiocytoma of bone; childhood, malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, Philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, bone cancer, brain tumor, lung carcinoma (including lung adenocarcinoma), small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In some embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated. In some embodiments, the cancer is selected from the group consisting of (advanced) non-small cell lung cancer, melanoma, head and neck squamous cell cancer, (advanced) urothelial bladder cancer, (advanced) kidney cancer (RCC), microsatellite instability-high cancer, classical Hodgkin lymphoma, (advanced) gastric cancer, (advanced) cervical cancer, primary mediastinal B-cell lymphoma, (advanced) hepatocellular carcinoma, colorectal cancer, gastrointestinal cancer, breast invasive carcinoma, bladder urothelial carcinoma, and (advanced) merkel cell carcinoma.

In addition, the compositions described herein may also be administered in combination therapy to further modulate a desired activity. Additional agents include, without limitations, chemotherapeutic agents, hormones, antiangiogens, radiolabelled, compounds, or with surgery, cryotherapy, and/or radiotherapy. The preceding treatment methods may be administered in conjunction with other forms of conventional therapy (e.g., standard-of-care treatments for cancer well-known to the skilled artisan), either consecutively with, pre- or post-conventional therapy. For example, these modulatory agents may be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and may be determined by the physician.

Therapy using one or more compositions described herein, either alone or in combination with other therapies, such as cancer therapies, may be used to contact MAGEA1-expressing cells and/or administered to a desired subject, such as a subject that is indicated as being a likely responder to therapy. In another embodiment, such therapy may be avoided once a subject is indicated as not being a likely responder to the therapy (e.g., as assessed according to a diagnostic or prognostic method described herein) and an alternative treatment regimen, such as targeted and/or untargeted cancer therapies, may be recommended and/or administered.

The term "targeted therapy" refers to administration of agents that selectively interact with a chosen biomolecule to thereby treat cancer. For example, targeted therapy regarding the inhibition of immune checkpoint inhibitor is useful in combination with the methods encompassed by the present invention.

The term "immunotherapy" or "immunotherapies" generally refers to any strategy for modulating an immune response in a beneficial manner and encompasses the treatment of a subject afflicted with, or at risk of contracting or suffering a recurrence of, a disease by a method comprising inducing, enhancing, suppressing or otherwise modifying an immune response, as well as any treatment that uses certain parts of a subject's immune system to fight diseases, such as cancer. The subject's own immune system is stimulated (or suppressed), with or without administration of one or more agent for that purpose. Immunotherapies that are designed to elicit or amplify an immune response are referred to as "activation immunotherapies" Immunotherapies that are designed to reduce or suppress an immune response are referred to as "suppression immunotherapies." In some embodiments, an immunotherapy is specific for cells of interest, such as cancer cells. In some embodiments, immunotherapy may be "untargeted," which refers to administration of agents that do not selectively interact with immune system cells, yet modulates immune system function. Representative examples of untargeted therapies include, without limitation, chemotherapy, gene therapy, and radiation therapy.

Some forms of immunotherapy are targeted therapies that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy may involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy may also focus on using the cytotoxic lymphocyte-recognized epitopes of cancer cell lines. Alternatively, antisense polynucleotides, ribozymes, RNA interference molecules, triple helix polynucleotides and the like, may be used to selectively modulate biomolecules that are linked to the initiation, progression, and/or pathology of a tumor or cancer. Similarly, immunotherapy may take the form of cell-based therapies. For example, adoptive cellular immunotherapy is a type of immunotherapy using immune cells, such as T cells, that have a natural or genetically engineered reactivity to a patient's cancer are generated and then transferred back into the cancer patient. The injection of a large number of activated tumor-specific T cells may induce complete and durable regression of cancers.

Immunotherapy may involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy may also focus on using the cytotoxic lymphocyte-recognized epitopes of cancer cell lines. Alternatively, antisense polynucleotides, ribozymes, RNA interference molecules, triple helix polynucleotides and the like, may be used to selectively modulate biomolecules that are linked to the initiation, progression, and/or pathology of a tumor or cancer.

In some embodiments, an immunotherapeutic agent is an agonist of an immune-stimulatory molecule; an antagonist of an immune-inhibitory molecule; an antagonist of a chemokine; an agonist of a cytokine that stimulates T cell activation; an agent that antagonizes or inhibits a cytokine that inhibits T cell activation; and/or an agent that binds to a membrane bound protein of the B7 family. In some embodiments, the immunotherapeutic agent is an antagonist of an immune-inhibitory molecule. In some embodiments, the immunotherapeutic agents may be agents for cytokines, chemokines and growth factors, for examples, neutralizing antibodies that neutralize the inhibitory effect of tumor associated cytokines, chemokines, growth factors and other soluble factors, including IL-10, TGF-β and VEGF.

In some embodiments, immunotherapy comprises inhibitors of one or more immune checkpoints. The term "immune checkpoint" refers to a group of molecules on the cell surface of CD4+ and/or CD8+ T cells that fine-tune immune responses by modulating anti-cancer immune responses, such as down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD200R, CD160, gp49B, PIR-B, KRLG-1, KIR family receptors, TIM-1, TIM-3, TIM-4, LAG-3 (CD223), IDO, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragments, as well as nucleic acids encoding full-length immune checkpoint proteins.

Some immune checkpoints are "immune-inhibitory immune checkpoints" encompassing molecules (e.g., proteins) that inhibit, down-regulate, or suppress a function of the immune system (e.g., an immune response). For example, PD-L1 (programmed death-ligand 1), also known as CD274 or B7-H1, is a protein that transmits an inhibitory signal that reduces proliferation of T cells to suppress the immune system. CTLA-4 (cytotoxic T-lymphocyte-associated protein 4), also known as CD152, is a protein receptor on the surface of antigen-presenting cells that serves as an immune checkpoint ("off" switch) to downregulate immune responses. TIM-3 (T-cell immunoglobulin and mucin-domain containing-3), also known as HAVCR2, is a cell surface protein that serves as an immune checkpoint to regulate macrophage activation. VISTA (V-domain Ig suppressor of T cell activation) is a type I transmembrane protein that functions as an immune checkpoint to inhibit T cell effector function and maintain peripheral tolerance. LAG-3 (lymphocyte-activation gene 3) is an immune checkpoint receptor that negatively regulates proliferation, activation, and homeostasis of T cells. BTLA (B- and T-lymphocyte attenuator) is a protein that displays T cell inhibition via interactions with tumor necrosis family receptors (TNF-R). KIR (killer-cell immunoglobulin-like receptor) is a family of proteins expressed on NK cells, and a minority of T cells, that suppress the cytotoxic activity of NK cells. In some embodiments, immunotherapeutic agents may be agents specific to immunosuppressive enzymes such as inhibitors that may block the activities of arginase (ARG) and indoleamine 2,3-dioxygenase (IDO), an immune checkpoint protein that suppresses T cells and NK cells, which change the catabolism of the amino acids arginine and tryptophan in the immunosuppressive tumor microenvironment. The inhibitors may include, but are not limited to, N-hydroxy-L-Arg (NOHA) targeting to ARG-expressing M2 macrophages, nitroaspirin or sildenafil (Viagra®), which blocks ARG and nitric oxide synthase (NOS) simultaneously; and IDO inhibitors, such as 1-methyl-tryptophan. The term further encompasses biologically active protein fragment, as well as nucleic acids encoding full-length immune checkpoint proteins and biologically active protein fragments thereof. In some embodiment, the term further encompasses any fragment according to homology descriptions provided herein.

By contrast, other immune checkpoints are "immune-stimulatory" encompassing molecules (e.g., proteins) that activate, stimulate, or promote a function of the immune system (e.g., an immune response). In some embodiments, the immune-stimulatory molecule is CD28, CD80 (B7.1), CD86 (B7.2), 4-1BB (CD137), 4-1BBL (CD137L), CD27, CD70, CD40, CD40L, CD122, CD226, CD30, CD30L, OX40, OX40L, HVEM, BTLA, GITR and its ligand GITRL, LIGHT, LTβR, LTαβ, ICOS (CD278), ICOSL (B7-H2), and NKG2D. CD40 (cluster of differentiation 40) is a costimulatory protein found on antigen presenting cells that is required for their activation. OX40, also known as tumor necrosis factor receptor superfamily member 4 (TNFRSF4) or CD134, is involved in maintenance of an immune response after activation by preventing T-cell death and subsequently increasing cytokine production. CD137 is a mgember of the tumor necrosis factor receptor (TNF-R) family that co-stimulates activated T cells to enhance proliferation and T cell survival. CD122 is a subunit of the interleukin-2 receptor (IL-2) protein, which promotes differentiation of immature T cells into regulatory, effector, or memory T cells. CD27 is a member of the tumor necrosis factor receptor superfamily and serves as a co-stimulatory immune checkpoint molecule. CD28 (cluster of differentiation 28) is a protein expressed on T cells that provides co-stimulatory signals required for T cell activation and survival. GITR (glucocorticoid-induced TNFR-related protein), also known as TNFRSF18 and AITR, is a protein that plays a key role in dominant immunological self-tolerance maintained by regulatory T cells. ICOS (inducible T-cell co-stimulator), also known as CD278, is a CD28-superfamily costimulatory molecule that is expressed on activated T cells and play a role in T cell signaling and immune responses.

Immune checkpoints and their sequences are well-known in the art and representative embodiments are described further below. Immune checkpoints generally relate to pairs of inhibitory receptors and the natural binding partners (e.g., ligands). For example, PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells. The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell inhibitory signals, and the ability to modulate the immune response. The term "PD-1 ligand" refers to binding partners of the PD-1 receptor and includes both PD-L1 (Freeman et al. (2000) *J. Exp. Med.* 192:1027-1034) and PD-L2 (Latchman et al. (2001) *Nat. Immunol.* 2:261). The term "PD-1 ligand activity" includes the ability of a PD-1 ligand polypeptide to bind its natural receptor(s) (e.g., PD-1 or B7-1), the ability to modulate immune cell inhibitory signals, and the ability to modulate the immune response.

As used herein, the term "immune checkpoint therapy" refers to the use of agents that inhibit immune-inhibitory immune checkpoints, such as inhibiting their nucleic acids and/or proteins. Inhibition of one or more such immune checkpoints may block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that may either bind and/or inactivate or inhibit immune checkpoint proteins, or fragments thereof; as well as RNA interference, antisense, nucleic acid aptamers, etc. that may downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g., the extracellular portion of an immune checkpoint inhibition protein fused to the Fc portion of an antibody or immunoglobulin) that bind to its natural receptor (s); nucleic acid molecules that block immune checkpoint nucleic acid transcription or translation; and the like. Such agents may directly block the interaction between the one or more immune checkpoints and its natural receptor(s) (e.g., antibodies) to prevent inhibitory signaling and upregulate an immune response. Alternatively, agents may indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain may binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. Therapeutic agents used for blocking the PD-1 pathway include antagonistic antibodies and soluble PD-L1 ligands. The antagonist agents against PD-1 and PD-L1/2 inhibitory pathway may include, but are not limited to, antagonistic antibodies to PD-1 or PD-L1/2 (e.g., 17D8, 2D3, 4H1, 5C4 (also known as nivolumab or BMS-936558), 4A11, 7D3 and 5F4 disclosed in U.S. Pat. No. 8,008,449; AMP-224, pidilizumab (CT-011), pembrolizumab, and antibodies disclosed in U.S. Pat. Nos. 8,779,105; 8,552,154; 8,217,149; 8,168,757; 8,008,449; 7,488,802; 7,943,743; 7,635,757; and 6,808,710. Similarly, additional representative checkpoint inhibitors may be, but are not limited to, antibodies against inhibitory regulator CTLA-4 (anti-cytotoxic T-lymphocyte antigen 4 anti-cytotoxic T-lymphocyte antigen 4), such as ipilimumab, tremelimumab (fully humanized), anti-CD28 antibodies, anti-CTLA-4 adnectins, anti-CTLA-4 domain antibodies, single chain anti-CTLA-4 antibody fragments, heavy chain anti-CTLA-4 fragments, light chain anti-CTLA-4 fragments, and other antibodies, such as those disclosed in U.S. Pat. Nos. 8,748,815; 8,529,902; 8,318,916; 8,017,114; 7,744,875; 7,605,238; 7,465,446; 7,109,003; 7,132,281; 6,984,720; 6,682,736; 6,207,156; and 5,977,318, as well as EP Pat. No. 1212422, U.S. Pat Publ. Numbers 2002/0039581 and 2002/086014, and Hurwitz et al. (1998) *Proc. Natl. Acad. Sci. U.S.A.* 95:10067-10071.

The representative definitions of immune checkpoint activity, ligand, blockade, and the like exemplified for PD-1, PD-L1, PD-L2, and CTLA-4 apply generally to other immune checkpoints.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary agents include, but are not limited to, alkylating agents: nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Similarly, additional exemplary agents including platinum-ontaining compounds (e.g., cisplatin, carboplatin, oxaliplatin), *vinca* alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE®)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genentech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of beta-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard et. al. (2003) *Exp. Hematol.* 31:446-454); Herceg (2001) *Mut. Res.* 477:97-110). Poly(ADP-ribose) polymerase 1 (PARP1) is a key molecule in the repair of DNA single-strand breaks (SSBs) (de Murcia J. et al. (1997) *Proc. Natl. Acad. Sci. U.S.A.* 94:7303-7307; Schreiber et al. (2006) *Nat. Rev. Mol. Cell Biol.* 7:517-528; Wang et al. (1997) *Genes Dev.* 11:2347-2358). Knockout of SSB repair by inhibition of PARP1 function induces DNA double-strand breaks (DSBs) that may trigger synthetic lethality in cancer cells with defective homology-directed DSB repair (Bryant et al. (2005) *Nature* 434:913-917; Farmer et al. (2005) *Nature* 434:917-921). The foregoing examples of chemotherapeutic agents are illustrative and are not intended to be limiting.

In another embodiment, radiation therapy is used. The radiation used in radiation therapy may be ionizing radiation. Radiation therapy may also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy may be administered as external beam radiation or teletherapy wherein the radiation is directed from a remote source. The radiation treatment may also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments may comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy may be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It may be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, may cause discomfort or even significant local pain in about half the patients treated. It may also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents may kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT may be directed through a fiber-optic (a very thin glass strand). The fiber-optic is placed close to the cancer to deliver the proper amount of light. The fiber-optic may be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and may include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also may be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser may remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser may penetrate deeper into tissue than light from the other types of lasers, and it may cause blood to clot quickly. It may be carried through optical fibers to less accessible parts of the body. This type of laser is sometimes used to treat throat cancers. Argon laser—This laser may pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light may be directed to parts of the body without making a large incision. More procedures may be done on an outpatient basis. Lasers may be used in two ways to treat cancer: by shrinking or destroying a tumor with heat, or by activating a chemical—known as a photosensitizing agent—that destroys cancer cells. In PDT, a photosensitizing agent is retained in cancer cells and may be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers may be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems may produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

In one aspect, provided herein is a method of eliciting in a subject an immune response to a cell that expresses MAGEA1. In some embodiments, the method comprises administering to the subject a pharmaceutical composition described herein, wherein the pharmaceutical composition, when administered to the subject, elicits an immune response to the cell that expresses MAGEA1.

In some embodiments, the immune response can include a cell-mediated immune response. A cellular immune response is a response that involves T cells and may be determined in vitro, ex vivo, or in vivo. For example, a general cellular immune response may be determined as the T cell proliferative activity in cells (e.g., peripheral blood leukocytes (PBLs)) sampled from the subject at a suitable time following the administering of a pharmaceutical composition. Following incubation of e.g., PBMCs with a stimulator for an appropriate period, [$^3$H]thymidine incorporation may be determined. The subset of T cells that is proliferating may be determined using flow cytometry.

In another aspect encompassed by the present invention, the methods provided herein include administering to both human and non-human mammals as described above. Veterinary applications also are contemplated. In some embodiments, the subject may be any living organism in which an immune response may be elicited.

In some embodiments, the pharmaceutical composition may be administered at any time that is appropriate. For example, the administering may be conducted before or during treatment of a subject having a disorder characterized by MAGEA1 expression, and continued after the disorder characterized by MAGEA1 expression becomes clinically undetectable. The administering also may be continued in a subject showing signs of recurrence.

In some embodiments, the pharmaceutical composition may be administered in a therapeutically or a prophylactically effective amount. Administering the pharmaceutical composition to the subject may be carried out using known procedures, and at dosages and for periods of time sufficient to achieve a desired effect.

In some embodiments, the pharmaceutical composition may be administered to the subject at any suitable site. Administration may be accomplished using methods generally known in the art. Agents, including cells, may be introduced to the desired site by direct injection, or by any other means used in the art including, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular administration. For example, subjects of interest may be engrafted with the transplanted cells by various routes. Such routes include, but are not limited to, intravenous administration, subcutaneous administration, administration to a specific tissue (e.g., focal transplantation), injection into the femur bone marrow cavity, injection into the spleen, administration under the renal capsule of fetal liver, and the like. In certain embodiment, the cancer vaccine encompassed by the present invention is injected to the subject intratumorally or subcutaneously. Cells may be administered in one infusion, or through successive infusions over a defined time period sufficient to generate a desired effect. Exemplary methods for transplantation, engraftment assessment, and marker phenotyping analysis of transplanted cells are well-known in the art (see, for example, Pearson et al. (2008) *Curr. Protoc. Immunol.* 81:15.21.1-15.21.21; Ito et al. (2002) *Blood* 100:3175-3182; Traggiai et al. (2004) *Science* 304:104-107; Ishikawa et al. *Blood* (2005) 106:1565-1573; Shultz et al. (2005) *J. Immunol.* 174:6477-6489; and Holyoake et al. (1999) *Exp. Hematol.* 27:1418-1427).

In some embodiments, the dose may be administered in an amount and for a period of time effective in bringing about a desired response, be it eliciting the immune response or the prophylactic or therapeutic treatment of a disorder characterized by MAGEA1 expression and/or symptoms associated therewith.

The pharmaceutical composition may be given subsequent to, preceding, or contemporaneously with other therapies including therapies that also elicit an immune response in the subject. For example, the subject may previously or concurrently be treated by other forms of immunomodulatory agents, such other therapies may be provided in such a way so as not to interfere with the immunogenicity of the compositions described herein.

Administering may be properly timed by the care giver (e.g., physician, veterinarian), and may depend on the clinical condition of the subject, the objectives of administering, and/or other therapies also being contemplated or administered. In some embodiments, an initial dose may be administered, and the subject monitored for an immunological and/or clinical response. Suitable means of immunological monitoring include using patient's peripheral blood lymphocyte (PBL) as responders and immunogenic peptides or peptide-MHC complexes described herein as stimulators. An immunological reaction also may be determined by a delayed inflammatory response at the site of administering. One or more doses subsequent to the initial dose may be given as appropriate, typically on a monthly, semimonthly, or a weekly basis, until the desired effect is achieved. Thereafter, additional booster or maintenance doses may be given as required, particularly when the immunological or clinical benefit appears to subside.

In general, an appropriate dosage and treatment regimen provides the active molecules or cells in an amount sufficient to provide a benefit. Such a response may be monitored by establishing an improved clinical outcome (e.g., more frequent remissions, complete or partial, or longer disease-free survival) in treated subjects as compared to non-treated subjects. Increases in preexisting immune responses to a viral protein generally correlate with an improved clinical outcome. Such immune responses may generally be evaluated using standard proliferation, cytotoxicity or cytokine assays, which are routine.

For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro, ex vivo, and in vivo animal studies) and clinical studies and analyzing data obtained therefrom by appropriate statistical, biological, and clinical methods and techniques, all of which can readily be practiced by an ordinarily skilled artisan.

As used herein, administration of a composition refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., engineered immune cells with one or more cytokines; immunosuppressive therapy such as calcineurin inhibitors, corticosteroids, microtubule inhibitors, low dose of a mycophenolic acid prodrug, or any combination thereof).

In some embodiments, a plurality of doses of a host cell (e.g., an engineered immune cell) described herein is administered to the subject, which may be administered at intervals between administrations of about two to about four weeks.

Treatment or prevention methods encompassed by the present invention may be administered to a subject as part of a treatment course or regimen, which may comprise additional treatments prior to, or after, administration of the instantly disclosed unit doses, cells, or compositions. For example, in some embodiments, a subject receiving a unit dose of the host cell (e.g., an engineered immune cell) is receiving or had previously received a hematopoietic cell transplant (HCT; including myeloablative and non-myeloablative HCT). In any of the foregoing embodiments, a hematopoietic cell used in an HCT may be a "universal donor" cell that is modified to reduce or eliminate expression of one or more endogenous genes that encode a polypeptide product selected from an MHC, antigen, and a binding protein (e.g., by a chromosomal gene knockout according to the methods described herein). In some embodiments, Techniques and regimens for performing cell transplantation are known in the art and may comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in some embodiments, a host cell (e.g., an engineered immune cell) encompassed by the present invention may be administered with or shortly after stem cell therapy.

Methods encompassed by the present invention may, in some embodiments, further include administering one or more additional agents to treat the disease or disorder (e.g., a disorder characterized by MAGEA1 expression) in a combination therapy. For example, in some embodiments, a combination therapy comprises administering host cell or binding protein encompassed by the present invention with (concurrently, simultaneously, or sequentially) an antiviral agent. In some embodiments, a combination therapy comprises administering a host cell or binding protein encompassed by the present invention with lopinavir/ritonavir, chloroquine, ribavirin, steroid drugs, hydroxychloroquine, and/or interferon α. In some embodiments, a combination therapy comprises administering a host cell, composition, or unit dose of the host cells encompassed by the present invention with a secondary therapy, such as a surgery, an antibody, a vaccine, or any combination thereof.

c. Screening Methods

Another aspect encompassed by the present invention encompasses screening assays.

In some embodiments, methods are provided for selecting agents that bind to a MAGEA1 immunogenic peptide or pMHC described herein. For example, a method of identifying a peptide-binding molecule, or antigen-binding fragment thereof, that binds to a peptide epitope selected from the peptide sequences listed in Table 1 comprising a) providing a cell presenting a peptide epitope selected from the peptide sequences listed in Table 1 in the context of an MHC molecule on the surface of the cell; b) determining binding of a plurality of candidate peptide-binding molecules or antigen-binding fragments thereof to the peptide epitope in the context of the MHC molecule on the cell; and c) identifying one or more peptide-binding molecules or antigen-binding fragments thereof that bind to the peptide epitope in the context of the MHC molecule, is provided.

In some embodiments, a method of identifying a peptide-binding molecule or antigen-binding fragment thereof that binds to a peptide epitope selected from the peptide sequences listed in Table 1 comprising: a) providing a peptide epitope either alone or in a stable MHC-peptide complex, comprising a peptide epitope selected from the peptide sequences listed in Table 1, either alone or in the context of an MHC molecule; b) determining binding of a plurality of candidate peptide-binding molecules or antigen-binding fragments thereof to the peptide or stable MHC-peptide complex; and c) identifying one or more peptide-binding molecules or antigen-binding fragments thereof that bind to the peptide epitope or the stable MHC-peptide complex, optionally wherein the MHC or MHC-peptide complex is as described herein, is provided.

In some embodiments, provide herein are methods of identifying a peptide-binding molecule or antigen-binding fragment thereof that binds to a peptide epitope selected from Table 1.

In some embodiments, the peptide binding molecule (e.g., MHC-peptide binding molecule) is a molecule or portion thereof that possesses the ability to bind (e.g., specifically and/or selectively) to a peptide epitope that is presented or displayed in the context of an MHC molecule (MHC-peptide complex), such as on the surface of a cell. Exemplary peptide binding molecules include T cell receptors or antibodies, or antigen-binding portions thereof, including single chain immunoglobulin variable regions (e.g., scTCR, scFv) thereof, that exhibit specific ability to bind to an MHC-peptide complex. In some embodiments, the peptide binding molecule is a TCR or antigen-binding fragment thereof. In some embodiments, the peptide binding molecule is an antibody, such as a TCR-like antibody or antigen-binding fragment thereof. In some embodiments, the peptide binding molecule is a TCR-like CAR that contains an antibody or antigen binding fragment thereof, such as a TCR-like antibody, such as one that has been engineered to bind to MHC-peptide complexes. In some embodiments, the peptide binding molecule may be derived from natural sources, or it may be partly or wholly synthetically or recombinantly produced.

In some embodiments, a binding molecule that binds to a peptide epitope may be identified by contacting one or more candidate peptide binding molecules, such as one or more candidate TCR molecules, antibodies, or antigen-binding fragments thereof, with an MHC-peptide complex, and assessing whether each of the one or more candidate binding molecules binds (e.g., specifically and/or selectively) to the MHC-peptide complex. The methods may be performed in vitro, ex vivo, or in vivo. Methods are well-known in the art for screening, such as described in U.S. Pat. Publ. 2020/0102553.

In some embodiments, the methods include contacting a plurality or library of binding molecules, such as a plurality or library of TCRs or antibodies, with an MHC-restricted epitope and identifying or selecting molecules that specifically and/or selectively bind such an epitope. In some embodiments, a library or collection containing a plurality of different binding molecules, such as a plurality of different TCRs or a plurality of different antibodies, may be screened or assessed for binding to an MHC-restricted epitope. In some embodiments, such as for selecting a binding protein that specifically and/or selectively binds an MHC-restricted peptide, hybridoma methods may be employed.

In some embodiments, screening methods may be employed in which a plurality of candidate binding molecules, such as a library or collection of candidate binding molecules, are individually contacted with an peptide binding molecule, either simultaneously or sequentially. Library members that specifically and/or selectively bind to a particular MHC-peptide complex may be identified or selected. In some embodiments, the library or collection of candidate binding molecules may contain at least 2, 5, 10, 100, $10^3$, $10^4$, $10^5$, $10^6$, $10^7$, $10^8$, $10^9$, or more different peptide binding molecules.

In some embodiments, the methods may be employed to identify a peptide binding molecule, such as a TCR or an antibody, that exhibits binding for more than one MHC haplotype or more than one MHC allele. In some embodiments, the peptide binding molecule, such as a TCR or antibody, specifically and/or selectively binds or recognizes a peptide epitope presented in the context of a plurality of MHC class I haplotypes or alleles. In some embodiments, the peptide binding molecule, such as a TCR or antibody, specifically and/or selectively binds or recognizes a peptide epitope presented in the context of a plurality of MHC class II haplotypes or alleles.

A variety of assays are known for assessing binding affinity and/or determining whether a binding molecule specifically and/or selectively binds to a particular ligand (e.g., MHC-peptide complex). It is within the level of a skilled artisan to determine the binding affinity of a TCR for a T cell epitope of a target polypeptide, such as by using any of a number of binding assays that are well-known in the art. For example, in some embodiments, a Biacore® machine may be used to determine the binding constant of a complex between two proteins. The dissociation constant ($K_D$) for the complex may be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy and surface plasmon resonance (Biacore®) analysis (see, e.g., Scatchard et al. (1949) *Ann. N.Y. Acad. Sci.* 51:660; Wilson (2002) *Science* 295:2103; Wolff et al. (1993) *Cancer Res.* 53:2560; and U.S. Pat. Nos. 5,283,173, 5,468,614, or the equivalent), flow cytometry, sequencing and other methods for detection of expressed nucleic acids. In one example, apparent affinity for a TCR is measured by assessing binding to various concentrations of tetramers, for example, by flow cytometry using labeled tetramers. In one example, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

In some embodiments, the methods may be used to identify binding molecules that bind only if the particular peptide is present in the complex, and not if the particular peptide is absent or if another, non-overlapping or unrelated peptide is present. In some embodiments, the binding molecule does not substantially bind the MHC in the absence of the bound peptide, and/or does not substantially bind the peptide in the absence of the MHC. In some embodiments, the binding molecules are at least partially specific. In some embodiments, an exemplary identified binding molecule may bind to an MHC-peptide complex if the particular peptide is present, and also bind if a related peptide that has one or two substitutions relative to the particular peptide is present.

In some embodiments, an identified antibody, such as a TCR-like antibody, may be used to produce or generate a chimeric antigen receptors (CARs) containing a non-TCR antibody that specifically and/or selectively binds to a MHC-peptide complex.

In some embodiments, the methods of identifying a peptide binding molecule, such as a TCR or TCR-like antibody or TCR-like CAR, may be used to engineer cells expressing or containing a peptide binding molecule. In some embodiments, a cell or engineered cell is a T cell. In some embodiments, the T cell is a CD4+ or CD8+ T cell. In some embodiments, the peptide binding molecule recognizes a MHC class I peptide complex, an MHC class II peptide complex and/or an MHC-E peptide complex. In some embodiments, a peptide binding molecule, such as a TCR or antibody or CAR, that specifically and/or selectively recognizes a peptide in the context of an MHC class I may be used to engineer CD8+ T cells. In some embodiments, also provided is a composition of engineered CD8+ T cells expressing or containing the TCR, antibody or CAR, for recognition of a peptide presented in the context of MHC class I. In any of such embodiments, the cells may be used in methods of adoptive cell therapy.

In some embodiments, TCR libraries may be generated by amplification of the repertoire of Vα and Vβ from T cells isolated from a subject, including cells present in PBMCs, spleen or other lymphoid organ. In some cases, T cells may be amplified from tumor-infiltrating lymphocytes (TILs). In some embodiments, TCR libraries may be generated from CD4+ or CD8+ cells. In some embodiments, the TCRs may be amplified from a T cell source of a normal of healthy subject, i.e., normal TCR libraries. In some embodiments, the TCRs may be amplified from a T cell source of a diseased subject, i.e., diseased TCR libraries. In some embodiments, degenerate primers are used to amplify the gene repertoire of Vα and VP, such as by RT-PCR in samples, such as T cells, obtained from humans. In some embodiments, scTv libraries may be assembled from naive Vα and Vβ libraries in which the amplified products are cloned or assembled to be separated by a linker. Depending on the source of the subject and cells, the libraries may be HLA allele-specific.

Alternatively, in some embodiments, TCR libraries may be generated by mutagenesis or diversification of a parent or scaffold TCR molecule. For example, in some aspects, a subject, e.g., human or other mammal such as a rodent, may be vaccinated with a peptide, such as a peptide identified by the present methods. In some embodiments, a sample may be obtained from the subject, such as a sample containing blood lymphocytes. In some instances, binding molecules, e.g., TCRs, may be amplified out of the sample, e.g., T cells contained in the sample. In some embodiments, antigen-specific T cells may be selected, such as by screening to assess CTL activity against the peptide. In some aspects, TCRs, e.g., present on the antigen-specific T cells, may be selected, such as by binding activity, e.g., particular affinity or avidity for the antigen. In some aspects, the TCRs are subjected to directed evolution, such as by mutagenesis, e.g., of the α or β chain. In some aspects, particular residues within CDRs of the TCR are altered. In some embodiments, selected TCRs may be modified by affinity maturation. In some aspects, a selected TCR may be used as a parent scaffold TCR against the antigen.

In some embodiments, the subject is a human, such as a human with a disorder characterized by MAGEA1 expression. In some embodiments, the subject is a rodent, such as a mouse. In some such embodiments, the mouse is a transgenic mouse, such as a mouse expressing human MHC (i.e., HLA) molecules, such as HLA-A2 (e.g., Nicholson et al. (2012) *Adv. Hematol.* 2012:404081).

In some embodiments, the subject is a transgenic mouse expressing human TCRs or is an antigen-negative mouse (e.g., Li et al. (2010) *Nat Med.* 161029-1034; Obenaus et al. (2015) *Nat. Biotechnol.* 33:402-407). In some embodiments, the subject is a transgenic mouse expressing human HLA molecules and human TCRs.

In some embodiments, such as where the subject is a transgenic HLA mouse, the identified TCRs are modified, e.g., to be chimeric or humanized. In some aspects, the TCR scaffold is modified, such as analogous to known antibody humanizing methods.

In some embodiments, such a scaffold molecule is used to generate a library of TCRs.

For example, in some embodiments, the library includes TCRs or antigen-binding portions thereof that have been modified or engineered compared to the parent or scaffold TCR molecule. In some embodiments, directed evolution methods may be used to generate TCRs with altered properties, such as with higher affinity for a specific MHC-peptide complex. In some embodiments, display approaches involve engineering, or modifying, a known, parent or reference TCR. For example, in some cases, a wild-type TCR may be used as a template for producing mutagenized TCRs in which in one or more residues of the CDRs are mutated, and mutants with an desired altered property, such as higher affinity for a desired target antigen, are selected. In some embodiments, directed evolution is achieved by display methods including, but not limited to, yeast display (Holler et al. (2003) *Nat. Immunol.* 4:55-62; Holler et al. (2000) *Proc. Natl. Acad. Sci. U.S.A.* 97:5387-5392), phage display (Li et al. (2005) *Nat. Biotechnol.* 23:349-354), or T cell display (Chervin et al. (2008) *J. Immunol. Methods* 339:175-184).

In some embodiments, the libraries may be soluble. In some embodiments, the libraries are display libraries in which the TCR is displayed on the surface of a phage or cell, or attached to a particle or molecule, such as a cell, ribosome or nucleic acid, e.g., RNA or DNA. Typically, the TCR libraries, including normal and disease TCR libraries or diversified libraries, may be generated in any form, including as a heterodimer or as a single chain form. In some embodiments, one or more members of the TCR may be a two-chain heterodimer. In some embodiments, pairing of the Vα and Vβ chains may be promoted by introduction of a disulfide bond. In some embodiments, members of the TCR library may be a TCR single chain (scTv or ScTCR), which, in some cases, may include a Vα and Vβ chain separated by a linker. Further, in some cases, upon screening and selection of a TCR from the library, the selected member may be generated in any form, such as a full-length TCR heterodimer or single-chain form or as antigen-binding fragments thereof.

Other methods of identifying molecules that bind to a peptide in the context of an MHC molecule are also described in U.S. Pat. Appl. No. 2020/0182884.

More generally, the present invention encompasses assays for screening agents, such as test proteins, that bind to, or modulate the activity of, MAGEA1 or an antigen thereof. Such agents include, without limitation, antibodies, proteins, fusion proteins, small molecules, and nucleic acids. In some embodiments, a method for identifying an agent which modulates an immune response entails determining the ability of the candidate agent to modulate MAGEA1 activity and further modulate an immune response of interest, such as modulated cytotoxic T cell activation and/or activity, sensitivity of cancer cells to immune checkpoint therapy, and the like.

In some embodiments, an assay is a cell-free or cell-based assay, comprising contacting a target, with a test agent, and determining the ability of the test agent to modulate (e.g., upregulate or downregulate) the amount and/or activity of the target, such as by measuring direct or indirect parameters as described below.

In some embodiments, an assay is a cell-based assay, such as one comprising contacting (a) a cell of interest with a test agent and determining the ability of the test agent to modulate the amount and/or activity of the target, such as binding characteristics. Determining the ability of the polypeptides to bind to, or interact with, each other may be accomplished, e.g., by measuring direct binding or by measuring a parameter of immune cell activation or function.

In another embodiment, an assay is a cell-based assay, comprising contacting a cell such as a cancer cell with immune cells (e.g., cytotoxic T cells) and a test agent, and determining the ability of the test agent to modulate the amount and/or activity of the target, and/or modulated immune responses, such as by measuring direct or indirect parameters as described below.

The methods described above and herein may also be adapted to test one or more agents that are already known to modulate the amount and/or activity of one or more biomarkers described herein to confirm modulation of the one or more biomarkers and/or to confirm the effects of the agents on readouts of a desired phenotype, such as modulated immune responses, sensitivity to immune checkpoint blockade, and the like.

In a direct binding assay, biomarker protein (or their respective target polypeptides or molecules) may be coupled with a radioisotope or enzymatic label such that binding may be determined by detecting the labeled protein or molecule in a complex. For example, the targets may be labeled with $^{125}I$ $^{35}S$, $^{14}C$, or $^{3}H$, either directly or indirectly, and the radioisotope detected by direct counting of radioemmission or by scintillation counting. Alternatively, the targets may be enzymatically labeled with, for example, horseradish peroxidase, alkaline phosphatase, or luciferase, and the enzymatic label detected by determination of conversion of an appropriate substrate to product. Determining the interaction between target and substrate may also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target may be accomplished in any vessel suitable for containing the reactants. Non-limiting examples of such vessels include microtiter plates, test tubes, and micro-centrifuge tubes. Immobilized forms of the antibodies encompassed by the present invention may also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

For example, in a direct binding assay, the polypeptides may be coupled with a radioisotope or enzymatic label such that polypeptide interactions and/or activity, such as binding events, may be determined by detecting the labeled protein in a complex. For example, the polypeptides may be labeled with $^{125}I$ $^{35}S$, $^{14}C$, or $^{3}H$, either directly or indirectly, and the radioisotope detected by direct counting of radioemmission or by scintillation counting. Alternatively, the polypeptides may be enzymatically labeled with, for example, horseradish peroxidase, alkaline phosphatase, or luciferase, and the enzymatic label detected by determination of conversion of an appropriate substrate to product.

It is also within the scope of the present invention to determine the ability of an agent to modulate a parameter of interest without the labeling of any of the interactants. For example, a microphysiometer may be used to detect interaction between polypeptides without the labeling of polypeptides to be monitored (McConnell et al. (1992) *Science* 257:1906-1912). As used herein, a "microphysiometer" (e.g., Cytosensor®) is an analytical instrument that measures the rate at which a cell acidifies its environment using a light-addressable potentiometric sensor (LAPS). Changes in this acidification rate may be used as an indicator of the interaction between compound and receptor.

In some embodiments, determining the ability of a test agent (e.g. antibodies, fusion proteins, peptides, or small molecules) to modulate the interaction between a given set of polypeptides may be accomplished by determining the activity of one or more members of the set of polypeptides. For example, the activity of a protein and/or one or more binding partners may be determined by detecting induction of a cellular second messenger (e.g., intracellular signaling), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the protein and/or the one or more binding partners. Determining the ability of the test agent to bind to or interact with said polypeptide may be accomplished, for example, by measuring the ability of a compound to modulate immune cell costimulation or inhibition in a proliferation assay, or by interfering with the ability of said polypeptide to bind to antibodies that recognize a portion thereof.

Agents that modulate target amount and/or activity, such as interactions with one or more binding partners, may be identified by their ability to inhibit immune cell proliferation, and/or effector function, or to induce anergy, clonal deletion, and/or exhaustion when added to an in vitro assay. For example, cells may be cultured in the presence of an agent that stimulates signal transduction via an activating receptor. A number of recognized readouts of cell activation may be employed to measure, cell proliferation or effector function (e.g., antibody production, cytokine production, phagocytosis) in the presence of the agent. The ability of a test agent to block this activation may be readily determined by measuring the ability of the agent to effect a decrease in proliferation or effector function being measured, using techniques known in the art.

For example, agents encompassed by the present invention may be tested for the ability to inhibit or enhance costimulation in a T cell assay, as described in Freeman et al. (2000) *J. Exp. Med.* 192:1027 and Latchman et al. (2001) *Nat. Immunol.* 2:261. CD4+ T cells may be isolated from human PBMCs and stimulated with activating anti-CD3 antibody. Proliferation of T cells may be measured by 3H thymidine incorporation. An assay may be performed with or without CD28 costimulation in the assay. Similar assays may be performed with Jurkat T cells and PHA-blasts from PBMCs.

Alternatively, agents encompassed by the present invention may be tested for the ability to modulate cellular production of cytokines which are produced by or whose production is enhanced or inhibited in immune cells in response to modulation of the one or more biomarkers. Indicative cytokines released by immune cells of interest may be identified by ELISA or by the ability of an antibody which blocks the cytokine to inhibit immune cell proliferation or proliferation of other cell types that is induced by the cytokine, such as those described in the Examples section. An in vitro immune cell costimulation assay may also be used in a method for identifying cytokines which may be modulated by modulation of the one or more biomarkers. For example, if a particular activity induced upon costimulation, e g, immune cell proliferation, cannot be inhibited by addition of blocking antibodies to known cytokines, the activity may result from the action of an unknown cytokine. Following costimulation, this cytokine may be purified from the media by conventional methods and its activity measured by its ability to induce immune cell proliferation. To identify cytokines which may play a role the induction of tolerance, an in vitro T cell costimulation assay as described above may be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance may be targeted for blockage in vivo in conjunction with reagents which block B lymphocyte antigens as a more efficient means to induce tolerance in transplant recipients or subjects with autoimmune diseases.

In some embodiments, an assay encompassed by the present invention is a cell-free assay for screening for agents that modulate the interaction between a biomarker and/or one or more binding partners, comprising contacting a polypeptide and one or more natural binding partners, or biologically active portion thereof, with a test agent and determining the ability of the test compound to modulate the interaction between the polypeptide and one or more natural binding partners, or biologically active portion thereof. Binding of the test compound may be determined either directly or indirectly as described above. In one embodiment, the assay includes contacting the polypeptide, or biologically active portion thereof, with its binding partner to form an assay mixture, contacting the assay mixture with a test compound, and determining the ability of the test agent to interact with the polypeptide in the assay mixture, wherein determining the ability of the test agent to interact with the polypeptide comprises determining the ability of the test agent to preferentially bind to the polypeptide or biologically active portion thereof, as compared to the binding partner.

In some embodiments, whether for cell-based or cell-free assays, a test agent may further be assayed to determine whether it affects binding and/or activity of the interaction between the polypeptide and the one or more binding partners, with other binding partners. Other useful binding analysis methods include the use of real-time Biomolecular Interaction Analysis (BIA) (Sjolander and Urbaniczky (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., Biacore®). Changes in the optical phenomenon of surface plasmon resonance (SPR) may be used as an indication of real-time reactions between biological polypeptides. Polypeptides of interest may be immobilized on a Biacore® chip and multiple agents (blocking antibodies, fusion proteins, peptides, or small molecules) may be tested for binding to the polypeptide of interest. An example of using the BIA technology is described by Fitz et al. (1997) *Oncogene* 15:613.

The cell-free assays encompassed by the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-R3-cholamidopropyl)dimethylamminiol-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either polypeptides to facilitate separation of complexed from uncomplexed forms of one or both of the proteins, as well as to accommodate automation of the assay. Binding of a test compound to a polypeptide, may be accomplished in any vessel suitable for containing the reactants. Examples of such vessels include microtiter plates, test tubes, and micro-centrifuge tubes. In one embodiment, a fusion protein may be provided which adds a domain that allows one or both of the proteins to be bound to a matrix. For example, glutathione-S-transferase-based polypeptide fusion proteins, or glutathione-S-transferase/target fusion proteins, may be adsorbed onto glutathione sepharose beads (Sigma Chemical, St. Louis, MO) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes may be dissociated from the matrix, and the level of polypeptide binding or activity determined using standard techniques.

The present invention further pertains to novel agents identified by the above-described screening assays. Accordingly, it is within the scope of the present invention to further use an agent identified as described herein in an appropriate model system. For example, an agent identified as described herein may be used in a model system to determine the efficacy, toxicity, or side effects of treatment with such an agent. Alternatively, an agent identified as described herein may be used in a model system to determine the mechanism of action of such an agent. Furthermore, the present invention pertains to uses of novel agents identified by the above-described screening assays for treatments as described herein.

d. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect encompassed by the present invention encompasses diagnostic assays for determining (e.g., detecting) the presence, absence, amount, and/or activity level of MAGEA1 or reactivity to MAGEA1 in the context of a biological sample (e.g., blood, serum, cells, or tissue) to thereby determine whether an individual afflicted with a disorder characterized by MAGEA1 expression is likely to respond to therapy, whether in an original state or as a recurrence. Such assays may be used for prognostic or predictive purpose to thereby prophylactically treat an individual prior to the onset or after recurrence of a disorder characterized by MAGEA1 expression.

The diagnostic methods described herein may furthermore be utilized to identify subjects having or at risk of developing a disorder associated with expression or lack thereof of MAGEA1. As used herein, the term "aberrant" includes an upregulation or downregulation of MAGEA1 from normal levels. Aberrant expression or activity includes increased or decreased expression or activity, as well as expression or activity which does not follow the normal developmental pattern of expression or the subcellular pattern of expression. For example, aberrant levels is intended to include the cases in which a mutation in the biomarker gene or regulatory sequence, or amplification of the chromosomal gene, thereof causes upregulation or downregulation of the biomarker of interest. As used herein, the term "unwanted" includes an unwanted phenomenon involved in a biological response, such as immune cell activity.

The assays described herein, such as the preceding diagnostic assays or the following assays, may be utilized to identify a subject having or at risk of developing a disorder associated with MAGEA1 misregulation. Thus, the present invention provides a method for identifying a disorder associated with aberrant or unwanted MAGEA1 regulation in which a test sample is obtained from a subject and MAGEA1 expression is detected, wherein the presence of MAGEA1 expression is diagnostic for a subject having or at risk of developing the disorder associated with aberrant or unwanted MAGEA1 expression. As used herein, a "test sample" refers to a biological sample obtained from a subject of interest. For example, a test sample may be a biological fluid (e.g., cerebrospinal fluid or serum), cell sample, or tissue, such as a histopathological slide of the tumor microenvironment, peritumoral area, and/or intratumoral area.

Furthermore, the prognostic assays described herein may be used to determine whether a subject may be administered an agent described herein to treat such a disorder associated with aberrant or unwanted MAGEA1 expression. For example, such methods may be used to determine whether a subject may be effectively treated with one or a combination of agents. Thus, the present invention provides methods for determining whether a subject may be effectively treated with one or more agents described herein for treating a disorder associated with aberrant or unwanted MAGEA1 expression.

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving the biomarker of interest.

Furthermore, any cell type or tissue in which the biomarker of interest is expressed may be utilized in the prognostic assays described herein.

e. Monitoring of Effects During Clinical Trials

Monitoring the influence of a disorder characterized by MAGEA1 expression therapy (e.g., compounds, drugs, vaccines, cell therapies, and the like) on immune responses, such as T cell reactivity (e.g., the presence of binding and/or T cell activation and/or effector function), may be applied not only in basic candidate MAGEA1 antigen binding molecule screening, but also in clinical trials. For example, the effectiveness of immunogenic peptides, pMHCs, engineered cells, binding proteins, and related compostions described herein to increase an immune response (e.g., T cell immune response) against cells of interest, such as hyperproliferative cells, expressing MAGEA1, may be monitored in clinical trials of subjects afflicted with a disorder characterized by MAGEA1 expression. In such clinical trials, the presence of binding and/or T cell activation and/or effector function (e.g., T cell proliferation, killing, and/or cytokine release), may be used as a "read out" or marker of the phenotype of a particular cell, tissue, or system. Similarly, the effectiveness of an adaptive T cell therapy with T cells engineered to express a binding protein (e.g., a TCR, an antigen-binding fragment of a TCR, a CAR, or a fusion protein comprising a TCR and an effector domain) as described herein to increase immune response to cells of interest, such as hyperproliferative cells, that are expressing MAGEA1, may be monitored in clinical trials of subjects having a disorder characterized by MAGEA1 expression. In such clinical trials, the presence of binding and/or T cell activation and/or effector function (e.g., T cell proliferation, killing, or cytokine release), may be used as a "read out" or marker of the phenotype of a particular cell, tissue, or system.

In some embodiments, the present invention provides a method for monitoring the effectiveness of treatment of a therapy (e.g., compounds, drugs, vaccines, cell therapies, and the like) including the steps of a) determining the absence, presence, or level of reactivity between a sample obtained from the subject and one or more binding proteins or related composition, in a first sample obtained from the subject prior to providing at least a portion of the therapy for the disorder characterized by MAGEA1 expression to the subject, and b) determining the absence, presence, or level of reactivity between the one or more binding proteins or related composition, and a sample obtained from the subject present in a second sample obtained from the subject following provision of the portion of the therapy, wherein the presence or a higher level of reactivity in the first sample, relative to the second sample, is an indication that the therapy is efficacious for treating the disorder characterized by MAGEA1 expression in the subject and wherein the absence or a lower level of reactivity in the first sample, relative to the second sample, is an indication that the therapy is not efficacious for treating the disorder characterized by MAGEA1 expression in the subject.

In some embodiments, the present invention provides a method for monitoring the effectiveness of treatment of a subject with an agent (e.g., antibodies, an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting MAGEA1 expression in the preadministration sample; (iii) obtaining one or more post-administration samples from the subject; (iv) detecting MAGEA1 expression in the post-administration samples; (v) comparing the MAGEA1 expression in the pre-administration sample with the MAGEA1 expression in the post-administration sample; and (vi) altering the administration of the agent to the subject accordingly. Biomarker polypeptide analysis, such as by immunohistochemistry (IHC), may also be used to select patients who will receive therapy, such as immunotherapy.

In addition, the prognostic methods described herein may be used to determine whether a subject may be administered a therapeutic agent to treat a disorder associated with MAGEA1 expression.

f. Clinical Efficacy

Clinical efficacy may be measured by any method known in the art. For example, the response to a therapy relates to any response of the disorder associated with MAGEA1 expression, e.g., a tumor, to the therapy, preferably to a change in the number of cancer cells, tumor mass, and/or tumor volume, such as after initiation of neoadjuvant or adjuvant chemotherapy. Tumor response may be assessed in a neoadjuvant or adjuvant situation where the size of a tumor after systemic intervention may be compared to the initial size and dimensions as measured by CT, PET, mammogram, ultrasound or palpation and the cellularity of a tumor may be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion such as percentage change in tumor volume or cellularity or by using a semi-quantitative scoring system such as residual cancer burden (Symmans et al. (2007) *J. Clin. Oncol.* 25:4414-4422) or Miller-Payne score (Ogston et al. (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy (e.g., after a few hours, days, weeks or preferably after a few months). A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular modulator of biomarkers listed in Table 1 therapeutic regimen is at least 25%, 30%, 35%, 40%, 45%, 50%, 55%, 60%, 65%, 70%, 75%, 80%, 85%, or more.

Additional criteria for evaluating the response to cancer therapy are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence, or metastasis). In addition, criteria for efficacy of treatment may be expanded to include response to chemotherapy, probability of survival, probability of metastasis within a given time period, and probability of tumor recurrence.

For example, in order to determine appropriate threshold values, a particular agent of interest may be administered to a population of subjects and the outcome may be correlated to biomarker measurements that were determined prior to administration of any therapy. The outcome measurement may be pathologic response to therapy given in the neoadjuvant setting. Alternatively, outcome measures, such as overall survival and disease-free survival may be monitored over a period of time for subjects following therapy for whom MAGEA1 expression values are known. In certain embodiments, the same doses of the agent are administered to each subject. The period of time for which subjects are monitored may vary. For example, subjects may be monitored for at least 1, 2, 3, 4, 5, 6, 7, 8, 9, 10, 11, 12, 14, 16, 18, 20, 25, 30, 35, 40, 45, 50, 55, 60 months, or longer. MAGEA1 measurement threshold values that correlate to outcome of a therapy may be determined using well-known methods, such as those described in the Examples section.

X. Cell Therapy

In another aspect encompassed by the present invention, the methods include adoptive cell therapy, whereby genetically engineered cells expressing the provided molecules targeting an MHC-restricted epitope (e.g., cells expressing a binding protein (e.g., a TCR or CAR) or antigen-binding fragment thereof) are administered to subjects. Such administration may promote activation of immune cells (e.g., T cell activation) in an antigen-targeted manner, such that the cells of interest, such as hyperproliferative cells, that express MAGEA1 are targeted for destruction.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated (e.g., via adoptive cell therapy, such as by adoptive T cell therapy). In some embodiments, the cells or compositions are administered to the subject, such as a subject having or at risk for the disease or condition. In some embodiments, the methods thereby treat, e.g., ameliorate one or more symptom of the disease or condition.

Methods for administration of cells for adoptive cell therapy are known and may be used in connection with the provided methods and compositions (e.g., U.S. Pat. Publ. No. 2003/0170238, U.S. Pat. No. 4,690,915, Rosenberg (2011) *Nat. Rev. Clin. Oncol.* 8:577-585, Themeli et al. (2013) *Nat. Biotechnol.* 31:928-933, Tsukahara et al. (2013) *Biochem. Biophys. Res. Commun.* 438:84-89, and Davila et al. (2013) *PLoS ONE* 8:e61338).

In some embodiments, cell therapy (e.g., adoptive cell therapy, such as adoptive T cell therapy) may be carried out by autologous transfer, in which the cells are isolated and/or otherwise prepared from the subject who is to receive the cell therapy, or from a sample derived from such a subject. Thus, in some embodiments, the cells are derived from a subject (e.g., patient) in need of a treatment and the cells, following isolation and processing are administered to the same subject.

In some embodiments, the cell therapy (e.g., adoptive cell therapy, such as adoptive T cell therapy) may be carried out by allogeneic transfer, in which the cells are isolated and/or otherwise prepared from a subject other than a subject who is to receive or who ultimately receives the cell therapy (e.g., a first subject). In such embodiments, the cells then are administered to a different subject (e.g., a second subject) of the same species. In some embodiments, the first and second subjects are genetically identical (syngeneic). In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the primate is a monkey or an ape. The subject may be male or female and may be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

The binding molecules, such as TCRs, antigen-binding fragments of TCRs (e.g., scTCRs) and chimeric receptors (e.g., CARs) containing the TCR, and cells expressing the same, may be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. Dosing and administration may depend in part on whether the administration is brief or chronic. Various dosing schedules include but are not limited to single or multiple administrations over various timepoints, bolus administration, and pulse infusion.

For the prevention or treatment of disease, the appropriate dosage of the binding molecule or cell may depend on the type of disease to be treated, the type of binding molecule, the severity and course of the disease, whether the binding molecule is administered for preventive or therapeutic purposes, previous therapy, the patient's clinical history and response to the binding molecule, and the discretion of the attending physician. The compositions and molecules and cells are in some embodiments suitably administered to the patient at one time or over a series of treatments.

In some embodiments, cells may be administered at $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $5.0\times10^6$, $1.0\times10^7$, $5.0\times10^7$, $1.0\times10^8$, $5.0\times10^8$, or more, or any range in between or any value in between, cells per kilogram of subject body weight. The number of cells transplanted may be adjusted based on the desired level of engraftment in a given amount of time. Generally, $1\times10^5$ to about $1\times10^9$ cells/kg of body weight, from about $1\times10^6$ to about $1\times10^8$ cells/kg of body weight, or about $1\times10^7$ cells/kg of body weight, or more cells, as necessary, may be transplanted. In some embodiment, transplantation of at least about $0.1\times10^6$, $0.5\times10^6$, $1.0\times10^6$, $2.0\times10^6$, $3.0\times10^6$, $4.0\times10^6$, or $5.0\times10^6$ total cells relative to an average size mouse is effective. For example, in some embodiments, cells, or individual populations of subtypes of cells, may be administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

Engraftment of transplanted cells may be assessed by any of various methods, such as, but not limited to, tumor volume, cytokine levels, time of administration, flow cytometric analysis of cells of interest obtained from the subject at one or more time points following transplantation, and the like. For example, a time-based analysis of waiting 1, 2, 3, 4, 5, 6, 7, 8, 9, 10, 11, 12, 13, 14, 15, 16, 17, 18, 19, 20, 21, 22, 23, 24, 25, 26, 27, 28 days or may signal the time for tumor harvesting. Any such metrics are variables that may be adjusted according to well-known parameters in order to determine the effect of the variable on a response to anticancer immunotherapy. In addition, the transplanted cells may be co-transplanted with other agents, such as cytokines, extracellular matrices, cell culture supports, and the like.

Cells may also be administered before, concurrently with, or after, other anti-cancer agents.

Two or more cell types may be combined and administered, such as cell-based therapy and adoptive cell transfer of stem cells, cancer vaccines and cell-based therapy, and the like. For example, adoptive cell-based immunotherapies may be combined with the cell-based therapies encompassed by the present invention. In some embodiments, the cell-based agents may be used alone or in combination with additional cell-based agents, such as immunotherapies like adoptive T cell therapy (ACT). For example, T cells genetically engineered to recognize CD19 used to treat follicular B cell lymphoma. Immune cells for ACT may be dendritic cells, T cells such as $CD8^+$ T cells and $CD4^+$ T cells, natural killer (NK) cells, NK T cells, cytotoxic T lymphocytes (CTLs), tumor infiltrating lymphocytes (TILs), lymphokine activated killer (LAK) cells, memory T cells, regulatory T cells (Tregs), helper T cells, cytokine-induced killer (CIK) cells, and any combination thereof. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies may be further modified to express one or more gene products to further modulate immune responses, such as expressing cytokines like GM-CSF, and/or to express tumor-associated antigen (TAA) antigens, such as Mage-1, gp-100, and the like. The ratio of an agent encompassed by the present invention, such as cancer cells, to another agent encompassed by the present invention or other composition may be 1:1 relative to each other (e.g., equal amounts of 2 agents, 3 agents, 4 agents, etc.), but may modulated in any amount desired (e.g., 1:1, 1.1:1, 1.2:1, 1.3:1, 1.4:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater).

In some embodiments, for example, where the subject is a human, the dose includes fewer than about $1\times10^8$ total binding protein (e.g., TCR- or CAR-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values.

In some embodiments, the cells or related compositions described herein, such as nucleic acids, host cells, pharmaceutical formulations, and the like, may be administered as part of a combination treatment, such as simultaneously with or sequentially with, in any order, another therapeutic intervention, such as another antibody or engineered cell or receptor or agent, such as a cytotoxic or therapeutic agent.

In some embodiments, the cells or related composition may be co-administered with one or more additional therapeutic agents or in connection with another therapeutic intervention, either simultaneously or sequentially in any order. In some contexts, the cells or related composition are co-administered with another therapy sufficiently close in time such that the cell populations enhance the effect of one or more additional therapeutic agents, or vice versa. In some embodiments, the cells or related composition are administered prior to the one or more additional therapeutic agents. In some embodiments, the cells or related composition are administered after to the one or more additional therapeutic agents.

In some embodiments, the biological activity of the cells or related composition is measured by any of a number of known methods once the cells or related composition are administered to a subject (e.g., a human) Parameters to assess include specific binding of an engineered or natural T cell or other immune cell to antigen, in vivo, e.g., by imaging, or in vitro/ex vivo, e.g., by ELISA or flow cytometry. In some embodiments, the ability of the cells to destroy target cells (cytotoxicity) may be measured using any suitable assay or method known in the art (e.g., Kochenderfer et al. (2009) *J. Immunother.* 32: 689-702 and Herman et al. (2004) *J. Immunol. Meth.* 285:25-40). In some embodiments, the biological activity of the cells also may be measured by assaying expression and/or secretion of certain cytokines, such as CD107a, IFNγ, IL-2, and TNF alpha. In some embodiments, the biological activity is measured by assessing clinical outcome, such as reduction in viral burden or load.

In some embodiments, cells are modified in any number of ways, such that their therapeutic or prophylactic efficacy is increased. For example, the binding protein (e.g., engineered TCR, CAR, or antigen-binding fragment thereof) expressed by the population may be conjugated either directly or indirectly through a linker to a targeting moiety. The practice of conjugating compounds to targeting moieties is well-known in the art (e.g., Wadwa et al. (1995) *J. Drug Targeting* 3:111 and U.S. Pat. No. 5,087,616).

Immune cells, such as cytotoxic lymphocytes, may be obtained from any suitable source such as peripheral blood, spleen, and lymph nodes. The immune cells may be used as crude preparations or as partially purified or substantially purified preparations, which may be obtained by standard techniques, including, but not limited to, methods involving immunomagnetic or flow cytometry techniques using antibodies.

In certain aspects, the MAGEA1 immunogenic peptides described herein, or a nucleic acid encoding such MAGEA1 immunogenic peptides, may be used in compositions and methods for providing MAGEA1-primed, antigen-presenting cells, and/or MAGEA1-specific lymphocytes generated with these antigen-presenting cells. In some embodiments, such antigen-presenting cells and/or lymphocytes are used in the treatment and/or prevention of a disorder associated with MAGEA1 expression.

In some aspects, provided herein are methods for making MAGEA1-primed, antigen-presenting cells by contacting antigen-presenting cells with a MAGEA1 immunogenic peptide described herein, or nucleic acids encoding the at least one MAGEA1 immunogenic peptide, alone or in combination with an adjuvant, in vitro under a condition sufficient for the at least one MAGEA1 immunogenic polypeptide to be presented by the antigen-presenting cells.

In some embodiments, MAGEA1 immunogenic polypeptide, or nucleic acid encoding the MAGEA1 immunogenic polypeptide, alone or in combination with an adjuvant, may be contacted with a homogenous, substantially homogenous, or heterogeneous composition comprising antigen-presenting cells. For example, the composition may include but is not limited to whole blood, fresh blood, or fractions thereof such as, but not limited to, peripheral blood mononuclear cells, buffy coat fractions of whole blood, packed red cells, irradiated blood, dendritic cells, monocytes, macrophages, neutrophils, lymphocytes, natural killer cells, and natural killer T cells. If, optionally, precursors of antigen-presenting cells are used, the precursors may be cultured under suitable culture conditions sufficient to differentiate the precursors into antigen-presenting cells. In some embodiments, the antigen-presenting cells (or precursors thereof) are selected from monocytes, macrophages, cells of myeloid lineage, B cells, dendritic cells, or Langerhans cells.

The amount of the MAGEA1 immunogenic polypeptide, or nucleic acid encoding the MAGEA1 immunogenic polypeptide, alone or in combination with an adjuvant, to be placed in contact with antigen-presenting cells may be determined by one of ordinary skill in the art by routine experimentation. Generally, antigen-presenting cells are contacted with the MAGEA1 immunogenic polypeptide, or nucleic acid encoding the MAGEA1 immunogenic polypeptide, alone or in combination with an adjuvant, for a period of time sufficient for cells to present the processed forms of the antigens for the modulation of T cells. In one embodiment, antigen-presenting cells are incubated in the presence of the MAGEA1 immunogenic polypeptide, or nucleic acid encoding the MAGEA1 immunogenic polypeptide, alone or in combination with an adjuvant, for less than about a week, illustratively, for about 1 minute to about 48 hours, about 2 minutes to about 36 hours, about 3 minutes to about 24 hours, about 4 minutes to about 12 hours, about 6 minutes to about 8 hours, about 8 minutes to about 6 hours, about 10 minutes to about 5 hours, about 15 minutes to about 4 hours, about 20 minutes to about 3 hours, about 30 minutes to about 2 hours, and about 40 minutes to about 1 hour. The time and amount of the MAGEA1 immunogenic polypeptide, or nucleic acid encoding the MAGEA1 immunogenic polypeptide, alone or in combination with an adjuvant, necessary for the antigen presenting cells to process and present the antigens may be determined, for example using pulse-chase methods wherein contact is followed by a washout period and exposure to a read-out system e.g., antigen reactive T cells.

In certain embodiments, any appropriate method for delivery of antigens to the endogenous processing pathway of the antigen-presenting cells may be used. Such methods include but are not limited to, methods involving pH-sensitive liposomes, coupling of antigens to adjuvants, apoptotic cell delivery, pulsing cells onto dendritic cells, delivering recombinant chimeric virus-like particles (VLPs) comprising antigen to the MHC class I processing pathway of a dendritic cell line.

In one embodiment, solubilized MAGEA1 immunogenic polypeptide is incubated with antigen-presenting cells. In some embodiments, the MAGEA1 immunogenic polypeptide may be coupled to a cytolysin to enhance the transfer of the antigens into the cytosol of an antigen-presenting cell for delivery to the MHC class I pathway. Exemplary cytolysins include saponin compounds such as saponin-containing Immune Stimulating Complexes (ISCOM5), pore-forming toxins (e.g., an alpha-toxin), and natural cytolysins of gram-positive bacteria such as listeriolysin O (LLO), streptolysin O (SLO), and perfringolysin O (PFO).

In some embodiments, antigen-presenting cells, such as dendritic cells and macrophage, may be isolated according to methods known in the art and transfected with polynucleotides by methods known in the art for introducing a nucleic acid encoding the MAGEA1 immunogenic polypeptide into the antigen-presenting cell. Transfection reagents and methods are known in the art and commercially available. For example, RNA encoding MAGEA1 immunogenic polypeptide may be provided in a suitable medium and combined with a lipid (e.g., a cationic lipid) prior to contact with antigen-presenting cells. Non-limiting examples of such lipids include LIPOFECTIN™ and LIPOFECTAMINE™. The resulting polynucleotide-lipid complex may then be contacted with antigen-presenting cells. Alternatively, the polynucleotide may be introduced into antigen-presenting cells using techniques such as electroporation or calcium phosphate transfection. The polynucleotide-loaded antigen-presenting cells may then be used to stimulate T lymphocyte (e.g., cytotoxic T lymphocyte) proliferation in vitro, ex vivo, or in vivo. In one embodiment, the ex vivo expanded T lymphocyte is administered to a subject in a method of adoptive immunotherapy.

In certain aspects, provided herein is a composition comprising antigen-presenting cells that have been contacted in vitro with a MAGEA1 immunogenic polypeptide, or a nucleic acid encoding a MAGEA1 immunogenic polypeptide, alone or in combination with an adjuvant under a condition sufficient for a MAGEA1 immunogenic epitope to be presented by the antigen-presenting cells.

In some aspects, provided herein is a method for preparing lymphocytes specific for a MAGEA1 protein. The method comprises contacting lymphocytes with the antigen-presenting cells described above under conditions sufficient to produce a MAGEA1 protein-specific lymphocyte capable of eliciting an immune response against a cell that is infected by the MAGEA1 virus. Thus, the antigen-presenting cells also may be used to provide lymphocytes, including T lymphocytes and B lymphocytes, for eliciting an immune response against cell that is infected by the MAGEA1 virus.

In some embodiments, a preparation of T lymphocytes is contacted with the antigen-presenting cells described above for a period of time, (e.g., at least about 24 hours) to priming the T lymphocytes to a MAGEA1 immunogenic epitope presented by the antigen-presenting cells.

In some embodiments, a population of antigen-presenting cells may be co-cultured with a heterogeneous population of peripheral blood T lymphocytes together with a MAGEA1 immunogenic polypeptide, or a nucleic acid encoding a MAGEA1 immunogenic polypeptide, alone or in combination with an adjuvant. The cells may be co-cultured for a period of time and under conditions sufficient for MAGEA1 epitopes included in the MAGEA1 polypeptides to be presented by the antigen-presenting cells and the antigen-presenting cells to prime a population of T lymphocytes to respond to cells is infected by the MAGEA1 virus. In certain embodiments, provided herein are T lymphocytes and B lymphocytes that are primed to respond to cells that is infected by the MAGEA1 virus.

T lymphocytes may be obtained from any suitable source such as peripheral blood, spleen, and lymph nodes. The T lymphocytes may be used as crude preparations or as partially purified or substantially purified preparations, which may be obtained by standard techniques including, but not limited to, methods involving immunomagnetic or flow cytometry techniques using antibodies.

In certain aspects, provided herein is a composition (e.g., a pharmaceutical composition) comprising the antigen-presenting cells or the lymphocytes described above, and a pharmaceutically acceptable carrier and/or diluent. In some embodiments, the composition further comprises an adjuvant as described above.

In certain aspects and as further described above, provided herein is a method for eliciting an immune response to the cell is infected by the MAGEA1 virus, the method comprising administering to the subject the antigen-presenting cells or the lymphocytes described above in effective amounts sufficient to elicit the immune response. In some embodiments, provided herein is a method for treatment or prophylaxis of a disorder characterized by MAGEA1 expression, the method comprising administering to the subject an effective amount of the antigen-presenting cells or the lymphocytes described above. In one embodiment, the antigen-presenting cells or the lymphocytes are administered systemically, preferably by injection. Alternately, one may administer locally rather than systemically, for example, via injection directly into tissue, preferably in a depot or sustained release formulation.

In certain embodiments, the antigen-primed antigen-presenting cells described herein and the antigen-specific T lymphocytes generated with these antigen-presenting cells may be used as active compounds in immunomodulating compositions for prophylactic or therapeutic treatment of a disorder characterized by MAGEA1 expression. In some embodiments, the MAGEA1-primed antigen-presenting cells described herein may be used for generating $CD8^+$ T lymphocytes, $CD4^+$ T lymphocytes, and/or B lymphocytes for adoptive transfer to the subject. Thus, for example, MAGEA1-specific lymphocyte may be adoptively transferred for therapeutic purposes in subjects afflicted with a disorder characterized by MAGEA1 expression.

In certain embodiments, the antigen-presenting cells and/or lymphocytes described herein may be administered to a subject, either by themselves or in combination, for eliciting an immune response, particularly for eliciting an immune response to cells expressing MAGEA1. In some embodiments, the antigen-presenting cells and/or lymphocytes may be derived from the subject (i.e., autologous cells) or from a different subject that is MHC matched or mismatched with the subject (e.g., allogeneic).

Single or multiple administrations of the antigen-presenting cells and lymphocytes may be carried out with cell numbers and treatment being selected by the care provider (e.g., physician). In some embodiments, the antigen-presenting cells and/or lymphocytes are administered in a pharmaceutically acceptable carrier. Suitable carriers may be growth medium in which the cells were grown, or any suitable buffering medium such as phosphate buffered saline. The cells may be administered alone or as an adjunct therapy in conjunction with other therapeutics.

In another aspect encompassed by the present invention, provided herein is a method for eliciting an immune response to a cell that expresses MAGEA1, the method comprising administering to the subject cells described herein expressing a binding protein (e.g., engineered TCR, CAR, or antigen-binding fragment thereof) in effective amounts sufficient to elicit the immune response. In some embodiments, provided herein is a method for treatment or prophylaxis of a disorder characterized by MAGEA1 expression, the method comprising administering to the subject an effective amount of the cells described herein expressing a binding protein (e.g., engineered TCR, CAR, or antigen-binding fragment thereof). In one embodiment, the cells are administered systemically, such as by injection. Alternately, one may administer locally rather than systemically, for example, via injection directly into tissue, such as in a depot or sustained release formulation.

In some embodiments, the cells described herein expressing a binding protein (e.g., engineered TCR, CAR, or antigen-binding fragment thereof) may be used as active compounds in immunomodulating compositions for prophylactic or therapeutic treatment of a disorder characterized by MAGEA1 expression. In some embodiments, MAGEA1-primed antigen-presenting cells may be used for generating lymphocytes (e.g., $CD8^+$ T lymphocytes, $CD4^+$ T lymphocytes, and/or B lymphocytes), for further use in adoptive transfer to the subject with the cells described herein expressing a binding protein (e.g., engineered TCR, CAR, or antigen-binding fragment thereof).

In some embodiments, the cells described herein expressing a binding protein (e.g., engineered TCR, CAR, or antigen-binding fragment thereof), either alone or in combination with the lymphocytes, may be administered to a subject for eliciting an immune response, particularly for eliciting an immune response to cells are expressing MAGEA1.

As described above, single or multiple administrations of the cells described herein expressing a binding protein (e.g., engineered TCR, CAR, or antigen-binding fragment thereof) cells, either alone or in combination with the lymphocytes, may be carried out with cell numbers and treatment being selected by the care provider (e.g., physician). Similarly, the cells, either alone or in combination with lymphocytes, may be administered in a pharmaceutically acceptable carrier. Suitable carriers may be growth medium in which the cells were grown, or any suitable buffering medium such as phosphate buffered saline. Cells may be administered alone or as an adjunct therapy in conjunction with other therapeutics.

XI. Kits and Devices

The present invention also encompasses kits and devices. For example, the kit or devie may comprise binding proteins, nucleic acids or vectors comprising sequences encoding binding proteins, host cells comprising nucleic acids or vectors and/or expressing the binding proteins as described herein, stable MHC-peptide complexes, adjuvants, detection reagents, and combinations thereof, packaged in a suitable container and may further comprise instructions for using such reagents. The kit may also contain other components, such as administration tools packaged in a separate container. The kit may be promoted, distributed, or sold as a unit for performing the methods encompassed by the present invention.

The disclosure is further illustrated by the following examples, which should not be construed as limiting.

EXAMPLES

Example 1: Materials and Methods for Example 2 a. Immunogenic Epitope Identification (i) Discovery and Design of TCR Pool

TCR sequences were obtained from a head and neck squamous cell carcinoma (HNSCC) patient that responded to immune checkpoint blockade (e.g., had 60% reduction in primary tumor size following anti-PD1 and anti-CTLA4 therapy). Individual paired TCR alpha and TCR beta sequences, previously obtained by single cell sequencing (10X Genomics) of dissociated tumor biopsies, were cloned into a single construct expressing mouse TRBC and TRAC regions to create human-mouse TCRs separated by a P2A. The TCR constructs were packaged with Lenti-X™ cells (Takara Bio USA, Mountain View, CA). Briefly, TCR constructs were mixed with packaging plasmids (pREV/pTAT/pVSVG/pGAGPOL) and incubated with jetPRIME® (Polyplus, Illkirch, France) reagent according to the manufacturer's protocol. After 24 hours, cultures were washed with Opti-Pro™ SFM medium (LifeTech). Viral supernatants were harvested 48 hours after transfection and were concentrated using Vivaspin® 20 centrifugal concentrators (Sartorius, Bohemia, NY) to desired volume (Sartorius, Bohemia, NY). Lentiviral titer was determined by GFP or TCRα/β expression using a $TCR^{-/-}$ Jurkat cell line. To quantify viral titers, GFP expression was assessed by flow cytometric analysis 48 to 72 hours post-transduction. Samples were analyzed using a CytoFLEX™ flow cytometer (Beckman Coulter). Titer was calculated as the percentage of cells expressing GFP as TU/ml using the formula: TU/ml=% of $GFP^+$×(number of cells used in transduction)×(dilution factor)×1000.

Ten orphan TCRs from this patient were pooled together to identify their cognate antigens using the genome-wide TargetScan technology. This screen identified MAGEA1 as a novel target. Validation and deconvolution of the orphan TCRs identified two TCRs (HN-32-41 and HN-32-39) recognizing the same novel epitope from MAGEA1 presented by HLA C*07:02, which is an HLA allele expressed by ~28% of the U.S. population. Note that the term "TCR32-39" may also be known as "TCR39" and the term "TCR32-41" may also be known as "TCR41".

(ii) T Cell Engineering

Primary $CD8^+$ T cells were isolated using the StraightFrom® Leukopak® CD8 Microbead Kit (Miltenyi Biotec) according to manufacturer's protocol. Isolated cells were frozen in CryoStor® CS10 (Stem Cell Technologies) and stored in liquid nitrogen until use. On day −1, $CD8^+$ T cells were thawed, washed with complete T cell medium (RPMI 1640 supplemented with 10% heat-inactivated fetal bovine serum (FBS), 100 IU/mL penicillin, 100 μg/mL streptomycin, recombinant human IL-2 [50 U/mL, PeproTech, Cranbury, NJ], recombinant human IL-15 [5 ng/mL, R&D Systems], and recombinant human IL-7 [5 ng/mL, (R&D Systems]). On day 0, $CD8^+$ T cells were washed and resuspended in fresh T cell medium and activated using ImmunoCult™ human CD3/CD28/CD2 T cell activator (5 μL/$1\times10^6$ $CD8^+$ T cells, Stem Cell Technologies). On day 1, cells were washed and resuspended in fresh complete T cell medium, and plated at $1\times10^6$ cells per well across 11 wells. Each well was transduced with lentiviral particles to express a unique orphan TCRs or a control TCR known to target a specific antigen (10 orphan TCRs+1 Control TCR;11 wells total). On day 2, cells were washed and resuspended in fresh complete T cell medium and expanded until day 5 in G-Rex®24 well plates (Wilson Wolf). On day 5, cells were harvested, individual transductions of 10 orphan TCRs were combined, whereas the cells transduced with Control TCR were maintained independently and cell concentrations were adjusted to $100\times10^6$ $CD8^+$ T cells/mL in MACS running buffer (Miltenyi) and anti-mTCR biotin antibody (BioLegend) was added a 1:50 dilution for 10 minutes at room temperature then washed with MACS running buffer. Anti-biotin microbeads (Miltenyi) were added at 1:5 dilution and incubated for 10 minutes at room temperature. Cells were washed with MACS running buffer and resuspended in MACS running buffer for manual magnetic separation using a QuadroMACS Separator and LS columns (Miltenyi). Isolated cells were washed and resuspended in fresh complete T cell medium and expanded in G-Rex®10 flasks (Wilson Wolf) until day 12, at which point cells were frozen in CryoStor® CS10 and stored at liquid nitrogen until used. CD8+ T cells expressing either the pool of 10 orphan TCRs or the positive control TCR were thawed, combined and restimulated (further expanded) by co-culturing T cells with irradiated (60 grays) allogeneic PBMCs in the presence of 0.1 μg/mL anti-CD3 (OKT3, eBioscience) and 50 U/mL recombinant IL-2 (Peprotech) in fresh T cell medium (RPMI 1640 supplemented with 10% heat-inactivated fetal bovine serum (FBS), 100 IU/mL penicillin, 100 μg/mL streptomycin, recombinant human IL-2 [50 U/mL, PeproTech]) in GRex®100 flasks (Wilson Wolf). 50 U/mL recombinant IL-2 was added to expanding cells every other day until day 6. On day 6, half of culture medium was replaced with fresh T cell medium containing 50 U/mL recombinant IL-2. Cells were used for screens on day 7.

Primary CD3+ T cells were isolated from Leukopaks using the StraightFrom® Leukopak® CD3 Microbead Kit (Miltenyi Biotec) according to manufacturer's protocol. Isolated cells were frozen in CryoStor® CS10 (Stem Cell Technologies) and stored in liquid nitrogen until use. On day −1, CD3+ T cells were thawed, washed with complete T cell medium (RPMI 1640 supplemented with 10% heat-inactivated fetal bovine serum (FBS), 100 IU/mL penicillin, 100 μg/mL streptomycin, recombinant human IL-2 [50 U/mL, PeproTech, Cranbury, NJ], recombinant human IL-15 [5 ng/mL, R&D Systems], and recombinant human IL-7 [5 ng/mL, (R&D Systems]). On day 0, $CD3^+$ T cells were washed and resuspended in fresh T cell medium and activated using ImmunoCult™ human CD3/CD28/CD2 T cell activator (5 μL/$1\times10^6$ $CD3^+$ T cells, Stem Cell Technologies). On day 1, cells were washed and resuspended in fresh complete T cell medium, and plated at $1\times10^6$ cells per well. Triplicate wells were transduced with lentiviral particles to express either TCR HN-32-41 or HN-32-39. On day 2, cells were washed, triplicates were resuspended and combined in fresh complete T cell medium, and expanded until day 5 in 1 well of a G-Rex® 6-well plate (Wilson Wolf). On day 5, cells were harvested, and cell concentrations were adjusted to $100\times10^6$ $CD3^+$ T cells/mL in EasySep buffer (StemCell Inc) and FcBlock solution with CD34 magnetic beads (Miltenyi) for 30 minutes at 4 C, washed with EasySep buffer, and separated using a QuadroMACS Separator and LS columns (Miltenyi). Isolated cells were washed and resuspended in fresh complete T cell medium and expanded in G-Rex® 10 flasks (Wilson Wolf) until day 12, at which point cells were frozen in CryoStor® CS10 and stored at liquid nitrogen until use.

(iii) Peptide Library Design

The human genome-wide peptide library was generated by tiling across the human genome coding sequences spanning all proteins of the human genome with overlapping 90-mer amino acid tiles. The tiles were synthesized on a silicon chip (Twist Bioscience) and cloned into a lentivirus expression vector.

(iv) Library Virus Packaging and Titering

To generate peptide library-expressing reporter cells, peptide library constructs were first packaged using Lenti-X™ cells (Takara Bio USA, Mountain View, CA). Briefly, the Lenti-X™ cells were plated at 75% confluency in a CellBIND® polysyrene CellSTACK® 5-stack chamber (Corning), and transfected using jetPRIME® transfection reagent (Polyplus, Illkirch, France). Peptide libraries were mixed with packaging plasmids (pREV/pTAT/pVSVG/pGAGPOL) and incubated with the jetPRIME® reagent according to the manufacturer's protocol. Opti-Pro™ SFM medium (LifeTech) was added at 24 hours post-transfection. Viral supernatants were harvested 48 hours after transfection and were concentrated using Vivaflow® 50 cassettes (Sartorius, Bohemia, NY). Lentiviral titer was determined by puromycin colonies formation using Lenti-X™ cells using serial dilution of viral supernatant. To quantify viral titers, puromycin resistance colonies were selected 48 hours post-transduction. Pruomycin resistance colonies were visualized by crystal violet staining and counted. Titer was calculated as the colony forming unit as TU/ml using the formula: TU/ml=Number of puromycin resistance colonies×dilution factor×1000.

Reporter cells were generated by knocking endogenous HLA-A/B/C out in HEK293T cells using CRISPR and engineered to express a granzyme-activated infrared fluorescent protein (IFP) and a granzyme-activated scramblase (Ferretti et al. (2020) *Immunity* 53:1095-1107). Reporter cells for screens were engineered to express all six HLA alleles expressed by the subject from which the TCRs were obtained: human HLA-A*01:01, A*03:01, B*07:02, B*08:01, C*07:01 and C*07:02 (V1 P32 HEK Screps).

Reporter cells (V1 P32 HEK Screps) were transduced with lentiviral particles to express the PEP LIB V2 PLUS library at an MOI of 5 in complete DMEM (1×DMEM supplemented with 10% fetal bovine serum, 100 IU/mL penicillin, 100 μg/mL streptomycin). This library is comprised of >600,000 constructs (tiles) comprised of 90 amino acids each, representative of the human proteome. The day after transduction, complete DMEM media was refreshed and cells were maintained in culture or frozen in complete DMEM supplemented with 10% DMSO until needed.

(v) Co-Culture and Enrichment of Granzyme-Killed Cells

On day 7 of T cell expansion, T cells were added to library-transduced reporter cells at and E:T ratio of 2:1 and incubated at 37° C. for four hours. After incubation, all cells were harvested by trypsinization and centrifugation, cells were resuspended in 1×Annexin V binding buffer (Miltenyi Biotec) and centrifuged. Cells were resuspended with Annexin V magnetic microbeads (Miltenyi Biotec) in 1×Annexin V binding buffer (1 mL microbeads in 9 mL Annexin V binding buffer per $1\times10^9$ total cells) and incubated at room temperature for 15 minutes. Cells were washed with 5× volume of Annexin V binding buffer and centrifuged. Cells were resuspended in Annexin V binding buffer and then divided over 2 "megareps" and filtered using a 70 μM cell strainer (Corning). Annexin V-labeled cells were positively selected using an AutoMACS Pro (Miltenyi Biotec). The elution of each "megarep" was further divided over four "replicates" for a total of 8 technical replicates per screen. IFP cells were sorted using a MoFlo Astrios EQ cell sorter (Beckman Coulter) and stored in DNA/RNA Shield™ (Zymo Research) for subsequent analysis.

(vi) Next-Generation Sequencing (NGS) and Data Analysis

Genomic DNA was extracted using GeneJET™ Genomic DNA Purification Kit (Thermo Fisher Scientific, Waltham, MA) and prepared for NGS sequencing using two rounds of PCR amplification. In brief, the first round PCR amplified the peptide cassette and the second round added sequencing adapter and sample indexes before sequencing using an Illumina NextSeg™ instrument (Illumina, San Diego, CA).

Nucleotide sequences were mapped to individual nucleotide tiles. The proportion of read counts for each tile was calculated for each screen replicate (n=8) and for the input for each pool of transduced reporter cells, and enrichments of each tile were calculated by dividing the proportion of the tile in the screen replicate by the proportion of the tile in the input library. A modified geometric mean of the enrichment of an identical tile across the 8 screen replicates was used to identify reproducible screen hits.

b. TCR Discovery (i) Identification of the HLA Restriction

Since the reporter cells used in the genome-wide screen expressed six HLA-alleles: A*01:01, A*03:01, B*07:02, B*08:01, C*07:01 and C*07:02; it was necessary to deconvolute the HLA-restriction for the identified MAGEA1 epitope. Monoalleleic HEK reporter cells individually expressing each of the 6 HLA alleles were transduced with with lentiviral particles at an MOI of 1 to express an individual 90-amino acid fragments representing the top-scoring MAGEA1 tile from the screen. Cells were selected with puromycin (1.5 ug/mL) in complete DMEM. Cells were seeded a day before co-culture with the pool of T cells at an E:T ratio of ~2:1. After 4 hours, the co-cultures were harvested by pipetting and fluorescence of the reporter was detected using a CytoFLEX™ S instrument (Beckman Coulter).

(ii) Identification of the Corresponding TCR

To identify the corresponding TCR from the pool of TCR-transduced T cells, MHC monoallelic C*07:02 HEK293T cells engineered to express the MAGEA1 90mer were co-cultured with the pool of T cells at an E:T ratio of 1:1 for 16-24 hours. The T cells were mixed, collected by pipetting, and labeled with a CD137 microbead kit (Miltenyi) following the manufacturer's instructions. In brief, T cells were first stained with PE-labeled anti-CD137 and AF647-labeled anti-CD69 (BioLegend), washed, and then labeled with anti-PE microbeads. Labeled cells were enriched with an autoMACS® Pro separator (Miltenyi) and CD137 and CD69 double-positive cells were sorted on a MoFlo® Astrios™ Cell Sorter (Beckman Coulter). Genomic DNA was extracted from the sorted cells and the TCR expression cassette was PCR amplified and prepared for next generation sequencing (NGS).

(iii) Peptide Prediction and Target Verification

Overlapping peptide sequences with a score >2.5 fold were used to predict MHC binding with NetMHC4.0 (available on the World Wide Web at cbs.dtu.dk) and the top predicted MHC binding peptides were synthesized (Genscript). Monoallelic C*07:02 HEK293T reporter cells were pulsed with serial dilutions 0-20,000 ng/ml of each peptide candidate for 1 hour and then co-cultured with TCR-transduced T cells (1-IN-32-39 or HN-32-41) at an E:T ratio of ~1:1. After 4 hours, the cultures were harvested by pipetting and fluorescence of the reporter was detected using a CytoFLEX™ S instrument (Beckman Coulter). Additionally, monoallelic C*07:02 HEK293 suspension cells were pulsed with serial dilutions 0-500 pM of peptide VBFFFPSL (SEQ ID NO: 1) for 2 hours and then co-cultured with TCR-transduced T cells (HN-32-39 or HN-32-41) at an E:T ratio of 1:1 overnight. Cells were then harvested by pipetting and centrifuged at 2,000 rpm for 2 minutes. The supernatant was collected for IFNγ measurement using a human IFNγ 3rd generation single-plex assay (Protein Simple).

c. TCR Characterization (i) T Cell Recognition Assay

To detect reactivity to cancer cell lines, wild-type cancer cell lines were seeded in a 96-well flat bottom plate and rested overnight at 37° C. in 5% $CO_2$. On the following day, T cells were thawed, washed in complete RPMI-1640 medium, and added to the wells for an effector to target (E:T) ratio of 1:1 for INFγ measurement or 1:4 for flow cytometry analysis of activation-induced markers. The co-culture was incubated overnight. Cells were then harvested by pipetting, transferred to V-bottom 96-well plates, and centrifuged at 2,000 rpm for 2 minutes. The supernatant was collected for IFNγ measurement using a human IFNγ 3rd generation single-plex assay (Protein Simple). For flow cytometry analysis (Cytoflex S™ instrument, Beckman Coulter), cell pellets were washed with FACS buffer (PBS, 0.5% BSA, 2 mM EDTA) and stained for activation-induced markers, including PE-conjugated anti-CD137 (Miltenyi), AF647-conjugated anti-CD69 (Biolegend), and BV421-conjugated anti-CD8 (BioLegend).

(ii) Cancer Cell Culture and Incucyte® NucLight™ Red Transduction

Cancer cell lines were purchased from ATCC (Manassas, $V_\alpha$.) and HEK293T cells were originally from Takara Bio (Shiga, Japan). All media were supplemented with 10% PBS, except U266B1 which required 15% FBS, and 1% penicillin and incubated at 37° C. in 5% $CO_2$. A101D (high MAGE-A1 expresing cells; TPM: 359), A2058 (medium MAGE-A1 expresing cells; TPM: 128), HS294T, and HEK293T cells were maintained in complete DMEM. SK-MEL-5 was cultured in complete EMEM, whereas U266B1, NCIH1437 and 786-O required complete RPMI. Untransduced cancer cells were maintained in preparation for the T cell recognition assay, and $10^6$ cells of each cell line were introduced with Incucyte® NucLight™ Red lentivirus reagent (Sartorius, Gottingen, Germany) Positively-labeled cells were selected using 1.5 ug/mL of puromycin over 72 hours.

(iii) Incucyte® Cytotoxicity Assay

Cancer cells selected for Incucyte® NucLight™ analysis were seeded into 96-well flat bottom plates (Corning, Flintshire, UK) at $10^4$ cells. On the same day, T cells were thawed, washed in complete RPMI-1640, and allowed to rest overnight in medium with 50 U/mL IL-2 (PeproTech), 5 ng/mL IL-7, and 5 ng/mL IL-15 (R&D Systems). All cells were rested overnight at 37° C. in 5% $CO_2$. Serial dilution of the T cells was performed for the effector to target ratios, with the highest E:T at 4:1, and the lowest at 1:4. One image per whole well from two technical replicates was taken every 2 hours over a 72 hour time course. Imaging utilized a 4× objective lens and data were analyzed using the Incucyte® Basic Software. Red channel acquisition time was 400 ms, and its background was subtracted by enabling Top-Hat segmentation. Edge split was applied so that the software can recognize closely spaced cells as multiple objects, rather than one object, if the setting were absent.

(d) Alloreactivity and Safety Screens (i) Generation of 96-Well-Based MHC-Expressing Arrays for Alloreactivity Screens Endogenous HLA-A/B/C were knocked out in HEK293T cells using CRISPR-Cas engineering. Guide RNAs (gRNAs) were designed against sequences conserved across the HLA-A, HLA-B and HLA-C loci using the multicrispr.net tool (Prykhozhij et al., *Plos One,* 2015). The following guides were selected: CRISPR-ALL-1: CGGCTACTACAACCAGAGCG (SEQ ID NO: 58), CRISPR-ALL-2: AGATCACACTGACCTGGCAG (SEQ ID NO: 59), CRISPR-ALL-3: AGGTCAGTGTGATCTCCGCA (SEQ ID NO: 60). gRNAs were cloned into the LentiCRISPR V2 vector using BsmBI sites. HEK293T cells were transfected with plasmid guide constructs using Mirus TransIT (Mirus Bio, Madison, WI). After 7 days, MHC-knockout (MHC-KO) cells were sorted using a pan-MHC antibody (BioLegend). Single-cell clones were expanded, and the absence of MHC was verified by flow cytometry. B2M-knockout (B2M-KO) cells were used as a positive control for the complete absence of surface MHC expression. B2M was knocked out in HEK293T cells by electroporating CRISPR RNPs targeting B2M using the guide RNA: GGCCACGGAGCGAGACATCT (SEQ ID NO: 61).

MHC-null HEK293T cells were transduced with IncuCyte® NucLight™ Red virus (Essen BioScience). Transduced cells were sorted for NucLight™ Red expression using a Sony SH800 sorter. To generate an MHC-expressing array, MHC-null NucLight™ Red-expressing HEK293T cells were transduced with the most common 110 MHCs (pHAGE-EF1a-MHC-UBC-NAT) in individual wells in 96-well plates. Transduced cells were selected with nourseothricin (400 μg/ml) for one week. Cells expressing the most common 110 MHCs were passaged and stored in 96-well plates as an array. Expression of individual MHC alleles was verified by staining using a pan-MHC antibody (BioLegend).

To generate the positive control for the assay, MHC-null HEK293T cells were transduced with IncuCyte® NucLight™ Red virus (Essen BioScience) and sorted for NucLight™ Red expression using a Sony SH800 sorter. HLA-C*07:02 (pHAGE-EF1a-MHC-UBC-NAT) was then introduced into the cells using lentiviral transduction. Transduced cells were selected with nourseothricin (400 μg/ml) for one week. These cells were then transduced with a 90-mer construct (pHAGE-CMV-FHA-MAGE-A1-EFS-AmCyan) expressing a fragment of MAGE-A1, which contains the MAGE-A1 epitope (VBFFFPSL (SEQ ID NO: 1)). Transduced cells were then sorted for AmCyan expression using a Bigfoot Spectral Cell Sorter (Thermo Fisher Scientific).

(ii) Lentiviral Packaging and Transduction

To package the lentiviruses of the 110 MHC expression constructs (pHAGE-EF1a-MHC-UBC-NAT), MHC-null HEK293T cells were plated at 75% confluency in 96 wells and transfected using jetPRIME® transfection reagent (Polyplus, Illkirch, France). Individual MHC expression constructs were mixed with packaging plasmids (pREV/pTAT/pVSVG/pGAGPOL) and incubated with jetPRIME® reagent according to the manufacturer's protocol, and DMEM medium was added at 24 hours post-transfection. Viral supernatants were harvested 48 hours after transfection and used for transduction of the 110 MHCs in a 96-well-based array format. To package the lentiviruses of other constructs, Lenti-X® cells (Takara Bio USA, Mountain View, CA) were plated at 75% confluency and transfected using jetPRIME® transfection reagent (Polyplus, Illkirch, France). Expression constructs were mixed with packaging plasmids (pREV/pTAT/pVSVG/pGAGPOL) and incubated with jetPRIME® reagent according to the manufacturer's protocol, and OptiPRO™ SFM medium was added at 24 hours post-transfection. Viral supernatants were harvested 48 hours after transfection and were concentrated using either Vivaspin® 20 centrifugal concentrators or Vivaflow® 50 cassettes (Sartorius, Bohemia, NY).

All viral transduction involving cell lines derived from HEK293T cells was done with polybrene (4 μg/ml).

(iii) Co-Culture for Alloreactivity Profiling

Pan T cells were engineered as described above and frozen. On Day 0, T cells were restimulated in upright T25 flasks with 1.0E+6 T cells, 20.0E+6 irradiated PBMCs, recombinant human IL-2, and CD3 monoclonal antibody (OKT3) [0.1 ug/mL, eBioscience]. Half the volume of media was exchanged on Days 2, 4, 5, and 6 with RPMI 1640 supplemented with 10% heat-inactivated fetal bovine serum [FBS], 100 IU/mL penicillin, 100 μg/mL streptomycin, and recombinant human IL-2 [50 U/mL, PeproTech, Cranbury, NJ]. Cells were harvested for assay on Day 7.

The assay was performed in triplicates. On Day 5, target cells in the 96-well array were passaged and seeded in 384-well plates. On Day 6, engineered CD8+ T cells expressing the HN-32-41 TCR or untransduced control T cells were added at an effector to target (E:T) ratio of 5:1 and incubated with target cells for 48 hours. Target cell numbers were measured over time using IncuCyte® by measuring the number of NucLight™ Red-positive cells. Cell inhibition at 48 h by the recombinant TCR of interest on each MHC in the assay was calculated as 1−(Cell doubling[Incubated with HN-32-41-expressing T cells]/Cell doubling[Incubated with untransduced control T cells]).

(iv) Generation of TCR HN-32-41-Expressing CD8 T Cells for Safety Screens

Primary CD8+ T cells were prepared as described above to express HN-P32-41. Triplicate wells transduced with lentiviral particles to express HN-32-41 combined in fresh complete T cell medium, and expanded until Day 5 in a G-Rex® 10 culture vessel (Wilson Wolf). On Day 5, cells were harvested, and cell concentrations were adjusted to $100\times10^6$ $CD3^+$ T cells/mL in EasySep buffer (StemCell Inc) and FcBlock solution with CD34 magnetic beads (Miltenyi) for 30 minutes at 4 C, washed with EasySep buffer, and separated using a QuadroMACS® Separator and LS columns (Miltenyi). Isolated cells were washed and resuspended in fresh complete T cell medium and expanded in G-Rex®10 flasks (Wilson Wolf) until day 12, at which point cells were frozen in CryoStor® CS10 and stored at liquid nitrogen until use.

CD8+ T cells expressing HN-32-41 were thawed and restimulated (further expanded) by co-culturing T cells with irradiated (60 grays) allogeneic PBMCs in the presence of 0.1 ug/mL anti-CD3 (OKT3, eBioscience) and 50 U/mL recombinant IL-2 (Peprotech) in fresh T cell medium (RPMI 1640 supplemented with 10% heat-inactivated fetal bovine serum (FBS), 100 IU/mL penicillin, 100 μg/mL streptomycin, recombinant human IL-2 [50 U/mL, PeproTech]) in GRex® 100 flasks (Wilson Wolf). 50 U/mL recombinant IL-2 was added to expanding cells every other day until day 6. On day 6, half of culture medium was replaced with fresh T cell medium containing 50 U/mL recombinant IL-2. Cells were used for screens on Day 7.

(v) Quality Control (QC) of T Cell On-Target Killing

On Day 5 of restimulation, reporter cells (expressing the peptidome library) were labeled with CellTrace™ Violet (Thermo Fisher) for 10 minutes at room temperature. The labeling reaction was quenched with a 5× excess of complete DMEM media (1×DMEM supplemented with 10% FBS, 100 IU/mL penicillin, 100 ug/mL streptomycin). After centrifugation, cells were seeded for subsequent assays. For off-target screening, $400\times10^6$ labeled reporter cells were seeded in a CellSTACK® flask. For QC of T cell on-target killing, 25,000 reporter cells were seeded per well of a 96-well flat bottom plate.

On Day 6 of HN-32-41 restimulation, T cells were tested for activity against MAGE-A1 peptide. As a positive control, a fraction of reporter cells was pulsed with 100 ng/mL of MAGE-A1 peptide (Genscript) for one hour. T cells were added to reporter cells at four effector:target (E:T) ratios (2:1, 1:1, 1:2, 1:4) in triplicate. After four hours of incubation at 37° C., cells were resuspended by pipetting up and down before data acquisition on a CytoFLEX flow cytometer (Beckman Coulter).

(vi) Screen Co-Culture, Target Cell Enrichment and Sorting

On Day 7 of HN-32-41 expansion, T cells were added to library-transduced reporter cells and incubated at 37° C. for four hours. After incubation, all cells were harvested by trypsinization and centrifugation, cells were resuspended in 1× Annexin V binding buffer (Miltenyi Biotec) and centrifuged. Cells were resuspended with Annexin V magnetic microbeads (Miltenyi Biotec) in 1× Annexin V binding buffer (1 mL microbeads in 9 mL Annexin V binding buffer per $1\times10^9$ total cells) and incubated at room temperature for 15 minutes. Cells were washed with 5× volume of Annexin V binding buffer and centrifuged. Cells were resuspended in Annexin V binding buffer and then divided over 2 "megareps" and filtered using a 70 uM cell strainer (Corning). Annexin V-labeled cells were positively selected using an autoMACS® Pro (Miltenyi Biotec). The elution of each "megarep" was further divided over four "replicates" for a total of 8 technical replicates per screen. IFP cells were sorted using a MoFlo® Astrios EQ cell sorter (Beckman Coulter).

(vii) Next Generation Sequencing

Genomic DNA (gDNA) was extracted from sorted cells using the GeneJET™ Genomic DNA Purification Kit (Thermo Fisher Scientific). The antigen cassette was amplified from the extracted gDNA by PCR then appended with sequencing adaptors and sample-specific index sequences in a second PCR reaction Amplicons were sequenced on an Illumina NextSeq™ machine using the standard Illumina sequencing primer.

(viii) Data Analysis

Nucleotide sequences were mapped to individual nucleotide tiles. The proportion of read counts for each tile was calculated for each screen replicate (n=8) and for the input for each pool of transduced reporter cells, and enrichments of each tile were calculated by dividing the proportion of the tile in the screen replicate by the proportion of the tile in the input library. A modified geometric mean of the enrichment of an identical tile across the 8 screen replicates was used to identify reproducible screen hits. Candidate epitopes for each tile were selected by identifying predicted strong-binding epitopes shared across overlapping adjacent and redundant tiles that were enriched in the screen.

e. Safety Evaluation of HN-32-41

(i) 90-Mer Validation

Strong hits from the safety screen were first evaluated using 90-mers. Monoalleleic HEK reporter cells espressing HLA C*07:02 were transduced with with lentiviral particles at an MOI of 1 to express an individual 90-amino acid fragments representing the top-scoring off-target tiles from the screen (e.g., LAMB4-IR, PIGO, SLC6A13, TLE3, BTBD2, SLC6A12, and RXFP1). Cells were selected with puromycin (1.5 ug/mL) in complete DMEM. Cells were seeded a day before co-culture with T cells expressing HN-32-41 at an E:T ratio of ~2:1. After 4 hours, the co-cultures were harvested by pipetting and fluorescence of the reporter was detected using a CytoFLEX™ S instrument (Beckman Coulter).

(ii) ORF Validation

Hit that validated as targets using 90-mers were advanced to testing against full protein open reading frames (ORFs). ORFs for TLE3 and SLC6A13 were cloned from the ORFeome Collaboration Library (Horizon). LAMB4 intron retention ORF was synthesized (GenScript). These clones were cloned into lentiviral over-expression vectors and delivered to C*07:02 HEK reporter cells by transduction followed by selection with puromycin. Cells were seeded a day before co-culture with T cells expressing HN-32-41 at an E:T ratio of ~2:1. After 4 hours, the co-cultures were harvested by pipetting and fluorescence of the reporter was detected using a CytoFLEX™ S instrument (Beckman Coulter). The PIGO ORF clone was purchased from Genscript in pcDNA3.1 overexpression vector and delivered by transient transfection using FuGENE6 reagent (Promega). C*07:02 HEK reporter cells were seeded to adhere overnigth, then transiently transfected with the PIGO ORF. The media was refreshed then cells expant overnight. Cells were co-cultured with T cells expressing HN-32-41 at an E:T of ~2:1. After 4 hours, the co-cultures were harvested by pipetting and fluorescence of the reporter was detected using a CytoFLEX™ S instrument (Beckman Coulter).

(iii) Peptide Validation

Targets that showed reactivity of HN-32-41 against full-length ORFs were advanced to testing against peptides. MHC-Flurry (O'Donnell et al. (2020) *Cell Systems* 42-48.e7) was used to predict peptides from LAMB4-IR with high-affinity binding to C*07:02. Predicted high-binding peptides were synthesized (GenScript). Monoallelic C*07:02 HEK293T reporter cells were pulsed with serial dilutions 0-20,000 ng/ml of the top peptide candidate for 1 hour and then co-cultured with TCR-transduced T cells (HN-32-41) at an E:T ratio of ~2:1. After 4 hours, the cultures were harvested by pipetting and fluorescence of the reporter was detected using a CytoFLEX™ S instrument (Beckman Coulter).

(iv) Co-Culture with Normal Primary Cells

Primary normal cells from C*07:02+ donors that were expanded, confirmed to maintain differentiation states, and frozen were obtained (Lonza). Tested samples include: Human umbilical vein endothelial cells (HUVEC (CC-2517)), lung small airway epithelial cells (SAEC (CC-2547)) and lung bronchial-tracheal epithelial cells (NHBE (CC-2540)).

Prior to co-culture assays, primary normal cells were thawed, washed, resuspended in RPMI media supplemented with IL-2, IL-7, and IL-15 and seeded in 96-well flat-bottom culture plates at a density of 200,000 cells/well and allowed to rest for 4 hours. Cells were pulsed with MAGE-A1 peptide for 1-2 hours or left un-pulsed in their respective media. HN-32-41 or untransduced (NTD) T cells were then added at a density of 100,000 cells/well in complete T cell media. 24 hours post co-culture, supernatants were collected and frozen at −80° C.). Supernatants were thawed and analyzed for IFN-γ levels by loading on a Simple Plex Human IFN-gamma (3rd Gen) Cartridge (ProteinSimple, San Jose, CA) using the Ella™ instrument.

For flow cytometry analysis (Cytoflex S™ instrument, Beckman Coulter), cell pellets were washed with FACS buffer (PBS, 0.5% BSA, 2 mM EDTA) and stained for activation-induced markers, including PE-conjugated anti-CD137 (Miltenyi), AF647-conjugated anti-CD69 (BioLegend), and BV421-conjugated anti-CD8 (BioLegend).

Figure 2A:
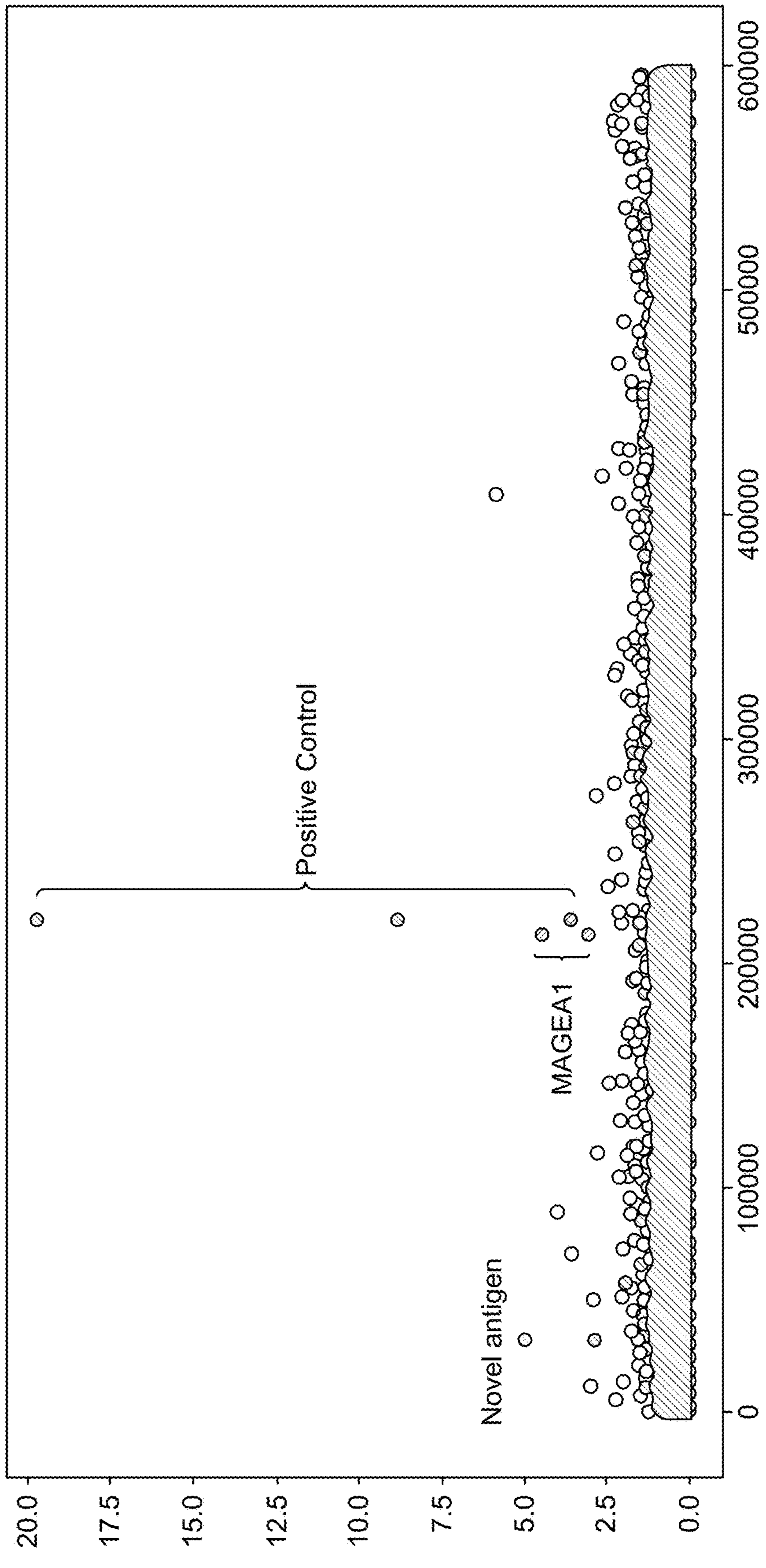
Figure 2A:
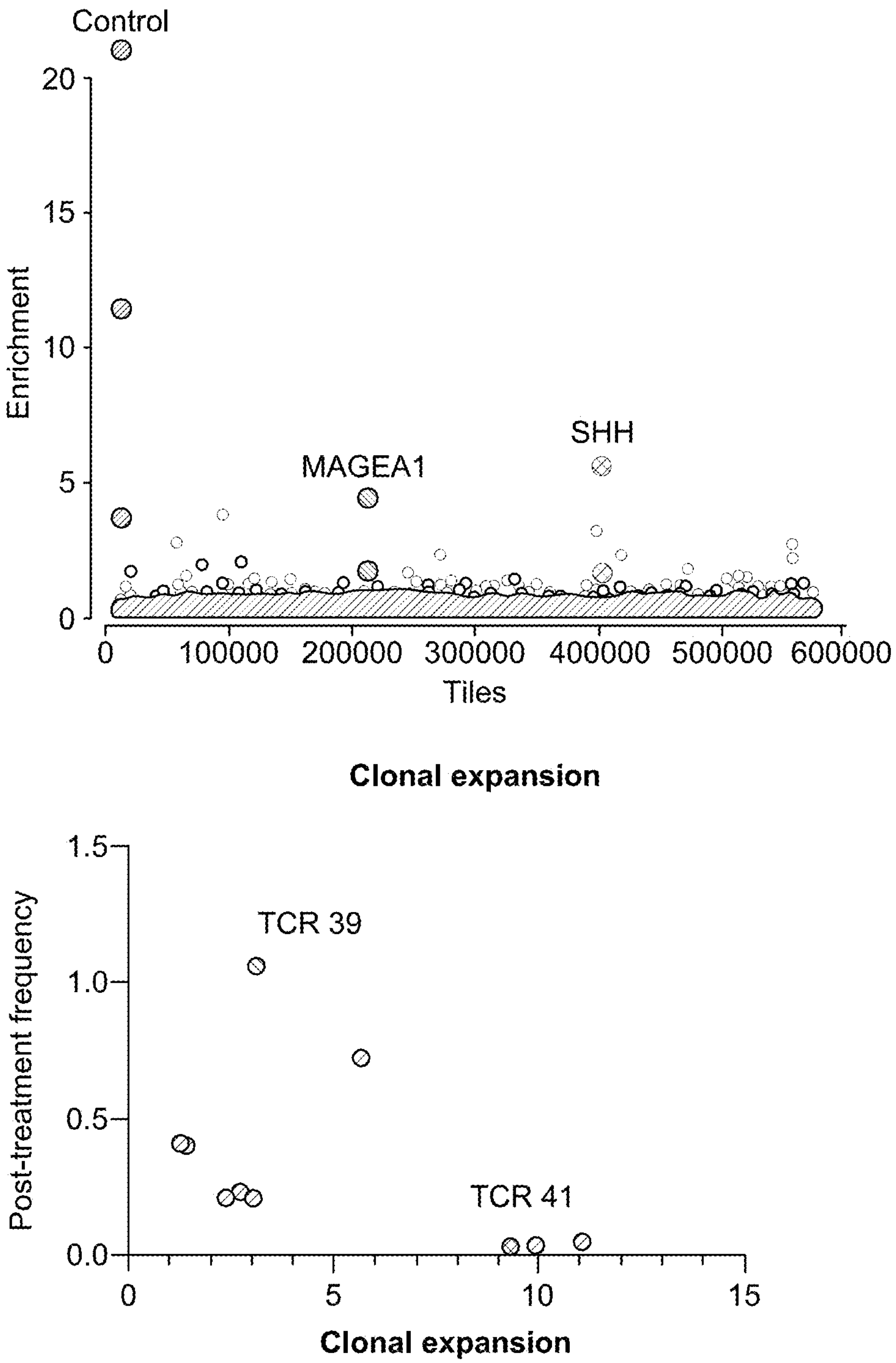
Figure 2B:
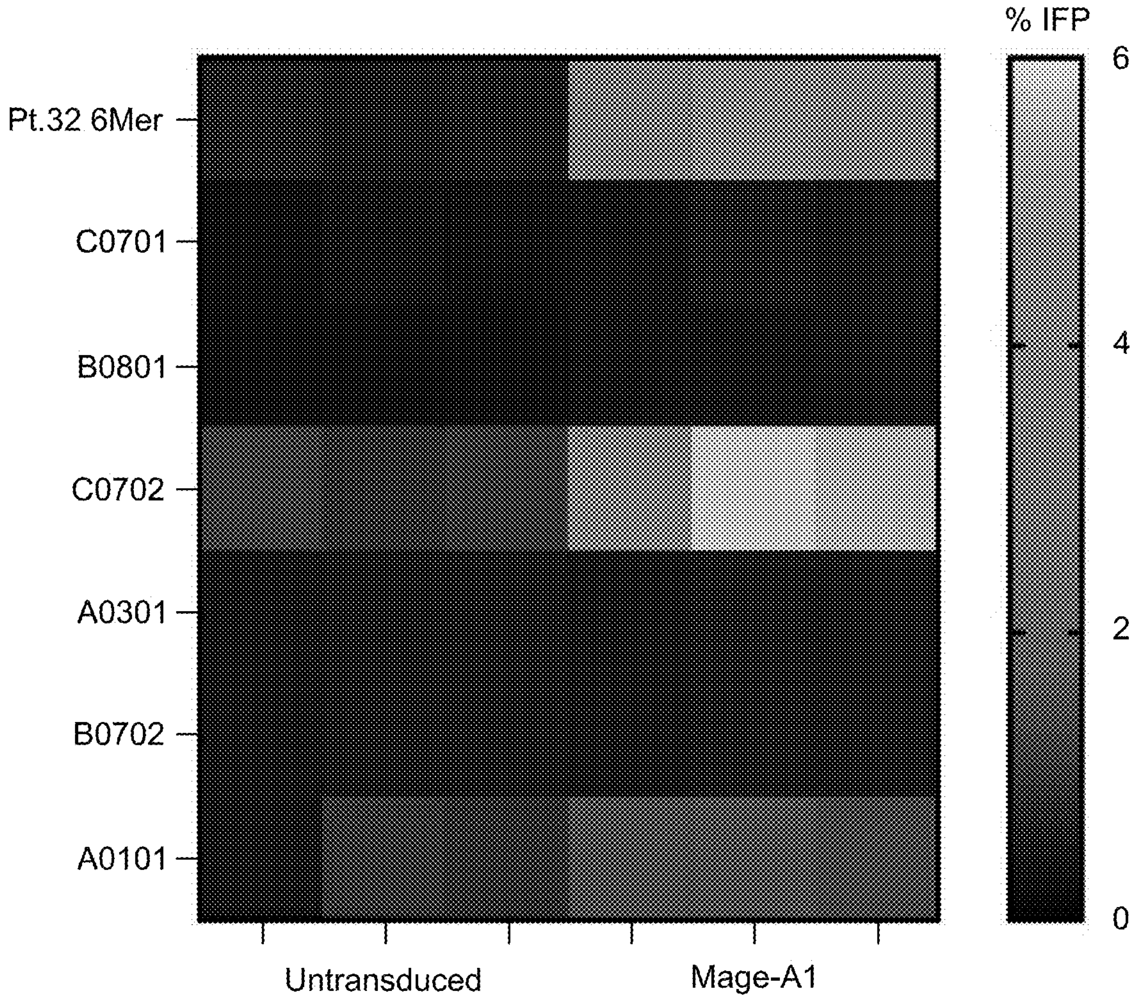

Example 2: Identification of MAGEA1 Immunogenic Epitopes and Binding Proteins Thereto A high-throughput antigen discovery platform that enables rapid identification of TCRs from a pool of TCRs obtained from a dissociated tumor sample that recognize immunogenic peptides presented by MHC molecules was developed and applied to identify the recognized immunogenic peptides (see Example 1). Antigenic peptides of MAGEA1, which is a gene whose expression is associated with certain disorders like cancer and not normally expressed in tissues outside of testis (FIG. 1), were identified as being recognized by TCRs that expanded following immune checkpoint blockade in head and neck tumor samples (FIG. 2A). Further evaluation revealed that the antigenic peptide was presented by HLA C*07:02 (FIG. 2B).

Common sequences shared by overlapping tiles of the searched sequence library and bioinformatics analyses allowed for the identification of immunogenic MAGEA1 peptide sequences (see Table 1 and FIG. 2C for representative immunogenic peptides). See also FIGS. 2D and 2E for a representative immunogenic peptide validation indicating that the peptide VBFFFPSL (SEQ ID NO: 1) exhibited the most favorable immunogenicity.

Figure 4B:
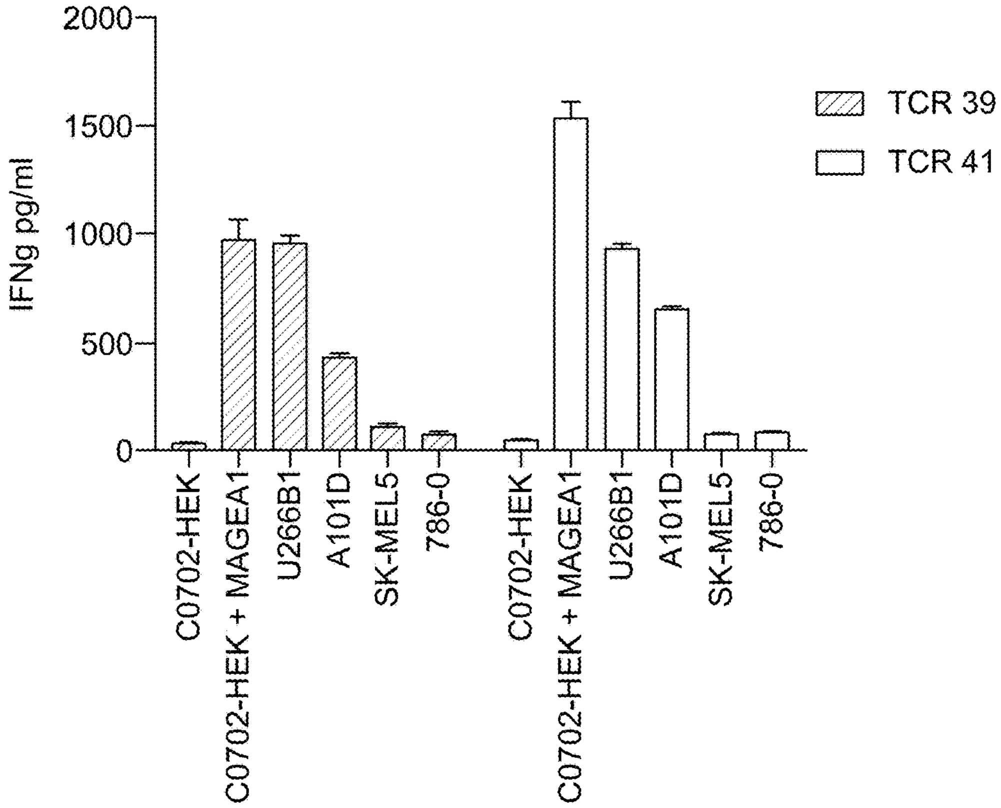
Figure 4C:
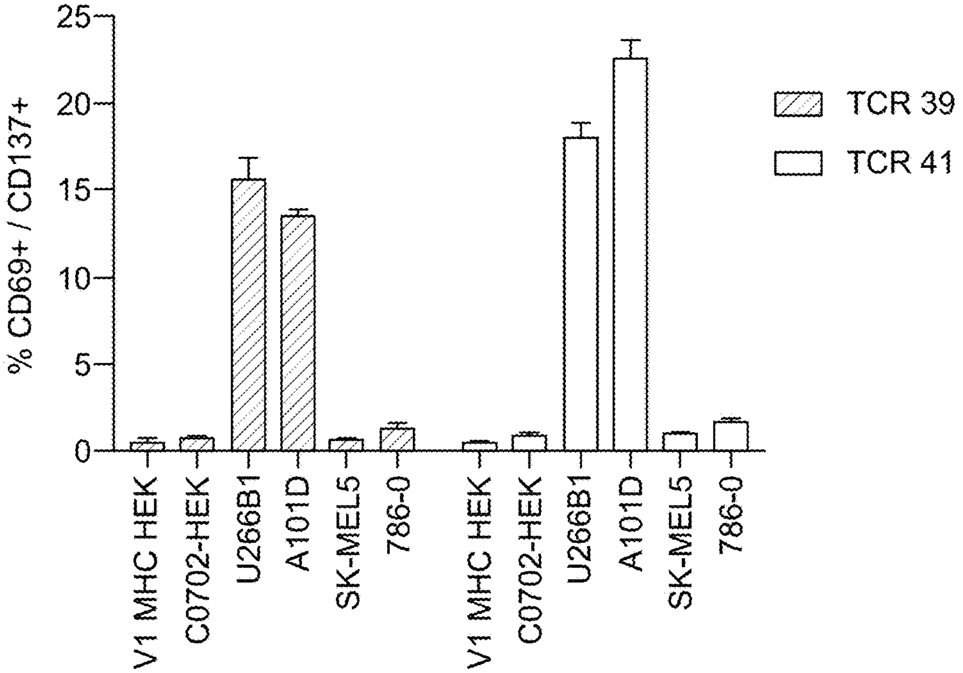
Figures 5A, 5B:
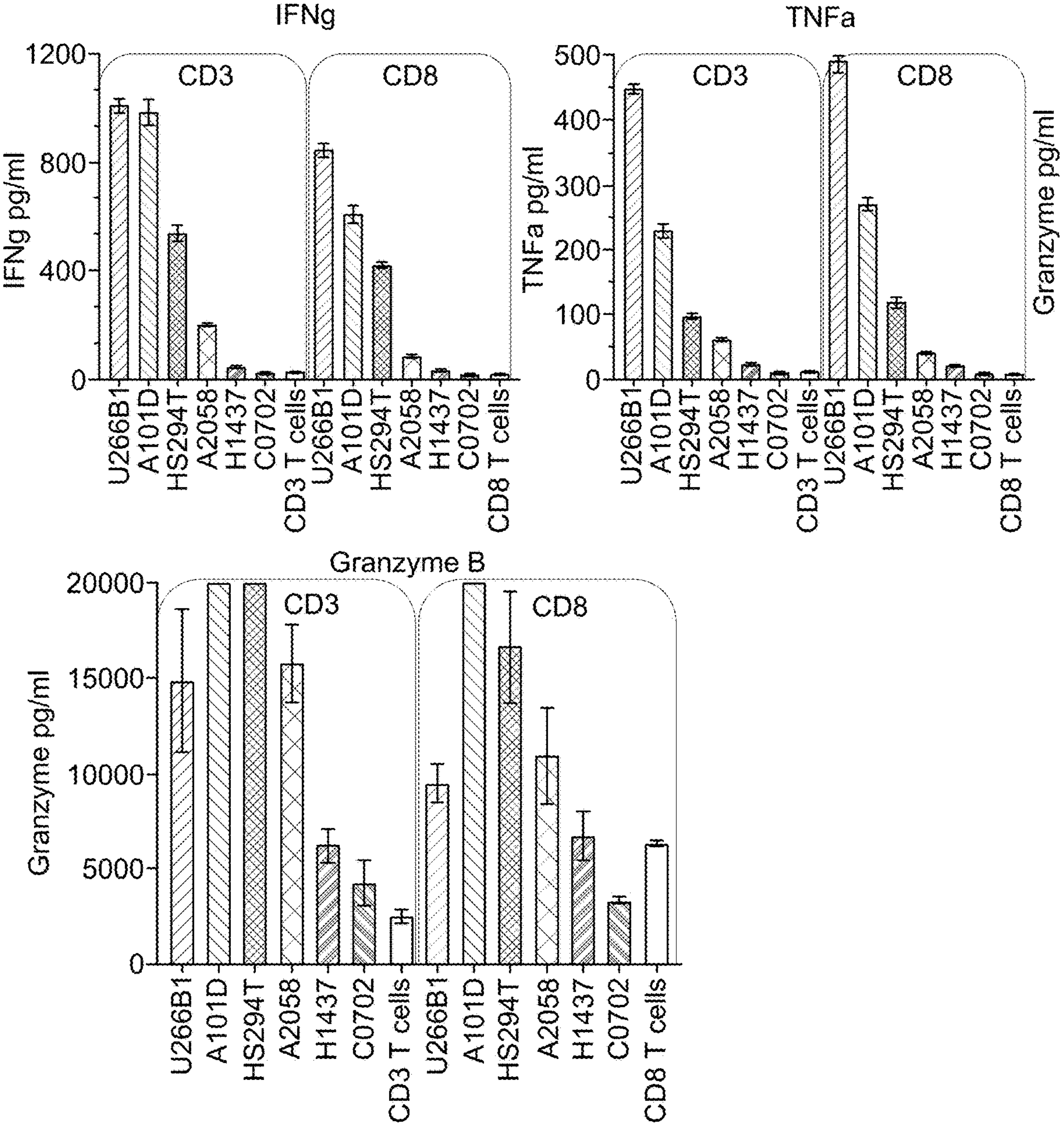
FIG. 5A-FIG. 5C show that TCR 32-41, transduced into pan-T-cells (CD3+: includes both CD4+ or CD8+ T-cells) ("TSC-204-C7") recognizes cancer cells that express MAGEA1. As described further below, the term "TSC-204-C7" refers to an engineered whole T cell population, including CD8+ T cells and CD4+ T cells, expressing TCR 32-41 in addition to other components, including CD8α, CD8β, and a CD34 enrichment tag. In some embodiments, TSC-204-C7 may further express a DN-TGF βRII.
Figure 5C:
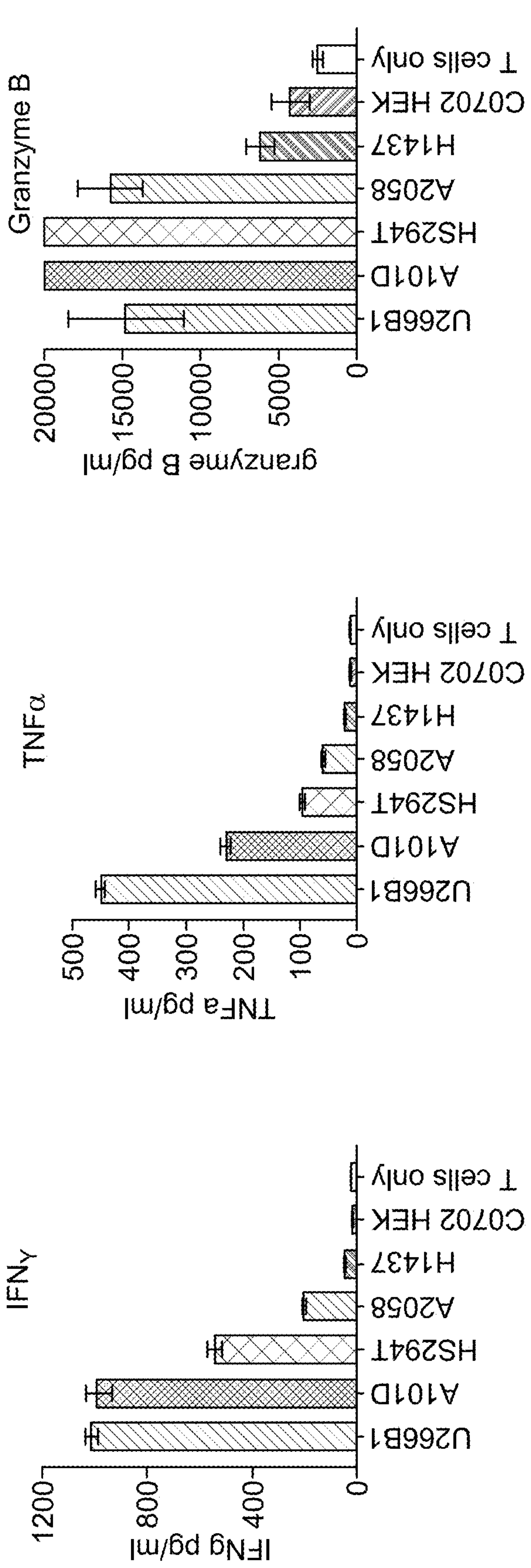
Figure 6A:
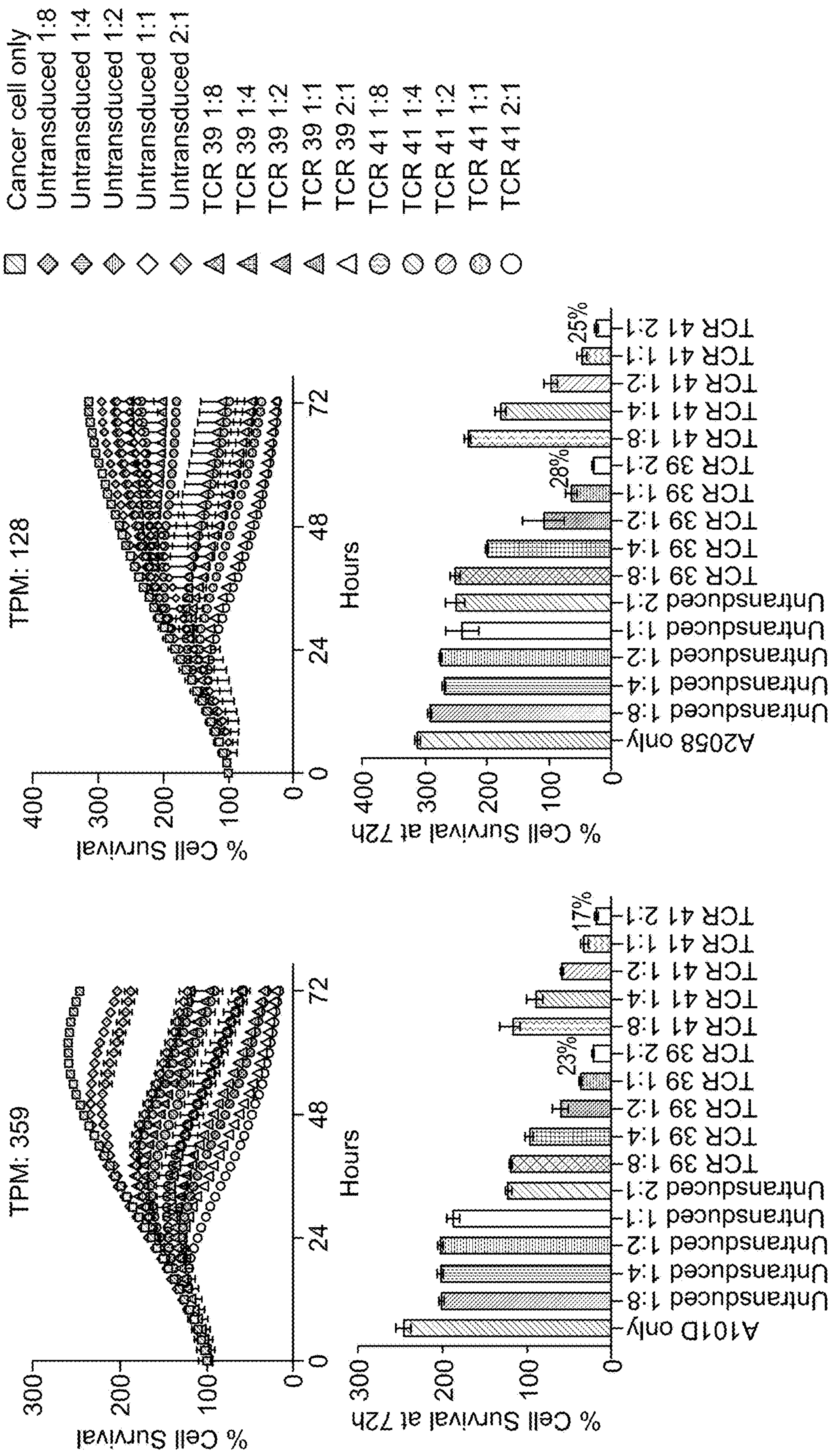
FIG. 6A-FIG. 6C demonstrate the cytotoxic activity of TCRs 32-39 or 32-41 on cell lines expressing variable levels of MAGEA1.
Figure 6B:
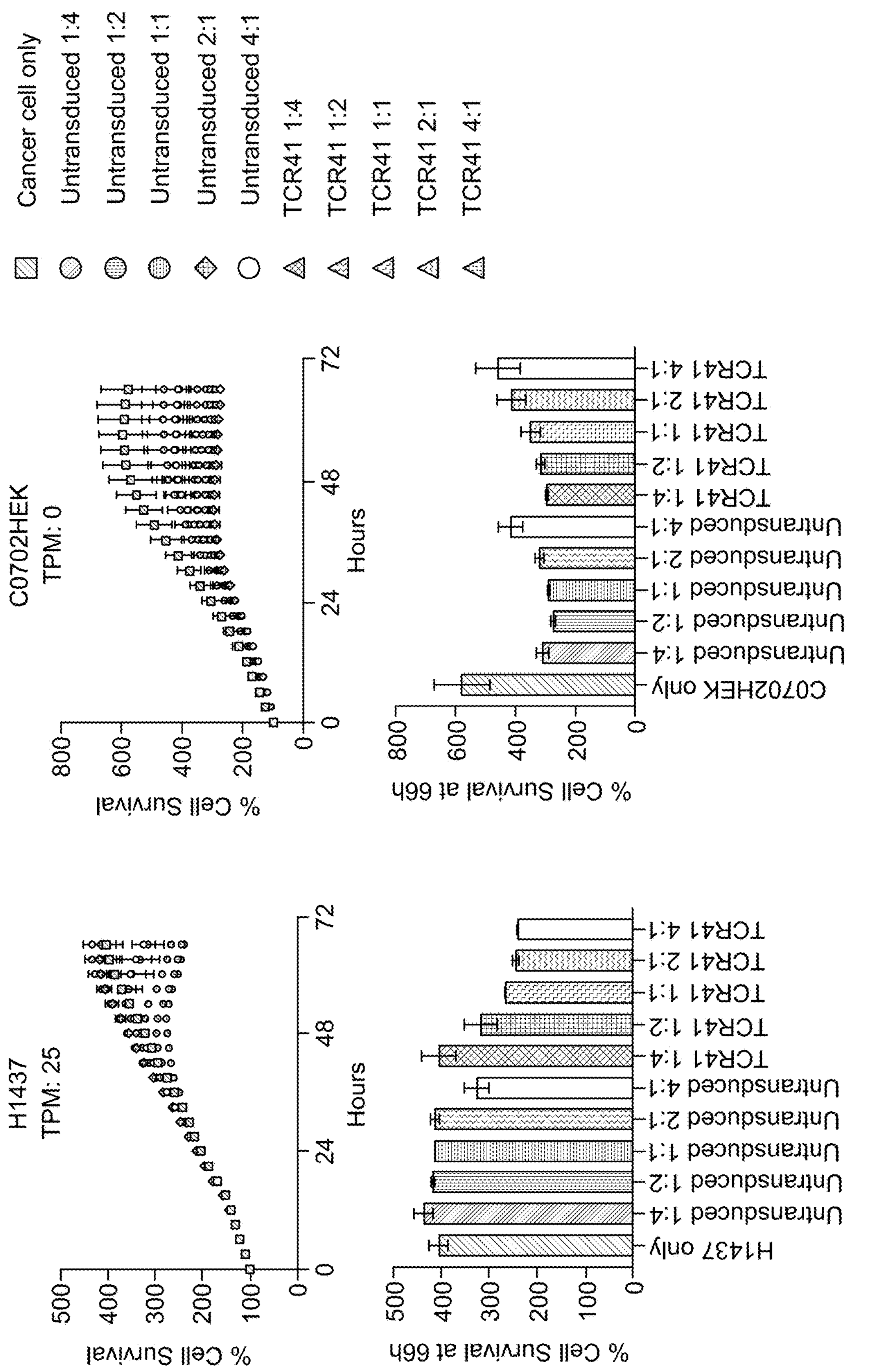
Figure 6C:
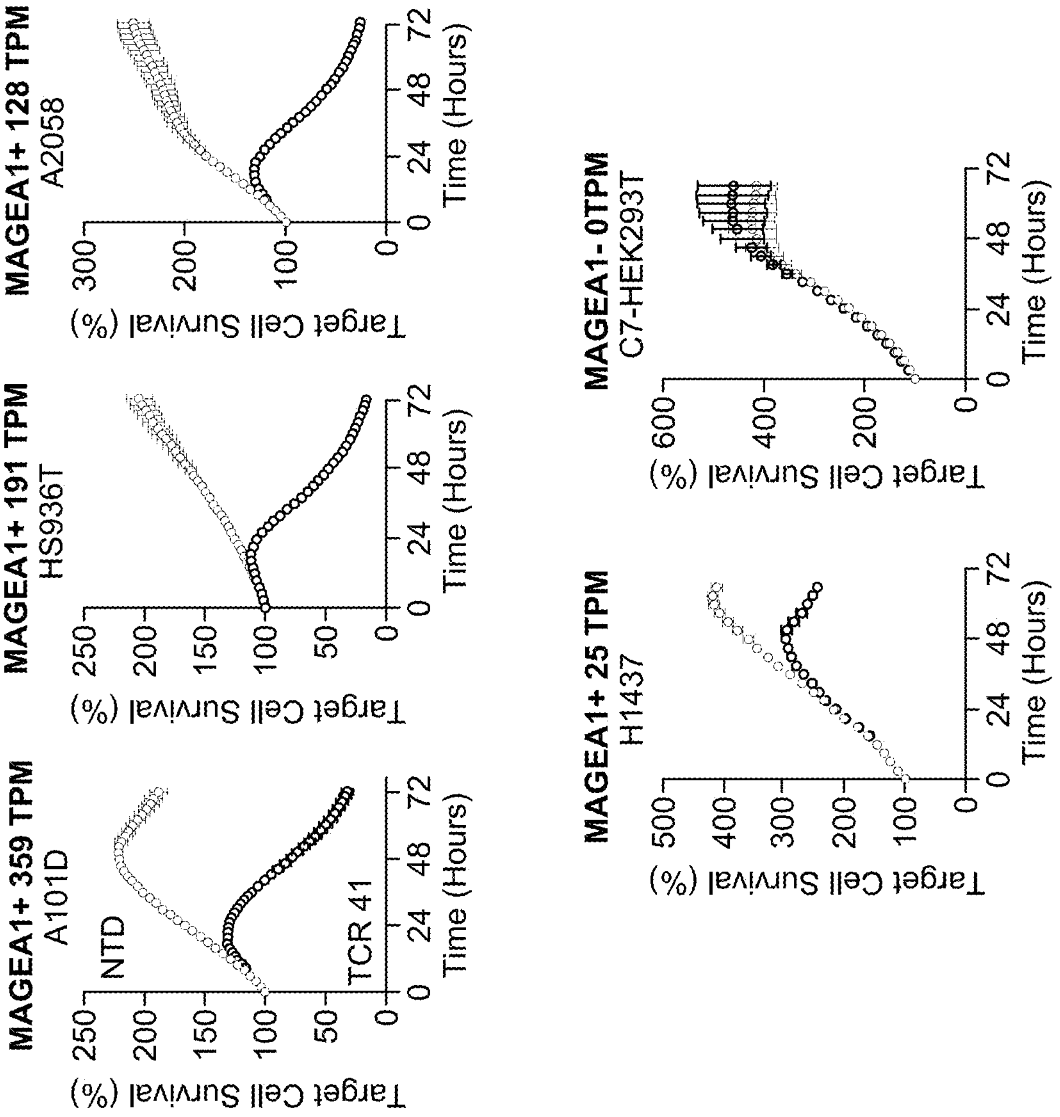
Figure 7:
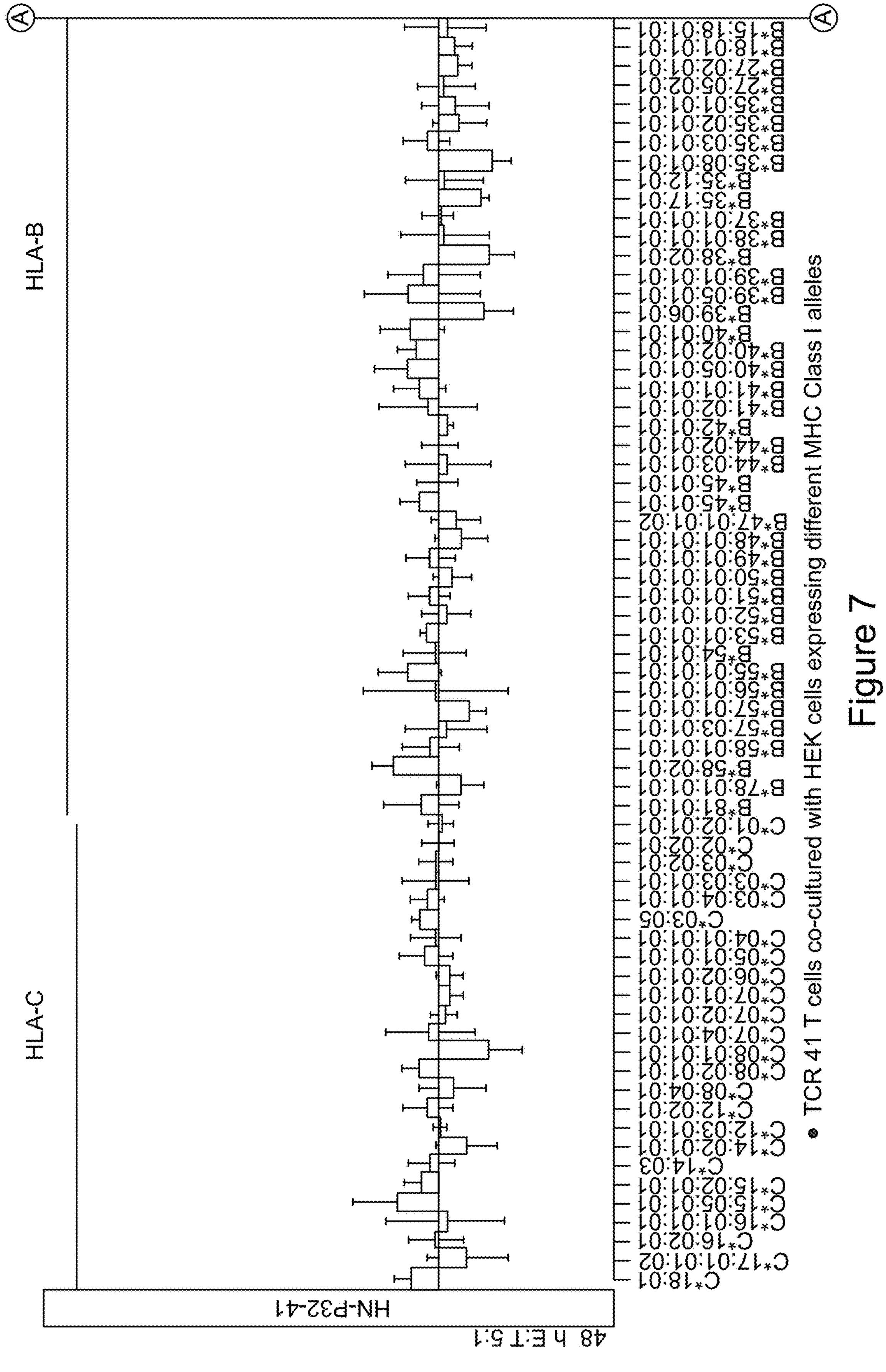
FIG. 7 shows that TCR 32-41 shows no allreactivity to the 110 most common MHC alleles (HLA types). TCR 32-41-expressing pan T cells or untransduced control T cells were co-cultured with MHC-null HEK293T cells re-expressing one of the 110 most frequently encountered Class I MHCs in the U.S. population for 48 hrs. A positive control consisting of HEK293T cells expressing both a fragment of MAGE-A1 which contains the epitope (VBFFFPSL (SEQ ID NO: 1)) and HLA-C*07:02 was included in the screen. The inhibition on target cell growth by the TCR 32-41-expressing pan T cells relative to that by the untransduced control T cells was measured after 48 hrs of co-culture as a readout of the reactivity of the TCR 32-41 to allogeneic MHC molecules. The positive control is indicated.
Figure 7:
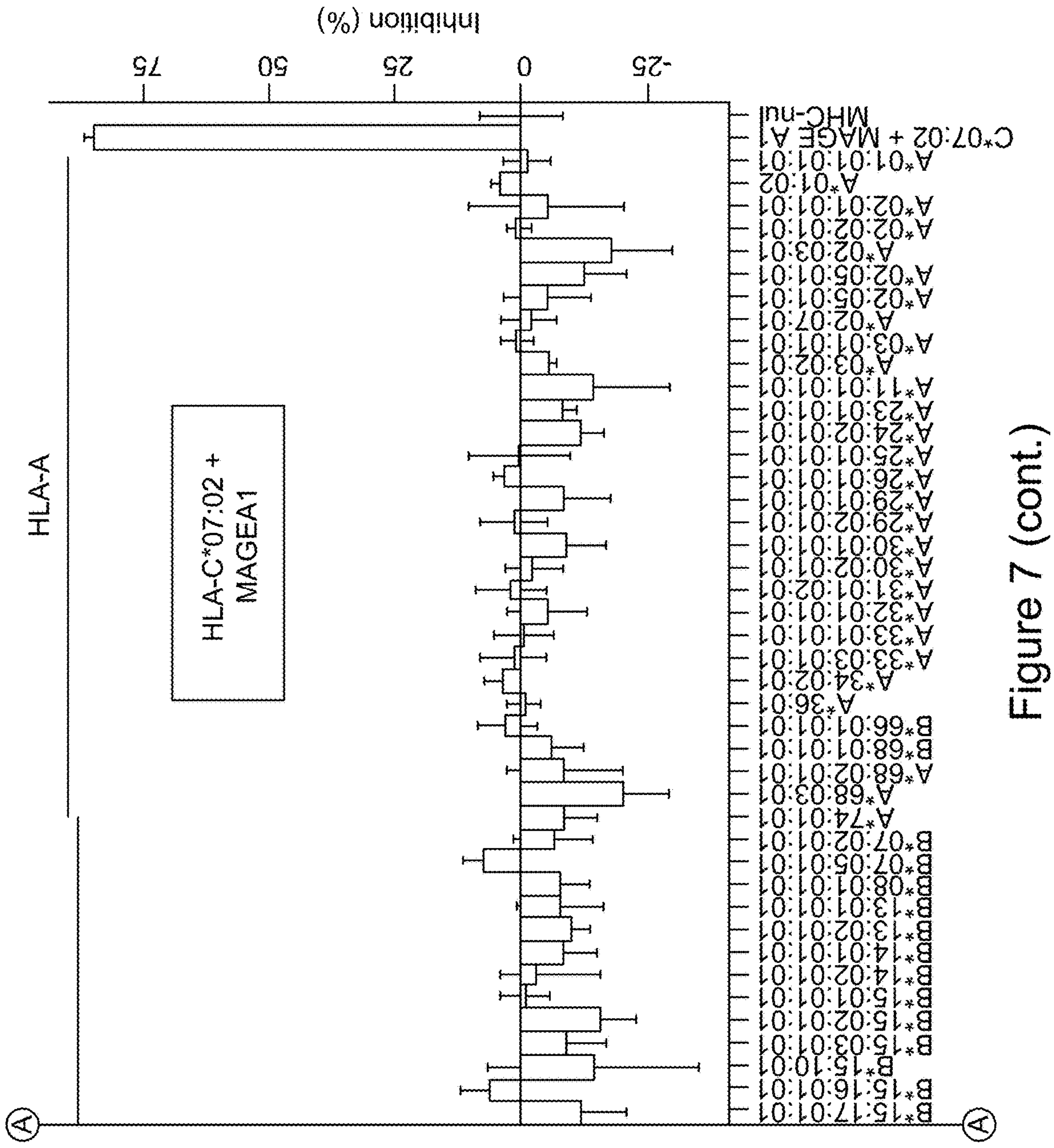
Figure 8:
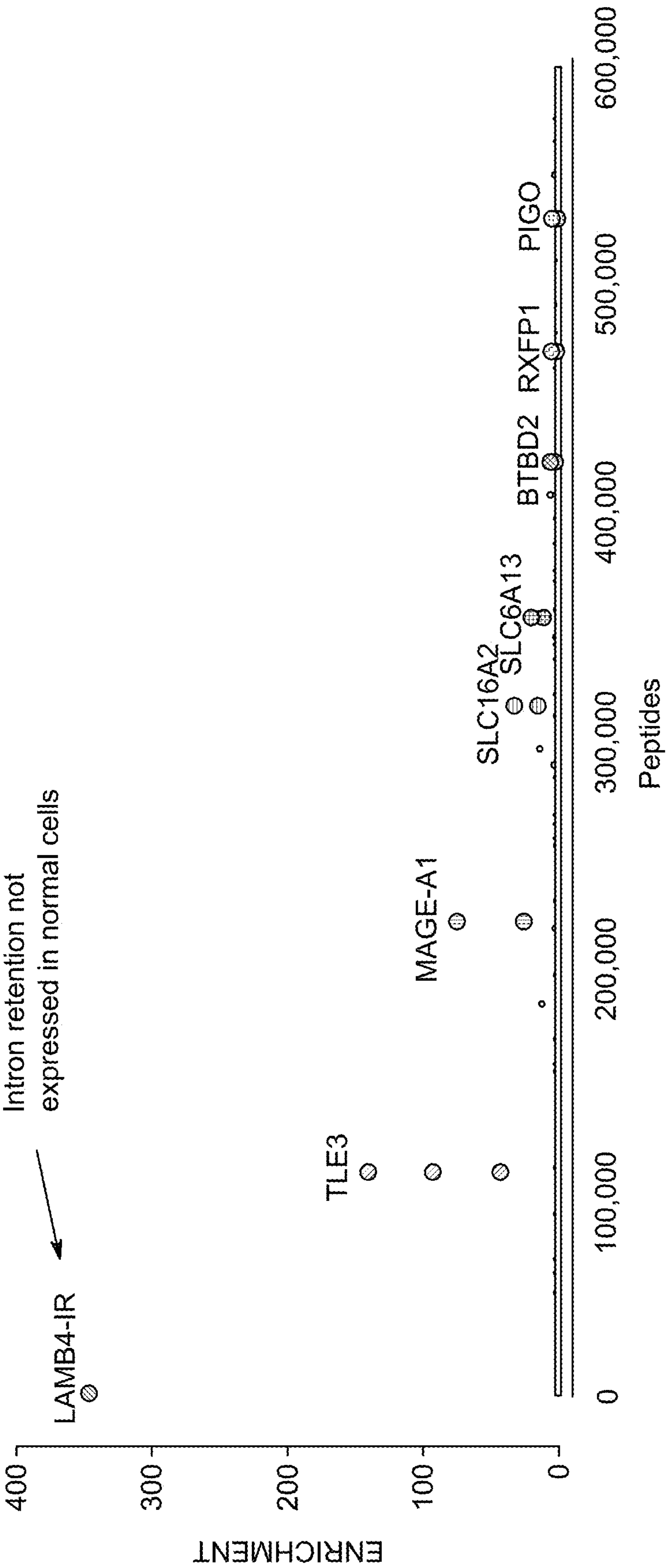
FIG. 8 shows results of a genome-wide SafetyScan screen to identify putative off-targets for TCR 32-41. SafetyScan screen data of TCR 32-41 identifying seven potential off-targets in a screen of >600,000 protein fragments spanning every wild-type (w.t.) human protein are shown. The screen is designed to overpredict off-targets by overexpressing 90-aa protein fragments, which are more efficiently processed than full-length proteins. Putative off-targets are identified by gene names. LAMB4-IR is a predicted cancer-specific intron retention transcript that has never been identified as expressed in normal cells. No expression of this variant was detected using RNA-seq analysis of normal tissue samples (Human Protein Atlas).
Figure 9:
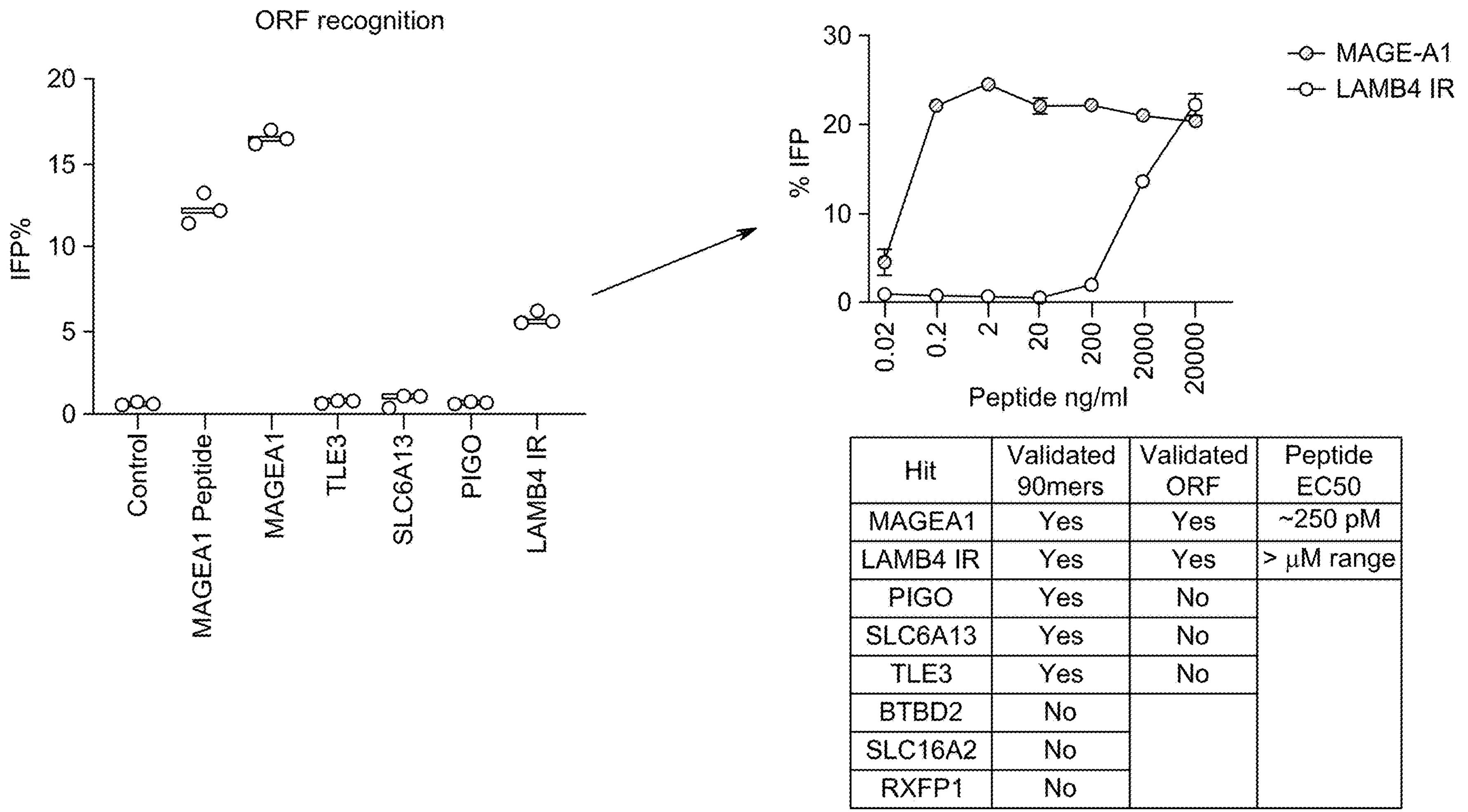
FIG. 9 shows that putative off-targets for TCR 32-41 are not recognized as full-length proteins.
Figure 10:
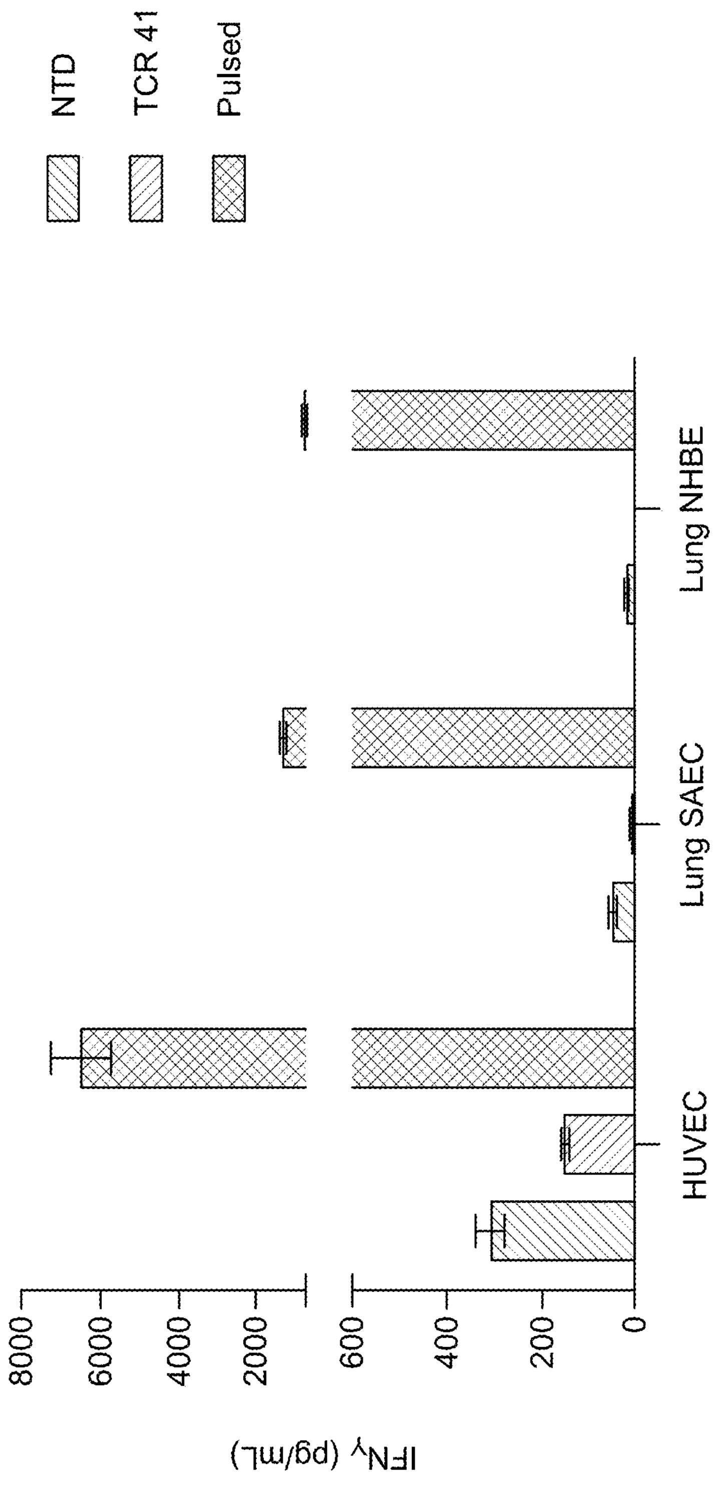
FIG. 10 shows that TCR 32-41 does not show reactivity to normal human cells. TCR 32-41-expressing pan T cells or untransduced (NTD) cells were tested for their reactivity to primary cells from healthy HLA-C*07:02+ human donors. Target cells that were pulsed with the MAGE-A1 peptide or non-pulsed, and co-cultured with TCR 32-41 or NTD cells. IFNγ secretion in culture supernatants was used as a readout of TCR 32-41's reactivity to target cells. Bars reflect the average of triplicates±SD.
Figure 11:
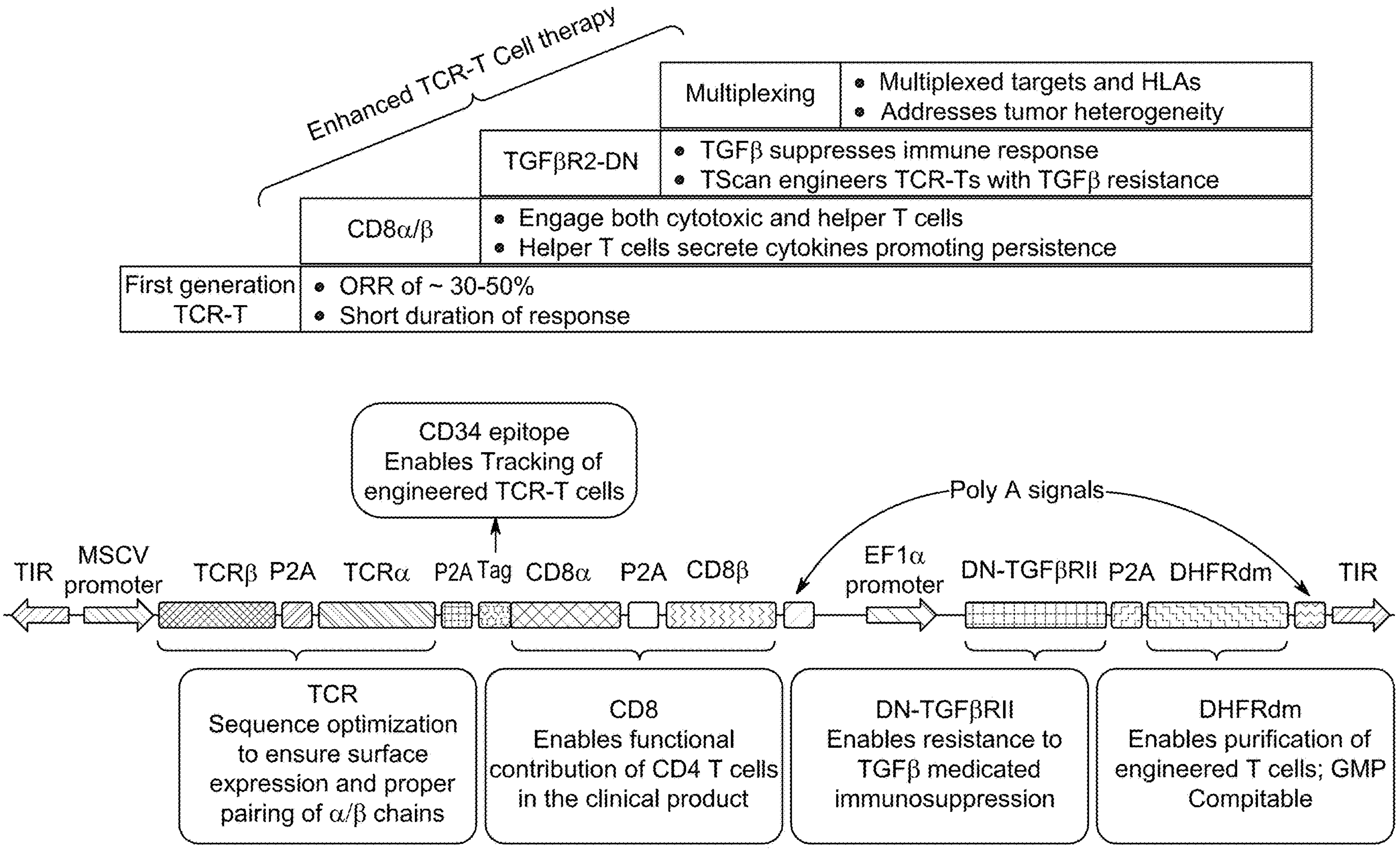
FIG. 11 provides a summary of enhanced TCR-T cell products encompassed by the present invention.
Figure 12:
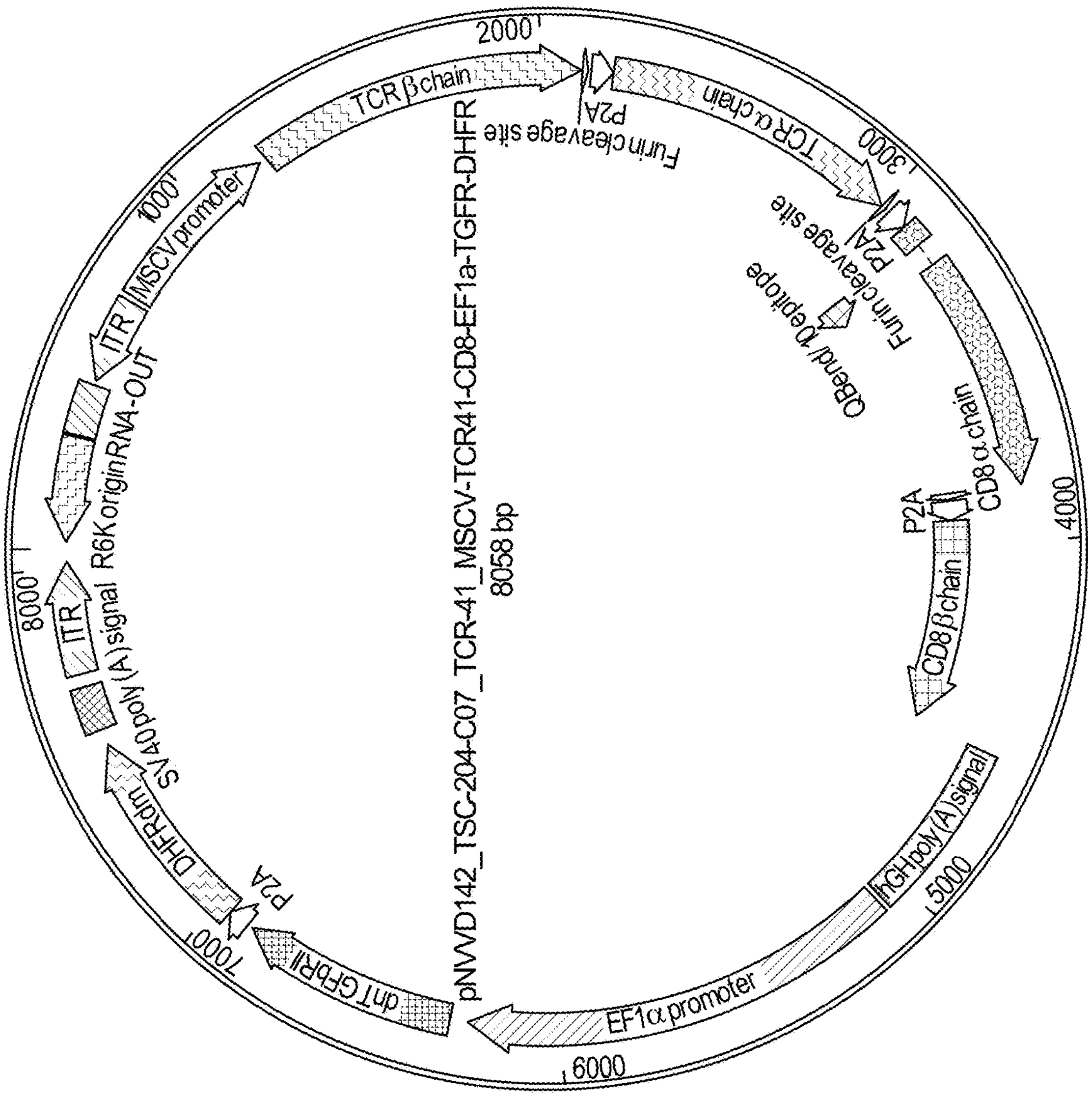
FIG. 12 shows the Map of the pNVVD142_TSC-204-C07_TCR-41_MSCV-TCR41-CD8-EF1a-TGFR-DHFR Vector. Key: CD: cluster of differentiation RNA-OUT: antisense RNA against the bacterial levansucrase encoded by sacB. SV: simian virus TCR: T Cell Receptor, TIR: terminal inverted repeat, QBend: Mouse anti Human CD34 antibody, dnTGFbRII: Dominant-negative TGF beta Receptor II, DHFR: Dihydrofolate reductase selection marker.

The representative immunogenic peptide within a 90-mer construct was then used to screen pools of TCR-transduced T cells and hits were identified, such as TCR 39 and TCR 41 (FIGS. 3A and 3B). The representative TCRs 39 and 41 were further demonstrated to recognize and kill cancer cells that express MAGEA1 at varying levels (FIGS. 4-6). In addition, representative TCR 41 was screened in an alloreactivity assay. TCR41 exhibited minimal allo-reactivity generally as defined by target cell inhibition of more than 20% (e.g., no detectable allo-reactivity to any of 110 different HLA types tested) (FIG. 7), did not appreciably react with cells expressing putative off-targets (FIGS. 8 and 9), and did not react with healthy human primary cells (FIG. 10). Moreover, it is believed that suppressing TGFβ signaling, such as by using DN-TGFβRII, can enhance anti-cancer effects and TCR efficacy (see FIG. 11, description provided herein, and Table 3 for representative, non-limiting expression constructs).

Thus, physiologically relevant TCR-antigen pairs in the context of MHC molecules have been identified.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web at tigr.org and/or the National Center for Biotechnology Information (NCBI) on the World Wide Web at ncbi.nlm.nih gov.

EQUIVALENTS AND SCOPE

The details of one or more embodiments encompassed by the present invention are set forth in the description above. Although representative, exemplary materials and methods have been described above, any materials and methods similar or equivalent to those described herein may be used in the practice or testing of embodiments encompassed by the present invention. Other features, objects and advantages related to the present invention are apparent from the description. Unless defined otherwise, all technical and scientific terms used herein have the same meaning as commonly understood by one of ordinary skill in the art to which the present invention belongs. In the case of conflict, the present description provided above will control.

Those skilled in the art will recognize or be able to ascertain using no more than routine experimentation, many equivalents to the specific embodiments encompassed by the present invention described herein. The scope encompassed by the present invention is not intended to be limited to the description provided herein and such equivalents are intended to be encompassed by the appended claims.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments encompassed by the present invention, to the tenth of the unit of the lower limit of the range, unless the context clearly dictates otherwise.

In addition, it is to be understood that any particular embodiment encompassed by the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions encompassed by the present invention (e.g., any antibiotic, therapeutic or active ingredient; any method of production; any method of use; etc.) may be excluded from any one or more claims, for any reason, whether or not related to the existence of prior art.

It is to be understood that the words which have been used are words of description rather than limitation, and that changes may be made within the purview of the appended claims without departing from the true scope and spirit encompassed by the present invention in its broader aspects.

While the present invention has been described at some length and with some particularity with respect to several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope encompassed by the present invention.

SEQUENCE LISTING

```
Sequence total quantity: 75
SEQ ID NO: 1            moltype = AA  length = 8
FEATURE                 Location/Qualifiers
source                  1..8
                        mol_type = protein
                        organism = Homo sapiens
SEQUENCE: 1
VRFFFPSL                                                                    8

SEQ ID NO: 2            moltype = AA  length = 9
FEATURE                 Location/Qualifiers
source                  1..9
                        mol_type = protein
                        organism = Homo sapiens
SEQUENCE: 2
FFFPSLREA                                                                   9

SEQ ID NO: 3            moltype = AA  length = 10
FEATURE                 Location/Qualifiers
source                  1..10
                        mol_type = protein
                        organism = Homo sapiens
SEQUENCE: 3
ARVRFFFPSL                                                                  10

SEQ ID NO: 4            moltype = AA  length = 9
FEATURE                 Location/Qualifiers
source                  1..9
                        mol_type = protein
                        organism = Homo sapiens
SEQUENCE: 4
VRFFFPSLR                                                                   9

SEQ ID NO: 5            moltype = AA  length = 9
FEATURE                 Location/Qualifiers
source                  1..9
                        mol_type = protein
                        organism = Homo sapiens
SEQUENCE: 5
RVRFFFPSL                                                                   9

SEQ ID NO: 6            moltype = AA  length = 10
FEATURE                 Location/Qualifiers
source                  1..10
                        mol_type = protein
                        organism = Homo sapiens
SEQUENCE: 6
RVRFFFPSLR                                                                  10

SEQ ID NO: 7            moltype = AA  length = 8
FEATURE                 Location/Qualifiers
source                  1..8
                        mol_type = protein
                        organism = Homo sapiens
SEQUENCE: 7
FFPSLREA                                                                    8

SEQ ID NO: 8            moltype = AA  length = 11
```

-continued

```
FEATURE                 Location/Qualifiers
source                  1..11
                        mol_type = protein
                        organism = Homo sapiens
SEQUENCE: 8
ARVRFFFPSL R                                                         11

SEQ ID NO: 9            moltype = AA  length = 8
FEATURE                 Location/Qualifiers
source                  1..8
                        mol_type = protein
                        organism = Homo sapiens
SEQUENCE: 9
SARVRFFF                                                             8

SEQ ID NO: 10           moltype = AA  length = 11
FEATURE                 Location/Qualifiers
source                  1..11
                        mol_type = protein
                        organism = Homo sapiens
SEQUENCE: 10
VRFFFPSLRE A                                                         11

SEQ ID NO: 11           moltype = AA  length = 10
FEATURE                 Location/Qualifiers
source                  1..10
                        mol_type = protein
                        organism = Homo sapiens
SEQUENCE: 11
RFFFPSLREA                                                           10

SEQ ID NO: 12           moltype = DNA  length = 834
FEATURE                 Location/Qualifiers
source                  1..834
                        mol_type = other DNA
                        organism = synthetic construct
SEQUENCE: 12
atggccatgc tcctgggggc atcagtgctg attctgtggc ttcagccaga ctgggttaac  60
agtcaacaga agaatgatga ccagcaagtt aagcaaaatt caccatccct gagcgtccag  120
gaaggaagaa tttctattct gaactgtgac tatactaaca gcatgtttga ttatttcctt  180
tggtacaaga aataccctgc tgaaggtcct acattcctga tttctattag ttccattaag  240
gataaaaatg aagatggaag attcactgtt ttccttaaca aaagtgccaa gcacctctct  300
ctgcacattg tgccctccca gcctggagac tctgcagtgt acttctgtgc agcaagcgct  360
cagaacaatg acatgcgctt tggagcaggg accagactga cagttaaacc aaatatccag  420
aaccctgacc ctgccgtgta ccagctgaga gactctaaat ccagtgacaa gtctgtctgc  480
ctattcaccg attttgattc tcaaacaaat gtgtcacaaa gtaaggattc tgatgtgtat  540
atcacagaca aaactgtgct agacatgagg tctatggact tcaagagcaa cagtgctgtg  600
gcctggagca acaaatctga ctttgcatgt gcaaacgcct tcaacaacag cattattcca  660
gaagacacct tcttccccag cccagaaagt tcctgtgatg tcaagctggt cgagaaaagc  720
tttgaaacag atacgaacct aaactttcaa aacctgtcag tgattgggtt ccgaatcctc  780
ctcctgaaag tggccgggtt taatctgctc atgacgctgc ggctgtggtc cagc        834

SEQ ID NO: 13           moltype = AA  length = 278
FEATURE                 Location/Qualifiers
source                  1..278
                        mol_type = protein
                        organism = synthetic construct
SEQUENCE: 13
MAMLLGASVL ILWLQPDWVN SQQKNDDQQV KQNSPSLSVQ EGRISILNCD YTNSMFDYFL  60
WYKKYPAEGP TFLISISSIK DKNEDGRFTV FLNKSAKHLS LHIVPSQPGD SAVYFCAASA  120
QNNDMRFGAG TRLTVKPNIQ NPDPAVYQLR DSKSSDKSVC LFTDFDSQTN VSQSKDSDVY  180
ITDKTVLDMR SMDFKSNSAV AWSNKSDFAC ANAFNNSIIP EDTFFPSPES SCDVKLVEKS  240
FETDTNLNFQ NLSVIGFRIL LLKVAGFNLL MTLRLWSS                         278

SEQ ID NO: 14           moltype = DNA  length = 921
FEATURE                 Location/Qualifiers
source                  1..921
                        mol_type = other DNA
                        organism = synthetic construct
SEQUENCE: 14
atggacacca gacttctctg ctgtgctgtc atctgtctcc tgggggcagg cctctcaaat  60
gccggcgtca tgcagaaccc aagacacctg gtcaggagga ggggacagga ggcaagactg  120
agatgcagcc caatgaaagg acacagtcat gtttactggt atcggcagct cccagaggaa  180
ggtctgaaat tcatggttta tctccagaaa gaaaatatca ttgatgagtc aggaatgcca  240
aaggaacgct tttctgctga atttcccaaa gagggcccca gcatcctgag gatccagcag  300
gttgtgcgcg gagattctgc agcttatttc tgtgccagct caccctccta cgagcagtac  360
ttcgggcctg gcaccaggct cactgtcaca gaggacctga acaaggtgtt cccacccgag  420
gtcgctgtgt ttgagccatc agaagcagag atctcccaca cccaaaaggc cacactggtg  480
tgcctggcca caggcttctt ccctgaccac gtggagctga gctggtgggt gaatgggaag  540
```

```
gaggtgcaca gtggggtcag cacggacccg cagcccctca aggagcagcc cgccctcaat  600
gactccagat actgcctgag cagccgcctg agggtctcgg ccaccttctg gcagaacccc  660
cgcaaccact tccgctgtca agtccagttc tacgggctct cggagaatga cgagtggacc  720
caggataggg ccaaacccgt cacccagatc gtcagcgccg aggcctgggg tagagcagac  780
tgtggcttta cctcggtgtc ctaccagcaa ggggtcctgt ctgccaccat cctctatgag  840
atcctgctag ggaaggccac cctgtatgct gtgctggtca gcgcccttgt gttgatggcc  900
atggtcaaga gaaaggattt c                                            921

SEQ ID NO: 15          moltype = AA  length = 307
FEATURE                Location/Qualifiers
source                 1..307
                       mol_type = protein
                       organism = synthetic construct
SEQUENCE: 15
MDTRLLCCAV ICLLGAGLSN AGVMQNPRHL VRRRGQEARL RCSPMKGHSH VYWYRQLPEE  60
GLKFMVYLQK ENIIDESGMP KERFSAEFPK EGPSILRIQQ VVRGDSAAYF CASSPSYEQY  120
FGPGTRLTVT EDLNKVFPPE VAVFEPSEAE ISHTQKATLV CLATGFFPDH VELSWWVNGK  180
EVHSGVSTDP QPLKEQPALN DSRYCLSSRL RVSATFWQNP RNHFRCQVQF YGLSENDEWT  240
QDRAKPVTQI VSAEAWGRAD CGFTSVSYQQ GVLSATILYE ILLGKATLYA VLVSALVLMA  300
MVKRKDF                                                            307

SEQ ID NO: 16          moltype = DNA  length = 813
FEATURE                Location/Qualifiers
source                 1..813
                       mol_type = other DNA
                       organism = synthetic construct
SEQUENCE: 16
atggtcctga aattctccgt gtccattctt tggattcagt tggcatgggt gagcacccag  60
ctgctggagc agagccctca gtttcttagc atccaagagg gagaaaatct cactgtgtac  120
tgcaactcct caagtgtttt ctccagcctt caatggtaca gacaggagcc tggggaaggt  180
cctgtcctcc tggtgacagt tgttactggt ggagaagtga agaagctgaa gagacttacc  240
tttcagtttg gtgatgcaag aaaggacagt tctctccaca tcactgcagc ccagcctggt  300
gatacaggcc tctacctctg tgcaggagat gaaagtatta gctatggaaa gctgacattt  360
ggacaaggga ccatcttgac tgtccatcca aatatccaga accctgaccc tgccgtgtac  420
cagctgagag actctaaatc cagtgacaag tctgtctgcc tattcaccga ttttgattct  480
caaacaaatg tgtcacaaag taaggattct gatgtgtata tcacagacaa aactgtgcta  540
gacatgaggt ctatggactt caagagcaac agtgctgtgg cctggagcaa caaatctgac  600
tttgcatgtg caaacgcctt caacaacagc attattccag aagacacctt cttccccagc  660
ccagaaagtt cctgtgatgt caagctggtc gagaaaagct ttgaaacaga tacgaaccta  720
aactttcaaa acctgtcagt gattgggttc cgaatcctcc tcctgaaagt ggccgggttt  780
aatctgctca tgacgctgcg gctgtggtcc agc                               813

SEQ ID NO: 17          moltype = AA  length = 271
FEATURE                Location/Qualifiers
source                 1..271
                       mol_type = protein
                       organism = synthetic construct
SEQUENCE: 17
MVLKFSVSIL WIQLAWVSTQ LLEQSPQFLS IQEGENLTVY CNSSSVFSSL QWYRQEPGEG  60
PVLLVTVVTG GEVKKLKRLT FQFGDARKDS SLHITAAQPG DTGLYLCAGD ESISYGKLTF  120
GQGTILTVHP NIQNPDPAVY QLRDSKSSDK SVCLFTDFDS QTNVSQSKDS DVYITDKTVL  180
DMRSMDFKSN SAVAWSNKSD FACANAFNNS IIPEDTFFPS PESSCDVKLV EKSFETDTNL  240
NFQNLSVIGF RILLLKVAGF NLLMTLRLWS S                                 271

SEQ ID NO: 18          moltype = DNA  length = 930
FEATURE                Location/Qualifiers
source                 1..930
                       mol_type = other DNA
                       organism = synthetic construct
SEQUENCE: 18
atgggctcct ggaccctctg ctgtgtgtcc ctttgcatcc tggttgcaaa gcacacagat  60
gctggagtta tccagtcacc ccggcacgag gtgacagaga tgggacaaga agtgactctg  120
agatgtaaac caatttcagg acatgactac cttttctggt acagacagac catgatgcgg  180
ggactggagt tgctcattta ctttaacaac aacgttccta ttgatgattc agggatgccc  240
gaggatcgct tctcagctaa gatgcctaat gcatcattct ccactctgaa gatccagccc  300
tcagaaccca gggactcagc tgtgtacttc tgtgccagca gttttctcgg ctggaatgaa  360
aaactgttct ttggcagtgg aacccagctc tctgtcttgg aggacctgaa caaggtgttc  420
ccacccgagg tcgctgtgtt tgagccatca gaagcagaga tctcccacac ccaaaaggcc  480
acactggtgt gcctggccac aggcttcttc cctgaccacg tggagctgag ctggtgggtg  540
aatgggaagg aggtgcacag tggggtcagc acggacccgc agcccctcaa ggagcagccc  600
gccctcaatg actccagata ctgcctgagc agccgcctga gggtctcggc caccttctgg  660
cagaaccccc gcaaccactt ccgctgtcaa gtccagttct acgggctctc ggagaatgac  720
gagtggaccc aggatagggc caaacccgtc acccagatcg tcagcgccga ggcctggggt  780
agagcagact gtggctttac ctcggtgtcc taccagcaag gggtcctgtc tgccaccatc  840
ctctatgaga tcctgctagg gaaggccacc ctgtatgctg tgctggtcag cgcccttgtg  900
ttgatggcca tggtcaagag aaaggatttc                                   930

SEQ ID NO: 19          moltype = AA  length = 310
FEATURE                Location/Qualifiers
```

```
source                  1..310
                        mol_type = protein
                        organism = synthetic construct
SEQUENCE: 19
MGSWTLCCVS LCILVAKHTD AGVIQSPRHE VTEMGQEVTL RCKPISGHDY LFWYRQTMMR  60
GLELLIYFNN NVPIDDSGMP EDRFSAKMPN ASFSTLKIQP SEPRDSAVYF CASSFLGWNE  120
KLFFGSGTQL SVLEDLNKVF PPEVAVFEPS EAEISHTQKA TLVCLATGFF PDHVELSWWV  180
NGKEVHSGVS TDPQPLKEQP ALNDSRYCLS SRLRVSATFW QNPRNHFRCQ VQFYGLSEND  240
EWTQDRAKPV TQIVSAEAWG RADCGFTSVS YQQGVLSATI LYEILLGKAT LYAVLVSALV  300
LMAMVKRKDF                                                        310

SEQ ID NO: 20           moltype = DNA  length = 822
FEATURE                 Location/Qualifiers
source                  1..822
                        mol_type = other DNA
                        organism = synthetic construct
SEQUENCE: 20
atggccatgc tcctgggggc atcagtgctg attctgtggc ttcagccaga ctgggttaac  60
agtcaacaga agaatgatga ccagcaagtt aagcaaaatt caccatccct gagcgtccag  120
gaaggaagaa tttctattct gaactgtgac tatactaaca gcatgtttga ttatttcctt  180
tggtacaaga aataccctgc tgaaggtcct acattcctga tttctattag ttccattaag  240
gataaaaatg aagatggaag attcactgtt ttccttaaca aaagtgccaa gcacctctct  300
ctgcacattg tgccctccca gcctggagac tctgcagtgt acttctgtgc agcaagcgct  360
cagaacaatg acatgcgctt tggagcaggg accagactga cagttaaacc aaacattcaa  420
aacccagaac ccgccgtcta ccagctgaaa gacccgaggt ctcaagactc tacgttgtgc  480
ttgttcaccg atttcgacag tcagataaat gtgcctaaga ccatggagag tggcactttc  540
atcactgaca aatgtgtgtt ggacatgaag gctatggaca gcaagtcaaa cggcgcgatt  600
gcttggtcca accaaacttc tttcacgtgc caggacatct tcaaggagac aaacgccacc  660
tatccatcct ctgatgttcc gtgcgatgcg actcttaccg agaaaagctt cgagacggac  720
atgaacttga acttccaaaa cctgcttgtg atggtactgc gaatacttct tcttaaggtg  780
gcgggcttca atttgctcat gacactcaga ctttggtcta gc                    822

SEQ ID NO: 21           moltype = AA  length = 274
FEATURE                 Location/Qualifiers
source                  1..274
                        mol_type = protein
                        organism = synthetic construct
SEQUENCE: 21
MAMLLGASVL ILWLQPDWVN SQQKNDDQQV KQNSPSLSVQ EGRISILNCD YTNSMFDYFL  60
WYKKYPAEGP TFLISISSIK DKNEDGRFTV FLNKSAKHLS LHIVPSQPGD SAVYFCAASA  120
QNNDMRFGAG TRLTVKPNIQ NPEPAVYQLK DPRSQDSTLC LFTDFDSQIN VPKTMESGTF  180
ITDKCVLDMK AMDSKSNGAI AWSNQTSFTC QDIFKETNAT YPSSDVPCDA TLTEKSFETD  240
MNLNFQNLLV MVLRILLLKV AGFNLLMTLR LWSS                              274

SEQ ID NO: 22           moltype = DNA  length = 909
FEATURE                 Location/Qualifiers
source                  1..909
                        mol_type = other DNA
                        organism = synthetic construct
SEQUENCE: 22
atggacacca gacttctctg ctgtgctgtc atctgtctcc tgggggcagg cctctcaaat  60
gccggcgtca tgcagaaccc aagacacctg gtcaggagga ggggacagga ggcaagactg  120
agatgcagcc caatgaaagg acacagtcat gtttactggt atcggcagct cccagaggaa  180
ggtctgaaat tcatggttta tctccagaaa gaaaatatca ttgatgagtc aggaatgcca  240
aaggaacgct tttctgctga atttcccaaa gagggcccca gcatcctgag gatccagcag  300
gttgtgcgcg gagattctgc agcttatttc tgtgccagct caccctccta cgagcagtac  360
ttcgggcctg gcaccaggct cactgtcaca gaagatcttc gaaacgtaac ccctccaaaa  420
gtgagtctct ttgaaccgag taaggctgag atcgcgaaca aacaaaaggc gaccctcgtc  480
tgtcttgcgc gaggattttt tcccgaccac gtggagttgt cttggtgggt aaacggtaag  540
gaagtacaca gcggtgtttg caccgaccct caagcctaca aggaatctaa ctattcatac  600
tgcctttcat cccgacttag ggtttctgct accttttggc acaatccgag gaatcacttt  660
aggtgtcaag tacagttcca cggattgtca gaggaggata aatggccgga gggctccccg  720
aagccggtta cgcagaacat tagtgcggaa gcctggggac gagcagactg cggtatcacg  780
tctgccagct atcagcaagg cgttctgtca gcgacaattc tgtacgaaat acttttgggt  840
aaggctacat tgtatgcggt attggtgtct acgctggtag tcatggccat ggtgaaacga  900
aaaaactca                                                         909

SEQ ID NO: 23           moltype = AA  length = 303
FEATURE                 Location/Qualifiers
source                  1..303
                        mol_type = protein
                        organism = synthetic construct
SEQUENCE: 23
MDTRLLCCAV ICLLGAGLSN AGVMQNPRHL VRRRGQEARL RCSPMKGHSH VYWYRQLPEE  60
GLKFMVYLQK ENIIDESGMP KERFSAEFPK EGPSILRIQQ VVRGDSAAYF CASSPSYEQY  120
FGPGTRLTVT EDLRNVTPPK VSLFEPSKAE IANKQKATLV CLARGFFPDH VELSWWVNGK  180
EVHSGVCTDP QAYKESNYSY CLSSRLRVSA TFWHNPRNHF RCQVQFHGLS EEDKWPEGSP  240
KPVTQNISAE AWGRADCGIT SASYQQGVLS ATILYEILLG KATLYAVLVS TLVVMAMVKR  300
KNS                                                               303
```

```
SEQ ID NO: 24          moltype = DNA  length = 1812
FEATURE                Location/Qualifiers
source                 1..1812
                       mol_type = other DNA
                       organism = synthetic construct
SEQUENCE: 24
atggacacca gacttctctg ctgtgctgtc atctgtctcc tgggggcagg cctctcaaat  60
gccggcgtca tgcagaaccc aagacacctg gtcaggagga ggggacagga ggcaagactg  120
agatgcagcc caatgaaagg acacagtcat gtttactggt atcggcagct cccagaggaa  180
ggtctgaaat tcatggttta tctccagaaa gaaaatatca ttgatgagtc aggaatgcca  240
aaggaacgct tttctgctga atttcccaaa gagggcccca gcatcctgag gatccagcag  300
gttgtgcgcg gagattctgc agcttatttc tgtgccagct caccctccta cgagcagtac  360
ttcgggcctg gcaccaggct cactgtcaca gaagatcttc gaaacgtaac cctccaaaa  420
gtgagtctct ttgaaccgag taaggctgag atcgcgaaca aacaaaaggc gaccctcgtc  480
tgtcttgcgc gaggattttt tcccgaccac gtggagttgt cttggtgggt aaacggtaag  540
gaagtacaca gcggtgtttg caccgaccct caagcctaca aggaatctaa ctattcatac  600
tgcctttcat cccgacttag ggtttctgct accttttggc acaatccgag gaatcacttt  660
aggtgtcaag tacagttcca cggattgtca gaggaggata aatggccgga gggctccccg  720
aagccggtta cgcagaacat tagtgcggaa gcctggggac gagcagactg cggtatcacg  780
tctgccagct atcagcaagg cgttctgtca gcgacaattc tgtacgaaat acttttgggt  840
aaggctacat tgtatgcggt attggtgtct acgctggtag tcatggccat ggtgaaacga  900
aaaaactcaa gagccaaaag aagcgggagc ggtgcgacaa actttagcct gttgaaacaa  960
gccggcgacg ttgaagagaa ccccggacct atggccatgc tcctgggggc atcagtgctg  1020
attctgtggc ttcagccaga ctgggttaac agtcaacaga agaatgatga ccagcaagtt  1080
aagcaaaatt caccatccct gagcgtccag gaaggaagaa tttctattct gaactgtgac  1140
tatactaaca gcatgtttga ttatttcctt tggtacaaga aataccctgc tgaaggtcct  1200
acattcctga tttctattag ttccattaag gataaaaatg aagatggaag attcactgtt  1260
ttccttaaca aaagtgccaa gcacctctct ctgcacattg tgccctccca gcctggagac  1320
tctgcagtgt acttctgtgc agcaagcgct cagaacaatg acatgcgctt tggagcaggg  1380
accagactga cagttaaacc aaacattcaa aacccagaac ccgccgtcta ccagctgaaa  1440
gacccgaggt ctcaagactc tacgttgtgc ttgttcaccg atttcgacag tcagataaat  1500
gtgcctaaga ccatggagag tggcactttc atcactgaca aatgtgtgtt ggacatgaag  1560
gctatggaca gcaagtcaaa cggcgcgatt gcttggtcca accaaacttc tttcacgtgc  1620
caggacatct tcaaggagac aaacgccacc tatccatcct ctgatgttcc gtgcgatgcg  1680
actcttaccg agaaaagctt cgagacggac atgaacttga acttccaaaa cctgcttgtg  1740
atggtactgc gaatacttct tcttaaggtg gcgggcttca atttgctcat gacactcaga  1800
ctttggtcta gc                                                    1812

SEQ ID NO: 25          moltype = AA  length = 604
FEATURE                Location/Qualifiers
source                 1..604
                       mol_type = protein
                       organism = synthetic construct
SEQUENCE: 25
MDTRLLCCAV ICLLGAGLSN AGVMQNPRHL VRRRGQEARL RCSPMKGHSH VYWYRQLPEE  60
GLKFMVYLQK ENIIDESGMP KERFSAEFPK EGPSILRIQQ VVRGDSAAYF CASSPSYEQY  120
FGPGTRLTVT EDLRNVTPPK VSLFEPSKAE IANKQKATLV CLARGFFPDH VELSWWVNGK  180
EVHSGVCTDP QAYKESNYSY CLSSRLRVSA TFWHNPRNHF RCQVQFHGLS EEDKWPEGSP  240
KPVTQNISAE AWGRADCGIT SASYQQGVLS ATILYEILLG KATLYAVLVS TLVVMAMVKR  300
KNSRAKRSGS GATNFSLLKQ AGDVEENPGP MAMLLGASVL ILWLQPDWVN SQQKNDDQQV  360
KQNSPSLSVQ EGRISILNCD YTNSMFDYFL WYKKYPAEGP TFLISISSIK DKNEDGRFTV  420
FLNKSAKHLS LHIVPSQPGD SAVYFCAASA QNNDMRFGAG TRLTVKPNIQ NPEPAVYQLK  480
DPRSQDSTLC LFTDFDSQIN VPKTMESGTF ITDKCVLDMK AMDSKSNGAI AWSNQTSFTC  540
QDIFKETNAT YPSSDVPCDA TLTEKSFETD MNLNFQNLLV MVLRILLLKV AGFNLLMTLR  600
LWSS                                                             604

SEQ ID NO: 26          moltype = DNA  length = 801
FEATURE                Location/Qualifiers
source                 1..801
                       mol_type = other DNA
                       organism = synthetic construct
SEQUENCE: 26
atggtcctga aattctccgt gtccattctt tggattcagt tggcatgggt gagcacccag  60
ctgctggagc agagccctca gtttcttagc atccaagagg gagaaaatct cactgtgtac  120
tgcaactcct caagtgtttt ctccagcctt caatggtaca gacaggagcc tggggaaggt  180
cctgtcctcc tggtgacagt tgttactggt ggagaagtga agaagctgaa gagacttacc  240
tttcagtttg gtgatgcaag aaaggacagt tctctccaca tcactgcagc ccagcctggt  300
gatacaggcc tctacctctg tgcaggagat gaaagtatta gctatggaaa gctgacattt  360
ggacaaggga ccatcttgac tgtccatcca aacattcaaa acccagaacc cgccgtctac  420
cagctgaaag acccgaggtc tcaagactct acgttgtgct tgttcaccga tttcgacagt  480
cagataaatg tgcctaagac catggagagt ggcactttca tcactgacaa atgtgtgttg  540
gacatgaagg ctatggacag caagtcaaac ggcgcgattg cttggtccaa ccaaacttct  600
ttcacgtgcc aggacatctt caaggagaca aacgccacct atccatcctc tgatgttccg  660
tgcgatgcga ctcttaccga gaaaagcttc gagacggaca tgaacttgaa cttccaaaac  720
ctgcttgtga tggtactgcg aatacttctt cttaaggtgg cgggcttcaa tttgctcatg  780
acactcagac tttggtctag c                                          801

SEQ ID NO: 27          moltype = AA  length = 267
```

```
FEATURE                Location/Qualifiers
source                 1..267
                       mol_type = protein
                       organism = synthetic construct
SEQUENCE: 27
MVLKFSVSIL WIQLAWVSTQ LLEQSPQFLS IQEGENLTVY CNSSSVFSSL QWYRQEPGEG  60
PVLLVTVVTG GEVKKLKRLT FQFGDARKDS SLHITAAQPG DTGLYLCAGD ESISYGKLTF  120
GQGTILTVHP NIQNPEPAVY QLKDPRSQDS TLCLFTDFDS QINVPKTMES GTFITDKCVL  180
DMKAMDSKSN GAIAWSNQTS FTCQDIFKET NATYPSSDVP CDATLTEKSF ETDMNLNFQN  240
LLVMVLRILL LKVAGFNLLM TLRLWSS                                     267

SEQ ID NO: 28          moltype = DNA  length = 918
FEATURE                Location/Qualifiers
source                 1..918
                       mol_type = other DNA
                       organism = synthetic construct
SEQUENCE: 28
atgggctcct ggaccctctg ctgtgtgtcc ctttgcatcc tggttgcaaa gcacacagat  60
gctggagtta tccagtcacc ccggcacgag gtgacagaga tgggacaaga agtgactctg  120
agatgtaaac caatttcagg acatgactac cttttctggt acagacagac catgatgcgg  180
ggactggagt tgctcattta ctttaacaac aacgttccta ttgatgattc agggatgccc  240
gaggatcgct tctcagctaa gatgcctaat gcatcattct ccactctgaa gatccagccc  300
tcagaaccca gggactcagc tgtgtacttc tgtgccagca gttttctcgg ctggaatgaa  360
aaactgttct ttggcagtgg aacccagctc tctgtcttgg aagatcttcg aaacgtaacc  420
cctccaaaag tgagtctctt tgaaccgagt aaggctgaga tcgcgaacaa acaaaaggcg  480
accctcgtct gtcttgcgcg aggatttttt cccgaccacg tggagttgtc ttggtgggta  540
aacggtaagg aagtacacag cggtgtttgc accgaccctc aagcctacaa ggaatctaac  600
tattcatact gcctttcatc ccgacttagg gtttctgcta ccttttggca caatccgagg  660
aatcacttta ggtgtcaagt acagttccac ggattgtcag aggaggataa atggccggag  720
ggctccccga agccggttac gcagaacatt agtgcggaag cctggggacg agcagactgc  780
ggtatcacgt ctgccagcta tcagcaaggc gttctgtcag cgacaattct gtacgaaata  840
cttttgggta aggctacatt gtatgcggta ttggtgtcta cgctggtagt catggccatg  900
gtgaaacgaa aaaactca                                               918

SEQ ID NO: 29          moltype = AA  length = 306
FEATURE                Location/Qualifiers
source                 1..306
                       mol_type = protein
                       organism = synthetic construct
SEQUENCE: 29
MGSWTLCCVS LCILVAKHTD AGVIQSPRHE VTEMGQEVTL RCKPISGHDY LFWYRQTMMR  60
GLELLIYFNN NVPIDDSGMP EDRFSAKMPN ASFSTLKIQP SEPRDSAVYF CASSFLGWNE  120
KLFFGSGTQL SVLEDLRNVT PPKVSLFEPS KAEIANKQKA TLVCLARGFF PDHVELSWWV  180
NGKEVHSGVC TDPQAYKESN YSYCLSSRLR VSATFWHNPR NHFRCQVQFH GLSEEDKWPE  240
GSPKPVTQNI SAEAWGRADC GITSASYQQG VLSATILYEI LLGKATLYAV LVSTLVVMAM  300
VKRKNS                                                            306

SEQ ID NO: 30          moltype = DNA  length = 1800
FEATURE                Location/Qualifiers
source                 1..1800
                       mol_type = other DNA
                       organism = synthetic construct
SEQUENCE: 30
atgggctcct ggaccctctg ctgtgtgtcc ctttgcatcc tggttgcaaa gcacacagat  60
gctggagtta tccagtcacc ccggcacgag gtgacagaga tgggacaaga agtgactctg  120
agatgtaaac caatttcagg acatgactac cttttctggt acagacagac catgatgcgg  180
ggactggagt tgctcattta ctttaacaac aacgttccta ttgatgattc agggatgccc  240
gaggatcgct tctcagctaa gatgcctaat gcatcattct ccactctgaa gatccagccc  300
tcagaaccca gggactcagc tgtgtacttc tgtgccagca gttttctcgg ctggaatgaa  360
aaactgttct ttggcagtgg aacccagctc tctgtcttgg aagatcttcg aaacgtaacc  420
cctccaaaag tgagtctctt tgaaccgagt aaggctgaga tcgcgaacaa acaaaaggcg  480
accctcgtct gtcttgcgcg aggatttttt cccgaccacg tggagttgtc ttggtgggta  540
aacggtaagg aagtacacag cggtgtttgc accgaccctc aagcctacaa ggaatctaac  600
tattcatact gcctttcatc ccgacttagg gtttctgcta ccttttggca caatccgagg  660
aatcacttta ggtgtcaagt acagttccac ggattgtcag aggaggataa atggccggag  720
ggctccccga agccggttac gcagaacatt agtgcggaag cctggggacg agcagactgc  780
ggtatcacgt ctgccagcta tcagcaaggc gttctgtcag cgacaattct gtacgaaata  840
cttttgggta aggctacatt gtatgcggta ttggtgtcta cgctggtagt catggccatg  900
gtgaaacgaa aaaactcaag agccaaaaga agcgggagcg gtgcgacaaa ctttagcctg  960
ttgaaacaag ccggcgacgt tgaagagaac cccggaccta tggtcctgaa attctccgtg  1020
tccattcttt ggattcagtt ggcatgggtg agcacccagc tgctggagca gagccctcag  1080
tttcttagca tccaagaggg agaaaatctc actgtgtact gcaactcctc aagtgttttc  1140
tccagccttc aatggtacag acaggagcct ggggaaggtc ctgtcctcct ggtgacagtt  1200
gttactggtg gagaagtgaa gaagctgaag agacttacct ttcagtttgg tgatgcaaga  1260
aaggacagtt ctctccacat cactgcagcc cagcctggtg atacaggcct ctacctctgt  1320
gcaggagatg aaagtattag ctatggaaag ctgacatttg gacaagggac catcttgact  1380
gtccatccaa acattcaaaa cccagaaccc gccgtctacc agctgaaaga cccgaggtct  1440
caagactcta cgttgtgctt gttcaccgat ttcgacagtc agataaatgt gcctaagacc  1500
atggagagtg gcactttcat cactgacaaa tgtgtgttgg acatgaaggc tatggacagc  1560
```

```
aagtcaaacg gcgcgattgc ttggtccaac caaacttctt tcacgtgcca ggacatcttc  1620
aaggagacaa acgccaccta tccatcctct gatgttccgt gcgatgcgac tcttaccgag  1680
aaaagcttcg agacggacat gaacttgaac ttccaaaacc tgcttgtgat ggtactgcga  1740
atacttcttc ttaaggtggc gggcttcaat ttgctcatga cactcagact ttggtctagc  1800

SEQ ID NO: 31          moltype = AA  length = 600
FEATURE                Location/Qualifiers
source                 1..600
                       mol_type = protein
                       organism = synthetic construct
SEQUENCE: 31
MGSWTLCCVS LCILVAKHTD AGVIQSPRHE VTEMGQEVTL RCKPISGHDY LFWYRQTMMR  60
GLELLIYFNN NVPIDDSGMP EDRFSAKMPN ASFSTLKIQP SEPRDSAVYF CASSFLGWNE  120
KLFFGSGTQL SVLEDLRNVT PPKVSLFEPS KAEIANKQKA TLVCLARGFF PDHVELSWWV  180
NGKEVHSGVC TDPQAYKESN YSYCLSSRLR VSATFWHNPR NHFRCQVQFH GLSEEDKWPE  240
GSPKPVTQNI SAEAWGRADC GITSASYQQG VLSATILYEI LLGKATLYAV LVSTLVVMAM  300
VKRKNSRAKR SGSGATNFSL LKQAGDVEEN PGPMVLKFSV SILWIQLAWV STQLLEQSPQ  360
FLSIQEGENL TVYCNSSSVF SSLQWYRQEP GEGPVLLVTV VTGGEVKKLK RLTFQFGDAR  420
KDSSLHITAA QPGDTGLYLC AGDESISYGK LTFGQGTILT VHPNIQNPEP AVYQLKDPRS  480
QDSTLCLFTD FDSQINVPKT MESGTFITDK CVLDMKAMDS KSNGAIAWSN QTSFTCQDIF  540
KETNATYPSS DVPCDATLTE KSFETDMNLN FQNLLVMVLR ILLLKVAGFN LLMTLRLWSS  600

SEQ ID NO: 32          moltype = DNA  length = 831
FEATURE                Location/Qualifiers
source                 1..831
                       mol_type = other DNA
                       organism = synthetic construct
SEQUENCE: 32
atggccatgc tcctgggggc atcagtgctg attctgtggc ttcagccaga ctgggttaac  60
agtcaacaga agaatgatga ccagcaagtt aagcaaaatt caccatccct gagcgtccag  120
gaaggaagaa tttctattct gaactgtgac tatactaaca gcatgtttga ttatttcctt  180
tggtacaaga aataccctgc tgaaggtcct acattcctga tttctattag ttccattaag  240
gataaaaatg aagatggaag attcactgtt ttccttaaca aaagtgccaa gcacctctct  300
ctgcacattg tgccctccca gcctggagac tctgcagtgt acttctgtgc agcaagcgct  360
cagaacaatg acatgcgctt tggagcaggg accagactga cagttaaacc aaacatccag  420
aaccccgacc ccgccgtgta ccagctgagg gactccaagt ccagcgacaa gagcgtgtgt  480
ctgtttacgg acttcgacag ccagaccaac gtgagtcaaa gcaaggacag cgacgtctac  540
ataacggata agaccgtgct ggacatgcgg agcatggact tcaagagcaa cagcgccgtg  600
gcctggtcca acaagagcga cttcgcctgc gccaacgcct tcaacaacag catcatcccc  660
gaggacacct tcttccccag cagcgacgtg ccctgcgacg tgaaactggt ggagaagtcc  720
ttcgagacag acaccaatct gaactttcag aacctgctgg tgatcgtgct gcggattctg  780
ctgctgaaag tggccggctt caatctgctg atgaccctgc ggctgtggag c           831

SEQ ID NO: 33          moltype = AA  length = 277
FEATURE                Location/Qualifiers
source                 1..277
                       mol_type = protein
                       organism = synthetic construct
SEQUENCE: 33
MAMLLGASVL ILWLQPDWVN SQQKNDDQQV KQNSPSLSVQ EGRISILNCD YTNSMFDYFL  60
WYKKYPAEGP TFLISISSIK DKNEDGRFTV FLNKSAKHLS LHIVPSQPGD SAVYFCAASA  120
QNNDMRFGAG TRLTVKPNIQ NPDPAVYQLR DSKSSDKSVC LFTDFDSQTN VSQSKDSDVY  180
ITDKTVLDMR SMDFKSNSAV AWSNKSDFAC ANAFNNSIIP EDTFFPSSDV PCDVKLVEKS  240
FETDTNLNFQ NLLVIVLRIL LLKVAGFNLL MTLRLWS                           277

SEQ ID NO: 34          moltype = DNA  length = 921
FEATURE                Location/Qualifiers
source                 1..921
                       mol_type = other DNA
                       organism = synthetic construct
SEQUENCE: 34
atggacacca gacttctctg ctgtgctgtc atctgtctcc tgggggcagg cctctcaaat  60
gccggcgtca tgcagaaccc aagacacctg gtcaggagga ggggacagga ggcaagactg  120
agatgcagcc caatgaaagg acacagtcat gtttactggt atcggcagct cccagaggaa  180
ggtctgaaat tcatggttta tctccagaaa gaaaatatca ttgatgagtc aggaatgcca  240
aaggaacgct tttctgctga atttcccaaa gagggcccca gcatcctgag gatccagcag  300
gttgtgcgcg gagattctgc agcttatttc tgtgccagct caccctccta cgagcagtac  360
ttcgggcctg gcaccaggct cactgtcaca gaagatctga acaaggtgtt ccctccagag  420
gtggccgtgt tcgagccttc taaggccgag atcgcccaca cacaaaaagc caccctcgtg  480
tgcctggcca ccggcttttt ccccgaccac gtggaactgt cttggtgggt caacggcaaa  540
gaggtgcact ccggcgtgtc aacggatccc cagcctctga aagaacagcc tgccctgaac  600
gacagccggt actgcctgag ctccagactg agagtgtccg ccaccttctg gcagaacccc  660
cggaaccact tcagatgcca ggtgcagttt tacggcctga gcgagaacga cgagtggacc  720
caggacagag ccaagcccgt gacacaaatc gtgtctgccg aagcctgggg aagagccgat  780
tgcggcatca ccagcgcctc ctatcaccag ggcgtgctga gcgccacaat cctgtacgaa  840
atcctgctgg gcaaggccac cctgtacgcc gtgctggtgt ctgctctggt gctgatggcc  900
atggtcaagc ggaaggactt t                                            921

SEQ ID NO: 35          moltype = AA  length = 307
```

```
FEATURE                Location/Qualifiers
source                 1..307
                       mol_type = protein
                       organism = synthetic construct
SEQUENCE: 35
MDTRLLCCAV ICLLGAGLSN AGVMQNPRHL VRRRGQEARL RCSPMKGHSH VYWYRQLPEE  60
GLKFMVYLQK ENIIDESGMP KERFSAEFPK EGPSILRIQQ VVRGDSAAYF CASSPSYEQY  120
FGPGTRLTVT EDLNKVFPPE VAVFEPSKAE IAHTQKATLV CLATGFFPDH VELSWWVNGK  180
EVHSGVSTDP QPLKEQPALN DSRYCLSSRL RVSATFWQNP RNHFRCQVQF YGLSENDEWT  240
QDRAKPVTQI VSAEAWGRAD CGITSASYHQ GVLSATILYE ILLGKATLYA VLVSALVLMA  300
MVKRKDF                                                           307

SEQ ID NO: 36          moltype = DNA  length = 1842
FEATURE                Location/Qualifiers
source                 1..1842
                       mol_type = other DNA
                       organism = synthetic construct
SEQUENCE: 36
atggacacca gacttctctg ctgtgctgtc atctgtctcc tgggggcagg cctctcaaat  60
gccggcgtca tgcagaaccc aagacacctg gtcaggagga ggggacagga ggcaagactg  120
agatgcagcc caatgaaagg acacagtcat gtttactggt atcggcagct cccagaggaa  180
ggtctgaaat tcatggttta tctccagaaa gaaaatatca ttgatgagtc aggaatgcca  240
aaggaacgct tttctgctga atttcccaaa gagggcccca gcatcctgag gatccagcag  300
gttgtgcgcg gagattctgc agcttatttc tgtgccagct caccctccta cgagcagtac  360
ttcgggcctg gcaccaggct cactgtcaca gaagatctga acaaggtgtt ccctccagag  420
gtggccgtgt tcgagcctte taaggccgag atcgcccaca cacaaaaagc caccctcgtg  480
tgcctggcca ccggcttttt ccccgaccac gtggaactgt cttggtgggt caacggcaaa  540
gaggtgcact ccggcgtgtc aacggatccc cagcctctga aagaacagcc tgccctgaac  600
gacagccggt actgcctgag ctccagactg agagtgtccg ccaccttctg gcagaacccc  660
cggaaccact tcagatgcca ggtgcagttt tacggcctga gcgagaacga cgagtggacc  720
caggacagag ccaagcccgt gacacaaatc gtgtctgccg aagcctgggg aagagccgat  780
tgcggcatca ccagcgcctc ctatcaccag ggcgtgctga gcgccacaat cctgtacgaa  840
atcctgctgg gcaaggccac cctgtacgcc gtgctggtgt ctgctctggt gctgatggcc  900
atggtcaagc ggaaggactt tggcagcggc agagccaaaa ggtccgggag cggtgcgaca  960
aactttagcc tgttgaaaca agccggcgac gttgaagaga accccggacc tatggccatg  1020
ctcctggggg catcagtgct gattctgtgg cttcagccag actgggttaa cagtcaacag  1080
aagaatgatg accagcaagt taagcaaaat tcaccatccc tgagcgtcca ggaaggaaga  1140
atttctattc tgaactgtga ctatactaac agcatgtttg attatttcct ttggtacaag  1200
aaataccctg ctgaaggtcc tacattcctg atttctatta gttccattaa ggataaaaat  1260
gaagatggaa gattcactgt tttccttaac aaaagtgcca agcacctctc tctgcacatt  1320
gtgccctccc agcctggaga ctctgcagtg tacttctgtg cagcaagcgc tcagaacaat  1380
gacatgcgct ttggagcagg gaccagactg acagttaaac caaacatcca gaaccccgac  1440
cccgccgtgt accagctgag ggactccaag tccagcgaca agagcgtgtg tctgtttacg  1500
gacttcgaca gccagaccaa cgtgagtcaa agcaaggaca gcgacgtcta cataacggat  1560
aagaccgtgc tggacatgcg gagcatggac ttcaagagca acagcgccgt ggcctggtcc  1620
aacaagagcg acttcgcctg cgccaacgcc ttcaacaaca gcatcatccc cgaggacacc  1680
ttcttcccca gcagcgacgt gccctgcgac gtgaaactgg tggagaagtc cttcgagaca  1740
gacaccaatc tgaactttca gaacctgctg gtgatcgtgc tgcggattct gctgctgaaa  1800
gtggccggct tcaatctgct gatgaccctg cggctgtgga gc                    1842

SEQ ID NO: 37          moltype = AA  length = 614
FEATURE                Location/Qualifiers
source                 1..614
                       mol_type = protein
                       organism = synthetic construct
SEQUENCE: 37
MDTRLLCCAV ICLLGAGLSN AGVMQNPRHL VRRRGQEARL RCSPMKGHSH VYWYRQLPEE  60
GLKFMVYLQK ENIIDESGMP KERFSAEFPK EGPSILRIQQ VVRGDSAAYF CASSPSYEQY  120
FGPGTRLTVT EDLNKVFPPE VAVFEPSKAE IAHTQKATLV CLATGFFPDH VELSWWVNGK  180
EVHSGVSTDP QPLKEQPALN DSRYCLSSRL RVSATFWQNP RNHFRCQVQF YGLSENDEWT  240
QDRAKPVTQI VSAEAWGRAD CGITSASYHQ GVLSATILYE ILLGKATLYA VLVSALVLMA  300
MVKRKDFGSG RAKRSGSGAT NFSLLKQAGD VEENPGPMAM LLGASVLILW LQPDWVNSQQ  360
KNDDQQVKQN SPSLSVQEGR ISILNCDYTN SMFDYFLWYK KYPAEGPTFL ISISSIKDKN  420
EDGRFTVFLN KSAKHLSLHI VPSQPGDSAV YFCAASAQNN DMRFGAGTRL TVKPNIQNPD  480
PAVYQLRDSK SSDKSVCLFT DFDSQTNVSQ SKDSDVYITD KTVLDMRSMD FKSNSAVAWS  540
NKSDFACANA FNNSIIPEDT FFPSSDVPCD VKLVEKSFET DTNLNFQNLL VIVLRILLLK  600
VAGFNLLMTL RLWS                                                   614

SEQ ID NO: 38          moltype = DNA  length = 810
FEATURE                Location/Qualifiers
source                 1..810
                       mol_type = other DNA
                       organism = synthetic construct
SEQUENCE: 38
atggtcctga aattctccgt gtccattctt tggattcagt tggcatgggt gagcacccag  60
ctgctggagc agagccctca gtttcttagc atccaagagg gagaaaatct cactgtgtac  120
tgcaactcct caagtgtttt ctccagcctt caatggtaca gacaggagcc tggggaaggt  180
cctgtcctcc tggtgacagt tgttactggt ggagaagtga agaagctgaa gagacttacc  240
tttcagtttg gtgatgcaag aaaggacagt tctctccaca tcactgcagc ccagcctggt  300
```

-continued

```
gatacaggcc tctacctctg tgcaggagat gaaagtatta gctatggaaa gctgacattt  360
ggacaaggga ccatcttgac tgtccatcca aacatccaga accccgaccc cgccgtgtac  420
cagctgaggg actccaagtc cagcgacaag agcgtgtgtc tgtttacgga cttcgacagc  480
cagaccaacg tgagtcaaag caaggacagc gacgtctaca taacggataa gaccgtgctg  540
gacatgcgga gcatggactt caagagcaac agcgccgtgg cctggtccaa caagagcgac  600
ttcgcctgcg ccaacgcctt caacaacagc atcatccccg aggacacctt cttccccagc  660
agcgacgtgc cctgcgacgt gaaactggtg gagaagtcct tcgagacaga caccaatctg  720
aactttcaga acctgctggt gatcgtgctg cggattctgc tgctgaaagt ggccggcttc  780
aatctgctga tgaccctgcg gctgtggagc                                     810
```

```
SEQ ID NO: 39          moltype = AA  length = 270
FEATURE                Location/Qualifiers
source                 1..270
                       mol_type = protein
                       organism = synthetic construct
SEQUENCE: 39
MVLKFSVSIL WIQLAWVSTQ LLEQSPQFLS IQEGENLTVY CNSSSVFSSL QWYRQEPGEG  60
PVLLVTVVTG GEVKKLKRLT FQFGDARKDS SLHITAAQPG DTGLYLCAGD ESISYGKLTF  120
GQGTILTVHP NIQNPDPAVY QLRDSKSSDK SVCLFTDFDS QTNVSQSKDS DVYITDKTVL  180
DMRSMDFKSN SAVAWSNKSD FACANAFNNS IIPEDTFFPS SDVPCDVKLV EKSFETDTNL  240
NFQNLLVIVL RILLLKVAGF NLLMTLRLWS                                     270
```

```
SEQ ID NO: 40          moltype = DNA  length = 930
FEATURE                Location/Qualifiers
source                 1..930
                       mol_type = other DNA
                       organism = synthetic construct
SEQUENCE: 40
atgggctcct ggaccctctg ctgtgtgtcc ctttgcatcc tggttgcaaa gcacacagat  60
gctggagtta tccagtcacc ccggcacgag gtgacagaga tgggacaaga agtgactctg  120
agatgtaaac caatttcagg acatgactac cttttctggt acagacagac catgatgcgg  180
ggactggagt tgctcattta ctttaacaac aacgttccta ttgatgattc agggatgccc  240
gaggatcgct tctcagctaa gatgcctaat gcatcattct ccactctgaa gatccagccc  300
tcagaaccca gggactcagc tgtgtacttc tgtgccagca gttttctcgg ctggaatgaa  360
aaactgttct ttggcagtgg aacccagctc tctgtcttgg aagatctgaa caaggtgttc  420
cctccagagg tggccgtgtt cgagccttct aaggccgaga tcgcccacac acaaaaagcc  480
accctcgtgt gcctggccac cggctttttc cccgaccacg tggaactgtc ttggtgggtc  540
aacggcaaag aggtgcactc cggcgtgtca acggatcccc agcctctgaa agaacagcct  600
gccctgaacg acagccggta ctgcctgagc tccagactga gagtgtccgc caccttctgg  660
cagaaccccc ggaaccactt cagatgccag gtgcagtttt acggcctgag cgagaacgac  720
gagtggaccc aggacagagc caagcccgtg acacaaatcg tgtctgccga agcctgggga  780
agagccgatt gcggcatcac cagcgcctcc tatcaccagg gcgtgctgag cgccacaatc  840
ctgtacgaaa tcctgctggg caaggccacc ctgtacgccg tgctggtgtc tgctctggtg  900
ctgatggcca tggtcaagcg gaaggacttt                                     930
```

```
SEQ ID NO: 41          moltype = AA  length = 310
FEATURE                Location/Qualifiers
source                 1..310
                       mol_type = protein
                       organism = synthetic construct
SEQUENCE: 41
MGSWTLCCVS LCILVAKHTD AGVIQSPRHE VTEMGQEVTL RCKPISGHDY LFWYRQTMMR  60
GLELLIYFNN NVPIDDSGMP EDRFSAKMPN ASFSTLKIQP SEPRDSAVYF CASSFLGWNE  120
KLFFGSGTQL SVLEDLNKVF PPEVAVFEPS KAEIAHTQKA TLVCLATGFF PDHVELSWWV  180
NGKEVHSGVS TDPQPLKEQP ALNDSRYCLS SRLRVSATFW QNPRNHFRCQ VQFYGLSEND  240
EWTQDRAKPV TQIVSAEAWG RADCGITSAS YHQGVLSATI LYEILLGKAT LYAVLVSALV  300
LMAMVKRKDF                                                           310
```

```
SEQ ID NO: 42          moltype = DNA  length = 1830
FEATURE                Location/Qualifiers
source                 1..1830
                       mol_type = other DNA
                       organism = synthetic construct
SEQUENCE: 42
atgggctcct ggaccctctg ctgtgtgtcc ctttgcatcc tggttgcaaa gcacacagat  60
gctggagtta tccagtcacc ccggcacgag gtgacagaga tgggacaaga agtgactctg  120
agatgtaaac caatttcagg acatgactac cttttctggt acagacagac catgatgcgg  180
ggactggagt tgctcattta ctttaacaac aacgttccta ttgatgattc agggatgccc  240
gaggatcgct tctcagctaa gatgcctaat gcatcattct ccactctgaa gatccagccc  300
tcagaaccca gggactcagc tgtgtacttc tgtgccagca gttttctcgg ctggaatgaa  360
aaactgttct ttggcagtgg aacccagctc tctgtcttgg aagatctgaa caaggtgttc  420
cctccagagg tggccgtgtt cgagccttct aaggccgaga tcgcccacac acaaaaagcc  480
accctcgtgt gcctggccac cggctttttc cccgaccacg tggaactgtc ttggtgggtc  540
aacggcaaag aggtgcactc cggcgtgtca acggatcccc agcctctgaa agaacagcct  600
gccctgaacg acagccggta ctgcctgagc tccagactga gagtgtccgc caccttctgg  660
cagaaccccc ggaaccactt cagatgccag gtgcagtttt acggcctgag cgagaacgac  720
gagtggaccc aggacagagc caagcccgtg acacaaatcg tgtctgccga agcctgggga  780
agagccgatt gcggcatcac cagcgcctcc tatcaccagg gcgtgctgag cgccacaatc  840
ctgtacgaaa tcctgctggg caaggccacc ctgtacgccg tgctggtgtc tgctctggtg  900
```

```
ctgatggcca tggtcaagcg gaaggacttt ggcagcggca gagccaaaag gtccgggagc  960
ggtgcgacaa actttagcct gttgaaacaa gccggcgacg ttgaagagaa ccccggacct  1020
atggtcctga aattctccgt gtccattctt tggattcagt tggcatgggt gagcacccag  1080
ctgctggagc agagccctca gtttcttagc atccaagagg gagaaaatct cactgtgtac  1140
tgcaactcct caagtgtttt ctccagcctt caatggtaca gacaggagcc tggggaaggt  1200
cctgtcctcc tggtgacagt tgttactggt ggagaagtga agaagctgaa gagacttacc  1260
tttcagtttg gtgatgcaag aaaggacagt tctctccaca tcactgcagc ccagcctggt  1320
gatacaggcc tctacctctg tgcaggagat gaaagtatta gctatggaaa gctgacattt  1380
ggacaaggga ccatcttgac tgtccatcca aacatccaga accccgaccc cgccgtgtac  1440
cagctgaggg actccaagtc cagcgacaag agcgtgtgtc tgtttacgga cttcgacagc  1500
cagaccaacg tgagtcaaag caaggacagc gacgtctaca taacggataa gaccgtgctg  1560
gacatgcgga gcatggactt caagagcaac agcgccgtgg cctggtccaa caagagcgac  1620
ttcgcctgcg ccaacgcctt caacaacagc atcatccccg aggacacctt cttccccagc  1680
agcgacgtgc cctgcgacgt gaaactggtg gagaagtcct tcgagacaga caccaatctg  1740
aactttcaga acctgctggt gatcgtgctg cggattctgc tgctgaaagt ggccggcttc  1800
aatctgctga tgaccctgcg gctgtggagc                                   1830

SEQ ID NO: 43          moltype = AA  length = 610
FEATURE                Location/Qualifiers
source                 1..610
                       mol_type = protein
                       organism = synthetic construct
SEQUENCE: 43
MGSWTLCCVS LCILVAKHTD AGVIQSPRHE VTEMGQEVTL RCKPISGHDY LFWYRQTMMR  60
GLELLIYFNN NVPIDDSGMP EDRFSAKMPN ASFSTLKIQP SEPRDSAVYF CASSFLGWNE  120
KLFFGSGTQL SVLEDLNKVF PPEVAVFEPS KAEIAHTQKA TLVCLATGFF PDHVELSWWV  180
NGKEVHSGVS TDPQPLKEQP ALNDSRYCLS SRLRVSATFW QNPRNHFRCQ VQFYGLSEND  240
EWTQDRAKPV TQIVSAEAWG RADCGITSAS YHQGVLSATI LYEILLGKAT LYAVLVSALV  300
LMAMVKRKDF GSGRAKRSGS GATNFSLLKQ AGDVEENPGP MVLKFSVSIL WIQLAWVSTQ  360
LLEQSPQFLS IQEGENLTVY CNSSSVFSSL QWYRQEPGEG PVLLVTVVTG GEVKKLKRLT  420
FQFGDARKDS SLHITAAQPG DTGLYLCAGD ESISYGKLTF GQGTILTVHP NIQNPDPAVY  480
QLRDSKSSDK SVCLFTDFDS QTNVSQSKDS DVYITDKTVL DMRSMDFKSN SAVAWSNKSD  540
FACANAFNNS IIPEDTFFPS SDVPCDVKLV EKSFETDTNL NFQNLLVIVL RILLLKVAGF  600
NLLMTLRLWS                                                         610

SEQ ID NO: 44          moltype = DNA  length = 930
FEATURE                Location/Qualifiers
source                 1..930
                       mol_type = genomic DNA
                       organism = Homo sapiens
SEQUENCE: 44
atgtctcttg agcagaggag tctgcactgc aagcctgagg aagcccttga ggcccaacaa  60
gaggccctgg gcctggtgtg tgtgcaggct gccacctcct cctcctctcc tctggtcctg  120
ggcaccctgg aggaggtgcc cactgctggg tcaacagatc ctccccagag tcctcaggga  180
gcctccgcct ttcccactac catcaacttc actcgacaga ggcaacccag tgagggttcc  240
agcagccgtg aagaggaggg gccaagcacc tcttgtatcc tggagtcctt gttccgagca  300
gtaatcacta agaaggtggc tgatttggtt ggttttctgc tcctcaaata tcgagccagg  360
gagccagtca caaaggcaga aatgctggag agtgtcatca aaaattacaa gcactgtttt  420
cctgagatct tcggcaaagc ctctgagtcc ttgcagctgg tctttggcat tgacgtgaag  480
gaagcagacc ccaccggcca ctcctatgtc cttgtcacct gcctaggtct ctcctatgat  540
ggcctgctgg gtgataatca gatcatgccc aagacaggct tcctgataat tgtcctggtc  600
atgattgcaa tggagggcgg ccatgctcct gaggaggaaa tctgggagga gctgagtgtg  660
atggaggtgt atgatgggag ggagcacagt gcctatgggg agcccaggaa gctgctcacc  720
caagatttgg tgcaggaaaa gtacctggag taccggcagg tgccggacag tgatcccgca  780
cgctatgagt tcctgtgggg tccaagggcc ctcgctgaaa ccagctatgt gaaagtcctt  840
gagtatgtga tcaaggtcag tgcaagagtt cgcttttttct tcccatccct gcgtgaagca  900
gctttgagag aggaggaaga gggagtctga                                   930

SEQ ID NO: 45          moltype = AA  length = 309
FEATURE                Location/Qualifiers
source                 1..309
                       mol_type = protein
                       organism = Homo sapiens
SEQUENCE: 45
MSLEQRSLHC KPEEALEAQQ EALGLVCVQA ATSSSSPLVL GTLEEVPTAG STDPPQSPQG  60
ASAFPTTINF TRQRQPSEGS SSREEEGPST SCILESLFRA VITKKVADLV GFLLLKYRAR  120
EPVTKAEMLE SVIKNYKHCF PEIFGKASES LQLVFGIDVK EADPTGHSYV LVTCLGLSYD  180
GLLGDNQIMP KTGFLIIVLV MIAMEGGHAP EEEIWEELSV MEVYDGREHS AYGEPRKLLT  240
QDLVQEKYLE YRQVPDSDPA RYEFLWGPRA LAETSYVKVL EYVIKVSARV RFFFPSLREA  300
ALREEEEGV                                                          309

SEQ ID NO: 46          moltype = DNA  length = 1101
FEATURE                Location/Qualifiers
source                 1..1101
                       mol_type = genomic DNA
                       organism = Homo sapiens
SEQUENCE: 46
atgcgcgtca tggctccacg cgccctcctc ctgctgctct cagggggcct ggccctgacc  60
gagacctggg cctgctccca ctccatgcgc tatttcgaca ccgccgtgtc ccgcccaggc  120
```

```
cgcggtgagc cacgcttcat ctcagtgggc tacgtggacg acactcagtt cgtgcgcttc  180
gacagcgacg ccgccagtcc tcgcggggag ccacgcgcac catgggtgga gcaggagggg  240
cctgagtatt gggaccgcga gacacagaag tacaagcgcc aggcacaggc tgaccgcgtg  300
agcctgcgca acctgcgcgg ctactacaac cagagcgagg acgggtctca caccctccag  360
cgcatgtctg gctgcgacct ggggcctgac gggcgcctcc tccgcgggta tgaccagtcc  420
gcctacgacg gcaaggatta catcgccctg aacgaggacc tgcgctcctg gaccgccgct  480
gacaccgccg ctcagatcac ccagcgcaag ttggaggctg cccgcgccgc tgagcagctg  540
cgcgcctacc tggagggcac atgcgtggag tggctccgcc gctacctgga gaacgggaag  600
gagaccctgc agcgcgcaga accaccaaag acacacgtga cccaccaccc tctctctgac  660
catgaggcca ccctgcgctg ctgggccctg ggcttctacc ctgctgagat cacactgacc  720
tggcagcgcg atggggagga ccagacccag gacaccgagc ttgtggagac ccgcccagca  780
ggtgatggca ccttccagaa gtgggcagct gtggtggtgc cttctgggca agagcagcgc  840
tacacatgcc atatgcagca cgaggggctg caagagccac tcaccctgag ctgggagcca  900
tcttcccagc caaccatccc aatcatgggc atcgttgctg gcctggctgt cctggttgtc  960
ctggctgtcc ttggtgctgt ggtcaccgct atgatgtgtc gccgcaagag ctcaggtggg  1020
aaaggtggga gctgctctca ggctgcatgc agcaacagtg cccagggctc tgatgagtct  1080
ctcatcactt gtaaagcctg a                                            1101

SEQ ID NO: 47          moltype = AA  length = 366
FEATURE                Location/Qualifiers
source                 1..366
                       mol_type = protein
                       organism = Homo sapiens
SEQUENCE: 47
MRVMAPRALL LLLSGGLALT ETWACSHSMR YFDTAVSRPG RGEPRFISVG YVDDTQFVRF  60
DSDAASPRGE PRAPWVEQEG PEYWDRETQK YKRQAQADRV SLRNLRGYYN QSEDGSHTLQ  120
RMSGCDLGPD GRLLRGYDQS AYDGKDYIAL NEDLRSWTAA DTAAQITQRK LEAARAAEQL  180
RAYLEGTCVE WLRRYLENGK ETLQRAEPPK THVTHHPLSD HEATLRCWAL GFYPAEITLT  240
WQRDGEDQTQ DTELVETRPA GDGTFQKWAA VVVPSGQEQR YTCHMQHEGL QEPLTLSWEP  300
SSQPTIPIMG IVAGLAVLVV LAVLGAVVTA MMCRRKSSGG KGGSCSQAAC SNSAQGSDES  360
LITCKA                                                             366

SEQ ID NO: 48          moltype = DNA  length = 4734
FEATURE                Location/Qualifiers
source                 1..4734
                       mol_type = other DNA
                       organism = synthetic construct
SEQUENCE: 48
atgcaatttc aactgaccct ttttttgcac cttgggtggc tcagttactc aaaagctcaa  60
gatgactgca acaggggtgc ctgtcatccc accactggtg atctcctggt gggcaggaac  120
acgcagctta tggcttcttc tacctgtggg ctgagcagag cccagaaata ctgcatcctc  180
agttacctgg agggggaaca aaaatgcttc atctgtgact ctagatttcc atatgatccg  240
tatgaccaac ccaacagcca caccattgag aatgtcattg taagttttga accagacaga  300
gaaaagaaat ggtggcaatc tgaaaatggt cttgatcatg tcagcatcag actggactta  360
gaggcattat ttcggttcag ccaccttatc ctgaccttta agacttttcg gcctgctgca  420
atgttagttg aacgttccac agactatgga cacaactgga aagtgttcaa atattttgca  480
aaagactgtg ccacttcctt tcctaacatc acatctggcc aggcccaggg agtgggagac  540
attgtttgtg actccaaata ctcggatatt gaaccctcaa caggtggaga ggttgtttta  600
aaagttttgg atcccagttt tgaaattgaa aacccttata gcccctacat ccaagacctt  660
gtgacattga caaacctgag gataaacttt accaagctcc acacccttgg ggatgctttg  720
cttggaagga ggcaaaatga ttcccttgat aaatactact atgctctgta cgagatgatt  780
gttcggggaa gctgcttttg caatggccat gctagcgaat gtcgccctat gcagaagatg  840
cggggagatg ttttcagccc tcctggaatg gttcacggtc agtgtgtgtg tcagcacaat  900
acagatggtc cgaactgtga gagatgcaag gacttcttcc aggatgctcc ttggaggcca  960
gctgcagacc tccaggacaa cgcttgcaga tcgtgcagct gtaatagcca ctccagccgc  1020
tgtcactttg acatgactac gtacctggca agcggtggcc tcagcggggg cgtgtgtgaa  1080
gactgccagc acaacactga ggggcagcac tgcgaccgct gcagacccct cttctacagg  1140
gacccgctca agaccatctc agatccctac gcgtgcattc cttgtgaatg tgaccccgat  1200
gggaccatat ctggtggcat ttgtgtgagc cactctgatc ctgccttagg gtctgtggcc  1260
ggccagtgcc tttgtaaaga gaacgtggaa ggagccaaat gcgaccagtg caaacccaac  1320
cactacggac taagcgccac cgacccccctg ggctgccagc cctgcgactg taacccccctt  1380
gggagtctgc cattcttgac ctgtgatgtg gatacaggcc aatgcttgtg cctgtcatat  1440
gtcaccggag cacactgcga agaatgcact gttggatact ggggcctggg aaatcatctc  1500
catgggtgtt ctccctgtga ctgtgatatt ggaggtgctt attctaacgt gtgctcaccc  1560
aagaatgggc agtgtgaatg ccgcccacat gtcactggcc gtagctgctc tgaaccagcc  1620
cctggctact tctttgctcc tttgaatttc tatctctacg aggcagagga agccacaaca  1680
ctccaaggac tggcgccttt gggctcggag acgtttggcc agagtcctgc tgttcacgtt  1740
gttttaggag agccagttcc tgggaaccct gttacatgga ctggacctgg atttgccagg  1800
gttctccctg gggctggctt gagatttgct gtcaacaaca ttccctttcc tgtggacttc  1860
accattgcca ttcactatga aacccagtct gcagctgact ggactgtcca gattgtggtg  1920
aacccccctg gagggagtga gcactgcata cccaagactc tacagtcaaa gcctcagtct  1980
tttgccttac cagcggctac gagaatcatg ctgcttccca cacccatctg tttagaacca  2040
gatgtacaat attccataga tgtctatttt tctcagcctt tgcaaggaga gtcccacgct  2100
cattcacatg tcctggtgga ctctcttggc cttattcccc aaatcaattc attggagaat  2160
ttctgcagca agcaggactt agatgagtat cagcttcaca actgtgttga aattgcctca  2220
gcaatgggac ctcaagtgct cccgggtgcc tgtgaaaggc tgatcatcag catgtctgcc  2280
aagctgcatg atggggctgt ggcctgcaag tgtcaccccc agggctcagt cggatccagc  2340
tgcagccgac ttggaggcca gtgccagtgt aaacctcttg tggtcgggcg ctgctgtgac  2400
aggtgctcaa ctggaagcta tgatttgggg catcacggct gtcacccatg tcactgccat  2460
```

```
cctcaaggat caaaggacac tgtatgtgac caagtaacag gacagtgccc ctgccatgga  2520
gaggtgtctg gccgccgctg tgatcgctgc ctggcaggct actttggatt tcccagctgc  2580
cacccttgcc cttgtaatag gtttgctgaa ctttgtgatc ctgagacagg gtcatgcttc  2640
aattgtggag gctttacaac tggcagaaac tgtgaaaggt gtattgatgg ttactatgga  2700
aatccttctt caggacagcc ctgtcgtcct tgcctgtgtc cagatgatcc ctcaagcaat  2760
cagtattttg cccattcctg ttatcagaat ctgtggagct cagatgtaat ctgcaattgt  2820
cttcaaggtt atacgggtac tcagtgtgga gaatgctcta ctggtttcta tggaaatcca  2880
agaatttcag gagcaccttg ccaaccatgt gcctgcaaca acaacataga tgtaaccgat  2940
ccagagtcct gcagccgggt aacaggggag tgccttcgat gtttgcacaa cactcagggc  3000
gcaaactgcc agctctgcaa accaggtcac tatggatcag ccctcaatca gacctgcaga  3060
agatgctcct gccatgcttc cggcgtgagt cccatggagt gtccccctgg tgggggagct  3120
tgcctctgtg accctgtcac tggtgcatgt ccttgtctgc cgaatgtcac aggcctggcc  3180
tgtgaccgtt gtgctgatgg atactggaat ctggtccctg gcagaggatg tcagtcatgt  3240
gactgtgacc ctaggacctc tcaaagtagc cactgtgacc agcttacagg ccagtgtccg  3300
tgtaaattag gttacggcgg gaaacgttgc agtgagtgcc aggaaaatta ttatggtgat  3360
ccacctgggc gatgcattcc atgtgattgt aacagggcag gtacccagaa gcccatctgt  3420
gatccagaca caggcatgtg ccgctgccgg gagggtgtca gcggccagag atgtgatcgc  3480
tgtgcccggg gacacagcca ggaattccct acttgtcttc aatgtcactt gtgctttgat  3540
cagtgggacc acaccatttc ttccctctcc aaagcggtgc aagggttaat gagactggct  3600
gctaacatgg aagataaaag agagaccctg cctgtctgtg aggcagactt caaagacctc  3660
agagggaacg tgtctgaaat agaaaggatt ttgaaacatc ctgttttccc atctgggaaa  3720
ttcttaaaag tcaaggatta tcatgactct gttagaagac aaatcatgca gctaaatgaa  3780
caactgaaag cagtgtatga atttcaagat ctgaaagata caatagaaag agcaaagaat  3840
gaagcagacc tcttacttga agaccttcag gaagaaattg atttgcaatc cagtgtcctt  3900
aatgcaagca ttgcggactc ctcagaaaac atcaagaaat attatcacat atcatcatct  3960
gctgaaaaga aaattaatga aactagttcc accattaata cctctgcaaa tacaaggaat  4020
gacttactta ccatcttaga tacactaacc tcaaaaggaa acttgtcatt ggaaagatta  4080
aagcagatta agataccaga tatccaaata ttgaatgaaa aggtgtgcgg agatccagga  4140
aatgtgccat gtgtgccctt gccctgtggc ggtgctctct gcacgggccg gaaggggcac  4200
aggaagtgta ggggtcccgg ctgtcacggc tccctgaccc tctcaacgaa tgccctccaa  4260
aaagcccagg aagcaaaatc cattattcgt aatttggaca aacaggttcg tgggttgaaa  4320
aatcagatcg aaagtataag tgaacaggca gaagtctcca aaaacaatgc cttacagctg  4380
agggaaaaac tgggaaatat aagaaaccaa agtgactctg aagaagaaaa catcaatctt  4440
ttcatcaaaa aagtgaaaaa ctttttgtta ggtaatttaa aaatatatat taggactagt  4500
ttttgttttt ttccctttttt aatgtatagt caaacatcat acgtgaaccc aggaggcgga  4560
gcttgcagtg agccgagatc gcgccactgc actccagcct gggcgacaga gcgagactcc  4620
gtctcaaaaa aaaaaaaaaa aaaaaaaaaa aaaaaaaaaa aaaaaaaaaa aaaaaaaacat  4680
catagccagt tccaaattat attaattgga aatgacaagc ctaaatcaga aaaa        4734
```

```
SEQ ID NO: 49          moltype = AA  length = 1578
FEATURE                Location/Qualifiers
source                 1..1578
                       mol_type = protein
                       organism = synthetic construct
SEQUENCE: 49
MQFQLTLFLH LGWLSYSKAQ DDCNRGACHP TTGDLLVGRN TQLMASSTCG LSRAQKYCIL  60
SYLEGEQKCF ICDSRFPYDP YDQPNSHTIE NVIVSFEPDR EKKWWQSENG LDHVSIRLDL  120
EALFRFSHLI LTFKTFRPAA MLVERSTDYG HNWKVFKYFA KDCATSFPNI TSGQAQGVGD  180
IVCDSKYSDI EPSTGGEVVL KVLDPSFEIE NPYSPYIQDL VTLTNLRINF TKLHTLGDAL  240
LGRRQNDSLD KYYYALYEMI VRGSCFCNGH ASECRPMQKM RGDVFSPPGM VHGQCVCQHN  300
TDGPNCERCK DFFQDAPWRP AADLQDNACR SCSCNSHSSR CHFDMTTYLA SGGLSGGVCE  360
DCQHNTEGQH CDRCRPLFYR DPLKTISDPY ACIPCECDPD GTISGGICVS HSDPALGSVA  420
GQCLCKENVE GAKCDQCKPN HYGLSATDPL GCQPCDCNPL GSLPFLTCDV DTGQCLCLSY  480
VTGAHCEECT VGYWGLGNHL HGCSPCDCDI GGAYSNVCSP KNGQCECRPH VTGRSCSEPA  540
PGYFFAPLNF YLYEAEEATT LQGLAPLGSE TFGQSPAVHV VLGEPVPGNP VTWTGPGFAR  600
VLPGAGLRFA VNNIPFPVDF TIAIHYETQS AADWTVQIVV NPPGGSEHCI PKTLQSKPQS  660
FALPAATRIM LLPTPICLEP DVQYSIDVYF SQPLQGESHA HSHVLVDSLG LIPQINSLEN  720
FCSKQDLDEY QLHNCVEIAS AMGPQVLPGA CERLIISMSA KLHDGAVACK CHPQGSVGSS  780
CSRLGGQCQC KPLVVGRCCD RCSTGSYDLG HHGCHPCHCH PQGSKDTVCD QVTGQCPCHG  840
EVSGRRCDRC LAGYFGFPSC HPCPCNRFAE LCDPETGSCF NCGGFTTGRN CERCIDGYYG  900
NPSSGQPCRP CLCPDDPSSN QYFAHSCYQN LWSSDVICNC LQGYTGTQCG ECSTGFYGNP  960
RISGAPCQPC ACNNNIDVTD PESCSRVTGE CLRCLHNTQG ANCQLCKPGH YGSALNQTCR  1020
RCSCHASGVS PMECPPGGGA CLCDPVTGAC PCLPNVTGLA CDRCADGYWN LVPGRGCQSC  1080
DCDPRTSQSS HCDQLTGQCP CKLGYGGKRC SECQENYYGD PPGRCIPCDC NRAGTQKPIC  1140
DPDTGMCRCR EGVSGQRCDR CARGHSQEFP TCLQCHLCFD QWDHTISSLS KAVQGLMRLA  1200
ANMEDKRETL PVCEADFKDL RGNVSEIERI LKHPVFPSGK FLKVKDYHDS VRRQIMQLNE  1260
QLKAVYEFQD LKDTIERAKN EADLLLEDLQ EEIDLQSSVL NASIADSSEN IKKYYHISSS  1320
AEKKINETSS TINTSANTRN DLLTILDTLT SKGNLSLERL KQIKIPDIQI LNEKVCGDPG  1380
NVPCVPLPCG GALCTGRKGH RKCRGPGCHG SLTLSTNALQ KAQEAKSIIR NLDKQVRGLK  1440
NQIESISEQA EVSKNNALQL REKLGNIRNQ SDSEEENINL FIKKVKNFLL GNLKIYIRTS  1500
FCFFPFLMYS QTSYVNPGGG ACSEPRSRHC TPAWATERDS VSKKKKKKKK KKKKKKKKKH  1560
HSQFQIILIG NDKPKSEK                                                1578
```

```
SEQ ID NO: 50          moltype = DNA  length = 9683
FEATURE                Location/Qualifiers
source                 1..9683
                       mol_type = other DNA
                       organism = synthetic construct
SEQUENCE: 50
```

-continued

```
tggaagggct aattcactcc caaagaagac aagatatcct tgatctgtgg atctaccaca  60
cacaaggcta cttccctgat tagcagaact acacaccagg gccaggggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agaccctttt agtcagtgtg gaaaatctct agcagtggcg cccgaacagg gacttgaaag  660
cgaaagggaa accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca gggggaaaga aaaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag tttttgctgt  1860
actttctata gtgaatagag ttaggcaggg atattcacca ttatcgtttc agacccacct  1920
cccaaccccg aggggacccg acaggcccga aggaatagaa gaagaaggtg gagagagaga  1980
cagagacaga tccattcgat tagtgaacgg atctcgacgg tatcgccgaa ttaattcaca  2040
aatggcagta ttcatccaca attttaaaag aaaagggggg attggggggt acagtgcagg  2100
ggaaagaata gtagacataa tagcaacaga catacaaact aaagaattac aaaaacaaat  2160
tacaaaaatt caaaattttc gggtttatta caggcgcgcc agagatccag tttggacctg  2220
caggtgaaag accccacctg taggtttggc aagttagctt aagtaacgcc attttgcaag  2280
gcatggaaaa tacataactg agaatagaga agttcagatc aaggttagga acagagagac  2340
agcagaatat gggccaaaca ggatatctgt ggtaagcagt tcctgccccg gctcagggcc  2400
aagaacagat ggtccccaga tgcggtcccg ccctcagcag tttctagcga accatcagat  2460
gtttccaggg tgccccaagg acctgaaatg accctgtgcc ttatttgaac taaccaatca  2520
gtttgcttct tgcttctgtt tgtgtgcttc tgctccctga gctcaataaa agagcccaca  2580
acccctcact tggtgggcca gtcctctgat agactgtgtc ccctggatac ccgtacggta  2640
ccgctagcgc caccatgggc accagcctcc tctgctggat ggccctgtgt ctcctggggg  2700
cagatcacgc agatactgga gtctcccagg accccagaca caagatcaca aagaggggac  2760
agaatgttac tttcaggtgt gatccaattt ctgaacacaa ccgcctttat tggtaccgcc  2820
agaccctggg gcagggccca gagtttctga cttacttcca gaatgaagct caacttgaaa  2880
aatcaaggct gctcagtgat cggttctctg cagagaggcc taagggatct ttctccacct  2940
tggagatcca gcgcacagag caggggggact ctgccatgta tctctgtgcc agcagccgca  3000
ctgctggaga tactcagtat tttggcccag gcacccggct gacagtgctc gaagatctga  3060
acaaggtgtt ccctccagag gtggccgtgt tcgagccttc taaggccgag atcgcccaca  3120
cacaaaaagc caccctcgtg tgcctggcca ccggcttttt ccccgaccac gtggaactgt  3180
cttggtgggt caacggcaaa gaggtgcact ccggcgtgtc aacggatccc cagcctctga  3240
aagaacagcc tgccctgaac gacagccggt actgcctgag ctccagactg agagtgtccg  3300
ccaccttctg gcagaacccc cggaaccact tcagatgcca ggtgcagttt tacggcctga  3360
gcgagaacga cgagtggacc caggacagag ccaagcccgt gacacaaatc gtgtctgccg  3420
aagcctgggg aagagccgat tgcggcatca ccagcgcctc ctatcaccag ggcgtgctga  3480
gcgccacaat cctgtacgaa atcctgctgg gcaaggccac cctgtacgcc gtgctggtgt  3540
ctgctctggt gctgatggcc atggtcaagc ggaaggactt tggcagcggc agagccaaaa  3600
ggtccgggag cggtgcgaca aactttagcc tgttgaaaca agccggcgac gttgaagaga  3660
accccggacc tatggaaacc ctcttgggcc tgcttatcct ttggctgcag ctgcaatggg  3720
tgagcagcaa acaggaggtg actcagattc ctgcagctct gagtgtccca gaaggagaaa  3780
acttggttct caactgcagt ttcactgata gcgctattta caacctccag tggtttaggc  3840
aggaccctgg gaaaggcctc acatctctgt tgcttattca gtcaagtcag agagagcaaa  3900
caagtggacg ccttaatgcc tctctggata aatcatcagg acgcagtact ctttacattg  3960
cagcttctca gcctggtgat tcagccacct acctgtgcgc tgtgaggggt ggtacctcag  4020
gaacctacaa atacatcttt ggaacaggca ccaggctgaa ggttcttgca aacatccaga  4080
accccgaccc cgccgtgtac cagctgaggg actccaagtc cagcgacaag agcgtgtgtc  4140
tgtttacgga cttcgacagc cagaccaacg tgagtcaaag caaggacagc gacgtctaca  4200
taacggataa gaccgtgctg gacatgcgga gcatggactt caagagcaac agcgccgtgg  4260
cctggtccaa caagagcgac ttcgcctgcg ccaacgcctt caacaacagc atcatccccg  4320
aggacacctt cttccccagc agcgacgtgc cctgcgacgt gaaactggtg gagaagtcct  4380
tcgagacaga caccaatctg aactttcaga acctgctggt gatcgtgctg cggattctgc  4440
tgctgaaagt ggccggcttc aatctgctga tgaccctgcg gctgtggagc agcagggcta  4500
agaggtccgg cagcggagcc accaattttt ccctgctgaa acaggctggt gacgtggaag  4560
aaaaccctgg ccccatggcg ctgcccgtca ccgcgctgct gctgcccctg gcgctgctgt  4620
tacacgccgc tcggccagag cttcccaccc agggcacatt ctccaacgtg tccaccaatg  4680
tgtcgggagg cggcggatcg tcccagttca gagtgtcccc tctggaccgc acctggaacc  4740
```

-continued

```
tgggcgagac cgtggagctg aaatgtcagg tcctgctgag caacccgacc tccgggtgca  4800
gttggctgtt ccagccgcgt ggtgctgccg caagccctac gttcctgctt tacctgagcc  4860
agaacaagcc caaggcggcc gagggcctgg acacccagag attctccggc aagcgcctgg  4920
gggacacatt cgtgcttact ttgagcgatt tccgcagaga gaacgagggc tactatttct  4980
gttcggcgct gagcaattcc atcatgtatt tcagccactt tgtgccagtg ttcctgcctg  5040
ccaagcctac cacaacacca gctccccgtc ccccgactcc ggcgcctacc atcgcgagtc  5100
aaccgttgag cctgaggcct gaggcttgtc ggcccgctgc ggggggtgcc gtccacacca  5160
ggggcctcga ctttgcgtgc gacatctata tttgggcgcc tctggcgggt acctgcgggg  5220
tgctgctgct gtcattggtg attaccctgt actgcaatca ccgcaaccgc cggcgggtct  5280
gtaagtgccc acggcctgtg gtcaagtccg gtgacaaacc gtcgctctcg gctcgctacg  5340
tgcgcgctaa gcgcagcggt tccggggcca ccaacttttc attgctgaag caggccggtg  5400
atgtggagga gaatccaggg cccatgcgcc ccaggcttgg gctccttctt gctgctcagc  5460
tcactgtctt gcatggcaac tccgttctgc agcagactcc cgcctacatc aaggtgcaga  5520
cgaacaagat ggtgatgctg tcatgcgagg ccaagatctc tctttcaaat atgagaattt  5580
attggctacg acagcgccag gccccctcca gcgacagcca ccacgagttc ctggcgcttt  5640
gggattctgc taaaggcacc atccatggag aggaggtgga acaggagaag atagctgtct  5700
tccgcgacgc atcccgcttc atcctgaacc tgaccagcgt gaagccggag gacagcggca  5760
tctacttctg tatgatcgtt ggctccccccg agctgacctt cggcaaaggc acccagctgt  5820
ccgtggtgga cttcctgccc accacagccc agccaaccaa gaaatccacc ctcaagaagc  5880
gcgtgtgccg actgccccgc cctgaaaccc agaagggccc tctgtgctcc cccatcaccc  5940
ttggactgct ggtggcggga gtcctggtgc tgctcgtatc tctgggtgtc gccatccacc  6000
tgtgctgccg ccgccgccgc gcccgcctga ggtttatgaa acagttttac aagtgataaa  6060
tcgatagatc ctaatcaacc tctggattac aaaatttgtg aaagattgac tggtattctt  6120
aactatgttg ctccttttac gctatgtgga tacgctgctt taatgccttt gtatcatgct  6180
attgcttccc gtatggcttt cattttctcc tccttgtata aatcctggtt gctgtctctt  6240
tatgaggagt tgtggcccgt tgtcaggcaa cgtggcgtgg tgtgcactgt gtttgctgac  6300
gcaaccccca ctggttgggg cattgccacc acctgtcagc tcctttccgg gactttcgct  6360
ttccccctcc ctattgccac ggcggaactc atcgccgcct gccttgcccg ctgctggaca  6420
ggggctcggc tgttgggcac tgacaattcc gtggtgttgt cggggaaatc atcgtccttt  6480
ccttggctgc tcgcctgtgt tgccacctgg attctgcgcg ggacgtcctt ctgctacgtc  6540
ccttcggccc tcaatccagc ggaccttcct tcccgcggcc tgctgccggc tctgcggcct  6600
cttccgcgtc ttcgccttcg ccctcagacg agtcggatct ccctttgggc cgcctccccg  6660
cctgagatcc tttaagacca atgacttaca aggcagctgt agatcttagc cactttttaa  6720
aagaaaaggg gggactggaa gggctaattc actcccaacg aagacaagat ctgctttttg  6780
cttgtactgg gtctctctgg ttagaccaga tctgagcctg ggagctctct ggctaactag  6840
ggaacccact gcttaagcct caataaagct tgccttgagt gcttcaagta gtgtgtgccc  6900
gtctgttgtg tgactctggt aactagagat ccctcagacc cttttagtca gtgtggaaaa  6960
tctctagcag tagtagttca tgtcatctta ttattcagta tttataactt gcaaagaaat  7020
gaatatcaga gagtgagagg cccgggttaa ttaaggaaag ggctagatca ttcttgaaga  7080
cgaaagggcc tcgtgatacg cctattttta taggttaatg tcatgataat aatggtttct  7140
tagacgtcag gtggcacttt tcggggaaat gtgcgcggaa cccctatttg tttatttttc  7200
taaatacatt caaatatgta tccgctcatg agacaataac cctgataaat gcttcaataa  7260
tattgaaaaa ggaagagtat gagtattcaa catttccgtg tcgcccttat tccctttttt  7320
gcggcatttt gccttcctgt ttttgctcac ccagaaacgc tggtgaaagt aaaagatgct  7380
gaagatcagt tgggtgcacg agtgggttac atcgaactgg atctcaacag cggtaagatc  7440
cttgagagtt ttcgccccga agaacgtttt ccaatgatga gcacttttaa agttctgcta  7500
tgtggcgcgg tattatcccg tgttgacgcc gggcaagagc aactcggtcg ccgcatacac  7560
tattctcaga atgacttggt tgagtactca ccagtcacag aaaagcatct tacggatggc  7620
atgacagtaa gagaattatg cagtgctgcc ataaccatga gtgataacac tgcggccaac  7680
ttacttctga caacgatcgg aggaccgaag gagctaaccg cttttttgca caacatgggg  7740
gatcatgtaa ctcgccttga tcgttgggaa ccggagctga atgaagccat accaaacgac  7800
gagcgtgaca ccacgatgcc tgtagcaatg gcaacaacgt tgcgcaaact attaactggc  7860
gaactactta ctctagcttc ccggcaacaa ttaatagact ggatggaggc ggataaagtt  7920
gcaggaccac ttctgcgctc ggcccttccg gctggctggt ttattgctga taaatctgga  7980
gccggtgagc gtgggtctcg cggtatcatt gcagcactgg ggccagatgg taagccctcc  8040
cgtatcgtag ttatctacac gacggggagt caggcaacta tggatgaacg aaatagacag  8100
atcgctgaga taggtgcctc actgattaag cattggtaac tgtcagacca agtttactca  8160
tatatacttt agattgattt aaaacttcat ttttaattta aaaggatcta ggtgaagatc  8220
ctttttgata atctcatgac caaaatccct taacgtgagt tttcgttcca ctgagcgtca  8280
gaccccgtag aaaagatcaa aggatcttct tgagatcctt tttttctgcg cgtaatctgc  8340
tgcttgcaaa caaaaaaacc accgctacca gcggtggttt gtttgccgga tcaagagcta  8400
ccaactcttt ttccgaaggt aactggcttc agcagagcgc agataccaaa tactgttctt  8460
ctagtgtagc cgtagttagg ccaccacttc aagaactctg tagcaccgcc tacatacctc  8520
gctctgctaa tcctgttacc agtggctgct gccagtggcg ataagtcgtg tcttaccggg  8580
ttggactcaa gacgatagtt accggataag gcgcagcggt cgggctgaac ggggggttcg  8640
tgcacacagc ccagcttgga gcgaacgacc tacaccgaac tgagatacct acagcgtgag  8700
ctatgagaaa gcgccacgct tcccgaaggg agaaaggcgg acaggtatcc ggtaagcggc  8760
agggtcggaa caggagagcg cacgagggag cttccagggg gaaacgcctg gtatctttat  8820
agtcctgtcg ggtttcgcca cctctgactt gagcgtcgat ttttgtgatg ctcgtcaggg  8880
gggcggagcc tatggaaaaa cgccagcaac gcggcctttt tacggttcct ggccttttgc  8940
tggccttttg ctcacatgtt ctttcctgcg ttatcccctg attctgtgga taaccgtatt  9000
accgcctttg agtgagctga taccgctcgc cgcagccgaa cgaccgagcg cagcgagtca  9060
gtgagcgagg aagcggaaga gcgcccaata cgcaaaccgc ctctccccgc gcgttggccg  9120
attcattaat gcagcaagct catggctgac taattttttt tatttatgca gaggccgagg  9180
ccgcctcggc ctctgagcta ttccagaagt agtgaggagg cttttttgga ggcctaggct  9240
tttgcaaaaa gctccccgtg gcacgacagg tttcccgact ggaaagcggg cagtgagcgc  9300
aacgcaatta atgtgagtta gctcactcat taggcacccc aggctttaca ctttatgctt  9360
ccggctcgta tgttgtgtgg aattgtgagc ggataacaat ttcacacagg aaacagctat  9420
gacatgatta cgaatttcac aaataaagca tttttttcac tgcattctag ttgtggtttg  9480
```

```
tccaaactca tcaatgtatc ttatcatgtc tggatcaact ggataactca agctaaccaa  9540
aatcatccca aacttcccac cccataccct attaccactg ccaattacct gtggtttcat  9600
ttactctaaa cctgtgattc ctctgaatta ttttcatttt aaagaaattg tatttgttaa  9660
atatgtacta caaacttagt agt                                          9683

SEQ ID NO: 51          moltype = DNA  length = 8789
FEATURE                Location/Qualifiers
source                 1..8789
                       mol_type = other DNA
                       organism = synthetic construct
SEQUENCE: 51
tggaagggct aattcactcc caaagaagac aagatatcct tgatctgtgg atctaccaca  60
cacaaggcta cttccctgat tagcagaact acacaccagg gccaggggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agaccctttt agtcagtgtg gaaaatctct agcagtggcg cccgaacagg gacttgaaag  660
cgaaagggaa accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca gggggaaaga aaaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag tttttgctgt  1860
actttctata gtgaatagag ttaggcaggg atattcacca ttatcgtttc agacccacct  1920
cccaaccccg aggggacccg acaggcccga aggaatagaa gaagaaggtg gagagagaga  1980
cagagacaga tccattcgat tagtgaacgg atctcgacgg tatcgccgaa ttaattcaca  2040
aatggcagta ttcatccaca attttaaaag aaaagggggg attggggggt acagtgcagg  2100
ggaaagaata gtagacataa tagcaacaga catacaaact aaagaattac aaaaacaaat  2160
tacaaaaatt caaaattttc gggtttatta caggcgcgcc agagatccag tttggacctg  2220
caggtgaaag accccacctg taggtttggc aagttagctt aagtaacgcc attttgcaag  2280
gcatggaaaa tacataactg agaatagaga agttcagatc aaggttagga acagagagac  2340
agcagaatat gggccaaaca ggatatctgt ggtaagcagt tcctgccccg gctcagggcc  2400
aagaacagat ggtccccaga tgcggtcccg ccctcagcag tttctagcga accatcagat  2460
gtttccaggg tgccccaagg acctgaaatg accctgtgcc ttatttgaac taaccaatca  2520
gtttgcttct tgcttctgtt tgtgtgcttc tgctccctga gctcaataaa agagcccaca  2580
acccctcact tggtgggcca gtcctctgat agactgtgtc ccctggatac ccgtacggta  2640
ccgctagcgc caccatgggc tcctggaccc tctgctgtgt gtccctttgc atcctggttg  2700
caaagcacac agatgctgga gttatccagt caccccggca cgaggtgaca gagatgggac  2760
aagaagtgac tctgagatgt aaaccaattt caggacatga ctaccttttc tggtacagac  2820
agaccatgat gcggggactg gagttgctca tttactttaa caacaacgtt cctattgatg  2880
attcagggat gcccgaggat cgcttctcag ctaagatgcc taatgcatca ttctccactc  2940
tgaagatcca gccctcagaa cccagggact cagctgtgta cttctgtgcc agcagttttc  3000
tcggctggaa tgaaaaactg ttctttggca gtggaaccca gctctctgtc ttggaagatc  3060
tgaacaaggt gttccctcca gaggtggccg tgttcgagcc ttctaaggcc gagatcgccc  3120
acacacaaaa agccaccctc gtgtgcctgg ccaccggctt tttccccgac cacgtggaac  3180
tgtcttggtg ggtcaacggc aaagaggtgc actccggcgt gtcaacggat ccccagcctc  3240
tgaaagaaca gcctgccctg aacgacagcc ggtactgcct gagctccaga ctgagagtgt  3300
ccgccacctt ctggcagaac ccccggaacc acttcagatg ccaggtgcag ttttacggcc  3360
tgagcgagaa cgacgagtgg acccaggaca gagccaagcc cgtgacacaa atcgtgtctg  3420
ccgaagcctg gggaagagcc gattgcggca tcaccagcgc ctcctatcac cagggcgtgc  3480
tgagcgccac aatcctgtac gaaatcctgc tgggcaaggc caccctgtac gccgtgctgg  3540
tgtctgctct ggtgctgatg gccatggtca agcggaagga ctttggcagc ggcagagcca  3600
aaaggtccgg gagcggtgcg acaaacttta gcctgttgaa acaagccggc gacgttgaag  3660
agaaccccgg acctatggtc ctgaaattct ccgtgtccat tctttggatt cagttggcat  3720
gggtgagcac ccagctgctg gagcagagcc ctcagtttct tagcatccaa gagggagaaa  3780
atctcactgt gtactgcaac tcctcaagtg ttttctccag ccttcaatgg tacagacagg  3840
agcctgggga aggtcctgtc ctcctggtga cagttgttac tggtggagaa gtgaagaagc  3900
tgaagagact tacctttcag tttggtgatg caagaaagga cagttctctc cacatcactg  3960
cagcccagcc tggtgataca ggcctctacc tctgtgcagg agatgaaagt attagctatg  4020
gaaagctgac atttggacaa gggaccatct tgactgtcca tccaaacatc cagaaccccg  4080
```

-continued accccgccgt gtaccagctg agggactcca agtccagcga caagagcgtg tgtctgttta 4140
cggacttcga cagccagacc aacgtgagtc aaagcaagga cagcgacgtc tacataacgg 4200
ataagaccgt gctggacatg cggagcatgg acttcaagag caacagcgcc gtggcctggt 4260
ccaacaagag cgacttcgcc tgcgccaacg ccttcaacaa cagcatcatc cccgaggaca 4320
ccttcttccc cagcagcgac gtgccctgcg acgtgaaact ggtggagaag tccttcgaga 4380
cagacaccaa tctgaacttt cagaacctgc tggtgatcgt gctgcggatt ctgctgctga 4440
aagtggccgg cttcaatctg ctgatgaccc tgcggctgtg gagcagcagg gctaagaggt 4500
ccggcagcgg agccaccaat ttttccctgc tgaaacaggc tggtgacgtg gaagaaaacc 4560
ctggccccat gggtcggggg ctgctcaggg gcctgtggcc gctgcacatc gtcctgtgga 4620
cgcgtatcgc cagcacgatc ccaccgcacg ttcagaagtc ggttaataac gacatgatag 4680
tcactgacaa caacggtgca gtcaagtttc cacaactgtg taaattttgt gatgtgagat 4740
tttccacctg tgacaaccag aaatcctgca tgagcaactg cagcatcacc tccatctgtg 4800
agaagccaca ggaagtctgt gtggctgtat ggagaaagaa tgacgagaac ataacactag 4860
agacagtttg ccatgacccc aagctcccct accatgactt tattctggaa gatgctgctt 4920
ctccaaagtg cattatgaag gaaaaaaaaa agcctggtga gactttcttc atgtgttcct 4980
gtagctctga tgagtgcaat gacaacatca tcttctcaga agaatataac accagcaatc 5040
ctgacttgtt gctagtcata tttcaagtga caggcatcag cctcctgcca ccactgggag 5100
ttgccatatc tgtcatcatc atcttctact gctaccgcgt taaccggcag cagaagtagt 5160
gataaatcga tagatcctaa tcaacctctg gattacaaaa tttgtgaaag attgactggt 5220
attcttaact atgttgctcc ttttacgcta tgtggatacg ctgctttaat gcctttgtat 5280
catgctattg cttcccgtat ggctttcatt ttctcctcct tgtataaatc ctggttgctg 5340
tctctttatg aggagttgtg gcccgttgtc aggcaacgtg gcgtggtgtg cactgtgttt 5400
gctgacgcaa cccccactgg ttggggcatt gccaccacct gtcagctcct ttccgggact 5460
ttcgctttcc ccctccctat tgccacggcg gaactcatcg ccgcctgcct tgcccgctgc 5520
tggacagggg ctcggctgtt gggcactgac aattccgtgg tgttgtcggg gaaatcatcg 5580
tcctttcctt ggctgctcgc ctgtgttgcc acctggattc tgcgcgggac gtccttctgc 5640
tacgtccctt cggccctcaa tccagcggac cttccttccc gcggcctgct gccggctctg 5700
cggcctcttc cgcgtcttcg ccttcgccct cagacgagtc ggatctccct ttgggccgcc 5760
tccccgcctg agatccttta agaccaatga cttacaaggc agctgtagat cttagccact 5820
ttttaaaaga aaaggggga ctggaagggc taattcactc ccaacgaaga caagatctgc 5880
tttttgcttg tactgggtct ctctggttag accagatctg agcctgggag ctctctggct 5940
aactagggaa cccactgctt aagcctcaat aaagcttgcc ttgagtgctt caagtagtgt 6000
gtgcccgtct gttgtgtgac tctggtaact agagatccct cagacccttt tagtcagtgt 6060
ggaaaatctc tagcagtagt agttcatgtc atcttattat tcagtattta taacttgcaa 6120
agaaatgaat atcagagagt gagaggcccg ggttaattaa ggaaagggct agatcattct 6180
tgaagacgaa agggcctcgt gatacgccta tttttatagg ttaatgtcat gataataatg 6240
gtttcttaga cgtcaggtgg cacttttcgg ggaaatgtgc gcggaacccc tatttgttta 6300
tttttctaaa tacattcaaa tatgtatccg ctcatgagac aataaccctg ataaatgctt 6360
caataatatt gaaaaaggaa gagtatgagt attcaacatt tccgtgtcgc ccttattccc 6420
ttttttgcgg cattttgcct tcctgttttt gctcacccag aaacgctggt gaaagtaaaa 6480
gatgctgaag atcagttggg tgcacgagtg ggttacatcg aactggatct caacagcggt 6540
aagatccttg agagttttcg ccccgaagaa cgttttccaa tgatgagcac ttttaaagtt 6600
ctgctatgtg gcgcggtatt atcccgtgtt gacgccgggc aagagcaact cggtcgccgc 6660
atacactatt ctcagaatga cttggttgag tactcaccag tcacagaaaa gcatcttacg 6720
gatggcatga cagtaagaga attatgcagt gctgccataa ccatgagtga taacactgcg 6780
gccaacttac ttctgacaac gatcggagga ccgaaggagc taaccgcttt tttgcacaac 6840
atgggggatc atgtaactcg ccttgatcgt tgggaaccgg agctgaatga agccatacca 6900
aacgacgagc gtgacaccac gatgcctgta gcaatggcaa caacgttgcg caaactatta 6960
actggcgaac tacttactct agcttcccgg caacaattaa tagactggat ggaggcggat 7020
aaagttgcag gaccacttct gcgctcggcc cttccggctg gctggtttat tgctgataaa 7080
tctggagccg gtgagcgtgg gtctcgcggt atcattgcag cactggggcc agatggtaag 7140
ccctcccgta tcgtagttat ctacacgacg gggagtcagg caactatgga tgaacgaaat 7200
agacagatcg ctgagatagg tgcctcactg attaagcatt ggtaactgtc agaccaagtt 7260
tactcatata tactttagat tgatttaaaa cttcattttt aatttaaaag gatctaggtg 7320
aagatccttt ttgataatct catgaccaaa atcccttaac gtgagttttc gttccactga 7380
gcgtcagacc ccgtagaaaa gatcaaagga tcttcttgag atcctttttt tctgcgcgta 7440
atctgctgct tgcaaacaaa aaaaccaccg ctaccagcgg tggtttgttt gccggatcaa 7500
gagctaccaa ctctttttcc gaaggtaact ggcttcagca gagcgcagat accaaatact 7560
gttcttctag tgtagccgta gttaggccac cacttcaaga actctgtagc accgcctaca 7620
tacctcgctc tgctaatcct gttaccagtg gctgctgcca gtggcgataa gtcgtgtctt 7680
accgggttgg actcaagacg atagttaccg gataaggcgc agcggtcggg ctgaacgggg 7740
ggttcgtgca cacagcccag cttggagcga acgacctaca ccgaactgag atacctacag 7800
cgtgagctat gagaaagcgc cacgcttccc gaagggagaa aggcggacag gtatccggta 7860
agcggcaggg tcggaacagg agagcgcacg agggagcttc caggggggaaa cgcctggtat 7920
ctttatagtc ctgtcgggtt tcgccacctc tgacttgagc gtcgattttt gtgatgctcg 7980
tcaggggggc ggagcctatg gaaaaacgcc agcaacgcgg cctttttacg gttcctggcc 8040
ttttgctggc cttttgctca catgttcttt cctgcgttat cccctgattc tgtggataac 8100
cgtattaccg cctttgagtg agctgatacc gctcgccgca gccgaacgac cgagcgcagc 8160
gagtcagtga gcgaggaagc ggaagagcgc ccaatacgca aaccgcctct ccccgcgcgt 8220
tggccgattc attaatgcag caagctcatg gctgactaat tttttttatt tatgcagagg 8280
ccgaggccgc ctcggcctct gagctattcc agaagtagtg aggaggcttt tttggaggcc 8340
taggcttttg caaaaagctc cccgtggcac gacaggtttc ccgactggaa agcgggcagt 8400
gagcgcaacg caattaatgt gagttagctc actcattagg caccccaggc tttacacttt 8460
atgcttccgg ctcgtatgtt gtgtggaatt gtgagcggat aacaatttca cacaggaaac 8520
agctatgaca tgattacgaa tttcacaaat aaagcatttt tttcactgca ttctagttgt 8580
ggtttgtcca aactcatcaa tgtatcttat catgtctgga tcaactggat aactcaagct 8640
aaccaaaatc atcccaaact tcccacccca taccctatta ccactgccaa ttacctgtgg 8700
tttcatttac tctaaacctg tgattcctct gaattatttt cattttaaag aaattgtatt 8760
tgttaaatat gtactacaaa cttagtagt 8789

```
SEQ ID NO: 52          moltype = DNA  length = 8058
FEATURE                Location/Qualifiers
source                 1..8058
                       mol_type = other DNA
                       organism = synthetic construct
SEQUENCE: 52
gaattcgtcg acgctagctg gcttgttgtc cacaaccatt aaaccttaaa agctttaaaa  60
gccttatata ttcttttttt tcttataaaa cttaaaacct tagaggctat ttaagttgct  120
gatttatatt aattttattg ttcaaacatg agagcttagt acgtgaaaca tgagagctta  180
gtacattagc catgagagct tagtacatta gccatgaggg tttagttcat taaacatgag  240
agcttagtac attaaacatg agagcttagt acatactatc aacaggttga actgctgatc  300
tgtacagtag aattggtaaa gagagttgtg taaaatattg agttcgcaca tcttgttgtc  360
tgattattga tttttggcga aaccatttga tcatatgaca agatgtgtat ctaccttaac  420
ttaatgattt tgataaaaat cattaggtac caattacatt gcttgcaatt aaccctttaa  480
cggttataag gatctagatg agatagaaag atttggtttt cggatttgtg ttacataaga  540
tgcctaaaat aaaaattgag attcaatttt ttttaaactt ttttttaatt ggtggtaaga  600
atattccctc tacctgtttg agagtaatga aattgtagta tgatttttca acaaactaaa  660
aaaacaacat aaatctcaca taataacttt atttcaatca cacaattgaa taccaatagg  720
ttgacagtac ttaccagcct gcaggtgaaa gaccccacct gtaggtttgg caagttagct  780
taagtaacgc cattttgcaa ggcatggaaa atacataact gagaatagag aagttcagat  840
caaggttagg aacagagaga cagcagaata tgggccaaac aggatatctg tggtaagcag  900
ttcctgcccc ggctcagggc caagaacaga tggtccccag atgcggtccc gccctcagca  960
gtttctagcg aaccatcaga tgtttccagg gtgccccaag gacctgaaat gaccctgtgc  1020
cttatttgaa ctaaccaatc agtttgcttc ttgcttctgt ttgtgtgctt ctgctccctg  1080
agctcaataa aagagcccac aacccctcac ttggtgggcc agtcctctga tagactgtgt  1140
cccctggata cccgtacggt accgctagcg ccaccatggg ctcctggacc ctctgctgtg  1200
tgtccctttg catcctggtt gcaaagcaca cagatgctgg agttatccag tcaccccggc  1260
acgaggtgac agagatggga caagaagtga ctctgagatg taaaccaatt tcaggacatg  1320
actacctttt ctggtacaga cagaccatga tgcggggact ggagttgctc atttacttca  1380
acaacaacgt tcctattgat gattcaggga tgcccgagga tcgcttctca gctaagatgc  1440
ctaatgcatc attctccact ctgaagatcc agccctcaga acccagggac tcagctgtgt  1500
acttctgtgc cagcagtttt ctcggctgga atgaaaaact gttctttggc agtggaaccc  1560
agctctctgt cttggaagat ctgaacaagg tgttccctcc agaggtggcc gtgttcgagc  1620
cttctaaggc cgagatcgcc cacacacaaa aagccaccct cgtgtgcctg gccaccggct  1680
tttccccga ccacgtggaa ctgtcttggt gggtcaacgg caaagaggtg cactccggcg  1740
tgtcaacgga tccccagcct ctgaaagaac agcctgccct gaacgacagc cggtactgcc  1800
tgagctccag actgagagtg tccgccacct tctggcagaa cccccggaac cacttcagat  1860
gccaggtgca gttttacggc ctgagcgaga acgacgagtg gacccaggac agagccaagc  1920
ccgtgacaca aatcgtgtct gccgaagcct ggggaagagc cgattgcggc atcaccagcg  1980
cctcctatca ccagggcgtg ctgagcgcca caatcctgta cgaaatcctg ctgggcaagg  2040
ccaccctgta cgccgtgctg gtgtctgctc tggtgctgat ggccatggtc aagcggaagg  2100
actttggcag cggcagagcc aaaaggtccg ggagcggtgc gacaaacttt agcctgttga  2160
aacaagccgg cgacgttgaa gagaaccccg gacctatggt cctgaaattc tccgtgtcca  2220
ttctttggat tcagttggca tgggtgagca cccagctgct ggagcagagc cctcagtttc  2280
ttagcatcca agagggagaa aatctcactg tgtactgcaa ctcctcaagt gttttctcca  2340
gccttcaatg gtacagacag gagcctgggg aaggtcctgt cctcctggtg acagttgtta  2400
ctggtggaga agtgaagaag ctgaagagac ttacctttca gtttggtgat gcaagaaagg  2460
acagttctct ccacatcact gcagcccagc ctggtgatac aggcctctac ctctgtgcag  2520
gagatgaaag tattagctat ggaaagctga catttggaca agggaccatc ttgactgtcc  2580
atccaaacat ccagaacccc gaccccgccg tgtaccagct gagggactcc aagtccagcg  2640
acaagagcgt gtgtctgttt acggacttcg acagccagac caacgtgagt caaagcaagg  2700
acagcgacgt ctacataacg gataagaccg tgctggacat gcggagcatg gacttcaaga  2760
gcaacagcgc cgtggcctgg tccaacaaga gcgacttcgc ctgcgccaac gccttcaaca  2820
acagcatcat ccccgaggac accttcttcc ccagcagcga cgtgccctgc gacgtgaaac  2880
tggtggagaa gtccttcgag acagacacca atctgaactt tcagaacctg ctggtgatcg  2940
tgctgcggat tctgctgctg aaagtggccg gcttcaatct gctgatgacc ctgcggctgt  3000
ggagcagcag ggctaagagg tccggcagcg gagccaccaa tttttccctg ctgaaacagg  3060
ctggtgacgt ggaagaaaac cctggcccca tggcgctgcc cgtcaccgcg ctgctgctgc  3120
ccctggcgct gctgttacac gccgctcggc cagagcttcc cacccagggc acattctcca  3180
acgtgtccac caatgtgtcg ggaggcggcg gatcgtccca gttcagagtg tcccctctgg  3240
accgcacctg gaacctgggc gagaccgtgg agctgaaatg tcaggtcctg ctgagcaacc  3300
cgacctccgg gtgcagttgg ctgttccagc cgcgtggtgc tgccgcaagc cctacgttcc  3360
tgctttacct gagccagaac aagcccaagg cggccgaggg cctggacacc cagagattct  3420
ccggcaagcg cctgggggac acattcgtgc ttactttgag cgatttccgc agagagaacg  3480
agggctacta tttctgttcg gcgctgagca attccatcat gtatttcagc cactttgtgc  3540
cagtgttcct gcctgccaag cctaccacaa caccagctcc ccgtccccg actccggcgc  3600
ctaccatcgc gagtcaaccg ttgagcctga ggcctgaggc ttgtcggccc gctgcggggg  3660
gtgccgtcca caccaggggc ctcgactttg cgtgcgacat ctatatttgg gcgcctctgg  3720
cgggtacctg cggggtgctg ctgctgtcat tggtgattac cctgtactgc aatcaccgca  3780
accgccggcg ggtctgtaag tgcccacggc ctgtggtcaa gtccggtgac aaaccgtcgc  3840
tctcggctcg ctacgtgcgc gctaagcgca gcggttccgg ggccaccaac ttttcattgc  3900
tgaagcaggc cggtgatgtg gaggagaatc cagggcccat gcgccccagg ctttggctcc  3960
ttcttgctgc tcagctcact gtcttgcatg gcaactccgt tctgcagcag actcccgcct  4020
acatcaaggt gcagacgaac aagatggtga tgctgtcatg cgaggccaag atctctcttt  4080
caaatatgag aatttattgg ctacgacagc gccaggcccc ctccagcgac agccaccacg  4140
agttcctggc gctttgggat tctgctaaag gcaccatcca tggagaggag gtggaacagg  4200
agaagatagc tgtcttccgc gacgcatccc gcttcatcct gaacctgacc agcgtgaagc  4260
cggaggacag cggcatctac ttctgtatga tcgttggctc cccgagctg accttcggca  4320
```

```
aaggcaccca gctgtccgtg gtggacttcc tgcccaccac agcccagcca accaagaaat  4380
ccaccctcaa gaagcgcgtg tgccgactgc cccgccctga aacccagaag ggccctctgt  4440
gctcccccat caccccttgga ctgctggtgg cgggagtcct ggtgctgctc gtatctctgg  4500
gtgtcgccat ccacctgtgc tgccgccgcc gccgcgcccg cctgaggttt atgaaacagt  4560
tttacaagtg ataaatcgat ggaagggtgg catccctgtg acccctcccc agtgcctctc  4620
ctggccctgg aagttgccac tccagtgccc accagccttg tcctaataaa attaagttgc  4680
atcattttgt ctgactaggt gtccttctat aatattatgg ggtggagggg ggtggtatgg  4740
agcaaggggc aagttgggaa gacaacctgt agggcctgcg gggtctattg ggaaccaagc  4800
tggagtgcag tggcacaatc ttggctcact gcaatctccg cctcctgggt tcaagcgatt  4860
ctcctgcctc agcctcccga gttgttggga ttccaggcat gcatgaccag gctcagctaa  4920
tttttgtttt tttggtagag acggggtttc accatattgg ccaggctggt ctccaactcc  4980
taatctcagg tgatctaccc accttggcct cccaaattgc tgggattaca ggcgtgaacc  5040
actgctccct tccctgtcct tctgattact agtggctccg gtgcccgtca gtgggcagag  5100
cgcacatcgc ccacagtccc cgagaagttg tggggagggg tcggcaattg aaccggtgcc  5160
tagagaaggt ggcgcggggt aaactgggaa agtgatgtcg tgtactggct ccgccttttt  5220
cccgagggtg ggggagaacc gtatataagt gcagtagtcg ccgtgaacgt tctttttcgc  5280
aacgggtttg ccgccagaac acaggtaagt gccgtgtgtg gttcccgcgg gcctggcctc  5340
tttacgggtt atggcccttg cgtgccttga attacttcca cctggctgca gtacgtgatt  5400
cttgatcccg agcttcgggt tggaagtggg tgggagagtt cgaggccttg cgcttaagga  5460
gccccttcgc ctcgtgcttg agttgaggcc tggcctgggc gctggggccg ccgcgtgcga  5520
atctggtggc accttcgcgc ctgtctcgct gctttcgata agtctctagc catttaaaat  5580
ttttgatgac ctgctgcgac gcttttttc tggcaagata gtcttgtaaa tgcgggccaa  5640
gatctgcaca ctggtatttc ggtttttggg gccgcgggcg gcgacggggc ccgtgcgtcc  5700
cagcgcacat gttcggcgag gcggggcctg cgagcgcggc caccgagaat cggacggggg  5760
tagtctcaag ctggccggcc tgctctggtg cctggcctcg cgccgccgtg tatcgccccg  5820
ccctgggcgg caaggctggc ccggtcggca ccagttgcgt gagcggaaag atggccgctt  5880
cccggccctg ctgcagggag ctcaaaatgg aggacgcggc gctcgggaga gcgggcgggt  5940
gagtcaccca cacaaaggaa aagggccttt ccgtcctcag ccgtcgcttc atgtgactcc  6000
acggagtacc gggcgccgtc caggcacctc gattagttct cgagcttttg gagtacgtcg  6060
tctttaggtt ggggggaggg gttttatgcg atggagtttc cccacactga gtgggtggag  6120
actgaagtta ggccagcttg gcacttgatg taattctcct tggaatttgc cctttttgag  6180
tttggatctt ggttcattct caagcctcag acagtggttc aaagtttttt tcttccattt  6240
caggtgtcgt gaactagtcc agtgtggtgg aattctgcag atatcacggc tagcgccacc  6300
atgggtcggg ggctgctcag ggcctgtggg ccgctgcaca tcgtcctgtg gacgcgtatc  6360
gccagcacga tcccaccgca cgttcagaag tcggtgaata acgacatgat agtcactgac  6420
aacaacggtg cagtcaagtt tccacaactg tgtaaatttt gtgatgtgag attttccacc  6480
tgtgacaacc agaaatcctg catgagcaac tgcagcatca cctccatctg tgagaagcca  6540
caggaagtct gtgtggctgt atggagaaag aatgacgaga acataacact agagacagtt  6600
tgccatgacc ccaagctccc ctaccatgac tttattctgg aagatgctgc ttctccaaag  6660
tgcattatga aggagaagaa aaagcctggt gagactttct tcatgtgttc ctgtagctct  6720
gatgagtgca atgacaacat catcttctca gaagaatata acaccagcaa tcctgacttg  6780
ttgctagtca tatttcaagt gacaggcatc agcctcctgc caccactggg agttgccata  6840
tctgtcatca tcatcttcta ctgctaccgc gtgaaccggc agcagaaggc tagtggttca  6900
ggcgcaacga atttctcttt gctgaagcag gctggggatg tcgaagaaaa tccgggtcca  6960
atggtgggct cgctcaactg catcgtagca gtctcccaga atatgggcat cgggaagaac  7020
ggtgatttcc cgtggccccc acttcgcaac gagagccgtt atttccaaag aatgactaca  7080
acctcctccg tggagggtaa gcagaacctg gtcatcatgg ggaagaagac ctggttctct  7140
atccctgaaa aaaaccgccc cctgaagggc cgcatcaacc tggtgctgag cagggaactc  7200
aaggagcctc ctcagggcgc gcattttctg agccgctcat tggatgacgc tctcaaactg  7260
accgaacagc cggagctagc caacaaggtg gacatggtgt ggatcgtcgg aggctcctcc  7320
gtgtacaagg aggccatgaa tcaccccggc cacttgaagc tgttcgtcac ccggatcatg  7380
caggacttcg agtcggacac gttctttcca gagattgacc tggagaagta caagctgctg  7440
cccgagtacc cgggagttct tagtgatgtg caggaggaga aaggcatcaa gtacaaattt  7500
gaggtgtacg agaagaacga ctaacggtcc gtcctgacca atgctggagt tcttcgccca  7560
ccccaacttg tttattgcag cttataatgg ttacaaataa agcaatagca tcacaaattt  7620
cacaaataaa gcattttttt cactgcattc tagttgtggt ttgtccaaac tcatcaatgt  7680
atcttatcat gtctgtatac aggttacctc agtctcctag gtacgtctta tatctatgaa  7740
aaaacattca aaagcacaac atctagaaga acttaccttt tttcaccact ctattgcaaa  7800
gatatgtacc gatttctctc gaagtacaaa aaaccgctag ttttcaaatt cacctcaaga  7860
ctttgaaaaa aaattgaatc tgtcaatgtc aaataaaatc agaaacaaat gtcataatgt  7920
tacgttaatg ttgtcaggtc gaaaaataaa attgcaaata gaaattttgt tcctttttta  7980
ttggttttta ttggtgggaa aaatattccc tctaactgca aaagggttaa ttatgttaga  8040
ggtagagtcg acaagctt                                                8058
```

```
SEQ ID NO: 53          moltype = AA  length = 20
FEATURE                Location/Qualifiers
source                 1..20
                       mol_type = protein
                       organism = synthetic construct
VARIANT                1..10
                       note = This region may encompass 0-10 residues
VARIANT                11..20
                       note = This region may encompass 0-10 residues
SEQUENCE: 53
GGGGGGGGGG SSSSSSSSSS                                          20

SEQ ID NO: 54          moltype = AA  length = 10
FEATURE                Location/Qualifiers
source                 1..10
```

```
                        mol_type = protein
                        organism = synthetic construct
SEQUENCE: 54
GGGGSGGGGS                                                  10

SEQ ID NO: 55           moltype = AA  length = 8
FEATURE                 Location/Qualifiers
source                  1..8
                        mol_type = protein
                        organism = synthetic construct
SEQUENCE: 55
GGGSGGGS                                                    8

SEQ ID NO: 56           moltype = AA  length = 11
FEATURE                 Location/Qualifiers
source                  1..11
                        mol_type = protein
                        organism = synthetic construct
SEQUENCE: 56
GGGSGGGSGG S                                                11

SEQ ID NO: 57           moltype = AA  length = 9
FEATURE                 Location/Qualifiers
source                  1..9
                        mol_type = protein
                        organism = unidentified
SEQUENCE: 57
LAGLIDADG                                                   9

SEQ ID NO: 58           moltype = DNA  length = 20
FEATURE                 Location/Qualifiers
source                  1..20
                        mol_type = other DNA
                        organism = synthetic construct
SEQUENCE: 58
cggctactac aaccagagcg                                       20

SEQ ID NO: 59           moltype = DNA  length = 20
FEATURE                 Location/Qualifiers
source                  1..20
                        mol_type = other DNA
                        organism = synthetic construct
SEQUENCE: 59
agatcacact gacctggcag                                       20

SEQ ID NO: 60           moltype = DNA  length = 20
FEATURE                 Location/Qualifiers
source                  1..20
                        mol_type = other DNA
                        organism = synthetic construct
SEQUENCE: 60
aggtcagtgt gatctccgca                                       20

SEQ ID NO: 61           moltype = DNA  length = 20
FEATURE                 Location/Qualifiers
source                  1..20
                        mol_type = other DNA
                        organism = synthetic construct
SEQUENCE: 61
ggccacggag cgagacatct                                       20

SEQ ID NO: 62           moltype = AA  length = 9
FEATURE                 Location/Qualifiers
source                  1..9
                        mol_type = protein
                        organism = Homo sapiens
SEQUENCE: 62
ALKDVEERV                                                   9

SEQ ID NO: 63           moltype = AA  length = 10
FEATURE                 Location/Qualifiers
source                  1..10
                        mol_type = protein
                        organism = Homo sapiens
SEQUENCE: 63
LLFGLALIEV                                                  10

SEQ ID NO: 64           moltype = AA  length = 9
FEATURE                 Location/Qualifiers
```

```
source                  1..9
                        mol_type = protein
                        organism = Homo sapiens
SEQUENCE: 64
SESIKKKVL                                                          9

SEQ ID NO: 65           moltype = AA  length = 9
FEATURE                 Location/Qualifiers
source                  1..9
                        mol_type = protein
                        organism = Homo sapiens
SEQUENCE: 65
ASSTLYLVF                                                          9

SEQ ID NO: 66           moltype = AA  length = 84
FEATURE                 Location/Qualifiers
source                  1..84
                        mol_type = protein
                        organism = Homo sapiens
SEQUENCE: 66
GREHSAYGEP RKLLTQDLVQ EKYLEYRQVP DSDPARYEFL WGPRALAETS YVKVLEYVIK  60
VSARVRFFFP SLREAALREE EEGV                                         84

SEQ ID NO: 67           moltype = AA  length = 5
FEATURE                 Location/Qualifiers
source                  1..5
                        mol_type = protein
                        organism = Homo sapiens
SEQUENCE: 67
SELSP                                                              5

SEQ ID NO: 68           moltype = AA  length = 62
FEATURE                 Location/Qualifiers
source                  1..62
                        mol_type = protein
                        organism = Homo sapiens
SEQUENCE: 68
YLEYRQVPDS DPARYEFLWG PRALAETSYV KVLEYVIKVS ARVRFFFPSL REAALREEEE  60
GV                                                                 62

SEQ ID NO: 69           moltype = AA  length = 11
FEATURE                 Location/Qualifiers
source                  1..11
                        mol_type = protein
                        organism = Homo sapiens
SEQUENCE: 69
SELSPRADPC V                                                       11

SEQ ID NO: 70           moltype = AA  length = 15
FEATURE                 Location/Qualifiers
source                  1..15
                        mol_type = protein
                        organism = Homo sapiens
SEQUENCE: 70
VDYSISRDGE THYRT                                                   15

SEQ ID NO: 71           moltype = AA  length = 8
FEATURE                 Location/Qualifiers
source                  1..8
                        mol_type = protein
                        organism = Homo sapiens
SEQUENCE: 71
FFFPSLEA                                                           8

SEQ ID NO: 72           moltype = AA  length = 9
FEATURE                 Location/Qualifiers
source                  1..9
                        mol_type = protein
                        organism = Homo sapiens
SEQUENCE: 72
FPSLREAAL                                                          9

SEQ ID NO: 73           moltype = AA  length = 10
FEATURE                 Location/Qualifiers
source                  1..10
                        mol_type = protein
                        organism = Homo sapiens
SEQUENCE: 73
ETSYVKVLEY                                                         10
```

-continued

```
SEQ ID NO: 74          moltype = AA  length = 9
FEATURE                Location/Qualifiers
source                 1..9
                       mol_type = protein
                       organism = Homo sapiens
SEQUENCE: 74
ALAETSYVK                                                        9

SEQ ID NO: 75          moltype = AA  length = 9
FEATURE                Location/Qualifiers
source                 1..9
                       mol_type = protein
                       organism = Homo sapiens
SEQUENCE: 75
TSYVKVLEY                                                        9
```

What is claimed is:

1. An isolated MAGEA1 (VRFFFPSL (SEQ ID NO: 1)) peptide-MHC (HLA-C*0702) (pMHC) complex binding protein comprising:

a) a T cell receptor (TCR) alpha chain variable domain comprising CDR1 comprising residues 45-49 of SEQ ID NO: 39, CDR2 comprising residues 67-73 of SEQ ID NO: 39, and CDR3 comprising residues 107-120 of SEQ ID NO: 39; and b) a TCR beta chain variable domain comprising CDR1 comprising residues 46-50 of SEQ ID NO: 41, CDR2 comprising residues 68-73 of SEQ ID NO: 41, and CDR3 comprising residues 111-124 of SEQ ID NO: 41.

2. The binding protein of claim 1 comprising:

a) a TCR alpha chain variable ($V_\alpha$) domain comprising an amino acid sequence comprising at least 80% identity, at least 85% identity, at least 90% identity, at least 95% identity, at least 99%, or 100% identity to residues 1-131 of SEQ ID NO: 39; and b) a TCR beta chain variable ($V_\beta$) domain comprising an amino acid sequence comprising at least 80% identity, at least 85% identity, at least 90% identity, at least 95% identity, at least 99%, or 100% identity to residues 1-134 of SEQ ID NO: 41.

3. The binding protein of claim 2 comprising:

a) a TCR alpha chain variable ($V_\alpha$) domain comprising an amino acid sequence comprising residues 1-131 of SEQ ID NO: 39; and b) a TCR beta chain variable ($V_\beta$) domain comprising an amino acid sequence comprising residues 1-134 of SEQ ID NO: 41.

4. The binding protein of claim 1 comprising:

a) a TCR alpha chain comprising an amino acid sequence comprising at least 80% identity, at least 85% identity, at least 90% identity, at least 95% identity, at least 99%, or 100% identity to the sequence of SEQ ID NO: 39; and b) a TCR beta chain comprising an amino acid sequence comprising at least 80% identity, at least 85% identity, at least 90% identity, at least 95% identity, at least 99%, or 100% identity to the sequence of SEQ ID NO: 41.

5. The binding protein of claim 4 comprising:

a) a TCR alpha chain comprising an amino acid sequence comprising the sequence of SEQ ID NO: 39; and b) a TCR beta chain comprising an amino acid sequence comprising the sequence of SEQ ID NO: 41.

6. The binding protein of any one of claims 1-5, wherein 1) the TCR Va domain is encoded by a TRAV27 gene and a TRAJ52 gene, and the TCR VB domain is encoded by a TRBV12-4 gene and a TRBJ1-4; or 2) the TCR alpha chain is encoded by a TRAV27 gene, a TRAJ52 gene, and an MGTM modified TRAC gene and the TCR beta chain is encoded by a TRBV12-4 gene, a TRBJ1-4 gene, and an MGTM modified TRBC1 gene.

7. The binding protein of any one of claims 1-5, wherein the binding protein is an antibody, an antigen-binding fragment of an antibody, a TCR, an antigen-binding fragment of a TCR, a single chain TCR (scTCR), a chimeric antigen receptor (CAR), or a fusion protein comprising a TCR and an effector domain.

8. The binding protein of claim 7, wherein the binding protein is a TCR.

9. The binding protein of any one of claims 1-5, wherein the binding protein is chimeric, humanized, or human.

10. The binding protein of any one of claims 1-5, wherein the binding protein comprises a binding domain, a transmembrane domain, and an intracellular effector domain.

11. The binding protein of any one of claims 1-5, wherein the TCR alpha chain and the TCR beta chain are covalently linked, wherein the covalent linkage is through a linker peptide.

12. The binding protein of any one of claims 1-5, wherein the TCR alpha chain and/or the TCR beta chain are covalently linked to an affinity tag or a label.

13. The binding protein of any one of claims 1-5, wherein the binding protein binds to the pMHC complex on a cell surface.

14. The binding protein of any one of claims 1-5, wherein binding of the binding protein to a MAGEA1 peptide-MHC (pMHC) complex elicits an immune response selected from the group consisting of a T cell response, a CD8+ T cell response, T cell expansion, cytokine release, and cytotoxic killing.

15. The binding protein of claim 14, wherein the binding protein is a TCR.

16. The binding protein of any one of claims 1-5, wherein the binding protein is capable of specifically and/or selectively binding to a MAGEA1 peptide-MHC (pMHC) complex with a $K_d$ less than or equal to about $1\times10^{-4}$ M.

17. The binding protein of any one of claims 1-5, wherein the binding protein does not bind to a peptide-MHC (pMHC) complex selected from the group consisting of ALKDVEERV (SEQ ID NO: 62)/HLA-A*02, LLFGLALIEV (SEQ ID NO: 63)/HLA-A*02, SESIKKKVL (SEQ ID NO: 64)/HLA-B*44, ASSTLYLVF (SEQ ID NO: 65)/HLA-B*57, and a pMHC complex comprising a LAMB4-IR, TLE3, SLC16A2, SLC6A13, BTBD2, RXFP1, and/or PIGO peptide epitope.

18. An isolated nucleic acid molecule that encodes the MAGEA1 (VRFFFPSL (SEQ ID NO: 1)) peptide-MHC (HLA-C*0702) (pMHC) complex binding protein of any one of claims 1-5.

19. The isolated nucleic acid molecule of claim 18, wherein the nucleic acid is codon optimized for expression in a host cell.

20. An isolated nucleic acid molecule that encodes the MAGEA1 (VRFFFPSL (SEQ ID NO: 1)) peptide-MHC (HLA-C*0702) (pMHC) complex binding protein of claim 15.

21. The isolated nucleic acid molecule of claim 20, wherein the nucleic acid is codon optimized for expression in a host cell.

22. A cloning vector, expression vector, or viral vector comprising the isolated nucleic acid of claim 19.

23. The vector of claim 22, further comprising a nucleic acid sequence encoding CD8α, CD8β, a dominant negative TGFβ receptor II (DN-TGFβRII), and/or a selectable protein marker, optionally wherein a) the selectable protein marker is dihydrofolate reductase (DHFR);

b) the nucleic acid sequence encoding CD8α, CD8β, the DN-TGFβRII, and/or the selectable protein marker is operably linked to a nucleic acid encoding a tag, optionally wherein 1) the nucleic acid encoding a tag is at the 5' upstream of the nucleic acid sequence encoding CD8α, CD8β, the DN-TGFβRII, and/or the selectable protein marker such that the tag is fused to the N-terminus of CD8α, CD8β, the DN-TGFβRII, and/or the selectable protein marker; and/or 2) the tag is a CD34 enrichment tag; and/or c) the nucleic acid sequence encoding TCRα, TCRβ, CD8α, CD8β, the DN-TGFβRII, and/or the selectable protein marker are interconnected with an internal ribosome entry site or a nucleic acid sequence encoding a self-cleaving peptide, optionally wherein the self-cleaving peptide is P2A, E2A, F2A or T2A.

24. The vector of claim 23 comprising a nucleic acid sequence encoding CD8α and CD8β.

25. The vector of claim 24 comprising a vector sequence of SEQ ID NO: 51 or 52.

26. A cloning vector, expression vector, or viral vector comprising the isolated nucleic acid of claim 21.

27. The vector of claim 26, further comprising a nucleic acid sequence encoding CD8α, CD8β, a dominant negative TGFβ receptor II (DN-TGFβRII), and/or a selectable protein marker, optionally wherein a) the selectable protein marker is dihydrofolate reductase (DHFR);

b) the nucleic acid sequence encoding CD8α, CD8β, the DN-TGFβRII, and/or the selectable protein marker is operably linked to a nucleic acid encoding a tag, optionally wherein 1) the nucleic acid encoding a tag is at the 5' upstream of the nucleic acid sequence encoding CD8α, CD8β, the DN-TGFβRII, and/or the selectable protein marker such that the tag is fused to the N-terminus of CD8α, CD8β, the DN-TGFβRII, and/or the selectable protein marker; and/or 2) the tag is a CD34 enrichment tag; and/or c) the nucleic acid sequence encoding TCRα, TCRβ, CD8α, CD8β, the DN-TGFβRII, and/or the selectable protein marker are interconnected with an internal ribosome entry site or a nucleic acid sequence encoding a self-cleaving peptide, optionally wherein the self-cleaving peptide is P2A, E2A, F2A or T2A.

28. The vector of claim 27 comprising a nucleic acid sequence encoding CD8α and CD8β.

29. A genetically engineered host cell which exogenously comprises the vector of claim 22.

30. The host cell of claim 29, wherein the host cell has one or more of the following properties:

1) comprises a chromosomal gene knockout of a TCR gene, an HLA gene, or both;

2) comprises a knockout of an HLA gene selected from an α1 macroglobulin gene, α2 macroglobulin gene, α3 macroglobulin gene, β1 microglobulin gene, β2 microglobulin gene, and combinations thereof;

3) comprises a knockout of a TCR gene selected from a TCRα variable region gene, TCRβ variable region gene, TCR constant region gene, and combinations thereof;

4) expresses CD8α, CD8β, a DN-TGFβRII, and/or a selectable protein marker, optionally wherein the selectable protein marker is DHFR, further optionally wherein the CD8α, CD8β, the DN-TGFβRII, and/or the selectable protein marker is fused to a CD34 enrichment tag, optionally wherein host cells are enriched using the CD34 enrichment tag;

5) is a hematopoietic progenitor cell, peripheral blood mononuclear cell (PBMC), cord blood cell, or immune cell, optionally wherein the immune cell is a T cell, cytotoxic lymphocyte, cytotoxic lymphocyte precursor cell, cytotoxic lymphocyte progenitor cell, cytotoxic lymphocyte stem cell, $CD4^+$ T cell, $CD8^+$ T cell, CD4/CD8 double negative T cell, gamma delta (γδ) T cell, natural killer (NK) cell, NK-T cell, dendritic cell, or a combination thereof, further optionally wherein the T cell is a) a naive T cell, central memory T cell, effector memory T cell, or a combination thereof;

b) a primary T cell or a cell of a T cell line; and/or c) does not express or has a lower surface expression of an endogenous TCR;

6) is capable of producing a cytokine or a cytotoxic molecule when contacted with a target cell that comprises a peptide-MHC (pMHC) complex comprising a MAGEA1 peptide epitope in the context of an MHC molecule, optionally wherein a) the host cell is contacted with the target cell in vitro, ex vivo, or in vivo;

b) the cytokine is TNF-α, IL-2, and/or IFN-γ;

c) the cytotoxic molecule is a perforin and/or a granzyme, optionally wherein the cytotoxic molecule is granzyme B;

d) the host cell is capable of producing a higher level of cytokine or a cytotoxic molecule when contacted with a target cell with a heterozygous expression of MAGEA1, optionally wherein the host cell is capable of producing an at least 1.05-fold higher level of cytokine or a cytotoxic molecule; and/or e) the target cell is a cell line or a primary cell, optionally wherein the target cell is selected from the group consisting of a HEK293 derived cell line, a cancer cell line, a primary cancer cell, a transformed cell line, and an immortalized cell line;

7) is capable of killing a target cell that comprises a peptide-MHC (pMHC) complex comprising the MAGEA1 peptide epitope in the context of an MHC molecule, optionally wherein a) the killing is determined by a killing assay;

b) the ratio of the host cell and the target cell in the killing assay is from 20:1 to 1:4;

c) the target cell is a target cell pulsed with 1 μg/mL to 50 μg/mL of MAGEA1 peptide, optionally wherein the target cell is a cell monoallelic for an MHC matched to the MAGEA1 peptide;

d) the host cell is capable of killing a higher number of target cells when contacted with target cells with a heterozygous expression of MAGEA1, optionally wherein the cell killing is at least 1.05-fold higher; and/or e) the target cell is a cell line or a primary cell, optionally wherein the target cell is selected from the group consisting of a HEK293 derived cell line, a cancer cell line, a primary cancer cell, a transformed cell line, and an immortalized cell line;

8) does not induce T cell expansion, cytokine release, or cytotoxic killing when contacted with a target cell that comprises a peptide-MHC (pMHC) complex comprising a LAMB4-IR, TLE3, SLC16A2, SLC6A13, BTBD2, RXFP1, and/or PIGO peptide epitope; and/or 9) does not express MAGEA1 antigen, is not of serotype HLA-C*07, and/or does not express an HLA-C*07 allele.

31. A genetically engineered host cell which exogenously comprises the vector of claim 24.

32. A genetically engineered host cell which exogenously comprises the vector of claim 28.

33. A method of producing a host cell expressing a binding protein, wherein the method comprises the steps of: (i) introducing a vector according to claim 22 into the host cell; and (ii) culturing the transformed host cell under conditions suitable to allow expression of said binding protein.

34. A method of producing a host cell expressing a binding protein, wherein the method comprises the steps of: (i) introducing a vector according to claim 24 into the host cell; and (ii) culturing the transformed host cell under conditions suitable to allow expression of said binding protein.

35. A method of producing a host cell expressing a binding protein, wherein the method comprises the steps of: (i) introducing a vector according to claim 28 into the host cell; and (ii) culturing the transformed host cell under conditions suitable to allow expression of said binding protein.

* * * * *